US010640778B2

(12) United States Patent
Barrangou et al.

(10) Patent No.: US 10,640,778 B2
(45) Date of Patent: May 5, 2020

(54) METHOD OF MODULATING CELL RESISTANCE

(71) Applicant: DUPONT NUTRITION BIOSCIENCES APS, Copenhagen K (DK)

(72) Inventors: Rodolphe Barrangou, Madison, WI (US); Patrick Boyaval, Dange Saint Romain (FR); Christophe Fremaux, Dange Saint Romain (FR); Philippe Horvath, Dange Saint Romain (FR); Dennis Romero, Oregon, WI (US)

(73) Assignee: DUPONT NUTRITION BIOSCIENCES APS (DK)

( * ) Notice: Subject to any disclaimer, the term of this patent is extended or adjusted under 35 U.S.C. 154(b) by 0 days.

(21) Appl. No.: 15/229,103

(22) Filed: Aug. 4, 2016

(65) Prior Publication Data

US 2017/0037416 A1 Feb. 9, 2017

Related U.S. Application Data

(63) Continuation of application No. 11/990,885, filed as application No. PCT/US2006/033167 on Aug. 25, 2006, now Pat. No. 10,066,233.

(Continued)

(51) Int. Cl.

*C12N 15/74* (2006.01)
*A23K 20/10* (2016.01)
*A23L 33/135* (2016.01)
*C12Q 1/689* (2018.01)
*C12Q 1/70* (2006.01)
*C12N 15/09* (2006.01)
*C12N 15/52* (2006.01)
*C12N 15/31* (2006.01)

(52) U.S. Cl.

CPC ............ *C12N 15/746* (2013.01); *A23K 20/10* (2016.05); *A23L 33/135* (2016.08); *C12N 15/74* (2013.01); *C12Q 1/689* (2013.01); *C12Q 1/70* (2013.01); *A23V 2002/00* (2013.01); *C12Q 2600/156* (2013.01)

(58) Field of Classification Search

None

See application file for complete search history.

(56) References Cited

U.S. PATENT DOCUMENTS 2,225,783 A 12/1940 Jensen et al.
3,024,116 A 3/1962 Engelland (Continued)

FOREIGN PATENT DOCUMENTS

CA 2183606 2/1997
JP 2005-500847 3/2003

(Continued)

OTHER PUBLICATIONS

Almendros C et al., Target Motifs Affecting Natural Immunity by a Consitutive CRISPR-Cas System in *Escherichia coli*, PLOS One 2012, vol. 7, No. 11, e50797.

(Continued)

*Primary Examiner* — Maria Marvich

(57) ABSTRACT

The present invention relates to the use of one or more cas genes for modulating resistance in a cell against a target nucleic acid or a transcription product thereof.

9 Claims, 22 Drawing Sheets

Figure 1:
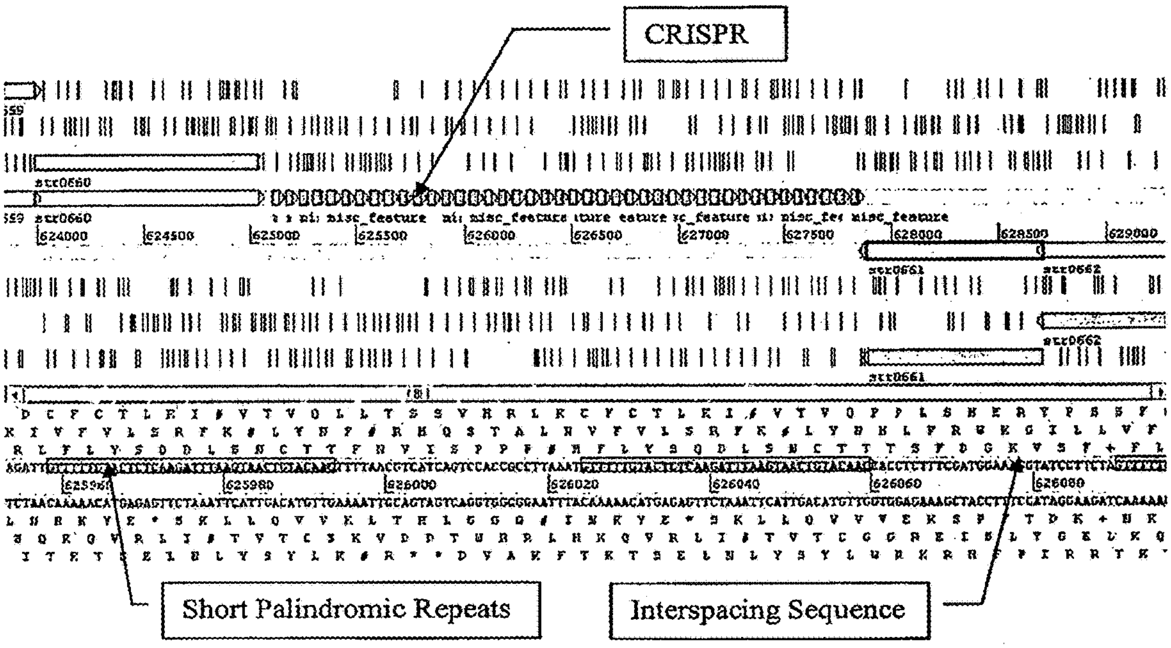

Specification includes a Sequence Listing.

Related U.S. Application Data

(60) Provisional application No. 60/747,683, filed on May 19, 2006, provisional application No. 60/711,396, filed on Aug. 26, 2005.

(56) References Cited

U.S. PATENT DOCUMENTS

| | | | | |
|---|---|---|---|---|
| 3,403,032 | A | 9/1968 | Etchells et al. | |
| 3,897,307 | A | 7/1975 | Porubcan et al. | |
| 3,932,674 | A | 1/1976 | Etchells et al. | |
| 4,140,800 | A | 2/1979 | Kline | |
| 4,423,079 | A | 12/1983 | Kline | |
| 4,621,058 | A | 11/1986 | Reddy | |
| 4,683,195 | A | 7/1987 | Mullis et al. | |
| 4,683,202 | A | 7/1987 | Mullis | |
| 5,097,025 | A | 3/1992 | Benfey et al. | |
| 5,538,864 | A | 7/1996 | Hill et al. | |
| 7,169,911 | B2 | 1/2007 | Durmaz et al. | |
| 2005/0130126 | A1 | 6/2005 | Durmaz et al. | |
| 2005/0232909 | A1 | 10/2005 | Farmer | |
| 2006/0194751 | A1 * | 8/2006 | Meinke | C07K 14/315 514/44 R |
| 2010/0093617 | A1 | 4/2010 | Barrangou et al. | |
| 2011/0300538 | A1 | 12/2011 | Barrangou et al. | |
| 2013/0288251 | A1 | 10/2013 | Horvath et al. | |
| 2014/0286989 | A1 | 9/2014 | Chang | |

FOREIGN PATENT DOCUMENTS

| | | |
|---|---|---|
| NZ | 565563 | 2/2012 |
| WO | 9951771 | 10/1999 |
| WO | 200104520 | 3/2001 |
| WO | 03/018760 | 3/2003 |
| WO | 2007/025097 | 3/2007 |
| WO | WO2012054726 | 4/2012 |

OTHER PUBLICATIONS

Supplementary online material for *Bolotin A. et al., Complete sequence and comparative genome analysis of the dairy bacterium *Streptococcus thermophilus*, Nature Biotechnology, 2004, vol. 22, No. 12, p. 1554-1558 )—10 tables and 3 figures.

Deskmukh, Vishal, A regenerative approach to the treatment of multiple sclerosis, Nature, vol. 502, Oct. 17, 2003, p. 327-349.

Guo et al, Protein tolerance to random amino acid change, PNAS, 2004, vol. 101 (25), pp. 9205-9210.

Lesk et al, Prediction of Protein Function from Protein Sequence and Structure, p. 27 and 28 downloaded Sep. 19, 2009.

O'Connor et al, (Appln Environ Microbiol, 62(9)3075-82, 1996).

Barrangou R, Diversity of CRISPR-Cas immune systems and molecular machines, Genome Biology, 2015 vol. 16 pp. 247.

Duplessis M et al., Characterization of *Streptococcus thermophilus*, Host Range Phage Mutants, Applied and Environmental Microbiology, Apr. 2006, vol. 72 No. 4, pp. 3036-3041.

Shah S A et al., "Protospacer recognition motifs", RNA Biology, vol. 10, No. 5, May 1, 2013, pp. 891-899.

Garvey P. et al., "Cloning and DNA sequence analysis of two abortive infection phage resistance determinants from Lactococcal plasmid PNP40", Applied and Environmental Microbiology, 1995, vol. 61, No. 1, p. 4321-4328.

McGrath S. et al., "Molecular characterization of a phage-encoded resistance system in Lactococcus lactis", Applied and Environmental Microbiology, 1999, vol. 65, No. 5, p. 1891-1899.

Viscardi M et al., "Selection of bacteriophage-resistant mutants of *Streptococcus thermophilus*", Journal of Microbiological Methods, 2003, vol. 55, No. 1, p. 109-119.

Coffey A et al., "Bacteriophage-resistance systems in dairy starter strains: molecular analysis to application", Antonie Van Leeuwenhoek, Aug. 2002, vol. 82, No. 1-2, p. 303-321.

Barrangou R et al., "CRISPR provides acquired resistance against viruses in prokaryotes", Science, Mar. 23, 2007, vol. 315, No. 5819, p. 1709-1712.

Wi Soo Jin, Park Ky Young, "Antisense expression of carnation cDNA encoding ACC synthase or ACC oxidase enhances polyamine content and abiotic stress tolerance in transgenic tobacco plants", Molecules and Cells, Apr. 30, 2002, vol. 13, No. 2, p. 209-220.

Ogryzko V V et al., "Antisense inhibition of CAS, the human homologue of the yeast chromosome segregation gene CSE1, interferes with mitosis in heal cells", Biochemistry, Jan. 1, 1997, vol. 31, No. 36, p. 9493-9500.

Makarova K. S. et al., A putative RNA-interference-based immune system in prokaryotes: computational analysis of the predicted enzymatic machinery, functional analogies with eukaryotic RNAi, and hypothetical mechanisms of action, Biology Direct, 2006, vol. 1, p. 7 DOI: 10.1186/1745-6150-1-7.

Sturino J. M. & Klaenhammer T. R., Bacteriophage Defense Systems and Strategies for Lactic Acid Bacteria, Advances in Applied Microbiology, 2004, vol. 56, p. 331-378.

O'Flynn G. et al., Evaluation of a cocktail of three bacteriophages for biocontrol of *Escherichia coli* O157:H7, Applied and Environmental Microbiology, 2004, vol. 70, No. 6, p. 3417-3424.

Lucchini S. et al., Broad-Range Bacteriophage Resistance in *Streptococcus thermophilus* by Insertional Mutagenesis, Virology, 2000, vol. 275, p. 267-277.

Mills S. et al., CRISPR analysis of bacteriophage-insensitive mutants (BIMs) of industrial *Streptococcus thermophilus*—implications for starter design, Journal Applied Microbiology, 2010, vol. 108, p. 945-955.

Krylov V.N. et al., Selection and properties of totally phage-resistant mutant Pseudomonas putida PpG1, Genetika, 1996, Mar, vol. 32, No. 3, p. 348-353 English Abstract, retrieved from PubMed.

Moineau S. Bacterophages and Phage Resistance in *Streptococcus thermophilus*: An update, Proc. From 34th Marshall Seminar, Sep. 17 & 18, 1997, p. 9-17.

Bacterophage not organism, says bacteriologist, J. Chem. Educ. 1930, vol. 7, No. 7, p. 1641.

Moineau S, Applications of phage resistance in lactic acid bacteria, Antonie van Leuvenhoek, 1999, vol. 76, p. 377-382.

Barrangou, Science 2007 vol. 315, p. 1709—supporting online material.

Kunin V. et al., Evolutionary conservation of sequence and secondary structures in CRISPR repeats, Genome Biology 2007, vol. 8, R61.

O'Connor, L. et al., AbiG, a Genotypically Novel Abortive Infection Mechanism Encoded by Plasmid pCI750 of *Lactococcus lactis* subsp. *cremoris* UC653; vol. 62, No. 9.

Duplessis, M., et al., Global gene expression analysis of two *Streptococcus thermophilus* bacteriophages using DNA microarray, Virology, 2005, vol. 340, No. 2, p. 192-208.

Ibrahim M et al., A genome-wide survey of short coding sequences in *Streptococci*, Microbiology, 2007, vol. 153, p. 3631-3644.

Brouns SJJ et al., Small CRISPR RNAs Guide Antiviral Defense in Prokaryotes, Science, 2008, vol. 321, p. 960-964.

Marraffini LA et al., CRISTPR Interference Limits Horizontal Gene Transfer in *Staphylococci* by Targeting DNA, Science, vol. 322, Dec. 19, 2008, p. 1843-1845.

Deveau H et al., Phage Response in CRISPR-Encoded Resistance in *Streptococcus thermophilus*, Journal of Bacteriology, Feb. 2008, vol. 190, No. 4, p. 1390-1400.

Horvath P et al., Comparative analysis of CRISPR loci in lactic acid bacteria genomes, International Journal of Food Microbiology, 2009, vol. 131, p. 62-70.

Horvath P et al., CRISPR/Cas, the Immune System of Bacteria and Archaea, Science, Jan. 8, 2010, vol. 327, 167-170.

Labrie SJ et al., Bacteriophage resistance mechanisms, Nature Reviews Microbiology, May 2010;8(5):317-27 and published online Mar. 29, 2010.

Hale CR et al., RNA-Guided RNA Cleavage by CRISPR RNA-Cas Protein Complex, Cell. Nov. 25, 2009;139(5):945-56.

Gameau JE et al., The CRISPR/Cas bacterial immune system cleaves bacteriophage and plasmid DNA, Nature, Nov. 4, 2010, vol. 468, p. 67-71.

(56) References Cited

OTHER PUBLICATIONS

Westra ER et al., H-NS-mediated repression of CRISPR-based immunity in *Escherichia coli* K12 can be relieved by the transcription activator LeuO, Molecular Microbiology, 2010, vol. 77, No. 6, p. 1380-1393.

Pougach K et al., Transcription, processing and function of CRISPR cassettes in *Esherichia coli*, Molecular Microbiology, Sep. 2010;77(6):1367-79.

Pul U et al., Identification and characterization of *E. coli* CRISPR-cas Promoters and their Silencing by H—NS, Molecular Microbiology, Mar. 2010;75(6):1495-512.

Sinkunas T et al., Cas3 is a single-stranded DNA nuclease and ATP-dependent helicase in CRISPR/Cas immune system, EMBO Journal 2011.

Deltcheva E et al., CRISPR RNA maturation by trans-encoded small RNA and host factor Rnase III, Nature, 2001 vol. 471, p. 602-606.

Makarova K. S. et al., Evolution and classification of the CRISPR-Cas systems, Nature Reviews 2011 v9 p. 467-477.

Sashital D G et al., Mechanism of Foreign DNA Selection in a Bacterial Adaptive Immune System, Molecular Cell, 2012, vol. 46, p. 606-615.

Westra ER et al., CRISPR Immunity Relies on the Consecutive Binding and Degradation of Negatively Supercoiled Invader DNA by Cascade and Cas3, Molecular Cell, 2012, vol. 46, p. 595-605.

Jinek M et al., A programmable dual-RNA-guided DNA endonuclease in adaptive bacterial immunity, Science, Aug. 17, 2012;337(6096):816-21.

Gasiunas G et al., Cas9-crRNA ribonucleoprotein complex mediates specific DNA cleavage for adaptive immunity in bacteria, Proc. Natl. Acad. Sci. USA, Sep. 25, 2012;109(39):E2579-86.

Sapranaushkas R et al., The *Streptococcus thermophilus* CRISPR/Cas system provides immunity in *Escherichia coli*, Nucleic Acids Research, 2011, p. 1-8.

Martinez et al., Clinical Microbiology Review, 2002, vol. 15, No. 4, pp. 647-679.

Sapranauskas, R. et al., "The *Streptococcus thermophilus* CRISPR/Cas system provides immunity in *Escherichia coli*," Nucleic Acids Research, 2011, vol. 39, No. 21, pp. 9375-9282 (p. 1-8).

Deveau, H. et al., "CRISPR/Cas System and its role in phage-bacteria interactions," Annu. Rev. Microbial., 2010, vol. 64, pp. 475-493.

Biswas, I. et al., "High-efficiency gene inactivation and replacement system for Gram-positive bacteria," Journal of Bacteriology, Jun. 1993, vol. 175, No. 11, pp. 3628-3635.

Mollet, B. et al., "Directed genomic integration, gene replacement, and integrative gene expression in *Streptococcus thermophilus*," Journal of Bacteriology, Jul. 1993 , vol. 175, No. 14, pp. 4315-4324.

Maguin, E. et al., "Efficient Insertional Mutagenesis in Lactococci and Other Gram-Posive Bacteria," Journal of Bacteriology (Feb. 1996) vol. 178, No. 3, p. 931-935.

The Concise Oxford Dictionary, 1999—definition of "suppress".

Horvath P. et al., Diversity, Activity, and Evolution of CRISPR loci in *Streptococcus thermophilus*, Journal of Bacteriology, Feb. 2008, vol. 190, No. 4, p. 1401-1412.

Horvath P. et al., CRISPR/Cas, the Immune System of Bacteria and Archaea, Science, 2010, vol. 327, p. 167.

Ellis H. M, et al., "High efficiency mutagenesis, repair and engineering of chromosomal DNA using single-stranded olignoucleotides", Proceedings of the National Academy of Science, 2001, vol. 98, No. 12, p. 6742-6746.

Pourcel C, Savignol G, & G Vergnaud (2005). CRISPR elements in Yersinia pestis aquire new repeats by preferential uptake of bacteriophage DNA and provide additional tools for evolutionary studies. Microbiology 151:653-663.

Jansen R. et al. 'Identification of genes that are associated with DNA repeats in prokaryotes' Molecular Microbiology, Feb. 2002, vol. 43, No. 6, p. 1565-1575.

Mojica F J. M. et al., "Intervening sequences of regularly spaced prokaryotic repeats derive from foreign genetic elements", Journal of Molecular Evolution, 2005, vol. 60, No. 2, p. 174-182.

Peng X, Brugger K, Shen L, She Q, & RA Garrett (2003). Genus-specific protein binding to the large clusters of DNA repeats (Short Regularly Spaced Repeats) present in Sulfolobus genomes. Journal of Bacteriology 185:2410-2417.

Koonin E, Archaeal diversity, poster at 158th Meeting of Society for General Microbiology, Apr. 3-6, 2006, University of Warwick.

Altschul S.F. et al., Basic Local Alignment Search Tool, J. Mol. Biol., 1990, vol. 215, p. 403-410.

Ausubel et al., Current Protocols in Molecular Biology, 1999, Wiley, New York, pp. 7-58 to 7-60.

Barrangou R. et al., Identification and Characterization of Leuconostoc fallax Strains isolated from an Industrial Sauerkraut Fermentation, Applied and Environmental Microbiology, 2002, vol. 68, p. 2877-2884.

Bolotin A, Quinquis B, Sorokin A, Ehrlich SD (2005). Clustered regularly interspaced short palindrome repeats (CRISPRs) have spacers of extrachromosomal origin. Microbiology 151(8):2551-2561.

Bolotin A. et al., Complete sequence and comparative genome analysis of the dairy bacterium *Streptococcus thermophilus*, Nature Biotechnology, 2004, vol. 22, No. 12, p. 1554-1558.

Devereux J. et al., A comprehensive set of sequence analysis programs for the VAX, Nucleic Acids Research, 1984, vol. 12, No. 1, p. 387-395.

Genbank accession No. DQ072990, Aug. 1, 2005.

Genbank accession No. DQ072991, Aug. 1, 2005.

Groenen PM, Bunschoten AE, van Soolingen D, & JD van Embden (1993). Nature of DNA polymorphism in the direct repeat cluster of *Mycobacterium tuberculosis*; application for strain differentiation by a novel typing method. Molecular Microbiology 10:1057-1065.

Haft D. H. et al., A Guild of 45 CRISPR-Assocation (Cas) Protein Families and Multiple CRISPR/Cas Subtypes Exist in Prokaryotic Genomes, Computational Biology, 2005, vol. 1, No. 6, e60.

Hoe N, Nakashima K, Grigsby D, Pan X, Dou SJ, Naidich S, Garcia M, Kahn E, Bergmire-Seat D, & JM Musser (1999). Rapid molecular genetic subtyping of serotype M1 group A *Streptococcus* strains. Emerging Infectious Diseases 5:254-263.

Horwell DC, The "peptoid" approach to the design of non-peptide, small molecule agonists and antagonists of neuropeptides, Trends Biotechnology, 1995, vol. 13, No. 4, p. 132-134.

Ishino Y. et al., Nucleotide Sequence of the iap Gene, Responsible for Alkaline Phosphatase Iszyme Conversion in *Escherichia coli*, and Identification of the Gene Product, J. Bacteriol., 1987, 169:5429-5433.

Jansen R, Van Embden JDA, Gaastra W, & LM Schouls (2002a). Identification of a novel family of sequence repeats among prokaryotes. OMICS 6:23-33.

Kamerbeek J, Schouls L, Kolk A, Van Agterveld M, Van Soolingen D, Kuijper S, Bunschoten A, Molhuizen H, Shaw R, Goyal M, & J Van Embden (1997). Simultaneous detection and strain differentiation of *Mycobacterium tuberculosis* for diagnosis and epidemiology. Journal of Clinical Microbiology 35:907-914.

Knorr D (editor), Food Biotechnology,1987, vol. 21, chapter 20, Bacterial Starter Cultures, p. 530, 538-539, 540.

Kosuge T. et al., Molecular cloning and sequence analysis of the proBA operon from an extremely thermophilic aubacterium Thermus Thermophilus, FEMS Microbiology Letters, 1994, vol. 123, No. 1-2, p. 55-62.

Kosuge T. et al, Construction of a Proline-Producing Mutant of the Extremely Thermophilic Eubacterium Thermus thermophilius HB27, Applied Environmental Microbiology, 1998, vol. 64, Issue: 11, pp. 4328-4332.

Levesque C. et al., Genomic Organization and Molecular Analysis of Virulent Bacteriophage 2972 Infecting an Exopolysaccharide-producing *Streptococcus thermophilus* Strain, Applied and Environmental Microbiology, 2005, 71:4057-4068.

Masepohl B. et al., Long tandemly repeated repetitive (LTRR) sequences in the filamentous cyanobacterium *Anabaena* sp. PCC 7120, Biochim. Biophys. Acta, 1996, 1307:26-30.

(56) References Cited

OTHER PUBLICATIONS

Mojica F.J.M. et al., Long stretches of short tandem repeats are present in the largest replicons of the Archaea Hasloferax mediterranei and Haloferax volcanii and could be involved in replicon partitioning, Mol. Microbiol., 1995, 17:85-93.
Mojica F.J.M., Diez-Villasenor C, Soria E, & G Juez (2000). Biological significance of a family of regularly spaced repeats in the genomes of Archaea, Bacteria and mitochondria. Molecular Microbiology 36:244-246.
Mongodin EF, Hance IR, DeBoy RT, Gill SR, Daugherty S, Huber R, Fraser CM, Stetter K, & KE Nelson (2005). Gene transfer and genome plasticity in Thermotoga maritima, a model hyperthermophilic species. Journal of Bacteriology 187:4935-4944.
Morinaga Y. et al., Improvement of Oligonucleotide-directed site-specific mutagenesis using double-stranded plasmid DNA, Biotechnology, 1984, vol. 2, p. 646-649 (634-639).
Nakata A. et al., Unusual Nucleotide Arrangement with Repeated Sequences in *Escherichia coli* K-12 Chromosome, Journal of Bacteriology, 1989, vol. 171, No. 6, p. 3553-3556.
Nelson R.M. et al., A General Method of Site-Specific Mutagenesis Using a Modification of the Thermus aquaticus, Analytical Biochemistry, 1989, vol. 180, p. 147-151.
Pederson C., Microbiology of Fermented Foods, 1979, 2nd edition, p. 135-151.
Pederson C., Microbiology of Fermented Foods, 1979, 2nd edition, p. 153-209.
Pederson C., Microbiology of Fermented Foods, 1979, 2nd edition, p. 210-234.
Rajagopal S.N. et al. Associative Growth and Proteolysis of *Streptococcus thermophilus* and Lactobacillus bulgaricus n. skim milk, Journal of Dairy Science, 1990, vol. 73, p. 894-899.
Russell, W.M., and T. R. Klaenhammer, Efficient System for Directed integration into the Lactobacillus acidophilus and Lactobacillus gasseri Chromosomes via Homolgous Recombination, Applied and Environmental Microbiology 2001, vol. 67, No. 9, p. 4361-4364.
Sarkar G. et al., The “Megaprimer” Method of Site-Directed Mutagenesis, Biotechniques, 1990, vol. 8, No. 4, p. 404-407.
Saunders NFW, Goodchild A, Raftery M, Guilhaus M, Curmi PMG, & R Cavicchioli (2005). Predicted roles for hypothetical proteins in the low-temperature expressed proteome of the Antarctic archaeon Methanococcoides burtonii. Journal of Proteome Research 4:464-472.
Simon R.J. et al., Peptoids: A modular approach to drug discovery, Proc. Natl. Acad. Sci. USA, 1992, vol. 89. No. 20, p. 9367-9371.
Tatusova T.A. et al., BLAST 2 Sequences, a new tool for comparing protein and nucleotide sequences, FEMS Microbiology Letters, 1999, vol. 174, No. 2, p. 247-250.
Tatusova T.A. et al., Erratum to BLAST 2 Sequences, a new tool for comparing protein and nucleotide sequences, FEMS Microbiology Letters, 1999, vol. 177, No. 1, p. 187-188.
Van Embden J.D.A. et al., Genetic Variation and Evolutionary Origin of the Direct Repeat Locus of *Mycobacterium tuberculosis* Complex Bacteria, Journal of Bacteriology, 2000, vol. 182, No. 9, p. 2393-2401.
Boucher I. et al., “DNA sequence analysis of three Lactococcus lactis plasmids encoding phage resistance mechanisms”, Journal of Dairy Science, 2001, vol. 84, No. 7, p. 1610-1620.
Cluzel P-J et al., “Phage abortive infection mechanism from Lactococcus-Lactis-SSP-Lactis expression of which is mediated by an ISO-ISS1 element”, Applied and Environmental Microbiology, 1991, vol. 57, No. 12, p. 3547-3551.

* cited by examiner

FIG. 3A

| Interspacing sequence number | Phages | | | | | | | | | | | | | | | | Number of matches |
|---|---|---|---|---|---|---|---|---|---|---|---|---|---|---|---|---|---|
| | Sfi19 | Sfi21 | Sfi11 | DT1 | MD2 | Sfi18 | Sfi21 | St3 | O1205 | Dt2 | 2972 | Dt4 | MD1 | Q5 | Kappa3 | 7201 | |
| 1 | | | | ■ | | | | | | | ■ | | | | ■ | | 3 |
| 3 | | | ■ | | | ■ | | | ■ | | | | | | | | 3 |
| 5 and 31 | | | ■ | ■ | | | | | ■ | | | | | | | | 3 |
| 6 | | | ■ | | | | | | ■ | | | | | | | | 2 |
| 8 | | | | ■ | | | | | | | | | | | | | 1 |
| 11 | | ■ | | ■ | | | | | | | | | | | | | 2 |
| 13 | ■ | ■ | ■ | ■ | | ■ | | | ■ | | | | | | | | 6 |
| 17 | ■ | ■ | | | | | | | | | | | | | | | 2 |
| 20 | | | ■ | | | | | | | | | ■ | ■ | ■ | | | 4 |
| 22 | ■ | ■ | ■ | | | ■ | ■ | ■ | ■ | | | | | | | | 7 |
| 23 | | | | | | | | | ■ | | ■ | | | | | | 2 |
| 25 | ■ | ■ | | | | | | | | | | | | | | | 2 |
| 27 | | | | ■ | | | | | | | | | | | | | 1 |
| 28 | ■ | ■ | | | | | | | | | | | | | | | 2 |
| 29 | ■ | ■ | ■ | | ■ | | | | ■ | ■ | ■ | | | | | ■ | 8 |
| 32 | | | | | | | | | ■ | | ■ | | | | | | 2 |
| 34 | ■ | ■ | | | | | | | | | | | | | | | 2 |
| 36 | | | | ■ | | | | | | | | | | | | | 1 |
| 37 | | | | | | | | | | | ■ | | | | | | 1 |
| 41 | | | ■ | | | | | | ■ | | | | | | | | 2 |

FIGURE 3B

```
>gi|5523999|gb|AF115102.1|AF115102  S. thermophilus phage Sfi19
        Query: 842    ttctggtagtggatttagtcaaacagatgt 871
                      |||||||||||| |||||||||||||||||
        Sbjct: 18912  ttctggtagtggttttagtcaaacagatgt 18941

>gi|5524032|gb|AF115103.1|AF115103  S thermophilus phage Sfi21
        Query: 842    ttctggtagtggatttagtcaaacagatgt 871
                      |||||||||||| |||||||||||||||||
        Sbjct: 17084  ttctggtagtggttttagtcaaacagatgt 17113

>gi|7669462|gb|AF158600.2|AF158600  S thermophilus phage Sfi11
        Query: 842    ttctggtagtggatttagtcaaacagatgt 871
                      ||||||||||||||||||||||||||||||
        Sbjct: 21396  ttctggtagtggatttagtcaaacagatgt 21425

>gi|61383211|gb|AF348736.2|  S thermophilus phage MD2
        Query: 842   ttctggtagtggatttagtcaaacagatgt 871
                     |||||||||||| |||||||||||||||||
        Sbjct: 9043  ttctggtagtggttttagtcaaacagatgt 9072

>gi|2444080|gb|U88974.1|  S thermophilus temperate phage O1205
        Query: 842    ttctggtagtggatttagtcaaacagatgt 871
                      |||||||||||| |||||||||||||||||
        Sbjct: 34602  ttctggtagtggttttagtcaaacagatgt 34631

>gi|15077558|gb|AF348739.1|  S thermophilus phage DT2
        Query: 843   tctggtagtggatttagtcaaac 865
                     |||||||||||||||||||||||
        Sbjct: 2575  tctggtagtggatttagtcaaac 2597

>gi|56718416|gb|AY699705.1|  S thermophilus phage 2972
        Query: 846    ggtagtggatttagtcaaacagatgt 871
                      |||||||| |||||||||||||||||
        Sbjct: 20033  ggtagtggctttagtcaaacagatgt 20058

>gi|7248462|gb|AF145054.1|AF145054  S thermophilus phage 7201
        Query: 842    ttctggtagtggatttagtcaaacagat 869
                      |||||| ||||| |||||||||||||||
        Sbjct: 29631  ttctggcagtggttttagtcaaacagat 29658
```

plt22jpg by D. Stewart and M. Zuker (c) 2003 Washington University dG = -7.4 [initially -7.4] sp

FIGURE 15

S2-TCCACTCACGTACAAATAGTGAGTGTACTC
P2 5'-AACGAGTACACTCACTATTTGTACG-3' this is the reverse complement of part of S2

P3 5' TCCACTCACGTACAAATAGTGAGTGTACTC
GTTTTTGTATTCTCAAGATTTAAGTAACTGTACAGT TTGATTCAACATAAAAAG -3'

Please note P3 was designed to contain:
- S2 TCCACTCACGTACAAATAGTGAGTGTACTC
- RT GTTTTTGTATTCTCAAGATTTAAGTAACTGTACAGT

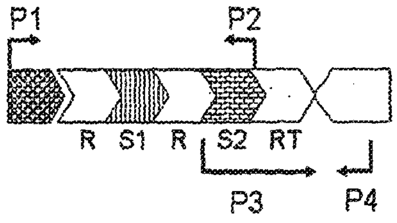

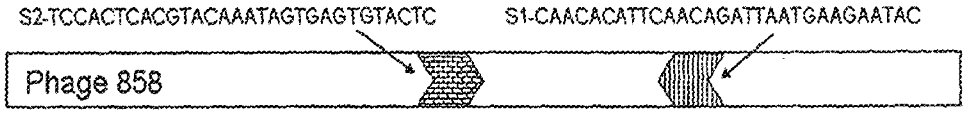

S1 and S2 both originate from phage 858. S1 is in ORF 38 at 31,381bp - S2 is in ORF 27 at 25,440bp

SEQUENCE LISTING

```
<160> NUMBER OF SEQ ID NOS: 712

<210> SEQ ID NO 1
<211> LENGTH: 36
<212> TYPE: DNA
<213> ORGANISM: Steptococcus thermophilus

<400> SEQUENCE: 1

gtttttgtac tctcaagatt taagtaactg tacaac                          36


<210> SEQ ID NO 2
<211> LENGTH: 36
<212> TYPE: DNA
<213> ORGANISM: Steptococcus thermophilus

<400> SEQUENCE: 2

gtttttgtat tctcaagatt taagtaactg tacagt                          36


<210> SEQ ID NO 3
<211> LENGTH: 36
<212> TYPE: DNA
<213> ORGANISM: Steptococcus thermophilus

<400> SEQUENCE: 3

gtttttgtac tctcaagatt taagtaactg tacagt                          36


<210> SEQ ID NO 4
<211> LENGTH: 36
<212> TYPE: DNA
<213> ORGANISM: Steptococcus thermophilus

<400> SEQUENCE: 4

gtttttgtac tctcaagatt taagtaaccg tacaac                          36


<210> SEQ ID NO 5
<211> LENGTH: 36
<212> TYPE: DNA
<213> ORGANISM: Steptococcus thermophilus

<400> SEQUENCE: 5

gtttttgtac tctcaagatt taagtaactg tgcaac                          36


<210> SEQ ID NO 6
```

<211> LENGTH: 36
<212> TYPE: DNA
<213> ORGANISM: Steptococcus thermophilus

<400> SEQUENCE: 6
gtttttgtac tctcaagatt taagtagctg tacagt 36

<210> SEQ ID NO 7
<211> LENGTH: 36
<212> TYPE: DNA
<213> ORGANISM: Steptococcus thermophilus

<400> SEQUENCE: 7
gtttttgtac tctcaagata taagtaactg tacaac 36

<210> SEQ ID NO 8
<211> LENGTH: 36
<212> TYPE: DNA
<213> ORGANISM: Steptococcus thermophilus

<400> SEQUENCE: 8
gtttttgtac tctcaagatc taagtaactg tacaac 36

<210> SEQ ID NO 9
<211> LENGTH: 36
<212> TYPE: DNA
<213> ORGANISM: Steptococcus thermophilus

<400> SEQUENCE: 9
gtttttgtac tctcaagatg taagtaactg tacaac 36

<210> SEQ ID NO 10
<211> LENGTH: 36
<212> TYPE: DNA
<213> ORGANISM: Steptococcus thermophilus

<400> SEQUENCE: 10
gtctttgtac tctcaagatt taagtaactg tacaac 36

<210> SEQ ID NO 11
<211> LENGTH: 36
<212> TYPE: DNA
<213> ORGANISM: Steptococcus thermophilus

<400> SEQUENCE: 11
aaaaaagtcc cctctcgagg taattaggtt tatatc 36

<210> SEQ ID NO 12
<211> LENGTH: 36
<212> TYPE: DNA
<213> ORGANISM: Steptococcus thermophilus

<400> SEQUENCE: 12
gtttccgtcc cctctcgagg taattaggtt tatatc 36

<210> SEQ ID NO 13
<211> LENGTH: 36
<212> TYPE: DNA
<213> ORGANISM: Steptococcus agalactiae

<400> SEQUENCE: 13
gttttagagc tgtgttgttt cgaatggttc caaaac 36

<210> SEQ ID NO 14
<211> LENGTH: 36
<212> TYPE: DNA
<213> ORGANISM: Steptococcus agalactiae

<400> SEQUENCE: 14
gttttaaagc tgtgctgtta ttatgctagg gcacca 36

<210> SEQ ID NO 15
<211> LENGTH: 36
<212> TYPE: DNA
<213> ORGANISM: Steptococcus agalactiae

<400> SEQUENCE: 15
gttttagagc tgtgctgttt cgaatggttc caaaac 36

<210> SEQ ID NO 16
<211> LENGTH: 36
<212> TYPE: DNA
<213> ORGANISM: Steptococcus agalactiae

<400> SEQUENCE: 16
gttttagagc tgtgctgtta ttatgctagg acatca 36

<210> SEQ ID NO 17
<211> LENGTH: 36
<212> TYPE: DNA
<213> ORGANISM: Steptococcus mutans

<400> SEQUENCE: 17
gttttagagc catgttagtt actgatttac taaaat 36

<210> SEQ ID NO 18
<211> LENGTH: 36
<212> TYPE: DNA
<213> ORGANISM: Steptococcus pyogenes

<400> SEQUENCE: 18
gttttagagc tatgctgttt tgaatggtcc caaaac 36

<210> SEQ ID NO 19
<211> LENGTH: 36
<212> TYPE: DNA
<213> ORGANISM: Steptococcus pyogenes

<400> SEQUENCE: 19
gttttagagc tatgctgttt tgaatggtct ccattc 36

<210> SEQ ID NO 20
<211> LENGTH: 33
<212> TYPE: DNA
<213> ORGANISM: Steptococcus pyogenes

<400> SEQUENCE: 20
ctttcaatcc actcacccat gaagggtgag acg 33

<210> SEQ ID NO 21
<211> LENGTH: 33
<212> TYPE: DNA
<213> ORGANISM: Steptococcus pyogenes

<400> SEQUENCE: 21
atttcaatcc actcacccat gaagggtgag act 33

<210> SEQ ID NO 22
<211> LENGTH: 33
<212> TYPE: DNA
<213> ORGANISM: Steptococcus pyogenes

<400> SEQUENCE: 22
atttcaatcc actcacccat gaagggtgag acc 33

<210> SEQ ID NO 23
<211> LENGTH: 30
<212> TYPE: DNA
<213> ORGANISM: Steptococcus thermophilus

<400> SEQUENCE: 23
agaacgtatt ccaaaacctc tttacgatta 30

<210> SEQ ID NO 24
<211> LENGTH: 30
<212> TYPE: DNA
<213> ORGANISM: Steptococcus thermophilus

<400> SEQUENCE: 24
ttaactgtta tcaaaatgat aagatagtct 30

<210> SEQ ID NO 25
<211> LENGTH: 30
<212> TYPE: DNA
<213> ORGANISM: Steptococcus thermophilus

<400> SEQUENCE: 25
cgttgatgtt tattcaagta aaataattaa 30

<210> SEQ ID NO 26
<211> LENGTH: 30
<212> TYPE: DNA
<213> ORGANISM: Steptococcus thermophilus

<400> SEQUENCE: 26
tcctttcacg ggtagcacac taacatacac 30

<210> SEQ ID NO 27
<211> LENGTH: 30
<212> TYPE: DNA
<213> ORGANISM: Steptococcus thermophilus

<400> SEQUENCE: 27
gttggcaatg caaacaacct ttatgaaccg 30

<210> SEQ ID NO 28
<211> LENGTH: 30
<212> TYPE: DNA
<213> ORGANISM: Steptococcus thermophilus

<400> SEQUENCE: 28
tttatttcct tgcgataacg ttccaccttt 30

<210> SEQ ID NO 29
<211> LENGTH: 30
<212> TYPE: DNA
<213> ORGANISM: Steptococcus thermophilus

<400> SEQUENCE: 29
agattataag gaacacaacc aactatatag 30

<210> SEQ ID NO 30
<211> LENGTH: 30
<212> TYPE: DNA
<213> ORGANISM: Steptococcus thermophilus

<400> SEQUENCE: 30
acgacatcaa gctgattgtc ttctacataa 30

<210> SEQ ID NO 31
<211> LENGTH: 30
<212> TYPE: DNA
<213> ORGANISM: Steptococcus thermophilus

<400> SEQUENCE: 31
tttggaatac tgaatgtttt actgaaaatc 30

<210> SEQ ID NO 32
<211> LENGTH: 30
<212> TYPE: DNA
<213> ORGANISM: Steptococcus thermophilus

<400> SEQUENCE: 32
acaccactat cttttcctcc tgaaaatgaa 30

<210> SEQ ID NO 33
<211> LENGTH: 30
<212> TYPE: DNA
<213> ORGANISM: Steptococcus thermophilus

<400> SEQUENCE: 33
gtaattccac gaaattatca accttatgca 30

<210> SEQ ID NO 34
<211> LENGTH: 29
<212> TYPE: DNA
<213> ORGANISM: Steptococcus thermophilus

<400> SEQUENCE: 34
ttggaggatt gccccatatt cccaagagt 29

<210> SEQ ID NO 35
<211> LENGTH: 30
<212> TYPE: DNA
<213> ORGANISM: Steptococcus thermophilus

<400> SEQUENCE: 35
gagaggcgtt aaatatagaa atgcaagatt 30

<210> SEQ ID NO 36
<211> LENGTH: 30
<212> TYPE: DNA
<213> ORGANISM: Steptococcus thermophilus

<400> SEQUENCE: 36
ttttaacgtc atcagtccac cgccttaaat 30

<210> SEQ ID NO 37
<211> LENGTH: 30
<212> TYPE: DNA
<213> ORGANISM: Steptococcus thermophilus

<400> SEQUENCE: 37
cacctctttc gatggaaagg tatccttcta 30

<210> SEQ ID NO 38
<211> LENGTH: 30
<212> TYPE: DNA
<213> ORGANISM: Steptococcus thermophilus

<400> SEQUENCE: 38
gaccaaagtt tgattataga gctatacacc 30

<210> SEQ ID NO 39
<211> LENGTH: 30
<212> TYPE: DNA
<213> ORGANISM: Steptococcus thermophilus

<400> SEQUENCE: 39
accatcattc ttaccattac aactgtaatg 30

<210> SEQ ID NO 40
<211> LENGTH: 30
<212> TYPE: DNA
<213> ORGANISM: Steptococcus thermophilus

<400> SEQUENCE: 40
atacgaattc ggttcgcaca attacaattc 30

<210> SEQ ID NO 41
<211> LENGTH: 32
<212> TYPE: DNA
<213> ORGANISM: Steptococcus thermophilus

<400> SEQUENCE: 41
tatcaacgca atcattacaa caacttcaaa ca 32

<210> SEQ ID NO 42
<211> LENGTH: 30
<212> TYPE: DNA
<213> ORGANISM: Steptococcus thermophilus

<400> SEQUENCE: 42
atctacgtgt caatacatat cacaaaacag 30

<210> SEQ ID NO 43
<211> LENGTH: 29
<212> TYPE: DNA
<213> ORGANISM: Steptococcus thermophilus

<400> SEQUENCE: 43
atttttagaa atttctgata taataatga 29

<210> SEQ ID NO 44
<211> LENGTH: 30
<212> TYPE: DNA
<213> ORGANISM: Steptococcus thermophilus

<400> SEQUENCE: 44
ttgttggaac aaggacgact tggtaaacta 30

<210> SEQ ID NO 45
<211> LENGTH: 30
<212> TYPE: DNA
<213> ORGANISM: Steptococcus thermophilus

<400> SEQUENCE: 45
catattaagc tgactgggcc taatgctttt 30

<210> SEQ ID NO 46
<211> LENGTH: 30
<212> TYPE: DNA
<213> ORGANISM: Steptococcus thermophilus

<400> SEQUENCE: 46
ttcatagcat accgtagttg taaaatctat 30

<210> SEQ ID NO 47
<211> LENGTH: 30
<212> TYPE: DNA
<213> ORGANISM: Steptococcus thermophilus

<400> SEQUENCE: 47
aacatttagg gaatgaaatt gataagactg 30

<210> SEQ ID NO 48
<211> LENGTH: 30
<212> TYPE: DNA
<213> ORGANISM: Steptococcus thermophilus

<400> SEQUENCE: 48
aacatgagaa actgtagaaa acaagcaata 30

<210> SEQ ID NO 49
<211> LENGTH: 31
<212> TYPE: DNA
<213> ORGANISM: Steptococcus thermophilus

<400> SEQUENCE: 49
tggtgaagat ggcagtcata aatggcacat t 31

<210> SEQ ID NO 50
<211> LENGTH: 30
<212> TYPE: DNA
<213> ORGANISM: Steptococcus thermophilus

<400> SEQUENCE: 50
aagggttgaa aaatgttggt atatcaaacg 30

<210> SEQ ID NO 51
<211> LENGTH: 30
<212> TYPE: DNA
<213> ORGANISM: Steptococcus thermophilus

<400> SEQUENCE: 51
ttctggtagt ggatttagtc aaacagatgt 30

<210> SEQ ID NO 52
<211> LENGTH: 30
<212> TYPE: DNA
<213> ORGANISM: Steptococcus thermophilus

<400> SEQUENCE: 52
tccatagagc gtcttaaaca aagaatagtc 30

<210> SEQ ID NO 53
<211> LENGTH: 30
<212> TYPE: DNA
<213> ORGANISM: Steptococcus thermophilus

<400> SEQUENCE: 53
ttatgattga atgacatggt tgtataagta 30

<210> SEQ ID NO 54
<211> LENGTH: 30
<212> TYPE: DNA
<213> ORGANISM: Steptococcus thermophilus

<400> SEQUENCE: 54
tttctttagg aataccaggg agttcagctt 30

<210> SEQ ID NO 55
<211> LENGTH: 30
<212> TYPE: DNA
<213> ORGANISM: Steptococcus thermophilus

<400> SEQUENCE: 55
tggcagagat tacacagcaa cggaaacagc 30

<210> SEQ ID NO 56
<211> LENGTH: 30
<212> TYPE: DNA
<213> ORGANISM: Steptococcus thermophilus

<400> SEQUENCE: 56
gggtatcatt gtatctagtg atggacctga 30

<210> SEQ ID NO 57
<211> LENGTH: 30
<212> TYPE: DNA
<213> ORGANISM: Steptococcus thermophilus

<400> SEQUENCE: 57
atttgaaaaa tgcacaacag cgtttgatag 30

<210> SEQ ID NO 58
<211> LENGTH: 30
<212> TYPE: DNA
<213> ORGANISM: Steptococcus thermophilus

<400> SEQUENCE: 58
gagctaccag ctaccccgta tgtcagagag 30

<210> SEQ ID NO 59
<211> LENGTH: 30
<212> TYPE: DNA
<213> ORGANISM: Steptococcus thermophilus

<400> SEQUENCE: 59
cgttcctttt ttcaaggtaa tctttgaaag 30

<210> SEQ ID NO 60
<211> LENGTH: 30
<212> TYPE: DNA
<213> ORGANISM: Steptococcus thermophilus

<400> SEQUENCE: 60
aagtccgtaa gcaccagttc caatcgtcat 30

<210> SEQ ID NO 61
<211> LENGTH: 30
<212> TYPE: DNA
<213> ORGANISM: Steptococcus thermophilus

<400> SEQUENCE: 61
ttgaatacca atgccagctt cttttaaggc 30

<210> SEQ ID NO 62
<211> LENGTH: 30
<212> TYPE: DNA
<213> ORGANISM: Steptococcus thermophilus

<400> SEQUENCE: 62
aacctcatac atggggaaaa ttggtaagta 30

<210> SEQ ID NO 63
<211> LENGTH: 30
<212> TYPE: DNA
<213> ORGANISM: Steptococcus thermophilus

<400> SEQUENCE: 63
taacttcatt agtgtagttg taattagcat 30

<210> SEQ ID NO 64
<211> LENGTH: 30
<212> TYPE: DNA
<213> ORGANISM: Steptococcus thermophilus

<400> SEQUENCE: 64
ttagctaccc aaatatcttc tgttttccaa 30

<210> SEQ ID NO 65
<211> LENGTH: 30
<212> TYPE: DNA
<213> ORGANISM: Steptococcus thermophilus

<400> SEQUENCE: 65
gagttttcaa tattggcaca ggagacaatt 30

<210> SEQ ID NO 66
<211> LENGTH: 30
<212> TYPE: DNA
<213> ORGANISM: Steptococcus thermophilus

<400> SEQUENCE: 66
tgatactatt ttagtcagat atgaaatatc 30

<210> SEQ ID NO 67
<211> LENGTH: 31
<212> TYPE: DNA
<213> ORGANISM: Steptococcus thermophilus

<400> SEQUENCE: 67
tcatcaatgt ttaaagccca acaatacatg a 31

<210> SEQ ID NO 68
<211> LENGTH: 30
<212> TYPE: DNA
<213> ORGANISM: Steptococcus thermophilus

<400> SEQUENCE: 68
tagatttaat cagtaatgag ttaggcataa 30

<210> SEQ ID NO 69
<211> LENGTH: 30
<212> TYPE: DNA

<213> ORGANISM: Steptococcus thermophilus

<400> SEQUENCE: 69
aggaaaatag catgagcgta caacaatcta 30

<210> SEQ ID NO 70
<211> LENGTH: 30
<212> TYPE: DNA
<213> ORGANISM: Steptococcus thermophilus

<400> SEQUENCE: 70
tgtctatcac gcttcctaag tgcatgaaaa 30

<210> SEQ ID NO 71
<211> LENGTH: 30
<212> TYPE: DNA
<213> ORGANISM: Steptococcus thermophilus

<400> SEQUENCE: 71
atgtcaccaa tcactaaaga acctacgctg 30

<210> SEQ ID NO 72
<211> LENGTH: 30
<212> TYPE: DNA
<213> ORGANISM: Steptococcus thermophilus

<400> SEQUENCE: 72
aacatcttcc tctccgattg caaatagtgc 30

<210> SEQ ID NO 73
<211> LENGTH: 29
<212> TYPE: DNA
<213> ORGANISM: Steptococcus thermophilus

<400> SEQUENCE: 73
catatttggt gcccgttcga taaagagta 29

<210> SEQ ID NO 74
<211> LENGTH: 30
<212> TYPE: DNA
<213> ORGANISM: Steptococcus thermophilus

<400> SEQUENCE: 74
cattaaatcg cttgaagcag acattgaagc 30

<210> SEQ ID NO 75
<211> LENGTH: 30
<212> TYPE: DNA
<213> ORGANISM: Steptococcus thermophilus

<400> SEQUENCE: 75
gacttatctt ggaaggtagt gaaggcactt 30

<210> SEQ ID NO 76
<211> LENGTH: 30
<212> TYPE: DNA
<213> ORGANISM: Steptococcus thermophilus

<400> SEQUENCE: 76
tccttgccat ctgcactgta agcccaagca 30

<210> SEQ ID NO 77
<211> LENGTH: 30

<212> TYPE: DNA
<213> ORGANISM: Steptococcus thermophilus

<400> SEQUENCE: 77
tagtacgcat aatcaattca tcaagcttga 30

<210> SEQ ID NO 78
<211> LENGTH: 30
<212> TYPE: DNA
<213> ORGANISM: Steptococcus thermophilus

<400> SEQUENCE: 78
gtagtgaccc aaaattctat gaccttgaaa 30

<210> SEQ ID NO 79
<211> LENGTH: 30
<212> TYPE: DNA
<213> ORGANISM: Steptococcus thermophilus

<400> SEQUENCE: 79
agattgtggt gcttacggaa aattccttgt 30

<210> SEQ ID NO 80
<211> LENGTH: 30
<212> TYPE: DNA
<213> ORGANISM: Steptococcus thermophilus

<400> SEQUENCE: 80
tggcaagaag tgtaagagat gcaatggata 30

<210> SEQ ID NO 81
<211> LENGTH: 30
<212> TYPE: DNA
<213> ORGANISM: Steptococcus thermophilus

<400> SEQUENCE: 81
tttattatca ttattcttct tcccaagcgt 30

<210> SEQ ID NO 82
<211> LENGTH: 30
<212> TYPE: DNA
<213> ORGANISM: Steptococcus thermophilus

<400> SEQUENCE: 82
ttttatagaa tttggtggtg aactttttca 30

<210> SEQ ID NO 83
<211> LENGTH: 29
<212> TYPE: DNA
<213> ORGANISM: Steptococcus thermophilus

<400> SEQUENCE: 83
aatgggtcac agattgccat aataaggag 29

<210> SEQ ID NO 84
<211> LENGTH: 30
<212> TYPE: DNA
<213> ORGANISM: Steptococcus thermophilus

<400> SEQUENCE: 84
ccgaggtcac tttagaaccc acaaaataag 30

<210> SEQ ID NO 85

<211> LENGTH: 30
<212> TYPE: DNA
<213> ORGANISM: Steptococcus thermophilus

<400> SEQUENCE: 85
atgagagaac acagtataga ccctgataca 30

<210> SEQ ID NO 86
<211> LENGTH: 30
<212> TYPE: DNA
<213> ORGANISM: Steptococcus thermophilus

<400> SEQUENCE: 86
cagtattaat gaggtttggg tggtcattcc 30

<210> SEQ ID NO 87
<211> LENGTH: 31
<212> TYPE: DNA
<213> ORGANISM: Steptococcus thermophilus

<400> SEQUENCE: 87
ccatactctc tatcagttca tttaattctt c 31

<210> SEQ ID NO 88
<211> LENGTH: 30
<212> TYPE: DNA
<213> ORGANISM: Steptococcus thermophilus

<400> SEQUENCE: 88
taatatgtcg ctctactgat tccaaaacgg 30

<210> SEQ ID NO 89
<211> LENGTH: 30
<212> TYPE: DNA
<213> ORGANISM: Steptococcus thermophilus

<400> SEQUENCE: 89
atgaattaca ttcatgattt tatcgagttt 30

<210> SEQ ID NO 90
<211> LENGTH: 29
<212> TYPE: DNA
<213> ORGANISM: Steptococcus thermophilus

<400> SEQUENCE: 90
cgtgccattg tttcggtcgg acgtgggca 29

<210> SEQ ID NO 91
<211> LENGTH: 30
<212> TYPE: DNA
<213> ORGANISM: Steptococcus thermophilus

<400> SEQUENCE: 91
ctttctaagt tgaattaaat tcaagttttg 30

<210> SEQ ID NO 92
<211> LENGTH: 30
<212> TYPE: DNA
<213> ORGANISM: Steptococcus thermophilus

<400> SEQUENCE: 92
tcgctactat ggttaacgat gaggaactct 30

<210> SEQ ID NO 93
<211> LENGTH: 30
<212> TYPE: DNA
<213> ORGANISM: Steptococcus thermophilus

<400> SEQUENCE: 93
agcaacttta aaactaaaag agctacttga 30

<210> SEQ ID NO 94
<211> LENGTH: 30
<212> TYPE: DNA
<213> ORGANISM: Steptococcus thermophilus

<400> SEQUENCE: 94
aaaaccctac acagtgtgtg agatgtgtca 30

<210> SEQ ID NO 95
<211> LENGTH: 30
<212> TYPE: DNA
<213> ORGANISM: Steptococcus thermophilus

<400> SEQUENCE: 95
aatgggtcac agattgccat aataaggagg 30

<210> SEQ ID NO 96
<211> LENGTH: 30
<212> TYPE: DNA
<213> ORGANISM: Steptococcus thermophilus

<400> SEQUENCE: 96
ttttttaaaa tccgtcatgc tatactatat 30

<210> SEQ ID NO 97
<211> LENGTH: 30
<212> TYPE: DNA
<213> ORGANISM: Steptococcus thermophilus

<400> SEQUENCE: 97
aattcaaact ttctccaata ataccctcca 30

<210> SEQ ID NO 98
<211> LENGTH: 30
<212> TYPE: DNA
<213> ORGANISM: Steptococcus thermophilus

<400> SEQUENCE: 98
catgctttca gttaataaga cgtgggacta 30

<210> SEQ ID NO 99
<211> LENGTH: 30
<212> TYPE: DNA
<213> ORGANISM: Steptococcus thermophilus

<400> SEQUENCE: 99
tggaaggggt gtctagtgaa gaaattgtcg 30

<210> SEQ ID NO 100
<211> LENGTH: 30
<212> TYPE: DNA
<213> ORGANISM: Steptococcus thermophilus

<400> SEQUENCE: 100
ctcgaagcgc ttcattgccc tattcctttc 30

<210> SEQ ID NO 101
<211> LENGTH: 29
<212> TYPE: DNA
<213> ORGANISM: Steptococcus thermophilus

<400> SEQUENCE: 101
atgtctaagg tatccactcg tgaaatcat 29

<210> SEQ ID NO 102
<211> LENGTH: 30
<212> TYPE: DNA
<213> ORGANISM: Steptococcus thermophilus

<400> SEQUENCE: 102
atattaatgg aaatttcatt caaacgcagt 30

<210> SEQ ID NO 103
<211> LENGTH: 30
<212> TYPE: DNA
<213> ORGANISM: Steptococcus thermophilus

<400> SEQUENCE: 103
tagagagttt atatcctgat ggaatcgatg 30

<210> SEQ ID NO 104
<211> LENGTH: 30
<212> TYPE: DNA
<213> ORGANISM: Steptococcus thermophilus

<400> SEQUENCE: 104
tggcgaatta gagagccaat ggcaagcaag 30

<210> SEQ ID NO 105
<211> LENGTH: 30
<212> TYPE: DNA
<213> ORGANISM: Steptococcus thermophilus

<400> SEQUENCE: 105
agaagaccaa taaacttgag aaaaagcaag 30

<210> SEQ ID NO 106
<211> LENGTH: 30
<212> TYPE: DNA
<213> ORGANISM: Steptococcus thermophilus

<400> SEQUENCE: 106
aaatggtcgt ttaattgtta atgtcaaagc 30

<210> SEQ ID NO 107
<211> LENGTH: 30
<212> TYPE: DNA
<213> ORGANISM: Steptococcus thermophilus

<400> SEQUENCE: 107
caattgattc taaaatgctt ggtacacgta 30

<210> SEQ ID NO 108
<211> LENGTH: 30
<212> TYPE: DNA
<213> ORGANISM: Steptococcus thermophilus

<400> SEQUENCE: 108
tcttcgtgtt atcacagctt ctacacgttg 30

<210> SEQ ID NO 109
<211> LENGTH: 30
<212> TYPE: DNA
<213> ORGANISM: Steptococcus thermophilus

<400> SEQUENCE: 109
gaaatctcat tgaaaccaac ttcaagacca 30

<210> SEQ ID NO 110
<211> LENGTH: 30
<212> TYPE: DNA
<213> ORGANISM: Steptococcus thermophilus

<400> SEQUENCE: 110
tgcttggtag ttgatgcact gcattagtaa 30

<210> SEQ ID NO 111
<211> LENGTH: 30
<212> TYPE: DNA
<213> ORGANISM: Steptococcus thermophilus

<400> SEQUENCE: 111
aatgtaccgg aatagcgtta cattgcacat 30

<210> SEQ ID NO 112
<211> LENGTH: 30
<212> TYPE: DNA
<213> ORGANISM: Steptococcus thermophilus

<400> SEQUENCE: 112
ttcataaatt ctcacttttc cttgctattc 30

<210> SEQ ID NO 113
<211> LENGTH: 30
<212> TYPE: DNA
<213> ORGANISM: Steptococcus thermophilus

<400> SEQUENCE: 113
tgtcgaaaaa attacctagt cacgacagac 30

<210> SEQ ID NO 114
<211> LENGTH: 30
<212> TYPE: DNA
<213> ORGANISM: Steptococcus thermophilus

<400> SEQUENCE: 114
caacaattac ttatgcatta ggaacatctg 30

<210> SEQ ID NO 115
<211> LENGTH: 30
<212> TYPE: DNA
<213> ORGANISM: Steptococcus thermophilus

<400> SEQUENCE: 115
aattcgtgaa aaacaataaa aacaaaaaaa 30

<210> SEQ ID NO 116
<211> LENGTH: 30
<212> TYPE: DNA
<213> ORGANISM: Steptococcus thermophilus

<400> SEQUENCE: 116
taacatttct gtccatttct tccttgatgc 30

<210> SEQ ID NO 117
<211> LENGTH: 28
<212> TYPE: DNA
<213> ORGANISM: Steptococcus thermophilus

<400> SEQUENCE: 117
caaggcaact caaccaacca aattgacc 28

<210> SEQ ID NO 118
<211> LENGTH: 30
<212> TYPE: DNA
<213> ORGANISM: Steptococcus thermophilus

<400> SEQUENCE: 118
ctaaaatcgt aaatggtaag ttgcacgatg 30

<210> SEQ ID NO 119
<211> LENGTH: 30
<212> TYPE: DNA
<213> ORGANISM: Steptococcus thermophilus

<400> SEQUENCE: 119
aacgtaagga gtttttttat ttctttgtta 30

<210> SEQ ID NO 120
<211> LENGTH: 30
<212> TYPE: DNA
<213> ORGANISM: Steptococcus thermophilus

<400> SEQUENCE: 120
gtggaaaatt tcacacccta catatatcaa 30

<210> SEQ ID NO 121
<211> LENGTH: 30
<212> TYPE: DNA
<213> ORGANISM: Steptococcus thermophilus

<400> SEQUENCE: 121
cctctgctaa tgacttaaac ggctcgtttt 30

<210> SEQ ID NO 122
<211> LENGTH: 30
<212> TYPE: DNA
<213> ORGANISM: Steptococcus thermophilus

<400> SEQUENCE: 122
aaaatcaaag ttttgggttt gtctacgttg 30

<210> SEQ ID NO 123
<211> LENGTH: 30
<212> TYPE: DNA
<213> ORGANISM: Steptococcus thermophilus

<400> SEQUENCE: 123
atatgtacat acctaaagaa aacacgggca 30

<210> SEQ ID NO 124
<211> LENGTH: 30
<212> TYPE: DNA
<213> ORGANISM: Steptococcus thermophilus

<400> SEQUENCE: 124
cgttgtcaaa atatgtgatt actttgtatt 30

<210> SEQ ID NO 125
<211> LENGTH: 30
<212> TYPE: DNA
<213> ORGANISM: Steptococcus thermophilus

<400> SEQUENCE: 125
ccatagctgt aatgttgttt gtgactgctt 30

<210> SEQ ID NO 126
<211> LENGTH: 30
<212> TYPE: DNA
<213> ORGANISM: Steptococcus thermophilus

<400> SEQUENCE: 126
cgctaagttt ggctttaagt ataacaagct 30

<210> SEQ ID NO 127
<211> LENGTH: 30
<212> TYPE: DNA
<213> ORGANISM: Steptococcus thermophilus

<400> SEQUENCE: 127
aaagtacgct tcaaggcacg ttgaagacat 30

<210> SEQ ID NO 128
<211> LENGTH: 30
<212> TYPE: DNA
<213> ORGANISM: Steptococcus thermophilus

<400> SEQUENCE: 128
ctttttaacg tgttagcgtc tttagctttg 30

<210> SEQ ID NO 129
<211> LENGTH: 30
<212> TYPE: DNA
<213> ORGANISM: Steptococcus thermophilus

<400> SEQUENCE: 129
ttggcttcgt gaataatttt taaaacgcat 30

<210> SEQ ID NO 130
<211> LENGTH: 30
<212> TYPE: DNA
<213> ORGANISM: Steptococcus thermophilus

<400> SEQUENCE: 130
tgttgaatca atacgctgaa acacactccc 30

<210> SEQ ID NO 131
<211> LENGTH: 30
<212> TYPE: DNA
<213> ORGANISM: Steptococcus thermophilus

<400> SEQUENCE: 131
cgttatcagt tgaaagtttc aactcgtaag 30

<210> SEQ ID NO 132
<211> LENGTH: 30
<212> TYPE: DNA
<213> ORGANISM: Steptococcus thermophilus

<400> SEQUENCE: 132
taaactagtt ggcatctatg ctccaggaag 30

<210> SEQ ID NO 133
<211> LENGTH: 30
<212> TYPE: DNA
<213> ORGANISM: Steptococcus thermophilus

<400> SEQUENCE: 133
tagaccacca tagccgagtt gtctttttcg 30

<210> SEQ ID NO 134
<211> LENGTH: 30
<212> TYPE: DNA
<213> ORGANISM: Steptococcus thermophilus

<400> SEQUENCE: 134
acatcccact ttctgggttt tttagccatg 30

<210> SEQ ID NO 135
<211> LENGTH: 30
<212> TYPE: DNA
<213> ORGANISM: Steptococcus thermophilus

<400> SEQUENCE: 135
agtatggcta ttgtcctgat actcatccac 30

<210> SEQ ID NO 136
<211> LENGTH: 30
<212> TYPE: DNA
<213> ORGANISM: Steptococcus thermophilus

<400> SEQUENCE: 136
cgctcttgac gtggctggtg acatctacgc 30

<210> SEQ ID NO 137
<211> LENGTH: 30
<212> TYPE: DNA
<213> ORGANISM: Steptococcus thermophilus

<400> SEQUENCE: 137
gagtacatgg agtttctgct agatacacta 30

<210> SEQ ID NO 138
<211> LENGTH: 29
<212> TYPE: DNA
<213> ORGANISM: Steptococcus thermophilus

<400> SEQUENCE: 138
taagttatga aatataaagt tattgtcta 29

<210> SEQ ID NO 139
<211> LENGTH: 30
<212> TYPE: DNA
<213> ORGANISM: Steptococcus thermophilus

<400> SEQUENCE: 139
aacgttatga catttaggag cttccaaatt 30

<210> SEQ ID NO 140
<211> LENGTH: 29
<212> TYPE: DNA
<213> ORGANISM: Steptococcus thermophilus

<400> SEQUENCE: 140
aacacagcaa gacaaaagga tgacacttt 29

<210> SEQ ID NO 141
<211> LENGTH: 30
<212> TYPE: DNA
<213> ORGANISM: Steptococcus thermophilus

<400> SEQUENCE: 141
caaccataac ttacgcatca ggtacatctg 30

<210> SEQ ID NO 142
<211> LENGTH: 29
<212> TYPE: DNA
<213> ORGANISM: Steptococcus thermophilus

<400> SEQUENCE: 142
acacgcgctt acctcgtata tcaaattca 29

<210> SEQ ID NO 143
<211> LENGTH: 30
<212> TYPE: DNA
<213> ORGANISM: Steptococcus thermophilus

<400> SEQUENCE: 143
tgcccgcaaa ctagcgatac acaacagcat 30

<210> SEQ ID NO 144
<211> LENGTH: 31
<212> TYPE: DNA
<213> ORGANISM: Steptococcus thermophilus

<400> SEQUENCE: 144
ctcaagctct tcatctgtga taggtgtttt g 31

<210> SEQ ID NO 145
<211> LENGTH: 30
<212> TYPE: DNA
<213> ORGANISM: Steptococcus thermophilus

<400> SEQUENCE: 145
atcactcttt gatagtatct caaacgctgg 30

<210> SEQ ID NO 146
<211> LENGTH: 30
<212> TYPE: DNA
<213> ORGANISM: Steptococcus thermophilus

<400> SEQUENCE: 146
gaaacagtca gaccagctaa ttcgccaatt 30

<210> SEQ ID NO 147
<211> LENGTH: 30
<212> TYPE: DNA
<213> ORGANISM: Steptococcus thermophilus

<400> SEQUENCE: 147
atatttcgaa agatacaagg acacttacac 30

<210> SEQ ID NO 148
<211> LENGTH: 30
<212> TYPE: DNA

<213> ORGANISM: Steptococcus thermophilus

<400> SEQUENCE: 148
gcggatgaaa cacaacttca attgtattca 30

<210> SEQ ID NO 149
<211> LENGTH: 30
<212> TYPE: DNA
<213> ORGANISM: Steptococcus thermophilus

<400> SEQUENCE: 149
taatgctaca tctcaaagga tgatcccaga 30

<210> SEQ ID NO 150
<211> LENGTH: 31
<212> TYPE: DNA
<213> ORGANISM: Steptococcus thermophilus

<400> SEQUENCE: 150
acgtctgtct aactggaaag tacctgctaa t 31

<210> SEQ ID NO 151
<211> LENGTH: 30
<212> TYPE: DNA
<213> ORGANISM: Steptococcus thermophilus

<400> SEQUENCE: 151
ctgttctcta atcgagaggc gcgtgattga 30

<210> SEQ ID NO 152
<211> LENGTH: 30
<212> TYPE: DNA
<213> ORGANISM: Steptococcus thermophilus

<400> SEQUENCE: 152
aaacctcact agtcacttag tgcggttagg 30

<210> SEQ ID NO 153
<211> LENGTH: 30
<212> TYPE: DNA
<213> ORGANISM: Steptococcus thermophilus

<400> SEQUENCE: 153
tattaagttt agtcccaggt ttcttatcgt 30

<210> SEQ ID NO 154
<211> LENGTH: 30
<212> TYPE: DNA
<213> ORGANISM: Steptococcus thermophilus

<400> SEQUENCE: 154
aaaccaataa acataccgat tgctgccaat 30

<210> SEQ ID NO 155
<211> LENGTH: 30
<212> TYPE: DNA
<213> ORGANISM: Steptococcus thermophilus

<400> SEQUENCE: 155
gcaaacgtta gcccaggaaa gcatcatgaa 30

<210> SEQ ID NO 156
<211> LENGTH: 30

<212> TYPE: DNA
<213> ORGANISM: Steptococcus thermophilus

<400> SEQUENCE: 156
aagagcaaaa aataactcta gctctcgtcc 30

<210> SEQ ID NO 157
<211> LENGTH: 30
<212> TYPE: DNA
<213> ORGANISM: Steptococcus thermophilus

<400> SEQUENCE: 157
aagaaacctc taagttgagc atttaatgat 30

<210> SEQ ID NO 158
<211> LENGTH: 29
<212> TYPE: DNA
<213> ORGANISM: Steptococcus thermophilus

<400> SEQUENCE: 158
atatagtttt aaactttctt gaccttctg 29

<210> SEQ ID NO 159
<211> LENGTH: 29
<212> TYPE: DNA
<213> ORGANISM: Steptococcus thermophilus

<400> SEQUENCE: 159
acgttgatga atattgttga taaacttta 29

<210> SEQ ID NO 160
<211> LENGTH: 30
<212> TYPE: DNA
<213> ORGANISM: Steptococcus thermophilus

<400> SEQUENCE: 160
caagaagtga acaaagtaca cgctggaagt 30

<210> SEQ ID NO 161
<211> LENGTH: 30
<212> TYPE: DNA
<213> ORGANISM: Steptococcus thermophilus

<400> SEQUENCE: 161
gacagcaaga tacacgtagt tgatgaattg 30

<210> SEQ ID NO 162
<211> LENGTH: 30
<212> TYPE: DNA
<213> ORGANISM: Steptococcus thermophilus

<400> SEQUENCE: 162
taagaaatca acgcagattt ttagccaaca 30

<210> SEQ ID NO 163
<211> LENGTH: 30
<212> TYPE: DNA
<213> ORGANISM: Steptococcus thermophilus

<400> SEQUENCE: 163
taacccaata attacagtga agcacaatag 30

<210> SEQ ID NO 164

<211> LENGTH: 29
<212> TYPE: DNA
<213> ORGANISM: Steptococcus thermophilus

<400> SEQUENCE: 164
caggcgtaag gtatgctaat tataacgat 29

<210> SEQ ID NO 165
<211> LENGTH: 30
<212> TYPE: DNA
<213> ORGANISM: Steptococcus thermophilus

<400> SEQUENCE: 165
gctatcgaac taatagctta gaggaactca 30

<210> SEQ ID NO 166
<211> LENGTH: 30
<212> TYPE: DNA
<213> ORGANISM: Steptococcus thermophilus

<400> SEQUENCE: 166
gtggaatatt aagcccgaat tgttgcagca 30

<210> SEQ ID NO 167
<211> LENGTH: 30
<212> TYPE: DNA
<213> ORGANISM: Steptococcus thermophilus

<400> SEQUENCE: 167
tattgcaata tttgcgtttg ggaaaccttc 30

<210> SEQ ID NO 168
<211> LENGTH: 30
<212> TYPE: DNA
<213> ORGANISM: Steptococcus thermophilus

<400> SEQUENCE: 168
cgtctgtcta actggaaagt accggctaat 30

<210> SEQ ID NO 169
<211> LENGTH: 30
<212> TYPE: DNA
<213> ORGANISM: Steptococcus thermophilus

<400> SEQUENCE: 169
aaagagatgt acccatccat tctaacaggt 30

<210> SEQ ID NO 170
<211> LENGTH: 30
<212> TYPE: DNA
<213> ORGANISM: Steptococcus thermophilus

<400> SEQUENCE: 170
ggggagttga tttcttacat caaaacaatg 30

<210> SEQ ID NO 171
<211> LENGTH: 30
<212> TYPE: DNA
<213> ORGANISM: Steptococcus thermophilus

<400> SEQUENCE: 171
catcaaagtt gaaaaggact acaacagccc 30

<210> SEQ ID NO 172
<211> LENGTH: 30
<212> TYPE: DNA
<213> ORGANISM: Steptococcus thermophilus

<400> SEQUENCE: 172
cttaaattta gagcgtggga tcttgaatat 30

<210> SEQ ID NO 173
<211> LENGTH: 30
<212> TYPE: DNA
<213> ORGANISM: Steptococcus thermophilus

<400> SEQUENCE: 173
atataccgat ggcacatctg aaactggctg 30

<210> SEQ ID NO 174
<211> LENGTH: 30
<212> TYPE: DNA
<213> ORGANISM: Steptococcus thermophilus

<400> SEQUENCE: 174
taactcatat gtatcttgac caactatttt 30

<210> SEQ ID NO 175
<211> LENGTH: 30
<212> TYPE: DNA
<213> ORGANISM: Steptococcus thermophilus

<400> SEQUENCE: 175
aaatagcacc tctaagcgtt aatggtattc 30

<210> SEQ ID NO 176
<211> LENGTH: 30
<212> TYPE: DNA
<213> ORGANISM: Steptococcus thermophilus

<400> SEQUENCE: 176
aatatctaca ggtcactaca aagctacgct 30

<210> SEQ ID NO 177
<211> LENGTH: 30
<212> TYPE: DNA
<213> ORGANISM: Steptococcus thermophilus

<400> SEQUENCE: 177
gttggggtgt gtttgtaacg gcgtatgcta 30

<210> SEQ ID NO 178
<211> LENGTH: 30
<212> TYPE: DNA
<213> ORGANISM: Steptococcus thermophilus

<400> SEQUENCE: 178
tcaatcaggt gacggtgatg cttatattaa 30

<210> SEQ ID NO 179
<211> LENGTH: 30
<212> TYPE: DNA
<213> ORGANISM: Steptococcus thermophilus

<400> SEQUENCE: 179
catacatgat agtttgtcaa cacttttgat 30

<210> SEQ ID NO 180
<211> LENGTH: 30
<212> TYPE: DNA
<213> ORGANISM: Steptococcus thermophilus

<400> SEQUENCE: 180
tcagcatttg gtttacatga cccacgtctg 30

<210> SEQ ID NO 181
<211> LENGTH: 30
<212> TYPE: DNA
<213> ORGANISM: Steptococcus thermophilus

<400> SEQUENCE: 181
caatcaacag gtttgactga ttataacggt 30

<210> SEQ ID NO 182
<211> LENGTH: 30
<212> TYPE: DNA
<213> ORGANISM: Steptococcus thermophilus

<400> SEQUENCE: 182
tagctacaca tgaattttat tacaatggtg 30

<210> SEQ ID NO 183
<211> LENGTH: 30
<212> TYPE: DNA
<213> ORGANISM: Steptococcus thermophilus

<400> SEQUENCE: 183
cttacgtttg aaaagaatat caaatcaatg 30

<210> SEQ ID NO 184
<211> LENGTH: 30
<212> TYPE: DNA
<213> ORGANISM: Steptococcus thermophilus

<400> SEQUENCE: 184
ttaaaaaagg gcctttctct aaatcaagta 30

<210> SEQ ID NO 185
<211> LENGTH: 30
<212> TYPE: DNA
<213> ORGANISM: Steptococcus thermophilus

<400> SEQUENCE: 185
tgctgaacgt atctgtccac tgtgtggcca 30

<210> SEQ ID NO 186
<211> LENGTH: 30
<212> TYPE: DNA
<213> ORGANISM: Steptococcus thermophilus

<400> SEQUENCE: 186
ccgttcttca aacgttaaat tccaaggtgt 30

<210> SEQ ID NO 187
<211> LENGTH: 30
<212> TYPE: DNA
<213> ORGANISM: Steptococcus thermophilus

<400> SEQUENCE: 187
gctgcgatta tgacaatgct gtctgtaagg 30

<210> SEQ ID NO 188
<211> LENGTH: 30
<212> TYPE: DNA
<213> ORGANISM: Steptococcus thermophilus

<400> SEQUENCE: 188
gaagaattta ttaataaaga tggttctgct 30

<210> SEQ ID NO 189
<211> LENGTH: 30
<212> TYPE: DNA
<213> ORGANISM: Steptococcus thermophilus

<400> SEQUENCE: 189
aggcagaaaa gaagtatttt ggtaagtatg 30

<210> SEQ ID NO 190
<211> LENGTH: 29
<212> TYPE: DNA
<213> ORGANISM: Steptococcus thermophilus

<400> SEQUENCE: 190
aaatggttta tcgacaagaa aatgaagct 29

<210> SEQ ID NO 191
<211> LENGTH: 30
<212> TYPE: DNA
<213> ORGANISM: Steptococcus thermophilus

<400> SEQUENCE: 191
ccaaatttgc attatacaaa acgctccttc 30

<210> SEQ ID NO 192
<211> LENGTH: 30
<212> TYPE: DNA
<213> ORGANISM: Steptococcus thermophilus

<400> SEQUENCE: 192
atcctaactg ctttgctaac tacatcatgg 30

<210> SEQ ID NO 193
<211> LENGTH: 29
<212> TYPE: DNA
<213> ORGANISM: Steptococcus thermophilus

<400> SEQUENCE: 193
taacaagata agattagcgt cttcaacat 29

<210> SEQ ID NO 194
<211> LENGTH: 30
<212> TYPE: DNA
<213> ORGANISM: Steptococcus thermophilus

<400> SEQUENCE: 194
aaaagcctat gtttgcccac tttgtggaag 30

<210> SEQ ID NO 195
<211> LENGTH: 30
<212> TYPE: DNA
<213> ORGANISM: Steptococcus thermophilus

<400> SEQUENCE: 195

```
tgtcactttc tctttctggg ttgtgccaat                                              30

<210> SEQ ID NO 196
<211> LENGTH: 31
<212> TYPE: DNA
<213> ORGANISM: Steptococcus thermophilus

<400> SEQUENCE: 196

catacttttc catctgtttg ttgtttgaaa a                                            31

<210> SEQ ID NO 197
<211> LENGTH: 30
<212> TYPE: DNA
<213> ORGANISM: Steptococcus thermophilus

<400> SEQUENCE: 197

tgagagtgtc tgatggattt attggcagcc                                              30

<210> SEQ ID NO 198
<211> LENGTH: 30
<212> TYPE: DNA
<213> ORGANISM: Steptococcus thermophilus

<400> SEQUENCE: 198

ggggttattt tccattttac cgtctatcta                                              30

<210> SEQ ID NO 199
<211> LENGTH: 30
<212> TYPE: DNA
<213> ORGANISM: Steptococcus thermophilus

<400> SEQUENCE: 199

tatcacgccc attttcattt cgccatctgt                                              30

<210> SEQ ID NO 200
<211> LENGTH: 30
<212> TYPE: DNA
<213> ORGANISM: Steptococcus thermophilus

<400> SEQUENCE: 200

aacattttaa tataatttct aaatctattg                                              30

<210> SEQ ID NO 201
<211> LENGTH: 30
<212> TYPE: DNA
<213> ORGANISM: Steptococcus thermophilus

<400> SEQUENCE: 201

tacaaaattc cttcaaacgc tatttattga                                              30

<210> SEQ ID NO 202
<211> LENGTH: 29
<212> TYPE: DNA
<213> ORGANISM: Steptococcus thermophilus

<400> SEQUENCE: 202

agagtttgaa aattattttt cagtttcta                                               29

<210> SEQ ID NO 203
<211> LENGTH: 30
<212> TYPE: DNA
<213> ORGANISM: Steptococcus thermophilus

<400> SEQUENCE: 203
```

ttcctcatct ttctccgctt ttgctagctt 30

<210> SEQ ID NO 204
<211> LENGTH: 31
<212> TYPE: DNA
<213> ORGANISM: Steptococcus thermophilus

<400> SEQUENCE: 204
ttgagcgttc tagtgtgtgg cttgtaatga a 31

<210> SEQ ID NO 205
<211> LENGTH: 30
<212> TYPE: DNA
<213> ORGANISM: Steptococcus thermophilus

<400> SEQUENCE: 205
tgaaagaaat acaatacaac gataatgacc 30

<210> SEQ ID NO 206
<211> LENGTH: 30
<212> TYPE: DNA
<213> ORGANISM: Steptococcus thermophilus

<400> SEQUENCE: 206
ctagttttaa gagatagctc tctaagtagg 30

<210> SEQ ID NO 207
<211> LENGTH: 29
<212> TYPE: DNA
<213> ORGANISM: Steptococcus thermophilus

<400> SEQUENCE: 207
aaattcgaca taagcactac agttatatt 29

<210> SEQ ID NO 208
<211> LENGTH: 30
<212> TYPE: DNA
<213> ORGANISM: Steptococcus thermophilus

<400> SEQUENCE: 208
ctattttcga gagaacgtca gtcattttaa 30

<210> SEQ ID NO 209
<211> LENGTH: 30
<212> TYPE: DNA
<213> ORGANISM: Steptococcus thermophilus

<400> SEQUENCE: 209
gtgctaacta tatcagtcgc atcaataaca 30

<210> SEQ ID NO 210
<211> LENGTH: 30
<212> TYPE: DNA
<213> ORGANISM: Steptococcus thermophilus

<400> SEQUENCE: 210
ttagcggtga ttggaataga ataagcgaat 30

<210> SEQ ID NO 211
<211> LENGTH: 30
<212> TYPE: DNA
<213> ORGANISM: Steptococcus thermophilus

<400> SEQUENCE: 211
cttctacagc agtttaagac acattatcat 30

<210> SEQ ID NO 212
<211> LENGTH: 29
<212> TYPE: DNA
<213> ORGANISM: Steptococcus thermophilus

<400> SEQUENCE: 212
cgtatcgaaa acggcgataa tccaacagt 29

<210> SEQ ID NO 213
<211> LENGTH: 31
<212> TYPE: DNA
<213> ORGANISM: Steptococcus thermophilus

<400> SEQUENCE: 213
caataccttt ttttaattca tcttgataag t 31

<210> SEQ ID NO 214
<211> LENGTH: 30
<212> TYPE: DNA
<213> ORGANISM: Steptococcus thermophilus

<400> SEQUENCE: 214
ttaagaacaa tatcatcaat acgactttca 30

<210> SEQ ID NO 215
<211> LENGTH: 30
<212> TYPE: DNA
<213> ORGANISM: Steptococcus thermophilus

<400> SEQUENCE: 215
catctatcaa attcaaattc ggataaacta 30

<210> SEQ ID NO 216
<211> LENGTH: 30
<212> TYPE: DNA
<213> ORGANISM: Steptococcus thermophilus

<400> SEQUENCE: 216
tgagagtgtc tgatggattt attggtaacc 30

<210> SEQ ID NO 217
<211> LENGTH: 29
<212> TYPE: DNA
<213> ORGANISM: Steptococcus thermophilus

<400> SEQUENCE: 217
acctcataca tggggaaaac ttgtaagta 29

<210> SEQ ID NO 218
<211> LENGTH: 30
<212> TYPE: DNA
<213> ORGANISM: Steptococcus thermophilus

<400> SEQUENCE: 218
tatttcacga atttctacac ttttcaacct 30

<210> SEQ ID NO 219
<211> LENGTH: 30
<212> TYPE: DNA
<213> ORGANISM: Steptococcus thermophilus

<400> SEQUENCE: 219
ctgaaacctt gttttgaagc gcttggaagt 30

<210> SEQ ID NO 220
<211> LENGTH: 30
<212> TYPE: DNA
<213> ORGANISM: Steptococcus thermophilus

<400> SEQUENCE: 220
gtcaattgat actgcaatct ctttaacatt 30

<210> SEQ ID NO 221
<211> LENGTH: 31
<212> TYPE: DNA
<213> ORGANISM: Steptococcus thermophilus

<400> SEQUENCE: 221
acttcaatat ggtcaacatc ttgatcaccg a 31

<210> SEQ ID NO 222
<211> LENGTH: 30
<212> TYPE: DNA
<213> ORGANISM: Steptococcus thermophilus

<400> SEQUENCE: 222
taaactcgac aaaagcacta catgaatatt 30

<210> SEQ ID NO 223
<211> LENGTH: 30
<212> TYPE: DNA
<213> ORGANISM: Steptococcus thermophilus

<400> SEQUENCE: 223
attttttaag gaaaggagga aaataatata 30

<210> SEQ ID NO 224
<211> LENGTH: 30
<212> TYPE: DNA
<213> ORGANISM: Steptococcus thermophilus

<400> SEQUENCE: 224
cgttcaaaac agcgaaaact taaccctaac 30

<210> SEQ ID NO 225
<211> LENGTH: 30
<212> TYPE: DNA
<213> ORGANISM: Steptococcus thermophilus

<400> SEQUENCE: 225
cattaagtcg cttgaggcag acattgaagc 30

<210> SEQ ID NO 226
<211> LENGTH: 30
<212> TYPE: DNA
<213> ORGANISM: Steptococcus thermophilus

<400> SEQUENCE: 226
ccaaactcaa attgtctata ataataaccg 30

<210> SEQ ID NO 227
<211> LENGTH: 30
<212> TYPE: DNA

<213> ORGANISM: Steptococcus thermophilus

<400> SEQUENCE: 227
tatctctatt tcaggtggtt taaaacattc 30

<210> SEQ ID NO 228
<211> LENGTH: 30
<212> TYPE: DNA
<213> ORGANISM: Steptococcus thermophilus

<400> SEQUENCE: 228
aaacgaagat ggaagcgttg atgtttattc 30

<210> SEQ ID NO 229
<211> LENGTH: 30
<212> TYPE: DNA
<213> ORGANISM: Steptococcus thermophilus

<400> SEQUENCE: 229
gattgcattt gccagtattt cttttgatta 30

<210> SEQ ID NO 230
<211> LENGTH: 29
<212> TYPE: DNA
<213> ORGANISM: Steptococcus thermophilus

<400> SEQUENCE: 230
tgaagacaac ggaaacaatc aacctatta 29

<210> SEQ ID NO 231
<211> LENGTH: 30
<212> TYPE: DNA
<213> ORGANISM: Steptococcus thermophilus

<400> SEQUENCE: 231
acttcttttt taatgtcatc taagacaata 30

<210> SEQ ID NO 232
<211> LENGTH: 30
<212> TYPE: DNA
<213> ORGANISM: Steptococcus thermophilus

<400> SEQUENCE: 232
gccaatgatg ttcaattcgt taatggaatt 30

<210> SEQ ID NO 233
<211> LENGTH: 30
<212> TYPE: DNA
<213> ORGANISM: Steptococcus thermophilus

<400> SEQUENCE: 233
tcaacatggg atatttcgtt ggtcaggatg 30

<210> SEQ ID NO 234
<211> LENGTH: 30
<212> TYPE: DNA
<213> ORGANISM: Steptococcus thermophilus

<400> SEQUENCE: 234
tatggctctc ttgttggaat aaagatgatt 30

<210> SEQ ID NO 235
<211> LENGTH: 30

<212> TYPE: DNA
<213> ORGANISM: Steptococcus thermophilus

<400> SEQUENCE: 235
ataacatagc agtctatttc tttgctgatg 30

<210> SEQ ID NO 236
<211> LENGTH: 30
<212> TYPE: DNA
<213> ORGANISM: Steptococcus thermophilus

<400> SEQUENCE: 236
gttaccacgc gccctactgt attagtggag 30

<210> SEQ ID NO 237
<211> LENGTH: 30
<212> TYPE: DNA
<213> ORGANISM: Steptococcus thermophilus

<400> SEQUENCE: 237
tacataccca aggttgtaag tcgttaaatt 30

<210> SEQ ID NO 238
<211> LENGTH: 30
<212> TYPE: DNA
<213> ORGANISM: Steptococcus thermophilus

<400> SEQUENCE: 238
tgtaagtagt caatattcac ttctgataac 30

<210> SEQ ID NO 239
<211> LENGTH: 30
<212> TYPE: DNA
<213> ORGANISM: Steptococcus thermophilus

<400> SEQUENCE: 239
gatagcaata gctttcttga cctaaaagac 30

<210> SEQ ID NO 240
<211> LENGTH: 30
<212> TYPE: DNA
<213> ORGANISM: Steptococcus thermophilus

<400> SEQUENCE: 240
gaggtctgta atttcattcc ctcgtaatct 30

<210> SEQ ID NO 241
<211> LENGTH: 29
<212> TYPE: DNA
<213> ORGANISM: Steptococcus thermophilus

<400> SEQUENCE: 241
aaaggtttct ctaaacacat gcggaatat 29

<210> SEQ ID NO 242
<211> LENGTH: 30
<212> TYPE: DNA
<213> ORGANISM: Steptococcus thermophilus

<400> SEQUENCE: 242
gtcatagtac caagcacaaa taacgttagt 30

<210> SEQ ID NO 243

```
<211> LENGTH: 30
<212> TYPE: DNA
<213> ORGANISM: Steptococcus thermophilus

<400> SEQUENCE: 243

gtgtatttag taatggtgat tttttaaatt                                30

<210> SEQ ID NO 244
<211> LENGTH: 30
<212> TYPE: DNA
<213> ORGANISM: Steptococcus thermophilus

<400> SEQUENCE: 244

cattcatttt ttatatatca ataaaacttt                                30

<210> SEQ ID NO 245
<211> LENGTH: 30
<212> TYPE: DNA
<213> ORGANISM: Steptococcus thermophilus

<400> SEQUENCE: 245

ggggattctt atttcactgt agttacgatg                                30

<210> SEQ ID NO 246
<211> LENGTH: 30
<212> TYPE: DNA
<213> ORGANISM: Steptococcus thermophilus

<400> SEQUENCE: 246

caaaaattga tgtcacaatt aataaaggtg                                30

<210> SEQ ID NO 247
<211> LENGTH: 30
<212> TYPE: DNA
<213> ORGANISM: Steptococcus thermophilus

<400> SEQUENCE: 247

ctatttctga caatggttga aattgtgttc                                30

<210> SEQ ID NO 248
<211> LENGTH: 29
<212> TYPE: DNA
<213> ORGANISM: Steptococcus thermophilus

<400> SEQUENCE: 248

ctttttttaa attaatttat cgtaagcaa                                 29

<210> SEQ ID NO 249
<211> LENGTH: 30
<212> TYPE: DNA
<213> ORGANISM: Steptococcus thermophilus

<400> SEQUENCE: 249

aacaaactta tgagaacggt tgaacggctt                                30

<210> SEQ ID NO 250
<211> LENGTH: 30
<212> TYPE: DNA
<213> ORGANISM: Steptococcus thermophilus

<400> SEQUENCE: 250

agcccgctta ttgcttcagt tggtttatat                                30
```

<210> SEQ ID NO 251
<211> LENGTH: 30
<212> TYPE: DNA
<213> ORGANISM: Steptococcus thermophilus

<400> SEQUENCE: 251
tggagcaaca agaatgatta actctaatgc 30

<210> SEQ ID NO 252
<211> LENGTH: 30
<212> TYPE: DNA
<213> ORGANISM: Steptococcus thermophilus

<400> SEQUENCE: 252
tttgatggat atcattgata aactatacga 30

<210> SEQ ID NO 253
<211> LENGTH: 30
<212> TYPE: DNA
<213> ORGANISM: Steptococcus thermophilus

<400> SEQUENCE: 253
taacgaaagc aataccaatc gtgctaaagc 30

<210> SEQ ID NO 254
<211> LENGTH: 30
<212> TYPE: DNA
<213> ORGANISM: Steptococcus thermophilus

<400> SEQUENCE: 254
tattcctatg gtcgatattc gaacagtcaa 30

<210> SEQ ID NO 255
<211> LENGTH: 30
<212> TYPE: DNA
<213> ORGANISM: Steptococcus thermophilus

<400> SEQUENCE: 255
caggggacaa ggactttgac ccaacagaag 30

<210> SEQ ID NO 256
<211> LENGTH: 30
<212> TYPE: DNA
<213> ORGANISM: Steptococcus thermophilus

<400> SEQUENCE: 256
agaaacacct aatggtctct tagaacccga 30

<210> SEQ ID NO 257
<211> LENGTH: 30
<212> TYPE: DNA
<213> ORGANISM: Steptococcus thermophilus

<400> SEQUENCE: 257
aagaagttaa agacaacttt gttaaagact 30

<210> SEQ ID NO 258
<211> LENGTH: 30
<212> TYPE: DNA
<213> ORGANISM: Steptococcus thermophilus

<400> SEQUENCE: 258
gaaaaagcat ccatgatagt gcttagacct 30

<210> SEQ ID NO 259
<211> LENGTH: 30
<212> TYPE: DNA
<213> ORGANISM: Steptococcus thermophilus

<400> SEQUENCE: 259
cggaatggta taaagaatac aaagaaaacg 30

<210> SEQ ID NO 260
<211> LENGTH: 29
<212> TYPE: DNA
<213> ORGANISM: Steptococcus thermophilus

<400> SEQUENCE: 260
ccaagtatca cgcaaagaaa tcaacgaga 29

<210> SEQ ID NO 261
<211> LENGTH: 31
<212> TYPE: DNA
<213> ORGANISM: Steptococcus thermophilus

<400> SEQUENCE: 261
ttgacctgtt tatccttgtt aactagaata g 31

<210> SEQ ID NO 262
<211> LENGTH: 30
<212> TYPE: DNA
<213> ORGANISM: Steptococcus thermophilus

<400> SEQUENCE: 262
agagcactag catactgttt agtccgaacg 30

<210> SEQ ID NO 263
<211> LENGTH: 30
<212> TYPE: DNA
<213> ORGANISM: Steptococcus thermophilus

<400> SEQUENCE: 263
aggcaaggta tttgatccaa cagaagccaa 30

<210> SEQ ID NO 264
<211> LENGTH: 29
<212> TYPE: DNA
<213> ORGANISM: Steptococcus thermophilus

<400> SEQUENCE: 264
catgatttac aaccacgcgc tagaccaag 29

<210> SEQ ID NO 265
<211> LENGTH: 30
<212> TYPE: DNA
<213> ORGANISM: Steptococcus thermophilus

<400> SEQUENCE: 265
acctagaagc atttgagcgt atattgattg 30

<210> SEQ ID NO 266
<211> LENGTH: 30
<212> TYPE: DNA
<213> ORGANISM: Steptococcus thermophilus

<400> SEQUENCE: 266
aattttgccc cttctttgcc ccttgactag 30

<210> SEQ ID NO 267
<211> LENGTH: 30
<212> TYPE: DNA
<213> ORGANISM: Steptococcus thermophilus

<400> SEQUENCE: 267
taatagttta ccaaatcgtc cttgttccaa 30

<210> SEQ ID NO 268
<211> LENGTH: 30
<212> TYPE: DNA
<213> ORGANISM: Steptococcus thermophilus

<400> SEQUENCE: 268
accattagca atcatttgtg cccattgagt 30

<210> SEQ ID NO 269
<211> LENGTH: 31
<212> TYPE: DNA
<213> ORGANISM: Steptococcus thermophilus

<400> SEQUENCE: 269
acgtctgtct aactggaaag tacctgttaa t 31

<210> SEQ ID NO 270
<211> LENGTH: 29
<212> TYPE: DNA
<213> ORGANISM: Steptococcus thermophilus

<400> SEQUENCE: 270
tttttatact ttgggtaatt acaaaatag 29

<210> SEQ ID NO 271
<211> LENGTH: 30
<212> TYPE: DNA
<213> ORGANISM: Steptococcus thermophilus

<400> SEQUENCE: 271
aagaaagaaa tattctagat atagatataa 30

<210> SEQ ID NO 272
<211> LENGTH: 30
<212> TYPE: DNA
<213> ORGANISM: Steptococcus thermophilus

<400> SEQUENCE: 272
caacgaccaa cacaacaact aaagttactg 30

<210> SEQ ID NO 273
<211> LENGTH: 30
<212> TYPE: DNA
<213> ORGANISM: Steptococcus thermophilus

<400> SEQUENCE: 273
tgattatggg tgttaaacaa ggagcttatg 30

<210> SEQ ID NO 274
<211> LENGTH: 30
<212> TYPE: DNA
<213> ORGANISM: Steptococcus thermophilus

<400> SEQUENCE: 274

-continued tgagtggtaa gtacaaatac gcaggactga 30

<210> SEQ ID NO 275
<211> LENGTH: 30
<212> TYPE: DNA
<213> ORGANISM: Steptococcus thermophilus

<400> SEQUENCE: 275
ttatttcctc ctttccttaa aaaaattaga 30

<210> SEQ ID NO 276
<211> LENGTH: 30
<212> TYPE: DNA
<213> ORGANISM: Steptococcus thermophilus

<400> SEQUENCE: 276
ggatgtatct gttgaaagag gtgtgtatat 30

<210> SEQ ID NO 277
<211> LENGTH: 30
<212> TYPE: DNA
<213> ORGANISM: Steptococcus thermophilus

<400> SEQUENCE: 277
aataggtgaa aaatatgcaa gtcacacaaa 30

<210> SEQ ID NO 278
<211> LENGTH: 30
<212> TYPE: DNA
<213> ORGANISM: Steptococcus thermophilus

<400> SEQUENCE: 278
aaaatggcat taaaaattaa cataggaata 30

<210> SEQ ID NO 279
<211> LENGTH: 30
<212> TYPE: DNA
<213> ORGANISM: Steptococcus thermophilus

<400> SEQUENCE: 279
tatcagctcg taaatgttcg atagactctt 30

<210> SEQ ID NO 280
<211> LENGTH: 30
<212> TYPE: DNA
<213> ORGANISM: Steptococcus thermophilus

<400> SEQUENCE: 280
attccattaa cgtatttgac ttcactagct 30

<210> SEQ ID NO 281
<211> LENGTH: 30
<212> TYPE: DNA
<213> ORGANISM: Steptococcus thermophilus

<400> SEQUENCE: 281
ctgttaccga tccaagagca gacatcatac 30

<210> SEQ ID NO 282
<211> LENGTH: 30
<212> TYPE: DNA
<213> ORGANISM: Steptococcus thermophilus

<400> SEQUENCE: 282
aagaagcggt taaatgcttc aactgaatag 30

<210> SEQ ID NO 283
<211> LENGTH: 30
<212> TYPE: DNA
<213> ORGANISM: Steptococcus thermophilus

<400> SEQUENCE: 283
aattgctaaa catctaaaag acttaacggg 30

<210> SEQ ID NO 284
<211> LENGTH: 30
<212> TYPE: DNA
<213> ORGANISM: Steptococcus thermophilus

<400> SEQUENCE: 284
gatgaagatt tgactgatga taaagagaaa 30

<210> SEQ ID NO 285
<211> LENGTH: 30
<212> TYPE: DNA
<213> ORGANISM: Steptococcus thermophilus

<400> SEQUENCE: 285
gacatcagaa agcagtttat aaatatttta 30

<210> SEQ ID NO 286
<211> LENGTH: 30
<212> TYPE: DNA
<213> ORGANISM: Steptococcus thermophilus

<400> SEQUENCE: 286
tttgaattta acaaccttga ttttgatatc 30

<210> SEQ ID NO 287
<211> LENGTH: 31
<212> TYPE: DNA
<213> ORGANISM: Steptococcus thermophilus

<400> SEQUENCE: 287
tgatacggtc aaagtttttc cactaatagc g 31

<210> SEQ ID NO 288
<211> LENGTH: 30
<212> TYPE: DNA
<213> ORGANISM: Steptococcus thermophilus

<400> SEQUENCE: 288
atggttttca tttcctgaac ccctaagagg 30

<210> SEQ ID NO 289
<211> LENGTH: 30
<212> TYPE: DNA
<213> ORGANISM: Steptococcus thermophilus

<400> SEQUENCE: 289
aagttattga aaaacgccaa catgatgagt 30

<210> SEQ ID NO 290
<211> LENGTH: 30
<212> TYPE: DNA
<213> ORGANISM: Steptococcus thermophilus

<400> SEQUENCE: 290
atataagtcc tcctattaat atccacaata 30

<210> SEQ ID NO 291
<211> LENGTH: 30
<212> TYPE: DNA
<213> ORGANISM: Steptococcus thermophilus

<400> SEQUENCE: 291
ttgcctcaag agatcctgct tgttgccaag 30

<210> SEQ ID NO 292
<211> LENGTH: 30
<212> TYPE: DNA
<213> ORGANISM: Steptococcus thermophilus

<400> SEQUENCE: 292
tcccatagtt ttaatgagtc ggttaactta 30

<210> SEQ ID NO 293
<211> LENGTH: 30
<212> TYPE: DNA
<213> ORGANISM: Steptococcus thermophilus

<400> SEQUENCE: 293
gtgtactaaa agtgtgctaa gttcataagg 30

<210> SEQ ID NO 294
<211> LENGTH: 30
<212> TYPE: DNA
<213> ORGANISM: Steptococcus thermophilus

<400> SEQUENCE: 294
atatagtgat tgtatccagc tgcggcgtag 30

<210> SEQ ID NO 295
<211> LENGTH: 29
<212> TYPE: DNA
<213> ORGANISM: Steptococcus thermophilus

<400> SEQUENCE: 295
aaaagcaaat cgcgagtata aaggatata 29

<210> SEQ ID NO 296
<211> LENGTH: 30
<212> TYPE: DNA
<213> ORGANISM: Steptococcus thermophilus

<400> SEQUENCE: 296
ttttaattga tctagacacc ctatgaaata 30

<210> SEQ ID NO 297
<211> LENGTH: 30
<212> TYPE: DNA
<213> ORGANISM: Steptococcus thermophilus

<400> SEQUENCE: 297
acagaggaga gaaaccatgg ctattttaga 30

<210> SEQ ID NO 298
<211> LENGTH: 29
<212> TYPE: DNA
<213> ORGANISM: Steptococcus thermophilus

<400> SEQUENCE: 298
tggcagcagt gaattcgatg ccgagcaat 29

<210> SEQ ID NO 299
<211> LENGTH: 30
<212> TYPE: DNA
<213> ORGANISM: Steptococcus thermophilus

<400> SEQUENCE: 299
ccaaggaata ccaggtccta aaggtgccga 30

<210> SEQ ID NO 300
<211> LENGTH: 29
<212> TYPE: DNA
<213> ORGANISM: Steptococcus thermophilus

<400> SEQUENCE: 300
ctaaatgaac tacaacaaca gcttgatga 29

<210> SEQ ID NO 301
<211> LENGTH: 30
<212> TYPE: DNA
<213> ORGANISM: Steptococcus thermophilus

<400> SEQUENCE: 301
taccttaaca ttttcgatat ttttcaaatt 30

<210> SEQ ID NO 302
<211> LENGTH: 30
<212> TYPE: DNA
<213> ORGANISM: Steptococcus thermophilus

<400> SEQUENCE: 302
tttgactgct tttttatctg aattgtaatt 30

<210> SEQ ID NO 303
<211> LENGTH: 30
<212> TYPE: DNA
<213> ORGANISM: Steptococcus thermophilus

<400> SEQUENCE: 303
cagtaaccta aagctctatc aagcctattt 30

<210> SEQ ID NO 304
<211> LENGTH: 30
<212> TYPE: DNA
<213> ORGANISM: Steptococcus thermophilus

<400> SEQUENCE: 304
cgtcaagctg acagaccttg acaacaaatc 30

<210> SEQ ID NO 305
<211> LENGTH: 29
<212> TYPE: DNA
<213> ORGANISM: Steptococcus thermophilus

<400> SEQUENCE: 305
aggcataaat aacattgata accctaaca 29

<210> SEQ ID NO 306
<211> LENGTH: 30
<212> TYPE: DNA

<213> ORGANISM: Steptococcus thermophilus

<400> SEQUENCE: 306
gccaacgagg tcaaatatgt caacggcatt 30

<210> SEQ ID NO 307
<211> LENGTH: 30
<212> TYPE: DNA
<213> ORGANISM: Steptococcus thermophilus

<400> SEQUENCE: 307
gaaataggaa cttcaaaggt aatttcttta 30

<210> SEQ ID NO 308
<211> LENGTH: 30
<212> TYPE: DNA
<213> ORGANISM: Steptococcus thermophilus

<400> SEQUENCE: 308
atttagagca aggaaagcag tacatcatta 30

<210> SEQ ID NO 309
<211> LENGTH: 30
<212> TYPE: DNA
<213> ORGANISM: Steptococcus thermophilus

<400> SEQUENCE: 309
ctgtaatcat ttttaaatca ggattatcaa 30

<210> SEQ ID NO 310
<211> LENGTH: 30
<212> TYPE: DNA
<213> ORGANISM: Steptococcus thermophilus

<400> SEQUENCE: 310
ttaaatgtat cctagtattt ttgtactata 30

<210> SEQ ID NO 311
<211> LENGTH: 30
<212> TYPE: DNA
<213> ORGANISM: Steptococcus thermophilus

<400> SEQUENCE: 311
ccatcagcca actgtatcgg ctactttcta 30

<210> SEQ ID NO 312
<211> LENGTH: 30
<212> TYPE: DNA
<213> ORGANISM: Steptococcus thermophilus

<400> SEQUENCE: 312
atgctcttgg cgactatctc atggagcgtg 30

<210> SEQ ID NO 313
<211> LENGTH: 30
<212> TYPE: DNA
<213> ORGANISM: Steptococcus thermophilus

<400> SEQUENCE: 313
aggaaaaaac ccaaacaacc caaaatgtta 30

<210> SEQ ID NO 314
<211> LENGTH: 30

<212> TYPE: DNA
<213> ORGANISM: Steptococcus thermophilus

<400> SEQUENCE: 314
tctaattctg tcaccacgac tatatcgcca 30

<210> SEQ ID NO 315
<211> LENGTH: 30
<212> TYPE: DNA
<213> ORGANISM: Steptococcus thermophilus

<400> SEQUENCE: 315
aatctgtgtg ggaagtaaag attgaagatg 30

<210> SEQ ID NO 316
<211> LENGTH: 30
<212> TYPE: DNA
<213> ORGANISM: Steptococcus thermophilus

<400> SEQUENCE: 316
atagtttgtt aagtcatacc cattaaattg 30

<210> SEQ ID NO 317
<211> LENGTH: 30
<212> TYPE: DNA
<213> ORGANISM: Steptococcus thermophilus

<400> SEQUENCE: 317
tccacatgat tacaaagcca cgcaagacct 30

<210> SEQ ID NO 318
<211> LENGTH: 29
<212> TYPE: DNA
<213> ORGANISM: Steptococcus thermophilus

<400> SEQUENCE: 318
gaagaccaaa atttgacaat gagtcctgc 29

<210> SEQ ID NO 319
<211> LENGTH: 30
<212> TYPE: DNA
<213> ORGANISM: Steptococcus thermophilus

<400> SEQUENCE: 319
attatattta agttgtaaat gttgcttttc 30

<210> SEQ ID NO 320
<211> LENGTH: 30
<212> TYPE: DNA
<213> ORGANISM: Steptococcus thermophilus

<400> SEQUENCE: 320
gcagacattg gctcaacaag tgattatgaa 30

<210> SEQ ID NO 321
<211> LENGTH: 30
<212> TYPE: DNA
<213> ORGANISM: Steptococcus thermophilus

<400> SEQUENCE: 321
tgttctcata aattgccttt cctttttatg 30

<210> SEQ ID NO 322

<211> LENGTH: 30
<212> TYPE: DNA
<213> ORGANISM: Steptococcus thermophilus

<400> SEQUENCE: 322
cttatcaaac atcaaggatt gtagatgagg 30

<210> SEQ ID NO 323
<211> LENGTH: 30
<212> TYPE: DNA
<213> ORGANISM: Steptococcus thermophilus

<400> SEQUENCE: 323
atttcattag tagcttgata aatgtttcta 30

<210> SEQ ID NO 324
<211> LENGTH: 30
<212> TYPE: DNA
<213> ORGANISM: Steptococcus thermophilus

<400> SEQUENCE: 324
gaaaatacta tactttaaaa gaaattttaa 30

<210> SEQ ID NO 325
<211> LENGTH: 30
<212> TYPE: DNA
<213> ORGANISM: Steptococcus thermophilus

<400> SEQUENCE: 325
tctcctccga cataatcttt tgtctttccg 30

<210> SEQ ID NO 326
<211> LENGTH: 30
<212> TYPE: DNA
<213> ORGANISM: Steptococcus thermophilus

<400> SEQUENCE: 326
acaaaagcac tgccacctat agaagcattt 30

<210> SEQ ID NO 327
<211> LENGTH: 30
<212> TYPE: DNA
<213> ORGANISM: Steptococcus thermophilus

<400> SEQUENCE: 327
aaaaacttta tgctatccgt gtcagtatat 30

<210> SEQ ID NO 328
<211> LENGTH: 30
<212> TYPE: DNA
<213> ORGANISM: Steptococcus thermophilus

<400> SEQUENCE: 328
ttttcaatga ttgaaagccc ataactaaca 30

<210> SEQ ID NO 329
<211> LENGTH: 30
<212> TYPE: DNA
<213> ORGANISM: Steptococcus thermophilus

<400> SEQUENCE: 329
ctttcatagt tgttacgaaa tgtttggcat 30

<210> SEQ ID NO 330
<211> LENGTH: 30
<212> TYPE: DNA
<213> ORGANISM: Steptococcus thermophilus

<400> SEQUENCE: 330
cgatttgcaa tatgatgata ttgatgaatt 30

<210> SEQ ID NO 331
<211> LENGTH: 30
<212> TYPE: DNA
<213> ORGANISM: Steptococcus thermophilus

<400> SEQUENCE: 331
tttagatgct agtcctaaga ctgtagagac 30

<210> SEQ ID NO 332
<211> LENGTH: 30
<212> TYPE: DNA
<213> ORGANISM: Steptococcus thermophilus

<400> SEQUENCE: 332
gtaatcaagc gtatataagt caggactatc 30

<210> SEQ ID NO 333
<211> LENGTH: 30
<212> TYPE: DNA
<213> ORGANISM: Steptococcus thermophilus

<400> SEQUENCE: 333
ataacagaag gagtagggga cgtaggcgcg 30

<210> SEQ ID NO 334
<211> LENGTH: 30
<212> TYPE: DNA
<213> ORGANISM: Steptococcus thermophilus

<400> SEQUENCE: 334
ttatttgata ggaatgtcag taatttttga 30

<210> SEQ ID NO 335
<211> LENGTH: 30
<212> TYPE: DNA
<213> ORGANISM: Steptococcus thermophilus

<400> SEQUENCE: 335
aacatttcag cgcttactta tcaatctaat 30

<210> SEQ ID NO 336
<211> LENGTH: 29
<212> TYPE: DNA
<213> ORGANISM: Steptococcus thermophilus

<400> SEQUENCE: 336
gtattagtag gcatacgatt atggaagta 29

<210> SEQ ID NO 337
<211> LENGTH: 30
<212> TYPE: DNA
<213> ORGANISM: Steptococcus thermophilus

<400> SEQUENCE: 337
catatatata tatatattta ttttaaatat 30

<210> SEQ ID NO 338
<211> LENGTH: 30
<212> TYPE: DNA
<213> ORGANISM: Steptococcus thermophilus

<400> SEQUENCE: 338
ttgtcataat aattaaatcc aataggactt 30

<210> SEQ ID NO 339
<211> LENGTH: 30
<212> TYPE: DNA
<213> ORGANISM: Steptococcus thermophilus

<400> SEQUENCE: 339
gaaaatttct gttgtgttct taatattagc 30

<210> SEQ ID NO 340
<211> LENGTH: 30
<212> TYPE: DNA
<213> ORGANISM: Steptococcus vestibularis

<400> SEQUENCE: 340
gtacttcaaa ggttctaact acataacaca 30

<210> SEQ ID NO 341
<211> LENGTH: 30
<212> TYPE: DNA
<213> ORGANISM: Steptococcus vestibularis

<400> SEQUENCE: 341
taaaaccaga tggtggttct tctgatacta 30

<210> SEQ ID NO 342
<211> LENGTH: 30
<212> TYPE: DNA
<213> ORGANISM: Steptococcus vestibularis

<400> SEQUENCE: 342
cattttcttc agtcaattcg ttctcaagcg 30

<210> SEQ ID NO 343
<211> LENGTH: 30
<212> TYPE: DNA
<213> ORGANISM: Steptococcus vestibularis

<400> SEQUENCE: 343
aaaggacggg ggcaatgaac aaacgacaac 30

<210> SEQ ID NO 344
<211> LENGTH: 29
<212> TYPE: DNA
<213> ORGANISM: Steptococcus vestibularis

<400> SEQUENCE: 344
taatatcatt gatagcttca tcaaaggct 29

<210> SEQ ID NO 345
<211> LENGTH: 29
<212> TYPE: DNA
<213> ORGANISM: Steptococcus vestibularis

<400> SEQUENCE: 345
taaattgttc cttgactccg aactgccct 29

<210> SEQ ID NO 346
<211> LENGTH: 30
<212> TYPE: DNA
<213> ORGANISM: Steptococcus vestibularis

<400> SEQUENCE: 346
aaacaatcgt ttatctatcc tcaaaggatg 30

<210> SEQ ID NO 347
<211> LENGTH: 30
<212> TYPE: DNA
<213> ORGANISM: Steptococcus vestibularis

<400> SEQUENCE: 347
ataaaaaaac gcctcaaaaa ccgagacaac 30

<210> SEQ ID NO 348
<211> LENGTH: 30
<212> TYPE: DNA
<213> ORGANISM: Steptococcus vestibularis

<400> SEQUENCE: 348
tggaaatccc ttatatcgac aaatacgtta 30

<210> SEQ ID NO 349
<211> LENGTH: 30
<212> TYPE: DNA
<213> ORGANISM: Steptococcus vestibularis

<400> SEQUENCE: 349
ttcccagtcg ttgattttta ttgaataccc 30

<210> SEQ ID NO 350
<211> LENGTH: 30
<212> TYPE: DNA
<213> ORGANISM: Steptococcus vestibularis

<400> SEQUENCE: 350
ggacatcgaa caagtcaatg ccgtaagctt 30

<210> SEQ ID NO 351
<211> LENGTH: 30
<212> TYPE: DNA
<213> ORGANISM: Steptococcus vestibularis

<400> SEQUENCE: 351
aatctttaac cggattgtag aaccgttcgg 30

<210> SEQ ID NO 352
<211> LENGTH: 30
<212> TYPE: DNA
<213> ORGANISM: Steptococcus vestibularis

<400> SEQUENCE: 352
tgcctttaaa ataactagat tttaccatca 30

<210> SEQ ID NO 353
<211> LENGTH: 29
<212> TYPE: DNA
<213> ORGANISM: Steptococcus vestibularis

<400> SEQUENCE: 353
gagcaagcac aagcaagctt tactatcct 29

<210> SEQ ID NO 354
<211> LENGTH: 30
<212> TYPE: DNA
<213> ORGANISM: Steptococcus vestibularis

<400> SEQUENCE: 354
cagattggtt tatcgaacaa ggtcgcaagt 30

<210> SEQ ID NO 355
<211> LENGTH: 31
<212> TYPE: DNA
<213> ORGANISM: Steptococcus vestibularis

<400> SEQUENCE: 355
caaaagctgt tggttaacgg tgctttgggc a 31

<210> SEQ ID NO 356
<211> LENGTH: 30
<212> TYPE: DNA
<213> ORGANISM: Steptococcus vestibularis

<400> SEQUENCE: 356
cttgtttttc ctctggggtc tctgcgactt 30

<210> SEQ ID NO 357
<211> LENGTH: 30
<212> TYPE: DNA
<213> ORGANISM: Steptococcus vestibularis

<400> SEQUENCE: 357
gaaataaact gcccaaacat ttttattttc 30

<210> SEQ ID NO 358
<211> LENGTH: 30
<212> TYPE: DNA
<213> ORGANISM: Steptococcus vestibularis

<400> SEQUENCE: 358
tgagtaagcg acaagctaga aatcaagtca 30

<210> SEQ ID NO 359
<211> LENGTH: 30
<212> TYPE: DNA
<213> ORGANISM: Steptococcus thermophilus

<400> SEQUENCE: 359
atagctaaga tggaagaagc atcaagcacc 30

<210> SEQ ID NO 360
<211> LENGTH: 30
<212> TYPE: DNA
<213> ORGANISM: Steptococcus thermophilus

<400> SEQUENCE: 360
cagtatctca aacgctggat acaacaagat 30

<210> SEQ ID NO 361
<211> LENGTH: 30
<212> TYPE: DNA
<213> ORGANISM: Steptococcus thermophilus

<400> SEQUENCE: 361
cctactcagt ggacacctgc aattgaagac 30

<210> SEQ ID NO 362
<211> LENGTH: 29
<212> TYPE: DNA
<213> ORGANISM: Steptococcus thermophilus

<400> SEQUENCE: 362
cgattggaac gggtgcttat ggccttaac 29

<210> SEQ ID NO 363
<211> LENGTH: 30
<212> TYPE: DNA
<213> ORGANISM: Steptococcus thermophilus

<400> SEQUENCE: 363
gcgaacaatt gaatttgtta gaaaatgtcg 30

<210> SEQ ID NO 364
<211> LENGTH: 30
<212> TYPE: DNA
<213> ORGANISM: Steptococcus thermophilus

<400> SEQUENCE: 364
gaagcattta ttaatataga tggttctgct 30

<210> SEQ ID NO 365
<211> LENGTH: 28
<212> TYPE: DNA
<213> ORGANISM: Steptococcus thermophilus

<400> SEQUENCE: 365
tgctgacgta tctgtccact gtgtgcca 28

<210> SEQ ID NO 366
<211> LENGTH: 30
<212> TYPE: DNA
<213> ORGANISM: Steptococcus thermophilus

<400> SEQUENCE: 366
tttttatact ttgggtaaat tacaaaatag 30

<210> SEQ ID NO 367
<211> LENGTH: 31
<212> TYPE: DNA
<213> ORGANISM: Steptococcus thermophilus

<400> SEQUENCE: 367
tcaaggtgtc gccttatgga aaagatgctt g 31

<210> SEQ ID NO 368
<211> LENGTH: 31
<212> TYPE: DNA
<213> ORGANISM: Steptococcus thermophilus

<400> SEQUENCE: 368
tgtaaaaatt tctagacgtt tagacacttt a 31

<210> SEQ ID NO 369
<211> LENGTH: 30
<212> TYPE: DNA
<213> ORGANISM: Steptococcus thermophilus

<400> SEQUENCE: 369
aaatgatgat tgaatgcttg agatagcagt 30

<210> SEQ ID NO 370
<211> LENGTH: 30
<212> TYPE: DNA
<213> ORGANISM: Steptococcus thermophilus

<400> SEQUENCE: 370
aataagaagt tcttgacgac caaccgacat 30

<210> SEQ ID NO 371
<211> LENGTH: 30
<212> TYPE: DNA
<213> ORGANISM: Steptococcus thermophilus

<400> SEQUENCE: 371
tcgtcaacgt cgatacagaa caacgtgctt 30

<210> SEQ ID NO 372
<211> LENGTH: 30
<212> TYPE: DNA
<213> ORGANISM: Steptococcus thermophilus

<400> SEQUENCE: 372
tgattagcaa atttaaaaca ggatatttgg 30

<210> SEQ ID NO 373
<211> LENGTH: 30
<212> TYPE: DNA
<213> ORGANISM: Steptococcus thermophilus

<400> SEQUENCE: 373
aaagacaagc ccaagggatt gaactagcaa 30

<210> SEQ ID NO 374
<211> LENGTH: 30
<212> TYPE: DNA
<213> ORGANISM: Steptococcus thermophilus

<400> SEQUENCE: 374
cgaacagttg gcgagaaatc cgtctggcgt 30

<210> SEQ ID NO 375
<211> LENGTH: 30
<212> TYPE: DNA
<213> ORGANISM: Steptococcus thermophilus

<400> SEQUENCE: 375
ctacattatt gatcatgttt tttctcctgt 30

<210> SEQ ID NO 376
<211> LENGTH: 30
<212> TYPE: DNA
<213> ORGANISM: Steptococcus thermophilus

<400> SEQUENCE: 376
tagaaggctc tggaaataca aagcaattct 30

<210> SEQ ID NO 377
<211> LENGTH: 31
<212> TYPE: DNA
<213> ORGANISM: Steptococcus thermophilus

<400> SEQUENCE: 377
tagaaggctc tggtaaatac aaagcaattc t 31

<210> SEQ ID NO 378
<211> LENGTH: 30
<212> TYPE: DNA
<213> ORGANISM: Steptococcus thermophilus

<400> SEQUENCE: 378
tctgatggct cttggtaggg aactggatat 30

<210> SEQ ID NO 379
<211> LENGTH: 30
<212> TYPE: DNA
<213> ORGANISM: Steptococcus thermophilus

<400> SEQUENCE: 379
tttgatggct cttggtaggg aactggatat 30

<210> SEQ ID NO 380
<211> LENGTH: 31
<212> TYPE: DNA
<213> ORGANISM: Steptococcus thermophilus

<400> SEQUENCE: 380
ttttgatggc tcttggtagg gaactggata t 31

<210> SEQ ID NO 381
<211> LENGTH: 29
<212> TYPE: DNA
<213> ORGANISM: Steptococcus thermophilus

<400> SEQUENCE: 381
acagaacaaa atggtagaat atatcatct 29

<210> SEQ ID NO 382
<211> LENGTH: 30
<212> TYPE: DNA
<213> ORGANISM: Steptococcus thermophilus

<400> SEQUENCE: 382
ccctggacaa gctatcagca catatccttg 30

<210> SEQ ID NO 383
<211> LENGTH: 30
<212> TYPE: DNA
<213> ORGANISM: Steptococcus thermophilus

<400> SEQUENCE: 383
cgctgttgat gtaacccgct ttatatatat 30

<210> SEQ ID NO 384
<211> LENGTH: 30
<212> TYPE: DNA
<213> ORGANISM: Steptococcus thermophilus

<400> SEQUENCE: 384
gaatgaatgt attagagcaa gcacttgacc 30

<210> SEQ ID NO 385
<211> LENGTH: 30
<212> TYPE: DNA

<213> ORGANISM: Steptococcus thermophilus

<400> SEQUENCE: 385
tagacgaaaa ggaaggaaaa tagcatgagc 30

<210> SEQ ID NO 386
<211> LENGTH: 30
<212> TYPE: DNA
<213> ORGANISM: Steptococcus thermophilus

<400> SEQUENCE: 386
ataactcgat tgctaactta agcaagcagt 30

<210> SEQ ID NO 387
<211> LENGTH: 30
<212> TYPE: DNA
<213> ORGANISM: Steptococcus thermophilus

<400> SEQUENCE: 387
ctgcatgtgt aaccatgact tcttcgtcgt 30

<210> SEQ ID NO 388
<211> LENGTH: 30
<212> TYPE: DNA
<213> ORGANISM: Steptococcus thermophilus

<400> SEQUENCE: 388
cttcgctgga aacttcgtag tcatacatac 30

<210> SEQ ID NO 389
<211> LENGTH: 30
<212> TYPE: DNA
<213> ORGANISM: Steptococcus thermophilus

<400> SEQUENCE: 389
aagaccgctg tactggttgg tattcgtacc 30

<210> SEQ ID NO 390
<211> LENGTH: 30
<212> TYPE: DNA
<213> ORGANISM: Steptococcus thermophilus

<400> SEQUENCE: 390
caaccaagcg aacacagcag tagcaccgca 30

<210> SEQ ID NO 391
<211> LENGTH: 29
<212> TYPE: DNA
<213> ORGANISM: Steptococcus thermophilus

<400> SEQUENCE: 391
atgatgatga agtatcgtca tctactaac 29

<210> SEQ ID NO 392
<211> LENGTH: 30
<212> TYPE: DNA
<213> ORGANISM: Steptococcus thermophilus

<400> SEQUENCE: 392
cttcacctca aatcttagag atggactaaa 30

<210> SEQ ID NO 393
<211> LENGTH: 30

<212> TYPE: DNA
<213> ORGANISM: Steptococcus thermophilus

<400> SEQUENCE: 393
aaaaggtgcg tatgaaactc atcccagcgg 30

<210> SEQ ID NO 394
<211> LENGTH: 30
<212> TYPE: DNA
<213> ORGANISM: Steptococcus thermophilus

<400> SEQUENCE: 394
aagggtttaa gtccttcata gagtggaaaa 30

<210> SEQ ID NO 395
<211> LENGTH: 30
<212> TYPE: DNA
<213> ORGANISM: Steptococcus thermophilus

<400> SEQUENCE: 395
cctcaaagct taaaattggg ctgaagtaga 30

<210> SEQ ID NO 396
<211> LENGTH: 30
<212> TYPE: DNA
<213> ORGANISM: Steptococcus thermophilus

<400> SEQUENCE: 396
gcaatttatt cgcttgatgt actcacgttt 30

<210> SEQ ID NO 397
<211> LENGTH: 30
<212> TYPE: DNA
<213> ORGANISM: Steptococcus thermophilus

<400> SEQUENCE: 397
tatttattgc aaatggttac catattttta 30

<210> SEQ ID NO 398
<211> LENGTH: 30
<212> TYPE: DNA
<213> ORGANISM: Steptococcus thermophilus

<400> SEQUENCE: 398
tattttagca ctacggtatc agcgtatctc 30

<210> SEQ ID NO 399
<211> LENGTH: 30
<212> TYPE: DNA
<213> ORGANISM: Steptococcus thermophilus

<400> SEQUENCE: 399
tgctacgtgc tctggacggg cgctatcagc 30

<210> SEQ ID NO 400
<211> LENGTH: 30
<212> TYPE: DNA
<213> ORGANISM: Steptococcus thermophilus

<400> SEQUENCE: 400
aaatgaacag acaagaagca acagaaattg 30

<210> SEQ ID NO 401

<211> LENGTH: 30
<212> TYPE: DNA
<213> ORGANISM: Steptococcus thermophilus

<400> SEQUENCE: 401
aagttgatcg tatctattta gaatatcgca 30

<210> SEQ ID NO 402
<211> LENGTH: 30
<212> TYPE: DNA
<213> ORGANISM: Steptococcus thermophilus

<400> SEQUENCE: 402
attcactttg acagatacta atgctacatc 30

<210> SEQ ID NO 403
<211> LENGTH: 30
<212> TYPE: DNA
<213> ORGANISM: Steptococcus thermophilus

<400> SEQUENCE: 403
caagcagtgt aaaggtggtt tatatgttaa 30

<210> SEQ ID NO 404
<211> LENGTH: 30
<212> TYPE: DNA
<213> ORGANISM: Steptococcus thermophilus

<400> SEQUENCE: 404
catagtatag ccgtcttctt tgattgattg 30

<210> SEQ ID NO 405
<211> LENGTH: 30
<212> TYPE: DNA
<213> ORGANISM: Steptococcus thermophilus

<400> SEQUENCE: 405
ccatgggtgc taaaggtgat gactaccgct 30

<210> SEQ ID NO 406
<211> LENGTH: 36
<212> TYPE: DNA
<213> ORGANISM: Steptococcus thermophilus

<400> SEQUENCE: 406
tttctaggaa tgggtaatta tagcgagcta gaaagc 36

<210> SEQ ID NO 407
<211> LENGTH: 38
<212> TYPE: DNA
<213> ORGANISM: Steptococcus thermophilus

<400> SEQUENCE: 407
agttgggaag gtcttggaaa atctatggca aaaaacct 38

<210> SEQ ID NO 408
<211> LENGTH: 35
<212> TYPE: DNA
<213> ORGANISM: Steptococcus thermophilus

<400> SEQUENCE: 408
tatatggttc aaatgcgatt caaagactat tcaaa 35

<210> SEQ ID NO 409
<211> LENGTH: 30
<212> TYPE: DNA
<213> ORGANISM: Steptococcus agalactiae

<400> SEQUENCE: 409
taattgccaa tgcttacaat atcttcgtca 30

<210> SEQ ID NO 410
<211> LENGTH: 30
<212> TYPE: DNA
<213> ORGANISM: Steptococcus agalactiae

<400> SEQUENCE: 410
atgttctgaa ttacctttct cgacactccg 30

<210> SEQ ID NO 411
<211> LENGTH: 30
<212> TYPE: DNA
<213> ORGANISM: Steptococcus agalactiae

<400> SEQUENCE: 411
accatcaagg ctcttatctg cagattgtta 30

<210> SEQ ID NO 412
<211> LENGTH: 30
<212> TYPE: DNA
<213> ORGANISM: Steptococcus agalactiae

<400> SEQUENCE: 412
aaatggttgc caatgacttt ctagagtgat 30

<210> SEQ ID NO 413
<211> LENGTH: 30
<212> TYPE: DNA
<213> ORGANISM: Steptococcus agalactiae

<400> SEQUENCE: 413
acaaaatctt ttgttgctcc tggacgtatt 30

<210> SEQ ID NO 414
<211> LENGTH: 30
<212> TYPE: DNA
<213> ORGANISM: Steptococcus agalactiae

<400> SEQUENCE: 414
atgtaaggta ttgtaaaact tcttcttgcg 30

<210> SEQ ID NO 415
<211> LENGTH: 30
<212> TYPE: DNA
<213> ORGANISM: Steptococcus agalactiae

<400> SEQUENCE: 415
actgttccta taattaaaat aaaagaggta 30

<210> SEQ ID NO 416
<211> LENGTH: 30
<212> TYPE: DNA
<213> ORGANISM: Steptococcus agalactiae

<400> SEQUENCE: 416
tgttccagta aaaagtaatt ttaaagcatt 30

<210> SEQ ID NO 417
<211> LENGTH: 30
<212> TYPE: DNA
<213> ORGANISM: Steptococcus agalactiae

<400> SEQUENCE: 417
cgctcgattg atgctatcaa ctatattgaa 30

<210> SEQ ID NO 418
<211> LENGTH: 30
<212> TYPE: DNA
<213> ORGANISM: Steptococcus agalactiae

<400> SEQUENCE: 418
ttcttcaaga gaacttgtag aacagcttca 30

<210> SEQ ID NO 419
<211> LENGTH: 30
<212> TYPE: DNA
<213> ORGANISM: Steptococcus agalactiae

<400> SEQUENCE: 419
aaggtacttt tagcttgttc ttgtggtgtt 30

<210> SEQ ID NO 420
<211> LENGTH: 30
<212> TYPE: DNA
<213> ORGANISM: Steptococcus agalactiae

<400> SEQUENCE: 420
acagctactg taaattctgc ttttacggtt 30

<210> SEQ ID NO 421
<211> LENGTH: 30
<212> TYPE: DNA
<213> ORGANISM: Steptococcus agalactiae

<400> SEQUENCE: 421
tagtgcagtt gtcaaggaga ttgtgagcga 30

<210> SEQ ID NO 422
<211> LENGTH: 30
<212> TYPE: DNA
<213> ORGANISM: Steptococcus agalactiae

<400> SEQUENCE: 422
tttaaccttt gaaaatgtga aaggctcgta 30

<210> SEQ ID NO 423
<211> LENGTH: 30
<212> TYPE: DNA
<213> ORGANISM: Steptococcus agalactiae

<400> SEQUENCE: 423
gcgatgatgg taagtcatca tggacagcgt 30

<210> SEQ ID NO 424
<211> LENGTH: 30
<212> TYPE: DNA
<213> ORGANISM: Steptococcus agalactiae

<400> SEQUENCE: 424
ttttacacac gatgtcagat ataatgtcaa 30

<210> SEQ ID NO 425
<211> LENGTH: 30
<212> TYPE: DNA
<213> ORGANISM: Steptococcus agalactiae

<400> SEQUENCE: 425
agtactgcac taggaattgt agagatcaaa 30

<210> SEQ ID NO 426
<211> LENGTH: 30
<212> TYPE: DNA
<213> ORGANISM: Steptococcus agalactiae

<400> SEQUENCE: 426
cgtaccatct atcaatttac cgcaagctgt 30

<210> SEQ ID NO 427
<211> LENGTH: 30
<212> TYPE: DNA
<213> ORGANISM: Steptococcus agalactiae

<400> SEQUENCE: 427
ttaaaagatt taaactatca agcgtcaatt 30

<210> SEQ ID NO 428
<211> LENGTH: 30
<212> TYPE: DNA
<213> ORGANISM: Steptococcus agalactiae

<400> SEQUENCE: 428
ttctaaatgc tggtgactgc tttgcataaa 30

<210> SEQ ID NO 429
<211> LENGTH: 31
<212> TYPE: DNA
<213> ORGANISM: Steptococcus agalactiae

<400> SEQUENCE: 429
ttgctgctag acccaaacag tttattttta g 31

<210> SEQ ID NO 430
<211> LENGTH: 30
<212> TYPE: DNA
<213> ORGANISM: Steptococcus agalactiae

<400> SEQUENCE: 430
tcctttttta gataatgtgc gatcacggac 30

<210> SEQ ID NO 431
<211> LENGTH: 29
<212> TYPE: DNA
<213> ORGANISM: Steptococcus agalactiae

<400> SEQUENCE: 431
ttttaccaat gcttccatat cgcttatat 29

<210> SEQ ID NO 432
<211> LENGTH: 30
<212> TYPE: DNA
<213> ORGANISM: Steptococcus agalactiae

<400> SEQUENCE: 432
tggttataca tttactaatc catcagcatt 30

<210> SEQ ID NO 433
<211> LENGTH: 30
<212> TYPE: DNA
<213> ORGANISM: Steptococcus agalactiae

<400> SEQUENCE: 433
aagctaattc tcatctcacc gagatggata 30

<210> SEQ ID NO 434
<211> LENGTH: 30
<212> TYPE: DNA
<213> ORGANISM: Steptococcus agalactiae

<400> SEQUENCE: 434
aaaaactctt accacttaca tacatgtatg 30

<210> SEQ ID NO 435
<211> LENGTH: 30
<212> TYPE: DNA
<213> ORGANISM: Steptococcus agalactiae

<400> SEQUENCE: 435
gctggagatt ttacaagcag tttgaatttc 30

<210> SEQ ID NO 436
<211> LENGTH: 30
<212> TYPE: DNA
<213> ORGANISM: Steptococcus agalactiae

<400> SEQUENCE: 436
atcacaccag tcgttatgat ggatgactat 30

<210> SEQ ID NO 437
<211> LENGTH: 30
<212> TYPE: DNA
<213> ORGANISM: Steptococcus agalactiae

<400> SEQUENCE: 437
tgtcaacagt acgtgagacg agtgtgtagg 30

<210> SEQ ID NO 438
<211> LENGTH: 30
<212> TYPE: DNA
<213> ORGANISM: Steptococcus agalactiae

<400> SEQUENCE: 438
tgaagttgat ggatatgttg atttagagct 30

<210> SEQ ID NO 439
<211> LENGTH: 30
<212> TYPE: DNA
<213> ORGANISM: Steptococcus agalactiae

<400> SEQUENCE: 439
taatcatttt atgagagata ccgcctcaag 30

<210> SEQ ID NO 440
<211> LENGTH: 30
<212> TYPE: DNA
<213> ORGANISM: Steptococcus agalactiae

<400> SEQUENCE: 440
tttaaagaga tatctgtttc atcttgcgga 30

<210> SEQ ID NO 441
<211> LENGTH: 30
<212> TYPE: DNA
<213> ORGANISM: Steptococcus agalactiae

<400> SEQUENCE: 441
aatcacttct gcataaatat cttttacttc 30

<210> SEQ ID NO 442
<211> LENGTH: 30
<212> TYPE: DNA
<213> ORGANISM: Steptococcus agalactiae

<400> SEQUENCE: 442
aaacatccgc aacgggataa ataaagctag 30

<210> SEQ ID NO 443
<211> LENGTH: 30
<212> TYPE: DNA
<213> ORGANISM: Steptococcus agalactiae

<400> SEQUENCE: 443
agtttcttgt gggttagctt gtccaccgta 30

<210> SEQ ID NO 444
<211> LENGTH: 30
<212> TYPE: DNA
<213> ORGANISM: Steptococcus agalactiae

<400> SEQUENCE: 444
gaacatgaaa gattttaaaa aagaacattt 30

<210> SEQ ID NO 445
<211> LENGTH: 30
<212> TYPE: DNA
<213> ORGANISM: Steptococcus agalactiae

<400> SEQUENCE: 445
agaggggaaa atatcaatgc cgaatgctga 30

<210> SEQ ID NO 446
<211> LENGTH: 30
<212> TYPE: DNA
<213> ORGANISM: Steptococcus agalactiae

<400> SEQUENCE: 446
gatggtacaa aatcatttgt tggtactgat 30

<210> SEQ ID NO 447
<211> LENGTH: 30
<212> TYPE: DNA
<213> ORGANISM: Steptococcus mutans

<400> SEQUENCE: 447
aaaaggaaac gccattaatt aatatggtga 30

<210> SEQ ID NO 448
<211> LENGTH: 30
<212> TYPE: DNA
<213> ORGANISM: Steptococcus mutans

<400> SEQUENCE: 448
gattgaacca gctagcgcag ttagtgctct 30

<210> SEQ ID NO 449
<211> LENGTH: 30
<212> TYPE: DNA
<213> ORGANISM: Steptococcus mutans

<400> SEQUENCE: 449
cgctaaaagc tgttgtgtca tcatagttag 30

<210> SEQ ID NO 450
<211> LENGTH: 30
<212> TYPE: DNA
<213> ORGANISM: Steptococcus mutans

<400> SEQUENCE: 450
taaatatttt caattagaca atagacaaac 30

<210> SEQ ID NO 451
<211> LENGTH: 30
<212> TYPE: DNA
<213> ORGANISM: Steptococcus mutans

<400> SEQUENCE: 451
tgcctatgta ttcggacatg acttgccaca 30

<210> SEQ ID NO 452
<211> LENGTH: 30
<212> TYPE: DNA
<213> ORGANISM: Steptococcus mutans

<400> SEQUENCE: 452
atgtgaaaag aaagtaacta ctacatttga 30

<210> SEQ ID NO 453
<211> LENGTH: 30
<212> TYPE: DNA
<213> ORGANISM: Steptococcus pyogenes

<400> SEQUENCE: 453
tgcgctggtt gatttcttct tgcgcttttt 30

<210> SEQ ID NO 454
<211> LENGTH: 30
<212> TYPE: DNA
<213> ORGANISM: Steptococcus pyogenes

<400> SEQUENCE: 454
ttatatgaac ataactcaat ttgtaaaaaa 30

<210> SEQ ID NO 455
<211> LENGTH: 30
<212> TYPE: DNA
<213> ORGANISM: Steptococcus pyogenes

<400> SEQUENCE: 455
aggaatatcc gcaataatta attgcgctct 30

<210> SEQ ID NO 456
<211> LENGTH: 30
<212> TYPE: DNA
<213> ORGANISM: Steptococcus pyogenes

<400> SEQUENCE: 456
taaatttgtt tagcaggtaa accgtgcttt 30

<210> SEQ ID NO 457
<211> LENGTH: 30
<212> TYPE: DNA
<213> ORGANISM: Steptococcus pyogenes

<400> SEQUENCE: 457
ttcagcacac tgagacttgt tgagttccat 30

<210> SEQ ID NO 458
<211> LENGTH: 33
<212> TYPE: DNA
<213> ORGANISM: Steptococcus pyogenes

<400> SEQUENCE: 458
ctgtgacatt gcgggatgta atcaaagtaa aaa 33

<210> SEQ ID NO 459
<211> LENGTH: 32
<212> TYPE: DNA
<213> ORGANISM: Steptococcus pyogenes

<400> SEQUENCE: 459
aaagcaaacc tagcagaagc agaaaatgac tt 32

<210> SEQ ID NO 460
<211> LENGTH: 34
<212> TYPE: DNA
<213> ORGANISM: Steptococcus pyogenes

<400> SEQUENCE: 460
tgatgtaatt ggtgattttc gtgatatgct tttt 34

<210> SEQ ID NO 461
<211> LENGTH: 5849
<212> TYPE: DNA
<213> ORGANISM: Steptococcus thermophilus

<400> SEQUENCE: 461
atgagtgact tagttttagg acttgatatc ggtataggtt ctgttggtgt aggtatcctt 60
aacaaagtga caggagaaat tatccataaa aactcacgca tcttcccagc agctcaagca 120
gaaaataacc tagtacgtag aacgaatcgt caaggaagac gcttgacacg acgtaaaaaa 180
catcgtatag ttcgtttaaa tcgtctattt gaggaaagtg gattaatcac cgattttacg 240
aagatttcaa ttaatcttaa cccatatcaa ttacgagtta agggcttgac cgatgaattg 300
tctaatgaag aactgtttat cgctcttaaa aatatggtga aacaccgtgg gattagttac 360
ctcgatgatg ctagtgatga cggaaattca tcagtaggag actatgcaca aattgttaag 420
gaaaatagta aacaattaga aactaagaca ccgggacaga tacagttgga acgctaccaa 480
acatatggtc aattacgtgg tgattttact gttgagaaag atggcaaaaa acatcgcttg 540
attaatgtct ttccaacatc agcttatcgt tcagaagcct taaggatact gcaaactcaa 600
caagaattta atccacagat tacagatgaa tttattaatc gttatctcga aattttaact 660
ggaaaacgga aatattatca tggacccgga aatgaaaagt cacggactga ttatggtcgt 720
tacagaacga gtggagaaac tttagacaat atttttggaa ttctaattgg gaaatgtaca 780

-continued

```
ttttatccag aagagtttag agcagcaaaa gcttcctaca cggctcaaga attcaatttg    840
ctaaatgatt tgaacaatct aacagttcct actgaaacca aaaagttgag caaagaacag    900
aagaatcaaa tcattaatta tgtcaaaaat gaaaaggcaa tggggccagc gaaacttttt    960
aaatatatcg ctaagttact ttcttgtgat gttgcagata tcaagggata ccgtatcgac   1020
aaatcaggta aggctgagat tcatactttc gaagcctatc gaaaaatgaa aacgcttgaa   1080
accttagata ttgaacaaat ggatagagaa acgcttgata aattagccta tgtcttaaca   1140
ttaaacactg agagggaagg tattcaagaa gccttagaac atgaatttgc tgatggtagc   1200
tttagccaga agcaagttga cgaattggtt caattccgca aagcaaatag ttccattttt   1260
ggaaaaggat ggcataattt ttctgtcaaa ctgatgatgg agttaattcc agaattgtat   1320
gagacgtcag aagagcaaat gactatcctg acacgacttg gaaaacaaaa acgacttcgt   1380
cttcaaataa aacaaaatat ttcaaataaa acaaaatata tagatgagaa actattaact   1440
gaagaaatct ataatcctgt tgttgctaag tctgttcgcc aggctataaa aatcgtaaat   1500
gcggcgatta aagaatacgg agactttgac aatattgtca tcgaaatggc tcgtgaaaca   1560
aatgaagatg atgaaaagaa agctattcaa aagattcaaa aagccaacaa agatgaaaaa   1620
gatgcagcaa tgcttaaggc tgctaaccaa tataatggaa aggctgaatt accacatagt   1680
gttttccacg gtcataagca attagcgact aaaatccgcc tttggcatca gcaaggagaa   1740
cgttgccttt atactggtaa gacaatctca atccatgatt tgataaataa tcctaatcag   1800
tttgaagtag atcatatttt acctctttct atcacattcg atgatagcct tgcaaataag   1860
gttttggttt atgcaactgc taaccaagaa aaaggacaac gaacacctta tcaggcttta   1920
gatagtatgg atgatgcgtg gtctttccgt gaattaaaag cttttgtacg tgagtcaaaa   1980
acactttcaa acaagaaaaa agaatacctc cttacagaag aagatatttc aaagtttgat   2040
gttcgaaaga aatttattga acgaaatctt gtagatacaa gatacgcttc aagagttgtc   2100
ctcaatgccc ttcaagaaca ctttagagct cacaagattg atacaaaagt ttccgtggtt   2160
cgtggccaat ttacatctca attgagacgc cattggggaa ttgagaagac tcgtgatact   2220
tatcatcacc atgctgtcga tgcattgatt attgccgcct caagtcagtt gaatttgtgg   2280
aaaaaacaaa agaataccct tgtaagttat tcagaagaac aactccttga tattgaaaca   2340
ggtgaactta ttagtgatga tgagtacaag gaatctgtgt tcaaagcccc ttatcaacat   2400
tttgttgata cattgaagag taaagaattt gaagacagta tcttattctc atatcaagtg   2460
gattctaagt ttaatcgtaa aatatcagat gccactattt atgcgacaag acaggctaaa   2520
gtgggaaaag ataagaagga tgaaacttat gtcttaggga aaatcaaaga tatctatact   2580
caggatggtt atgatgcctt tatgaagatt tataagaagg ataagtcaaa attcctcatg   2640
tatcgtcacg acccacaaac ctttgagaaa gttatcgagc caattttaga gaactatcct   2700
aataagcaaa tgaatgaaaa aggaaaagag gtaccatgta atcctttcct aaaatataaa   2760
gaagaacatg gctatattcg taaatatagt aaaaaaggca atggtcctga aatcaagagt   2820
cttaaatact atgatagtaa gcttttaggt aatcctattg atattactcc agagaatagt   2880
aaaaataaag ttgtcttaca gtcattaaaa ccttggagaa cagatgtcta tttcaataag   2940
gctactggaa aatacgaaat ccttggatta aaatatgctg atctacaatt tgagaaaggg   3000
acaggaacat ataagatttc ccaggaaaaa tacaatgaca ttaagaaaaa agagggtgta   3060
gattctgatt cagaattcaa gtttacactt tataaaaatg atttgttact cgttaaagat   3120
acagaaacaa aagaacaaca gcttttccgt tttctttctc gaactttacc taaacaaaag   3180
```

```
cattatgttg aattaaaacc ttatgataaa cagaaatttg aaggaggtga ggcgttaatt   3240
aaagtgttgg gtaacgttgc taatggtggt caatgcataa aaggactagc aaaatcaaat   3300
atttctattt ataaagtaag aacagatgtc ctaggaaatc agcatatcat caaaaatgag   3360
ggtgataagc ctaagctaga tttttaatat taattgttag aaagtgttgc aattatagtt   3420
atcatatgct ataataatcg tgtaagggac gccttacaca gttacttaaa tcttgcagaa   3480
gctacaaaga taaggcttca tgccgaaatc aacaccctgt cattttatgg cagggtgttt   3540
tcgttattta aagaggagaa gaaatgactt ggagagttgt acatgtcagt caaagtgaga   3600
agatgcgctt aaagcttgat aacttattag tgcaaaaaat gggacaagag tttacggtgc   3660
cactaagtga tatttcgata atcgttgcag aaggtgggga tacagttgtt acccttcgtc   3720
tattaagtgc cttaagtaaa tataatattg ccttggtcgt ttgtgataac gaacatttac   3780
caacaggaat ttatcactca caaaatgggc actttagagc gtacaagcgc ttgaaagaac   3840
agctggattg gtctcagaaa caaaaggaca aggcatggca gattgtaact tattataaaa   3900
tcaataacca agaggatgtt ctagccatgt ttgaaaaaag tctggacaac attagattac   3960
tttcagacta taaagagcag atagaacctg gtgatagaac gaatagagag ggacatgctg   4020
ccaaggtcta ctttaatgag ctctttggta aacaatttgt cagagtaact cagcaagaag   4080
ctgatgtcat caatgctggt ttaaactatg gctatgctat catgagggct cagatggcta   4140
gaatagtggc gggttatggt ttaaatggcc tattaggaat cttccataaa aatgaataca   4200
atcagtttaa tttggttgac gatttgatgg agccatttag acagattgta gatgtttggg   4260
tatatgataa tctacgagat caggaattcc ttaagtatga gtataggttg ggattgacag   4320
atttactcaa tgctaaaatc aaatatggca aagagacttg ctcagtgaca gttgctatgg   4380
acaaatatgt caaaggcttt atcaaatata tttcggaaaa agatagtagt aaatttcact   4440
gcccagtggt atcaagttta gagtggagaa aataagatga ggtatgaagc attgagatta   4500
ttatgttttt ttgatttacc aatggaatcc aaggatgaaa aaagaatata tcgtaatttt   4560
cgtaaagaat taatttcaaa tgggtttgaa atgttacaat tttcggtcta ctatcgcact   4620
tgtcctaata gaagctttgc aaataaattt tataagaagt taaagattag caatcttcct   4680
gctgggaatg tgagactttt ggcagttact gaaaaacaat tttcagagat gacattaatt   4740
ataggtggta aaactaagca agaagaaatc gtcagtgata ataagttggt ggttatatga   4800
aatattttgt acaacatcct tacaaagaac gtattgaatt aaatattggt gcaatcacac   4860
aaattgttgg tcagaataaa gaactcaaat attatatttg gcaaattttg agctggtatt   4920
ttggcggaaa aaaatactca agtgaggact taagtatttt tgattatgag gaacctacta   4980
tacttgatga gtctggagaa atagtgaagc gaagtagcta tcactatatc gacatttcaa   5040
gttttaagga tttactggag cagatggaat acaagaaagg aacacttgct cagggttacc   5100
ttagtaaaat tctcaatcag gttgatattg taggccattt ggagaaaatt aatgaacaag   5160
tagagcttat agaaggagca atgaatcagc atataaactt aaactgtggt caggtggagt   5220
accatttgga gaatcaccct ctaacactag accaattact ttcaaaaaat tttagtccct   5280
tttttgctat cgagaataag aatttatctt ttgaatgggt ttcaaatact gataaacttt   5340
ctctctttct agaaatgtta gaccgccttc tgtcacaaac aacagagaag tatctcattg   5400
tgctaaaaaa tattgatggc tttatctcag aagaatctta tactattttt tataggcaaa   5460
tctgtcatct ggtcaagaag tatccaaatc taacctttat tttgtttcct agtgaccaag   5520
```

-continued

```
gctatttaaa aattgatgaa gaaaatagta ggttcgtcaa tattttatct gaccaggtgg   5580

agcatttgta tgatgttgag tttatgtatg aaagagtaat gaaatattat ccaagtaatg   5640

attttccgac gagagaaggt tttaggatgt ctttagaaac tgtgacacct tatttattga   5700

caaaaatgct gagacaacct agtctctcac ttgttgattc agtaatattg aatatcctaa   5760

atcagttgtt tcattttagt taccgtataa gatattctca gacacctgat aaggaactat   5820

tacataaatt tttagaaagt aaggattga                                     5849
```

<210> SEQ ID NO 462
<211> LENGTH: 3387
<212> TYPE: DNA
<213> ORGANISM: Steptococcus thermophilus

<400> SEQUENCE: 462

```
atgagtgact tagttttagg acttgatatc ggtataggtt ctgttggtgt aggtatcctt     60

aacaaagtga caggagaaat tatccataaa aactcacgca tcttcccagc agctcaagca    120

gaaaataacc tagtacgtag aacgaatcgt caaggaagac gcttgacacg acgtaaaaaa    180

catcgtatag ttcgtttaaa tcgtctattt gaggaaagtg gattaatcac cgattttacg    240

aagatttcaa ttaatcttaa cccatatcaa ttacgagtta agggcttgac cgatgaattg    300

tctaatgaag aactgtttat cgctcttaaa aatatggtga aacaccgtgg gattagttac    360

ctcgatgatg ctagtgatga cggaaattca tcagtaggag actatgcaca aattgttaag    420

gaaaatagta aacaattaga aactaagaca ccgggacaga tacagttgga acgctaccaa    480

acatatggtc aattacgtgg tgattttact gttgagaaag atggcaaaaa acatcgcttg    540

attaatgtct ttccaacatc agcttatcgt tcagaagcct taaggatact gcaaactcaa    600

caagaattta atccacagat tacagatgaa tttattaatc gttatctcga aattttaact    660

ggaaaacgga aatattatca tggacccgga aatgaaaagt cacggactga ttatggtcgt    720

tacagaacga gtggagaaac tttagacaat atttttggaa ttctaattgg gaaatgtaca    780

ttttatccag aagagtttag agcagcaaaa gcttcctaca cggctcaaga attcaatttg    840

ctaaatgatt tgaacaatct aacagttcct actgaaacca aaaagttgag caaagaacag    900

aagaatcaaa tcattaatta tgtcaaaaat gaaaaggcaa tggggccagc gaaacttttt    960

aaatatatcg ctaagttact ttcttgtgat gttgcagata tcaagggata ccgtatcgac   1020

aaatcaggta aggctgagat tcatactttc gaagcctatc gaaaaatgaa aacgcttgaa   1080

accttagata ttgaacaaat ggatagagaa acgcttgata aattagccta tgtcttaaca   1140

ttaaacactg agagggaagg tattcaagaa gccttagaac atgaatttgc tgatggtagc   1200

tttagccaga agcaagttga cgaattggtt caattccgca aagcaaatag ttccattttt   1260

ggaaaaggat ggcataattt ttctgtcaaa ctgatgatgg agttaattcc agaattgtat   1320

gagacgtcag aagagcaaat gactatcctg acacgacttg gaaaacaaaa acgacttcgt   1380

cttcaaataa aacaaaatat ttcaaataaa acaaaatata tagatgagaa actattaact   1440

gaagaaatct ataatcctgt tgttgctaag tctgttcgcc aggctataaa aatcgtaaat   1500

gcggcgatta aagaatacgg agactttgac aatattgtca tcgaaatggc tcgtgaaaca   1560

aatgaagatg atgaaaagaa agctattcaa aagattcaaa aagccaacaa agatgaaaaa   1620

gatgcagcaa tgcttaaggc tgctaaccaa tataatggaa aggctgaatt accacatagt   1680

gttttccacg gtcataagca attagcgact aaaatccgcc tttggcatca gcaaggagaa   1740

cgttgccttt atactggtaa gacaatctca atccatgatt tgataaataa tcctaatcag   1800
```

```
tttgaagtag atcatatttt acctctttct atcacattcg atgatagcct tgcaaataag   1860
gttttggttt atgcaactgc taaccaagaa aaaggacaac gaacacctta tcaggcttta   1920
gatagtatgg atgatgcgtg gtctttccgt gaattaaaag cttttgtacg tgagtcaaaa   1980
acactttcaa acaagaaaaa agaatacctc cttacagaag aagatatttc aaagtttgat   2040
gttcgaaaga aatttattga acgaaatctt gtagatacaa gatacgcttc aagagttgtc   2100
ctcaatgccc ttcaagaaca ctttagagct cacaagattg atacaaaagt ttccgtggtt   2160
cgtggccaat ttacatctca attgagacgc cattggggaa ttgagaagac tcgtgatact   2220
tatcatcacc atgctgtcga tgcattgatt attgccgcct caagtcagtt gaatttgtgg   2280
aaaaaacaaa agaataccct tgtaagttat tcagaagaac aactccttga tattgaaaca   2340
ggtgaactta ttagtgatga tgagtacaag gaatctgtgt tcaaagcccc ttatcaacat   2400
tttgttgata cattgaagag taaagaattt gaagacagta tcttattctc atatcaagtg   2460
gattctaagt ttaatcgtaa aatatcagat gccactattt atgcgacaag acaggctaaa   2520
gtgggaaaag ataagaagga tgaaacttat gtcttaggga aaatcaaaga tatctatact   2580
caggatggtt atgatgcctt tatgaagatt tataagaagg ataagtcaaa attcctcatg   2640
tatcgtcacg acccacaaac ctttgagaaa gttatcgagc caattttaga gaactatcct   2700
aataagcaaa tgaatgaaaa aggaaaagag gtaccatgta atcctttcct aaaatataaa   2760
gaagaacatg gctatattcg taaatatagt aaaaaaggca atggtcctga aatcaagagt   2820
cttaaatact atgatagtaa gcttttaggt aatcctattg atattactcc agagaatagt   2880
aaaaataaag ttgtcttaca gtcattaaaa ccttggagaa cagatgtcta tttcaataag   2940
gctactggaa aatacgaaat ccttggatta aaatatgctg atctacaatt tgagaaaggg   3000
acaggaacat ataagatttc ccaggaaaaa tacaatgaca ttaagaaaaa agagggtgta   3060
gattctgatt cagaattcaa gtttacactt tataaaaatg atttgttact cgttaaagat   3120
acagaaacaa aagaacaaca gcttttccgt tttctttctc gaactttacc taaacaaaag   3180
cattatgttg aattaaaacc ttatgataaa cagaaatttg aaggaggtga ggcgttaatt   3240
aaagtgttgg gtaacgttgc taatggtggt caatgcataa aaggactagc aaaatcaaat   3300
atttctattt ataaagtaag aacagatgtc ctaggaaatc agcatatcat caaaaatgag   3360
ggtgataagc ctaagctaga tttttaa                                       3387
```

<210> SEQ ID NO 463
<211> LENGTH: 912
<212> TYPE: DNA
<213> ORGANISM: Steptococcus thermophilus

<400> SEQUENCE: 463

```
atgacttgga gagttgtaca tgtcagtcaa agtgagaaga tgcgcttaaa gcttgataac     60
ttattagtgc aaaaaatggg acaagagttt acggtgccac taagtgatat ttcgataatc    120
gttgcagaag gtggggatac agttgttacc cttcgtctat taagtgcctt aagtaaatat    180
aatattgcct tggtcgtttg tgataacgaa catttaccaa caggaattta tcactcacaa    240
aatgggcact ttagagcgta caagcgcttg aaagaacagc tggattggtc tcagaaacaa    300
aaggacaagg catggcagat tgtaacttat tataaaatca ataaccaaga ggatgttcta    360
gccatgtttg aaaaaagtct ggacaacatt agattacttt cagactataa agagcagata    420
gaacctggtg atagaacgaa tagagaggga catgctgcca aggtctactt taatgagctc    480
```

-continued

```
tttggtaaac aatttgtcag agtaactcag caagaagctg atgtcatcaa tgctggttta    540

aactatggct atgctatcat gagggctcag atggctagaa tagtggcggg ttatggttta    600

aatggcctat taggaatctt ccataaaaat gaatacaatc agtttaattt ggttgacgat    660

ttgatggagc catttagaca gattgtagat gtttgggtat atgataatct acgagatcag    720

gaattcctta agtatgagta taggttggga ttgacagatt tactcaatgc taaaatcaaa    780

tatggcaaag agacttgctc agtgacagtt gctatggaca aatatgtcaa aggctttatc    840

aaatatattt cggaaaaaga tagtagtaaa tttcactgcc cagtggtatc aagtttagag    900

tggagaaaat aa                                                        912
```

<210> SEQ ID NO 464
<211> LENGTH: 324
<212> TYPE: DNA
<213> ORGANISM: Steptococcus thermophilus

<400> SEQUENCE: 464

```
atgaggtatg aagcattgag attattatgt ttttttgatt taccaatgga atccaaggat     60

gaaaaaagaa tatatcgtaa ttttcgtaaa gaattaattt caaatgggtt tgaaatgtta    120

caattttcgg tctactatcg cacttgtcct aatagaagct ttgcaaataa attttataag    180

aagttaaaga ttagcaatct tcctgctggg aatgtgagac ttttggcagt tactgaaaaa    240

caattttcag agatgacatt aattataggt ggtaaaacta agcaagaaga aatcgtcagt    300

gataataagt tggtggttat atga                                           324
```

<210> SEQ ID NO 465
<211> LENGTH: 1053
<212> TYPE: DNA
<213> ORGANISM: Steptococcus thermophilus

<400> SEQUENCE: 465

```
atgaaatatt ttgtacaaca tccttacaaa gaacgtattg aattaaatat tggtgcaatc     60

acacaaattg ttggtcagaa taaagaactc aaatattata tttggcaaat tttgagctgg    120

tattttggcg gaaaaaaata ctcaagtgag gacttaagta tttttgatta tgaggaacct    180

actatacttg atgagtctgg agaaatagtg aagcgaagta gctatcacta tatcgacatt    240

tcaagtttta aggatttact ggagcagatg gaatacaaga aaggaacact tgctcagggt    300

taccttagta aaattctcaa tcaggttgat attgtaggcc atttggagaa aattaatgaa    360

caagtagagc ttatagaagg agcaatgaat cagcatataa acttaaactg tggtcaggtg    420

gagtaccatt tggagaatca ccctctaaca ctagaccaat tactttcaaa aaattttagt    480

cccttttttg ctatcgagaa taagaattta tcttttgaat gggtttcaaa tactgataaa    540

ctttctctct ttctagaaat gttagaccgc cttctgtcac aaacaacaga gaagtatctc    600

attgtgctaa aaaatattga tggctttatc tcagaagaat cttatactat tttttatagg    660

caaatctgtc atctggtcaa gaagtatcca aatctaacct ttattttgtt tcctagtgac    720

caaggctatt taaaaattga tgaagaaaat agtaggttcg tcaatatttt atctgaccag    780

gtggagcatt tgtatgatgt tgagtttatg tatgaaagag taatgaaata ttatccaagt    840

aatgattttc cgacgagaga aggttttagg atgtctttag aaactgtgac accttattta    900

ttgacaaaaa tgctgagaca acctagtctc tcacttgttg attcagtaat attgaatatc    960

ctaaatcagt tgtttcattt tagttaccgt ataagatatt ctcagacacc tgataaggaa   1020

ctattacata aatttttaga aagtaaggat tga                                1053
```

<210> SEQ ID NO 466
<211> LENGTH: 4123
<212> TYPE: DNA
<213> ORGANISM: Steptococcus thermophilus

<400> SEQUENCE: 466
atgagcgatt tatatagtca aaggtccaat tattacctgt ccttatctga acaaagaatt 60
atcattaaaa atgataataa agagattgtc aaagaagtgt ccatttcact cgttgataat 120
gtattacttt ttggtaatgc acaactgacc acccaactca tcaaagcctt gtcaaagaac 180
aaggtgaatg tttactattt ctcaaatgtt ggtcaattta tttctagtat tgaaacccac 240
aggcaggacg aattccaaaa gcaagagttg caagcaaagg cttattttga agaggatttc 300
cgtttagagg ttgcgaggag tattgctacg accaaggtga ggcacccaat tgccttactt 360
agagagtttg atacggatgg tctactagat acctcagatt attctaggtt tgaagatagt 420
gtcaatgata ttcagaaagc ttattccatt acagaaatta tgggttacga aggtcgcctt 480
gcgaaatcct atttttacta tctgaattta ctcgttccta atgactttca ttttaatggt 540
aggagtagac ggcctgggga ggattgtttt aacagtgccc tcaattttgg ctatagtatc 600
ttatattctt gcttaatggg ctgattaaga aaaacgggct aagcttggga tttggggtaa 660
ttcacaagca tcatcagcat catgcgacct tggccagtga tttaatggaa gaatggagac 720
ctatcatcgt cgataatacg cttatggagt tggtacgaaa tggtaaactt cttttaagtc 780
attttgaaaa taaggatcaa gacttcatac tcacccatga aggcagagaa atctttgcac 840
gggctttacg ttcaagaata ttagaagtcc atcagtatat tgagttagat aaaaaacgct 900
attcttttct ttatacagca gataggcaaa tcaagagttt gattagggct tttagagaac 960
ttgaccctag tctctatgag acaagttaca caggagggca ttaatgggac tttactttaa 1020
cctcagcgaa gaagagcgtg agtttgccaa acaaaaaaac catgttttgt ctgattattt 1080
atgatattcg aagtaacaaa cgtagactta aactctcgaa attacttgag ggttatggcg 1140
tgagggtgca aaaatcctgt ttcgaagtcg acctgtcaag aaatgattat cagtctctcc 1200
ttaaggatat cgagggcttc tccaaggctg atgaagaaga cagcataata gtgtatgtgc 1260
caaccaaaga agaggtgact agttttagcc cctaccatag tgctgaaaaa ttagatgaca 1320
ttctcttccc ctaagccttt atagaccttt aatcatatgg tacactatag atagtgtttc 1380
cagaggctct taaggaaatc aaagatagag agacacttca aagattttgt agatatatgg 1440
aagcattagt agcctatttc aagttttatg gaggtaaaga ttaatgacat tcgctaagat 1500
taaattttca gctcaaattc gtttagagac aggcctccat attggtggaa gcgatgcttt 1560
tgcagccatt ggtgcaatcg attcgcctgt tattaaagat cctattacca acctaccgat 1620
cattcctggt tcaagtctca aaggaaaaat gagaacgctt cttgccaagg tttataatga 1680
aaaggtagct gagaaaccaa gcgatgacag tgatattctt agccgtttat ttgggaatag 1740
taaagataaa cgattcaaaa tgggacgctt gatttttcgt gatgccttct tgtcaaacgc 1800
tgatgagcta gactctcttg ggtaagaag ttatacagaa gtaaaatttg aaaatacaat 1860
tgaccgtatc actgccgaag ctaatccaag acaaattgaa cgtgctattc gtaccagtac 1920
ttttgatttc gagttgattt atgaaattac agatgagaat gaaaatcaag tcgaagaaga 1980
ttccaaagtg attcgagatg gtttaaaact gcttgaactt gattatcttg gtggttctgg 2040
atctcgaggt tacggtaagg ttgcttttga aaacctcaaa gctactaccg tatttggtaa 2100
ttatgatgtt aaaacattaa atgaactttt aactgcggag gtctaatatg acctataaac 2160
tgtatattat gacctttcag aatgctcatt ttggttcggg cactcttgat agctcaaaat 2220
taacattctc agcagaccgt atcttctcag cactagtgct agaatcccta aaaatgggaa 2280
aactcgatgc atttcttgcg gaagctaacc aagacaagtt cacgctcaca gatgcctttc 2340
catttcaatt tggtcccttt ttgccgaaac ctattggtta tcccaaacat gaccaaatag 2400
atcaatcagt tgatgtcaaa gaggttcgcc gtcaagcaaa attgtctaag aaactgcaat 2460
ttcttgctct agaaaatgtt gacgattata tcaatggaga gttatttgaa aatgaagagc 2520
atgcagtcat cgatactgtg acaaaaaatc aaccacataa ggacggcaat ctttatcagg 2580
tagctacaac cagattttca aatgatacgt cgctttacgt catcgcaaac gaatctgatt 2640
tgcttaatga gttgatgtct agtcttcagt attcaggtct tggtggaaag cgttcaagtg 2700
gttttggtcg ttttgagtta gatattcaaa atatcccact agaattgtca gatagactga 2760
ctaagaatca ttcagataaa gtgatgagtc ttacgacagc acttcctgta gatgctgacc 2820
ttgaagaagc aatggaagat ggacattact tattaactaa atcaagtggt tttgcattta 2880
gtcatgccac caatgagaat tatcgtaagc aggatcttta caaatttgct tctggttcaa 2940
cttttagtaa aacatttgaa ggtcagattg ttgatgtgag accacttgat ttccctcatg 3000
ctgttttaaa ttatgctaaa ccactcttct ttaaattgga ggtataaaaa tgaaaaatga 3060
ctatagaaca tttaaattaa gcctcctgac acttgctcca attcatattg gtaatggaga 3120
gaagtatacc tctagagaat ttatctatga aaataaaaag ttttactttc ctgacatggg 3180
gaaattctat aataaaatgg tggagaagag gcttgctgaa aagtttgaag catttctaat 3240
tcaaactcgt ccaaatgcac gtaataatcg tcttatttcc ttcttaaatg ataaccgaat 3300
tgcagagcgt tcttttggag gttatagtat ctctgaaaca ggtttagaat cggacaaaaa 3360
tcctgattca accggagcta ttaacgaagt taataaattt attcgagatg cttttggaaa 3420
tccctacatt cctggtagct cactaaaagg tgctattcgt accattttaa tgaatactac 3480
ccctaagtgg aataatgaaa atgctgtaaa tgactttgga agatttccga aagagaataa 3540
gaaccttatc ccttggggac caaaaaaggg aaaagaatac gatgatttgt ttaacgcaat 3600
tcgtgtgagt gatagtaagc cttttgataa taagagtctt atcttagtgc agaaatggga 3660
ttattcagcg aaaacaaata aagctaaacc acttcccttg tatagagaat caatctctcc 3720
attaacaaaa attgaatttg agattacaac aaccactgat gaagctggaa gattgattga 3780
agaattaggt aagagagcac aagcgtttta taaagactat aaggcatttt tcctatctga 3840
atttcctgat gataagattc aagccaatct acaataccca atttatttag gtgcggggag 3900
cggtgcttgg acaaagactc tatttaagca agctgatggt attttacaaa gacgatacag 3960
tcgaatgaaa actaaaatgg ttaaaaaagg agttcttaag ctcacaaaag cacctcttaa 4020
aacagttaag attccatctg gtaatcattc attagtcaag aaccacgagt ccttttatga 4080
aatgggaaaa gctaatttca tgattaagga gattgataaa tga 4123

<210> SEQ ID NO 467
<211> LENGTH: 624
<212> TYPE: DNA
<213> ORGANISM: Steptococcus thermophilus

<400> SEQUENCE: 467
atgagcgatt tatatagtca aaggtccaat tattacctgt ccttatctga acaaagaatt 60
atcattaaaa atgataataa agagattgtc aaagaagtgt ccatttcact cgttgataat 120
gtattacttt ttggtaatgc acaactgacc acccaactca tcaaagcctt gtcaaagaac 180
aaggtgaatg tttactattt ctcaaatgtt ggtcaattta tttctagtat tgaaacccac 240
aggcaggacg aattccaaaa gcaagagttg caagcaaagg cttattttga agaggatttc 300
cgtttagagg ttgcgaggag tattgctacg accaaggtga ggcacccaat tgccttactt 360
agagagtttg atacggatgg tctactagat acctcagatt attctaggtt tgaagatagt 420
gtcaatgata ttcagaaagc ttattccatt acagaaatta tgggttacga aggtcgcctt 480
gcgaaatcct atttttacta tctgaattta ctcgttccta atgactttca ttttaatggt 540
aggagtagac ggcctgggga ggattgtttt aacagtgccc tcaattttgg ctatagtatc 600
ttatattctt gcttaatggg ctga 624

<210> SEQ ID NO 468
<211> LENGTH: 396
<212> TYPE: DNA
<213> ORGANISM: Steptococcus thermophilus

<400> SEQUENCE: 468
ttgcttaatg ggctgattaa gaaaaacggg ctaagcttgg gatttggggt aattcacaag 60
catcatcagc atcatgcgac cttggccagt gatttaatgg aagaatggag acctatcatc 120
gtcgataata cgcttatgga gttggtacga aatggtaaac ttcttttaag tcattttgaa 180
aataaggatc aagacttcat actcacccat gaaggcagag aaatctttgc acgggcttta 240
cgttcaagaa tattagaagt ccatcagtat attgagttag ataaaaaacg ctattctttt 300
ctttatacag cagataggca aatcaagagt ttgattaggg cttttagaga acttgaccct 360
agtctctatg agacaagtta cacaggaggg cattaa 396

<210> SEQ ID NO 469
<211> LENGTH: 273
<212> TYPE: DNA
<213> ORGANISM: Steptococcus thermophilus

<400> SEQUENCE: 469
atgttttgtc tgattattta tgatattcga agtaacaaac gtagacttaa actctcgaaa 60
ttacttgagg gttatggcgt gagggtgcaa aaatcctgtt tcgaagtcga cctgtcaaga 120
aatgattatc agtctctcct taaggatatc gagggcttct ccaaggctga tgaagaagac 180
agcataatag tgtatgtgcc aaccaaagaa gaggtgacta gttttagccc ctaccatagt 240
gctgaaaaat tagatgacat tctcttcccc taa 273

<210> SEQ ID NO 470
<211> LENGTH: 663
<212> TYPE: DNA
<213> ORGANISM: Steptococcus thermophilus

<400> SEQUENCE: 470
atgacattcg ctaagattaa attttcagct caaattcgtt tagagacagg cctccatatt 60
ggtggaagcg atgcttttgc agccattggt gcaatcgatt cgcctgttat taaagatcct 120
attaccaacc taccgatcat tcctggttca agtctcaaag gaaaaatgag aacgcttctt 180
gccaaggttt ataatgaaaa ggtagctgag aaaccaagcg atgacagtga tattcttagc 240
cgtttatttg ggaatagtaa agataaacga ttcaaaatgg gacgcttgat tttcgtgat 300 gccttcttgt caaacgctga tgagctagac tctcttgggg taagaagtta tacagaagta 360

-continued

```
aaatttgaaa atacaattga ccgtatcact gccgaagcta atccaagaca aattgaacgt    420

gctattcgta ccagtacttt tgatttcgag ttgatttatg aaattacaga tgagaatgaa    480

aatcaagtcg aagaagattc caaagtgatt cgagatggtt taaaactgct tgaacttgat    540

tatcttggtg gttctggatc tcgaggttac ggtaaggttg cttttgaaaa cctcaaagct    600

actaccgtat ttggtaatta tgatgttaaa acattaaatg aacttttaac tgcggaggtc    660

taa                                                                  663
```

<210> SEQ ID NO 471
<211> LENGTH: 900
<212> TYPE: DNA
<213> ORGANISM: Steptococcus thermophilus

<400> SEQUENCE: 471

```
atgacctata aactgtatat tatgaccttt cagaatgctc attttggttc gggcactctt     60

gatagctcaa aattaacatt ctcagcagac cgtatcttct cagcactagt gctagaatcc    120

ctaaaaatgg gaaaactcga tgcatttctt gcggaagcta accaagacaa gttcacgctc    180

acagatgcct ttccatttca atttggtccc tttttgccga aacctattgg ttatcccaaa    240

catgaccaaa tagatcaatc agttgatgtc aaagaggttc gccgtcaagc aaaattgtct    300

aagaaactgc aatttcttgc tctagaaaat gttgacgatt atatcaatgg agagttattt    360

gaaaatgaag agcatgcagt catcgatact gtgacaaaaa atcaaccaca taaggacggc    420

aatctttatc aggtagctac aaccagattt tcaaatgata cgtcgcttta cgtcatcgca    480

aacgaatctg atttgcttaa tgagttgatg tctagtcttc agtattcagg tcttggtgga    540

aagcgttcaa gtggttttgg tcgttttgag ttagatattc aaaatatccc actagaattg    600

tcagatagac tgactaagaa tcattcagat aaagtgatga gtcttacgac agcacttcct    660

gtagatgctg accttgaaga agcaatggaa gatggacatt acttattaac taaatcaagt    720

ggttttgcat ttagtcatgc caccaatgag aattatcgta agcaggatct ttacaaattt    780

gcttctggtt caacttttag taaaacattt gaaggtcaga ttgttgatgt gagaccactt    840

gatttccctc atgctgtttt aaattatgct aaaccactct tctttaaatt ggaggtataa    900
```

<210> SEQ ID NO 472
<211> LENGTH: 1074
<212> TYPE: DNA
<213> ORGANISM: Steptococcus thermophilus

<400> SEQUENCE: 472

```
atgaaaaatg actatagaac atttaaatta agcctcctga cacttgctcc aattcatatt     60

ggtaatggag agaagtatac ctctagagaa tttatctatg aaaataaaaa gttttacttt    120

cctgacatgg ggaaattcta taataaaatg gtggagaaga ggcttgctga aaagtttgaa    180

gcatttctaa ttcaaactcg tccaaatgca cgtaataatc gtcttatttc cttcttaaat    240

gataaccgaa ttgcagagcg ttcttttgga ggttatagta tctctgaaac aggtttagaa    300

tcggacaaaa atcctgattc aaccggagct attaacgaag ttaataaatt tattcgagat    360

gcttttggaa atccctacat tcctggtagc tcactaaaag gtgctattcg taccatttta    420

atgaatacta cccctaagtg gaataatgaa aatgctgtaa atgactttgg aagatttccg    480

aaagagaata agaaccttat cccttgggga ccaaaaaagg gaaaagaata cgatgatttg    540

tttaacgcaa ttcgtgtgag tgatagtaag ccttttgata ataagagtct tatcttagtg    600

cagaaatggg attattcagc gaaaacaaat aaagctaaac cacttccctt gtatagagaa    660
```

```
tcaatctctc cattaacaaa aattgaattt gagattacaa caaccactga tgaagctgga    720

agattgattg aagaattagg taagagagca caagcgtttt ataaagacta taaggcattt    780

ttcctatctg aatttcctga tgataagatt caagccaatc tacaataccc aatttattta    840

ggtgcgggga gcggtgcttg gacaaagact ctatttaagc aagctgatgg tattttacaa    900

agacgataca gtcgaatgaa aactaaaatg gttaaaaaag gagttcttaa gctcacaaaa    960

gcacctctta aaacagttaa gattccatct ggtaatcatt cattagtcaa gaaccacgag   1020

tccttttatg aaatgggaaa agctaatttc atgattaagg agattgataa atga         1074
```

<210> SEQ ID NO 473
<211> LENGTH: 5832
<212> TYPE: DNA
<213> ORGANISM: Steptococcus thermophilus

<400> SEQUENCE: 473

```
atgagtgact tagttttagg acttgatatc ggtataggtt ctgttggtgt aggtatcctt     60

aacaaagtga caggagaaat tatccataaa aactcacgca tcttcccagc agctcaagca    120

gaaaataacc tagtacgtag aacgaatcgt caaggaagac gcttgacacg acgtaaaaaa    180

catcgtatag ttcgtttaaa tcgtctattt gaggaaagtg gattaatcac cgattttacg    240

aagatttcaa ttaatcttaa cccatatcaa ttacgagtta agggcttgac cgatgaattg    300

tctaatgaag aactgtttat cgctcttaaa aatatggtga aacaccgtgg gattagttac    360

ctcgatgatg ctagtgatga cggaaattca tcagtaggag actatgcaca aattgttaag    420

gaaaatagta aacaattaga aactaagaca ccgggacaga tacagttgga acgctaccaa    480

acatatggtc aattacgtgg tgattttact gttgagaaag atggcaaaaa acatcgcttg    540

attaatgtct ttccaacatc agcttatcgt tcagaagcct taaggatact gcaaactcaa    600

caagaattta attcacagat tacagatgaa tttattaatc gttatctcga aattttaact    660

ggaaaacgga aatattatca tggacccgga aatgaaaagt cacggactga ttatggtcgt    720

tacagaacga atggagaaac tttagacaat atttttggaa ttctaattgg gaaatgtaca    780

ttttatccag acgagtttag agcagcaaaa gcttcctaca cggctcaaga attcaatttg    840

ctaaatgatt tgaacaatct aacagttcct actgaaacca aaaagttgag caaagaacag    900

aagaatcaaa tcattaatta tgtcaaaaat gaaaaggtaa tggggccagc gaaacttttt    960

aaatatatcg ctaaattact ttcttgtgat gttgcagata tcaagggaca ccgtatcgac   1020

aaatcaggta aggctgagat tcatactttc gaagcctatc gaaaaatgaa aacgcttgaa   1080

accttagata ttgagcaaat ggatagagaa acgcttgata aattagccta tgtcttaaca   1140

ttaaacactg agagggaagg tattcaagaa gctttagaac atgaatttgc tgatggtagc   1200

tttagccaga agcaagttga cgaattggtt caattccgca aagcaaatag ttccattttt   1260

ggaaaaggat ggcataattt ttctgtcaaa ctgatgatgg agttaattcc agaattgtat   1320

gagacgtcag aagagcaaat gactatcctg acacgacttg gaaaacaaaa aacaacttcg   1380

tcttcaaata aaacaaaata tatagatgag aaactattaa ctgaagaaat ctataatcct   1440

gttgttgcta agtctgttcg ccaggctata aaaatcgtaa atgcggcgat taaagaatac   1500

ggagactttg acaatattgt catcgaaatg gctcgtgaaa caaatgaaga tgatgaaaag   1560

aaagctattc aaaagattca aaaagccaac aaagatgaaa aagatgcagc aatgcttaag   1620

gctgctaacc aatataatgg aaaggctgaa ttaccacata gtgttttcca cggtcataag   1680
```

```
caattagcga ctaaaatccg cctttggcat cagcaaggag aacgttgcct ttatactggt   1740
aagacaatct caatccatga tttgataaat aatcctaatc agtttgaagt agatcatatt   1800
ttacctcttt ctatcacatt cgatgatagc cttgcaaata aggttttggt ttatgcaact   1860
gctaaccaag aaaaaggaca acgaacacct tatcaggctt tagatagtat ggatgatgcg   1920
tggtctttcc gtgaattaaa agcttttgta cgtgagtcaa aaacactttc aaacaagaaa   1980
aaagaatacc tccttacaga agaagatatt tcaaagtttg atgttcgaaa gaaatttatt   2040
gaacgaaatc ttgtagatac aagatacgct tcaagagttg tcctcaatgc ccttcaagaa   2100
cactttagag ctcacaagat tgatacaaaa gtttccgtgg ttcgtggcca atttacatct   2160
caattgagac gccattgggg aattgagaag actcgtgata cttatcatca ccatgctgtc   2220
gatgcattga ttattgccgc ctcaagtcag ttgaatttgt ggaaaaaaca aaagaatacc   2280
cttgtaagtt attcagaaga acaactcctt gatattgaaa caggtgaact tattagtgat   2340
gatgagtaca aggaatctgt gttcaaagcc ccttatcaac attttgttga tacattgaag   2400
agtaaagaat ttgaagacag tatcttattc tcatatcaag tggattctaa gtttaatcgt   2460
aaaatatcag atgccactat ttatgcgaca agacaggcta aagtgggaaa agataagaag   2520
gatgaaactt atgtcttagg gaaaatcaaa gatatctata ctcaggatgg ttatgatgcc   2580
tttatgaaga tttataagaa ggataagtca aaattcctca tgtatcgtca cgacccacaa   2640
acctttgaga aagttatcga gccaatttta gagaactatc ctaataagga aatgaatgaa   2700
aaagggaaag aagtaccatg taatcctttc ctaaaatata aagaagaaca tggctatatt   2760
cgtaaatata gtaaaaaagg caatggtcct gaaatcaaga gtcttaaata ctatgatagt   2820
aagcttttag gtaatcctat tgatattact ccagagaata gtaaaaataa agttgtctta   2880
cagtcattaa aaccttggag aacagatgtc tatttcaata aaaatactgg taaatatgaa   2940
attttaggac tgaaatatgc tgatttacaa tttgaaaaga agacaggaac atataagatt   3000
tcccaggaaa aatacaatgg cattatgaaa gaagagggtg tagattctga ttcagaattc   3060
aagtttacac tttataaaaa tgatttgtta ctcgttaaag atacagaaac aaaagaacaa   3120
cagcttttcc gttttctttc tcgaactatg cctaatgtga aatattatgt agagttaaag   3180
ccttattcaa aagataaatt tgagaagaat gagtcactta ttgaaatttt aggttctgca   3240
gataagtcag gacgatgtat aaaagggcta ggaaaatcaa atatttctat ttataaggta   3300
agaacagatg tcctaggaaa tcagcatatc atcaaaaatg agggtgataa gcctaagcta   3360
gatttttaat attaattgtt aaaaaagtgt tgcaattata gttatcatat gctataataa   3420
tcgtgtaagg gacgccttac acagttactt aaatcttgca gaagctacaa agataaggct   3480
tcatgccgaa atcaacaccc tgtcatttta tggcagggtg ttttcgttat ttaaagagga   3540
gaagaaatga cttggagagt tgtacatgtc agtcaaagtg agaagatgcg cttaaagctt   3600
gataacttat tagtgcaaaa gatgggacaa gagtttacgg tgccactaag tgatatttcg   3660
ataatcgttg cagaaggtgg ggatacagtt gttacccttc gtctattaag tgccttaagt   3720
aaatataata ttgccttggt cgtttgtgat aacgaacatt taccaacagg aatttatcac   3780
tcacaaaatg ggcactttag agcgtacaag cgcttgaaag aacagctgga ttggtctcag   3840
aaacaaaagg aaaaggcatg gcagattgta acttattata aaatcaataa ccaagaggat   3900
gtcctagcca tgtttgaaaa aagtctggac aacattagat tactttcaga ctataaagag   3960
cagatagaac ctggtgatag aacgaataga gagggacatg ctgccaaggt ctactttaat   4020
gagctctttg gtaaacaatt tgtcagagta actcagcaag aagctgatgt catcaatgct   4080
```

ggtttaaact atggctatgc tatcatgagg gctcagatgg ctagaatagt ggcgggttat 4140
ggtttaaatg gcctattagg aatcttccat aaaaatgaat acaatcagtt taatttggtt 4200
gacgatttga tggagccatt tagacagatt gtagatgttt gggtatatga taatctacga 4260
gatcaggaat tccttaagta tgagtatagg ttgggattga cagatttact caatgctaaa 4320
atcaaatatg gcaaagagac ttgctcagtg acagttgcta tggacaaata tgtcaaaggc 4380
tttatcaaat atatttcgga aaaagatagt agtaaatttc actgcccagt ggtatcaagt 4440
ttagagtgga gaaaataaga tgaggtatga agcattgaga ttattatgtt tttttgattt 4500
accaatggaa tccaaggatg aaaaaagaat atatcgtaat tttcgtaaag aattaatttc 4560
aaatgggttt gaaatgttac aattttcggt ctactatcgc acttgtccta atagaagctt 4620
tgcaaataaa ttttataaga agttaaagat gagcaatctt cctgctggga atgtgagact 4680
tttggcagtt actgaaaaac aattttcaga gatgacatta attataggtg gtaaaactaa 4740
gcaagaagaa atcgtcagtg ataataagtt ggtgatcata tgaaattttt tgtacaacat 4800
ccttacaaag aacgtattga attaaatatt ggtgcaatca cacaaattgt tggtcagaat 4860
aatgaactca aatattatac ttggcagatt ttgagctggt attttggtgg aaaaaaatac 4920
tcaagtgagg acttaagtat ttttgattat gaggagccta ccatacttga tgaggccaga 4980
gaaatagtga aacgaagtag ctatcactat atcgacattt caagttttaa ggatttactg 5040
gagcagatgg aatacaagaa aggaacactt gctcagggtt accttcgtaa aattgtcaat 5100
caagttgata ttgtaggcca tttggagaaa attaatgaac aagtagagct tattgaagaa 5160
gctatgaatc ggcatataaa cttaaactgt ggacaggtag aataccattt ggagaatctc 5220
cctctaacac tagaccaact actcacaaaa aattttagcc catttttttgc cattgagaac 5280 aagaatctat cttttgaatg ggtttctaat attgataaac tatccctctt tttagaaatg 5340
ttagaccatc ttctttcaca aacaacagag aagtatctca ttgtgctaaa aaatattgat 5400
ggctttatct cagaagaatc ttatactatt ttttataggc aaatctgtca tctggtcaag 5460
aagtatccaa atctaacctt tattttgttt cctagtgacc aaggctattt aaaaattgat 5520
gaagaaaata gtaggttcgt caatatttta tctgaccagg tggaacattt gtatgatgtt 5580
gagtttatgt atgaaagggt aatgaaatat tatccaagta atgattttcc gacgagagaa 5640
ggttttagga tgtctttaga aactgtgaca ccttatttat tgacaaaaat gctgagacaa 5700
cctagtctct cacttgttga ttcagtaata ttgaatatcc taaatcagct gtttcatttt 5760
agttaccgta taagatgttc tcagacacct gataaggaac tattacagaa atttttagaa 5820
agtaaggatt ga 5832

<210> SEQ ID NO 474
<211> LENGTH: 3369
<212> TYPE: DNA
<213> ORGANISM: Steptococcus thermophilus

<400> SEQUENCE: 474
atgagtgact tagttttagg acttgatatc ggtataggtt ctgttggtgt aggtatcctt 60
aacaaagtga caggagaaat tatccataaa aactcacgca tcttcccagc agctcaagca 120
gaaaataacc tagtacgtag aacgaatcgt caaggaagac gcttgacacg acgtaaaaaa 180
catcgtatag ttcgtttaaa tcgtctattt gaggaaagtg gattaatcac cgattttacg 240
aagatttcaa ttaatcttaa cccatatcaa ttacgagtta agggcttgac cgatgaattg 300

-continued

```
tctaatgaag aactgtttat cgctcttaaa aatatggtga aacaccgtgg gattagttac    360
ctcgatgatg ctagtgatga cggaaattca tcagtaggag actatgcaca aattgttaag    420
gaaaatagta aacaattaga aactaagaca ccgggacaga tacagttgga acgctaccaa    480
acatatggtc aattacgtgg tgattttact gttgagaaag atggcaaaaa acatcgcttg    540
attaatgtct ttccaacatc agcttatcgt tcagaagcct taaggatact gcaaactcaa    600
caagaattta attcacagat tacagatgaa tttattaatc gttatctcga aattttaact    660
ggaaaacgga aatattatca tggacccgga aatgaaaagt cacggactga ttatggtcgt    720
tacagaacga atggagaaac tttagacaat atttttggaa ttctaattgg gaaatgtaca    780
ttttatccag acgagtttag agcagcaaaa gcttcctaca cggctcaaga attcaatttg    840
ctaaatgatt tgaacaatct aacagttcct actgaaacca aaaagttgag caaagaacag    900
aagaatcaaa tcattaatta tgtcaaaaat gaaaaggtaa tggggccagc gaaacttttt    960
aaatatatcg ctaaattact ttcttgtgat gttgcagata tcaagggaca ccgtatcgac   1020
aaatcaggta aggctgagat tcatactttc gaagcctatc gaaaaatgaa aacgcttgaa   1080
accttagata ttgagcaaat ggatagagaa acgcttgata aattagccta tgtcttaaca   1140
ttaaacactg agagggaagg tattcaagaa gctttagaac atgaatttgc tgatggtagc   1200
tttagccaga agcaagttga cgaattggtt caattccgca aagcaaatag ttccattttt   1260
ggaaaaggat ggcataattt ttctgtcaaa ctgatgatgg agttaattcc agaattgtat   1320
gagacgtcag aagagcaaat gactatcctg acacgacttg gaaaacaaaa aacaacttcg   1380
tcttcaaata aaacaaaata tatagatgag aaactattaa ctgaagaaat ctataatcct   1440
gttgttgcta agtctgttcg ccaggctata aaaatcgtaa atgcggcgat taaagaatac   1500
ggagactttg acaatattgt catcgaaatg gctcgtgaaa caaatgaaga tgatgaaaag   1560
aaagctattc aaaagattca aaaagccaac aaagatgaaa aagatgcagc aatgcttaag   1620
gctgctaacc aatataatgg aaaggctgaa ttaccacata gtgttttcca cggtcataag   1680
caattagcga ctaaaatccg cctttggcat cagcaaggag aacgttgcct ttatactggt   1740
aagacaatct caatccatga tttgataaat aatcctaatc agtttgaagt agatcatatt   1800
ttacctcttt ctatcacatt cgatgatagc cttgcaaata aggttttggt ttatgcaact   1860
gctaaccaag aaaaaggaca acgaacacct tatcaggctt tagatagtat ggatgatgcg   1920
tggtctttcc gtgaattaaa agcttttgta cgtgagtcaa aaacactttc aaacaagaaa   1980
aaagaatacc tccttacaga agaagatatt tcaaagtttg atgttcgaaa gaaatttatt   2040
gaacgaaatc ttgtagatac aagatacgct tcaagagttg tcctcaatgc ccttcaagaa   2100
cactttagag ctcacaagat tgatacaaaa gtttccgtgg ttcgtggcca atttacatct   2160
caattgagac gccattgggg aattgagaag actcgtgata cttatcatca ccatgctgtc   2220
gatgcattga ttattgccgc ctcaagtcag ttgaatttgt ggaaaaaaca aaagaatacc   2280
cttgtaagtt attcagaaga acaactcctt gatattgaaa caggtgaact tattagtgat   2340
gatgagtaca aggaatctgt gttcaaagcc ccttatcaac attttgttga tacattgaag   2400
agtaaagaat ttgaagacag tatcttattc tcatatcaag tggattctaa gtttaatcgt   2460
aaaatatcag atgccactat ttatgcgaca agacaggcta aagtgggaaa agataagaag   2520
gatgaaactt atgtcttagg gaaaatcaaa gatatctata ctcaggatgg ttatgatgcc   2580
tttatgaaga tttataagaa ggataagtca aaattcctca tgtatcgtca cgacccacaa   2640
acctttgaga aagttatcga gccaatttta gagaactatc ctaataagga aatgaatgaa   2700
```

-continued aaagggaaag aagtaccatg taatcctttc ctaaaatata aagaagaaca tggctatatt 2760
cgtaaatata gtaaaaaagg caatggtcct gaaatcaaga gtcttaaata ctatgatagt 2820
aagcttttag gtaatcctat tgatattact ccagagaata gtaaaaataa agttgtctta 2880
cagtcattaa aaccttggag aacagatgtc tatttcaata aaaatactgg taaatatgaa 2940
attttaggac tgaaatatgc tgatttacaa tttgaaaaga agacaggaac atataagatt 3000
tcccaggaaa aatacaatgg cattatgaaa gaagagggtg tagattctga ttcagaattc 3060
aagtttacac tttataaaaa tgatttgtta ctcgttaaag atacagaaac aaaagaacaa 3120
cagcttttcc gttttctttc tcgaactatg cctaatgtga aatattatgt agagttaaag 3180
ccttattcaa aagataaatt tgagaagaat gagtcactta ttgaaatttt aggttctgca 3240
gataagtcag gacgatgtat aaaagggcta ggaaaatcaa atatttctat ttataaggta 3300
agaacagatg tcctaggaaa tcagcatatc atcaaaaatg agggtgataa gcctaagcta 3360
gatttttaa 3369

<210> SEQ ID NO 475
<211> LENGTH: 912
<212> TYPE: DNA
<213> ORGANISM: Steptococcus thermophilus

<400> SEQUENCE: 475
atgacttgga gagttgtaca tgtcagtcaa agtgagaaga tgcgcttaaa gcttgataac 60
ttattagtgc aaaagatggg acaagagttt acggtgccac taagtgatat ttcgataatc 120
gttgcagaag gtggggatac agttgttacc cttcgtctat taagtgcctt aagtaaatat 180
aatattgcct tggtcgtttg tgataacgaa catttaccaa caggaattta tcactcacaa 240
aatgggcact ttagagcgta caagcgcttg aaagaacagc tggattggtc tcagaaacaa 300
aaggaaaagg catggcagat tgtaacttat tataaaatca ataaccaaga ggatgtccta 360
gccatgtttg aaaaaagtct ggacaacatt agattacttt cagactataa agagcagata 420
gaacctggtg atagaacgaa tagagaggga catgctgcca aggtctactt taatgagctc 480
tttggtaaac aatttgtcag agtaactcag caagaagctg atgtcatcaa tgctggttta 540
aactatggct atgctatcat gagggctcag atggctagaa tagtggcggg ttatggttta 600
aatggcctat taggaatctt ccataaaaat gaatacaatc agtttaattt ggttgacgat 660
ttgatggagc catttagaca gattgtagat gtttgggtat atgataatct acgagatcag 720
gaattcctta agtatgagta taggttggga ttgacagatt tactcaatgc taaaatcaaa 780
tatggcaaag agacttgctc agtgacagtt gctatggaca aatatgtcaa aggctttatc 840
aaatatattt cggaaaaaga tagtagtaaa tttcactgcc cagtggtatc aagtttagag 900
tggagaaaat aa 912

<210> SEQ ID NO 476
<211> LENGTH: 324
<212> TYPE: DNA
<213> ORGANISM: Steptococcus thermophilus

<400> SEQUENCE: 476
atgaggtatg aagcattgag attattatgt ttttttgatt taccaatgga atccaaggat 60
gaaaaaagaa tatatcgtaa ttttcgtaaa gaattaattt caaatgggtt tgaaatgtta 120
caattttcgg tctactatcg cacttgtcct aatagaagct ttgcaaataa atttataag 180

-continued aagttaaaga tgagcaatct tcctgctggg aatgtgagac ttttggcagt tactgaaaaa 240
caattttcag agatgacatt aattataggt ggtaaaacta agcaagaaga aatcgtcagt 300
gataataagt tggtgatcat atga 324

<210> SEQ ID NO 477
<211> LENGTH: 1053
<212> TYPE: DNA
<213> ORGANISM: Steptococcus thermophilus

<400> SEQUENCE: 477
atgaaatttt ttgtacaaca tccttacaaa gaacgtattg aattaaatat tggtgcaatc 60
acacaaattg ttggtcagaa taatgaactc aaatattata cttggcagat tttgagctgg 120
tattttggtg gaaaaaaata ctcaagtgag gacttaagta tttttgatta tgaggagcct 180
accatacttg atgaggccag agaaatagtg aaacgaagta gctatcacta tatcgacatt 240
tcaagtttta aggatttact ggagcagatg gaatacaaga aaggaacact tgctcagggt 300
taccttcgta aaattgtcaa tcaagttgat attgtaggcc atttggagaa aattaatgaa 360
caagtagagc ttattgaaga agctatgaat cggcatataa acttaaactg tggacaggta 420
gaataccatt tggagaatct ccctctaaca ctagaccaac tactcacaaa aaattttagc 480 ccatttttttg ccattgagaa caagaatcta tcttttgaat gggtttctaa tattgataaa 540
ctatccctct ttttagaaat gttagaccat cttctttcac aaacaacaga gaagtatctc 600
attgtgctaa aaaatattga tggctttatc tcagaagaat cttatactat tttttatagg 660
caaatctgtc atctggtcaa gaagtatcca aatctaacct ttattttgtt tcctagtgac 720
caaggctatt taaaaattga tgaagaaaat agtaggttcg tcaatatttt atctgaccag 780
gtggaacatt tgtatgatgt tgagtttatg tatgaaaggg taatgaaata ttatccaagt 840
aatgattttc cgacgagaga aggttttagg atgtctttag aaactgtgac accttattta 900
ttgacaaaaa tgctgagaca acctagtctc tcacttgttg attcagtaat attgaatatc 960
ctaaatcagc tgtttcattt tagttaccgt ataagatgtt ctcagacacc tgataaggaa 1020
ctattacaga aatttttaga aagtaaggat tga 1053

<210> SEQ ID NO 478
<211> LENGTH: 7900
<212> TYPE: DNA
<213> ORGANISM: Steptococcus thermophilus

<400> SEQUENCE: 478
atgagcgatt tatatagtca aaggtccaat tattacctgt ccttatctga acaaagaatt 60
atcattaaaa atgataataa agagattgtc aaagaagtgt ccatttcact cgttgataat 120
gtattacttt ttggtaatgc acaactgacc acccaactca tcaaagcctt gtcaaagaac 180
aaggtgaatg tttactattt ctcaaatgtt ggtcaattta tttctagtat tgaaacccac 240
aggcaggacg aattccaaaa gcaagagttg caagcaaagg cttattttga agaggatttc 300
cgtttagagg ttgcgaggag tattgctacg accaaggtga ggcacccaat tgccttactt 360
agagagtttg atacggatgg tctactagat acctcagatt attctaggtt tgaagatagt 420
gtcaatgata ttcagaaagc ttattccatt acagaaatta tgggttacga aggtcgcctt 480
gcgaaatcct atttttacta tctgaattta ctcgttccta atgactttca ttttaatggt 540
aggagtagac ggcctgggga ggattgtttt aacagtgccc tcaattttgg ctatagtatc 600
ttatattctt gcttaatggg ctgattaaga aaaacgggct aagcttggga tttggggtaa 660

```
ttcacaagca tcatcagcat catgcgacct tggccagtga tttaatggaa gaatggagac     720
ctatcatcgt cgataatacg cttatggagt tggtacgaaa tggtaaactt cttttaagtc     780
atttgaaaa taaggatcaa gacttcatac tcacccatga aggcagagaa atctttgcac     840
gggctttacg ttcaagaata ttagaagtcc atcagtatat tgagttagat aaaaaacgct     900
attcttttct ttatacagca gataggcaaa tcaagagttt gattagggct tttagagaac     960
ttgaccctag tctctatgag acaagttaca caggagggca ttaatgggac tttactttaa    1020
cctcagcgaa gaagagcgtg agtttgccaa acaaaaaacc atgttttgtc tgattattta    1080
tgatattcga agtaacaaac gtagacttaa actctcgaaa ttacttgagg gttatggcgt    1140
gagggtgcaa aaatcctgtt tcgaagtcaa cctgtcaaga aatgattatc agtctctcct    1200
taaggatatc gagggcttct acaaggctga tgaagaagac agcataatag tgtatgtgac    1260
aaccaaagaa gaggtgacta gttttagccc ctaccatagt gctgaaaaat tagatgacat    1320
tctcttcttc taagccttta tagaccttta atcatatggt acactataga tagtgtttcc    1380
agtaggtcct acatcttgtg cctctagcaa ctgcctagag cacaagatat ggggatataa    1440
acctaattac ctcgagaggg gacggaaacg ctttctagct cgctataatt acccattcct    1500
agaaagatat aaacctaatt acctcgagag gggacggaaa ctttgaatag tctttgaatc    1560
gcatttgaac catatagata taaacctaat tacctcgaga ggggacggaa acaggttttt    1620
tgccatagat tttccaagac cttcccaact gatataaacc taattacctc gagaggggac    1680
ggaaacgctt tctagctcgc tataattacc cattcctaga aagatataaa cctaattacc    1740
tcgagagggg actttttga aaatttgaa aacagtattg ataccgcttc cagaaagtgt    1800
tagactaaaa gcacattaag ggcgccccaa tgagttgaaa agtactttca gcttttgggg    1860
tttttcata caaagatgaa ggagtcgaat gaaaaaatta gtatttactt ttaaaaggat    1920
cgaccatcct gcacaagatt tggctgttaa atttcatggc ttcttgatgg agcagttgga    1980
tagtgactat gttgattatc tgcatcagca gcaaacaaat ccctatgcga ccaaggtaat    2040
ccaagggaaa gaaaacacgc agtgggttgt acatctgctc acagacgaca tcgaggataa    2100
ggtttttatg accttattac agattaaaga ggtgtcctta aacgatctgc ctaaactcag    2160
tgtcgaaaaa gttgagattc aggagttggg ggcagataaa ctgttagaga ttttcaatag    2220
tgaggaaaat caaacctatt tttcaattat ttttgagact ccaacaggtt ttaaatctca    2280
aggttcctac gtcatcttcc cgtctatgcg tttgattttt caaagtttga tgcaaaagta    2340
tggaaggttg gttgaaaatc aacctgaaat tgaagaggat accttagatt acctatctga    2400
acacagcact atcacgaatt atcgcttgga gacgagttat ttcagggtgc acaggcaacg    2460
aattcctgcc tttagaggaa agttaacctt taaagtacaa ggcgcccaaa ctctaaaagc    2520
ttatgtcaaa atgcttctaa cattcggtga atattcaggt cttggcatga aaacgagtct    2580
cggtatggga gggataaagc ttgaagaaag aaaagattga tttattttac ggagctcttt    2640
tgcatgatat cggtaaggtc attcaaaggg cgacaggaga acgaaaaaaa cacgccttgg    2700
taggcgcgga ttggtttgat gagattgctg ataatcaagt tatttccgat caaattagat    2760
atcacatggc taactaccag agtgataaac ttggaaatga ccatcttgct tacataactt    2820
atatcgctga taacattgcc tctggtgtcg acagaagaca gtcaaatgag gagagtgacg    2880
aggatacatc agctaagatt tgggatacct atacaaacca ggctgatatt tttaacgttt    2940
ttggggcaca aacggataaa cgctacttta aaccgacggt tctaaacttg aaatctaaac    3000
```

```
ctaactttgc gtcggcaaca tatgaacctt tctcaaaagg tgattatgcg gcaattgcga   3060
ctcgtatcaa aaatgaattg gcagaatttg agtttaatca agtacaaatt gactctttgt   3120
taaatctgtt cgaagcaacc ctctcttttg tgccttcttc gactaatact aaagaaatcg   3180
ctgatatttc acttgctgat catagtcgtc tgacagcagc ttttgctcta gccatctatg   3240
attacttgga agacaaaggt cgtcataact ataaggagga cttgtttact aaagcatcag   3300
ccttttatga ggaagaagct ttctcctag ctagctttga cttatcaggg attcaagact    3360
ttatctataa tattaatatt gcgacgaatg gtgctgctaa acaattgaag gctagatctt   3420
tatatcttga ctttatgagc gagtatatag cagacagttt acttgataaa ctaggcctca   3480
atcgggctaa tatgctctat gtcggtgggg gacatgctta ctttgtccta gccaatactg   3540
aaaaaacggt agaaacactc gttcaatttg aaaaagattt caatcaattt ttattggcaa   3600
atttccaaac cagattatat gttgcctttg gttggggaag ctttgcggct aaggatatca   3660
tgagcgaact gaactcacct gaaagctata gacaggtcta tcaaaaggct agtcgcatga   3720
tttctgagaa aaaaatctca aggtatgatt atcaaaccct tatgttgttg aacaggggcg   3780
gtaaatcttc tgaaagagag tgcgagattt gtcattccgt tgagaattta gttgcttatc   3840
atgaccaaaa agtgtgtgac atttgtcgag gcttgtatca attttctaaa gagattgccc   3900
atgaccattt cattatcact gaaaatgaag ggcttcctat tggtccgaac gcatgtctta   3960
agggtgttgc atttgaaaag ctgagccaag aagctttttc ccgtgtctat gtcaaaaatg   4020
actataaggc tggtacagtt aaggcaaccc atgtttttgt tggagattac cagtatgatg   4080
aaatatacaa ttatgctgcc ttatctaaaa acgaaaatgg gttaggtatt aaacgtttag   4140
ctgttgtacg tcttgacgtg gatgatttgg gagcagcctt tatggctggc ttctcccaac   4200
aaggaaatgg gcaatatagt actctatcac gctcagccac tttctctcga agcatgagtc   4260
ttttcttcaa ggtttatatt aaccagtttg ctagtgataa gaagctctct atcatctatg   4320
ccggtgggga tgatgttttt gctattggct cttggcaaga tattattgcc tttactgttg   4380
aacttcgtga gaacttcatt aaatggacaa atggaaaact aacactatca gctggtatcg   4440
gtctgtttgc tgataagacc cctattagct taatggcaca tcaaacaggg gagctagaag   4500
aaacagctaa aggcaatgag aaagatagta tttcactctt tagttccgac tataccttta   4560
aatttgatcg gtttatcact aatgtttacg acgataagtt agagcagatt cgctatttct   4620
ttaatcacca agatgaacga ggcaagaatt tcatttataa attgattgaa ttgcttcgaa   4680
attatgatcg tatgaatatg gcacgtttag cttattattt aacacgactt gaagaattga   4740
cgcgtgaaac agacagggat aaatttaaaa catttaaaaa tttattctat tcttggtaca   4800
caaataagga tgataaggat agaaaagaag cagagttagc cttgcttctc tatatctatg   4860
agattagaaa ggattaggat atgacaatct tgactgatga gaattacgtt gatattgcag   4920
aaaaagcaat tctaaaacta gaaagaaata ctaggaacag aaagaatcct gatgccttct   4980
ttcttacaac aagtaagctc agaaacttgc tgagcttaac tagtacactt tttgatgaga   5040
gtaaggtcaa agaatatgat gctctccttg atcgtattgc ttatttaaga gtacaatttg   5100
tctaccaagc aggtagagag attgcagtaa aagatctgat agaaaaggct caaattcttg   5160
aggctcttaa ggaaatcaaa gatagagaga cacttcaaag attttgtaga tatatggaag   5220
cattagtagc ctatttcaag ttttatggag gtaaagatta atgacattcg ctaagattaa   5280
attttcagct caaattcgtt tagagacagg cctccatatt ggtggaagcg atgcttttgc   5340
agccattggt gcaatcgatt cgcctgttat taaagatcct attaccaacc taccgatcat   5400
```

```
tcctggttca agtctcaaag gaaaaatgag aacgcttctt gccaaggttt ataatgaaaa   5460
ggtagctgag aaaccaagcg atgacagtga tattcttagc cgtttatttg ggaatagtaa   5520
agataaacga ttcaaaatgg gacgcttgat ttttcgtgat gccttcttgt caaacgctga   5580
tgagctagac tctcttgggg taagaagtta tacagaagta aaatttgaaa atacaattga   5640
ccgtatcact gccgaagcta atccaagaca aattgaacgt gctattcgta ccagtacttt   5700
tgatttcgag ttgatttatg aaattacaga tgagaatgaa aatcaagtcg aagaagattt   5760
caaagtgatt cgagatggtt taaaactgct tgaacttgat tatcttggtg gttctggatc   5820
tcgaggttac ggtaaggttg cttttgaaaa actcaaagct actaccgtat ttggtaatta   5880
tgatgttaaa acattaaatg aacttttaac tgcggaggtc taatatgacc tataaactgt   5940
atattatgac ctttcagaat gctcattttg gttcgggcac tcttgatagc tcaaaattaa   6000
cattctcagc agaccgtatc ttctcagcac tagtgctaga atccctaaaa atgggaaaac   6060
tcgatgcatt tcttgcggaa gctaaccaag acaagttcac gctcacagat gcctttccat   6120
ttcaatttgg tccctttttg ccgaaaccga ttggttatcc caaacatgac caaatagatc   6180
aatcagttga tgtcaaagag gttcgccgtc aagcaaaatt gtctaagaaa ctgcaatttc   6240
ttgctctaga aaatgttgac gattatctca atggagagtt atttgaaaat gaagagcatg   6300
cagtcatcga tactgtgaca aaaaatcaac cacataagga cggcaatctt tatcaggtag   6360
ctacaaccag attttcaaat gatacgtcgc tttacgtcat cgcaaacgaa tctgatttgc   6420
ttaatgagtt gatgtctagt cttcagtatt caggtcttgg tggaaagcgt tcaagtggtt   6480
ttggtcgttt tgagttagat attcaaaata tcccactaga attgtcagat agactgacta   6540
agaatcattc agataaagtg atgagtctta cgacagcact tcctgtagat gctgaccttg   6600
aagaagcaat ggaagatgga cattacttat taactaaatc aagtggtttt gcatttagtc   6660
atgctaccaa tgagaattat cgtaagcagg atctttacaa atttgcttct ggttcaactt   6720
ttagtaaaac atttgaaggt cagattgttg atgtgagacc acttgatttc cctcatgctg   6780
ttttaaatta tgctaaacca ctcttcttta aattggaggt ataaaaatga aaaatgacta   6840
tagaacattt aaattaagcc tcctgacact tgctccaatt catattggta atggagagaa   6900
gtatacctct agagaattta tctatgaaaa taagaagttt tactttcctg acatggggaa   6960
attctataat aaaatggtgg agaagaggct tgctgaaaag tttgaagcat ttctaattca   7020
aactcgtcca aatgcacgta ataatcgtct tatttccttc ttaaatgata accgaattgc   7080
agagcgttct tttggaggtt atagtatctc tgaaacaggt ttagaatcgg acaaaaatcc   7140
tgattcagcc ggagctatta acgaagttaa taaatttatt cgagatgctt ttggaaatcc   7200
ctacattcct ggtagctcac taaaaggtgc tattcgtacc attttaatga atactacccc   7260
taagtggaat aatgaaaatg ctgtaaatga ctttggaaga tttccgaaag agaataagaa   7320
ccttatccct tggggaccaa aaaagggaaa agaatacgat gatttgttta acgcaattcg   7380
tgtgagtgat agtaagcctt ttgataataa gagtcttatc ttagtgcaga aatgggatta   7440
ttcagcgaaa acaaataaag ctaaaccact tcccttgtat agagaatcaa tctctccatt   7500
aacaaaaatt gaatttgaga ttacaacaac cactgatgaa gctggaagat tgattgaaga   7560
attaggtaag agagcacaag cgttttataa agactataag gcatttttcc tatctgaatt   7620
tcctgatgat aagattcaag ccaatctaca atacccaatt tatttaggtg cggggagcgg   7680
tgcttggaca aagactctat ttaagcaagc tgatggtatt ttacaaagac gatacagtcg   7740
```

-continued

```
aatgaaaact aaaatggtta aaaaaggagt tcttaagctc acaaaagcac ctcttaaaac   7800

agttaagatt ccatctggta atcattcatt agtcaagaac cacgagtcct tttatgaaat   7860

gggaaaagct aatttcatga ttaaggagat tgataaatga                         7900
```

<210> SEQ ID NO 479
<211> LENGTH: 624
<212> TYPE: DNA
<213> ORGANISM: Steptococcus thermophilus

<400> SEQUENCE: 479

```
atgagcgatt tatatagtca aaggtccaat tattacctgt ccttatctga acaaagaatt     60

atcattaaaa atgataataa agagattgtc aaagaagtgt ccatttcact cgttgataat    120

gtattacttt ttggtaatgc acaactgacc acccaactca tcaaagcctt gtcaaagaac    180

aaggtgaatg tttactattt ctcaaatgtt ggtcaattta tttctagtat tgaaacccac    240

aggcaggacg aattccaaaa gcaagagttg caagcaaagg cttattttga agaggatttc    300

cgtttagagg ttgcgaggag tattgctacg accaaggtga ggcacccaat tgccttactt    360

agagagtttg atacggatgg tctactagat acctcagatt attctaggtt tgaagatagt    420

gtcaatgata ttcagaaagc ttattccatt acagaaatta tgggttacga aggtcgcctt    480

gcgaaatcct atttttacta tctgaattta ctcgttccta atgactttca ttttaatggt    540

aggagtagac ggcctgggga ggattgtttt aacagtgccc tcaattttgg ctatagtatc    600

ttatattctt gcttaatggg ctga                                           624
```

<210> SEQ ID NO 480
<211> LENGTH: 396
<212> TYPE: DNA
<213> ORGANISM: Steptococcus thermophilus

<400> SEQUENCE: 480

```
ttgcttaatg ggctgattaa gaaaaacggg ctaagcttgg gatttggggt aattcacaag     60

catcatcagc atcatgcgac cttggccagt gatttaatgg aagaatggag acctatcatc    120

gtcgataata cgcttatgga gttggtacga aatggtaaac ttcttttaag tcattttgaa    180

aataaggatc aagacttcat actcacccat gaaggcagag aaatctttgc acgggcttta    240

cgttcaagaa tattagaagt ccatcagtat attgagttag ataaaaaacg ctattctttt    300

ctttatacag cagataggca aatcaagagt ttgattaggg cttttagaga acttgaccct    360

agtctctatg agacaagtta cacaggaggg cattaa                              396
```

<210> SEQ ID NO 481
<211> LENGTH: 330
<212> TYPE: DNA
<213> ORGANISM: Steptococcus thermophilus

<400> SEQUENCE: 481

```
atgggacttt actttaacct cagcgaagaa gagcgtgagt ttgccaaaca aaaaaccatg     60

ttttgtctga ttatttatga tattcgaagt aacaaacgta gacttaaact ctcgaaatta    120

cttgagggtt atggcgtgag ggtgcaaaaa tcctgtttcg aagtcaacct gtcaagaaat    180

gattatcagt ctctccttaa ggatatcgag ggcttctaca aggctgatga agaagacagc    240

ataatagtgt atgtgacaac caaagaagag gtgactagtt ttagccccta ccatagtgct    300

gaaaaattag atgacattct cttcttctaa                                     330
```

<210> SEQ ID NO 482
<211> LENGTH: 732
<212> TYPE: DNA
<213> ORGANISM: Steptococcus thermophilus

<400> SEQUENCE: 482
atgaaaaaat tagtatttac ttttaaaagg atcgaccatc ctgcacaaga tttggctgtt 60
aaatttcatg gcttcttgat ggagcagttg gatagtgact atgttgatta tctgcatcag 120
cagcaaacaa atccctatgc gaccaaggta atccaaggga aagaaaacac gcagtgggtt 180
gtacatctgc tcacagacga catcgaggat aaggttttta tgaccttatt acagattaaa 240
gaggtgtcct taaacgatct gcctaaactc agtgtcgaaa aagttgagat tcaggagttg 300
ggggcagata aactgttaga gattttcaat agtgaggaaa atcaaaccta tttttcaatt 360
atttttgaga ctccaacagg ttttaaatct caaggttcct acgtcatctt cccgtctatg 420
cgtttgattt ttcaaagttt gatgcaaaag tatggaaggt tggttgaaaa tcaacctgaa 480
attgaagagg ataccttaga ttacctatct gaacacagca ctatcacgaa ttatcgcttg 540
gagacgagtt atttcagggt gcacaggcaa cgaattcctg cctttagagg aaagttaacc 600
tttaaagtac aaggcgccca aactctaaaa gcttatgtca aaatgcttct aacattcggt 660
gaatattcag gtcttggcat gaaaacgagt ctcggtatgg gagggataaa gcttgaagaa 720
agaaaagatt ga 732

<210> SEQ ID NO 483
<211> LENGTH: 2277
<212> TYPE: DNA
<213> ORGANISM: Steptococcus thermophilus

<400> SEQUENCE: 483
ttgaagaaag aaaagattga tttattttac ggagctcttt tgcatgatat cggtaaggtc 60
attcaaaggg cgacaggaga acgaaaaaaa cacgccttgg taggcgcgga ttggtttgat 120
gagattgctg ataatcaagt tatttccgat caaattagat atcacatggc taactaccag 180
agtgataaac ttggaaatga ccatcttgct tacataactt atatcgctga taacattgcc 240
tctggtgtcg acagaagaca gtcaaatgag gagagtgacg aggatacatc agctaagatt 300
tgggatacct atacaaacca ggctgatatt tttaacgttt ttggggcaca aacggataaa 360
cgctacttta aaccgacggt tctaaacttg aaatctaaac ctaactttgc gtcggcaaca 420
tatgaacctt tctcaaaagg tgattatgcg gcaattgcga ctcgtatcaa aaatgaattg 480
gcagaatttg agtttaatca agtacaaatt gactctttgt taaatctgtt cgaagcaacc 540
ctctcttttg tgccttcttc gactaatact aaagaaatcg ctgatatttc acttgctgat 600
catagtcgtc tgacagcagc ttttgctcta gccatctatg attacttgga agacaaaggt 660
cgtcataact ataaggagga cttgtttact aaagcatcag ccttttatga ggaagaagct 720
tttctcctag ctagctttga cttatcaggg attcaagact ttatctataa tattaatatt 780
gcgacgaatg gtgctgctaa acaattgaag gctagatctt tatatcttga ctttatgagc 840
gagtatatag cagacagttt acttgataaa ctaggcctca atcgggctaa tatgctctat 900
gtcggtgggg gacatgctta ctttgtccta gccaatactg aaaaaacggt agaaacactc 960
gttcaatttg aaaaagattt caatcaattt ttattggcaa atttccaaac cagattatat 1020
gttgcctttg gttggggaag ctttgcggct aaggatatca tgagcgaact gaactcacct 1080
gaaagctata gacaggtcta tcaaaaggct agtcgcatga tttctgagaa aaaaatctca 1140

```
aggtatgatt atcaaaccct tatgttgttg aacaggggcg gtaaatcttc tgaaagagag   1200

tgcgagattt gtcattccgt tgagaattta gttgcttatc atgaccaaaa agtgtgtgac   1260

atttgtcgag gcttgtatca attttctaaa gagattgccc atgaccattt cattatcact   1320

gaaaatgaag ggcttcctat tggtccgaac gcatgtctta agggtgttgc atttgaaaag   1380

ctgagccaag aagctttttc ccgtgtctat gtcaaaaatg actataaggc tggtacagtt   1440

aaggcaaccc atgtttttgt tggagattac cagtatgatg aaatatacaa ttatgctgcc   1500

ttatctaaaa acgaaaatgg gttaggtatt aaacgtttag ctgttgtacg tcttgacgtg   1560

gatgatttgg gagcagcctt tatggctggc ttctcccaac aaggaaatgg gcaatatagt   1620

actctatcac gctcagccac tttctctcga agcatgagtc ttttcttcaa ggtttatatt   1680

aaccagtttg ctagtgataa gaagctctct atcatctatg ccggtgggga tgatgttttt   1740

gctattggct cttggcaaga tattattgcc tttactgttg aacttcgtga gaacttcatt   1800

aaatggacaa atggaaaact aacactatca gctggtatcg gtctgtttgc tgataagacc   1860

cctattagct taatggcaca tcaaacaggg gagctagaag aaacagctaa aggcaatgag   1920

aaagatagta tttcactctt tagttccgac tataccttta aatttgatcg gtttatcact   1980

aatgtttacg acgataagtt agagcagatt cgctatttct ttaatcacca agatgaacga   2040

ggcaagaatt tcatttataa attgattgaa ttgcttcgaa attatgatcg tatgaatatg   2100

gcacgtttag cttattattt aacacgactt gaagaattga cgcgtgaaac agacagggat   2160

aaatttaaaa catttaaaaa tttattctat tcttggtaca caaataagga tgataaggat   2220

agaaaagaag cagagttagc cttgcttctc tatatctatg agattagaaa ggattag      2277
```

<210> SEQ ID NO 484
<211> LENGTH: 381
<212> TYPE: DNA
<213> ORGANISM: Steptococcus thermophilus

<400> SEQUENCE: 484

```
atgacaatct tgactgatga gaattacgtt gatattgcag aaaaagcaat tctaaaacta     60

gaaagaaata ctaggaacag aaagaatcct gatgccttct ttcttacaac aagtaagctc    120

agaaacttgc tgagcttaac tagtacactt tttgatgaga gtaaggtcaa agaatatgat    180

gctctccttg atcgtattgc ttatttaaga gtacaatttg tctaccaagc aggtagagag    240

attgcagtaa aagatctgat agaaaaggct caaattcttg aggctcttaa ggaaatcaaa    300

gatagagaga cacttcaaag attttgtaga tatatggaag cattagtagc ctatttcaag    360

ttttatggag gtaaagatta a                                              381
```

<210> SEQ ID NO 485
<211> LENGTH: 663
<212> TYPE: DNA
<213> ORGANISM: Steptococcus thermophilus

<400> SEQUENCE: 485

```
atgacattcg ctaagattaa attttcagct caaattcgtt tagagacagg cctccatatt     60

ggtggaagcg atgcttttgc agccattggt gcaatcgatt cgcctgttat taaagatcct    120

attaccaacc taccgatcat tcctggttca agtctcaaag gaaaaatgag aacgcttctt    180

gccaaggttt ataatgaaaa ggtagctgag aaaccaagcg atgacagtga tattcttagc    240

cgtttatttg ggaatagtaa agataaacga ttcaaaatgg gacgcttgat tttcgtgat    300

gccttcttgt caaacgctga tgagctagac tctcttgggg taagaagtta tacagaagta    360
```

aaatttgaaa atacaattga ccgtatcact gccgaagcta atccaagaca aattgaacgt 420
gctattcgta ccagtacttt tgatttcgag ttgatttatg aaattacaga tgagaatgaa 480
aatcaagtcg aagaagattt caaagtgatt cgagatggtt taaaactgct tgaacttgat 540
tatcttggtg gttctggatc tcgaggttac ggtaaggttg cttttgaaaa actcaaagct 600
actaccgtat ttggtaatta tgatgttaaa acattaaatg aacttttaac tgcggaggtc 660
taa 663

<210> SEQ ID NO 486
<211> LENGTH: 900
<212> TYPE: DNA
<213> ORGANISM: Steptococcus thermophilus

<400> SEQUENCE: 486
atgacctata aactgtatat tatgaccttt cagaatgctc attttggttc gggcactctt 60
gatagctcaa aattaacatt ctcagcagac cgtatcttct cagcactagt gctagaatcc 120
ctaaaaatgg gaaaactcga tgcatttctt gcggaagcta accaagacaa gttcacgctc 180
acagatgcct ttccatttca atttggtccc tttttgccga aaccgattgg ttatcccaaa 240
catgaccaaa tagatcaatc agttgatgtc aaagaggttc gccgtcaagc aaaattgtct 300
aagaaactgc aatttcttgc tctagaaaat gttgacgatt atctcaatgg agagttattt 360
gaaaatgaag agcatgcagt catcgatact gtgacaaaaa atcaaccaca taaggacggc 420
aatctttatc aggtagctac aaccagattt tcaaatgata cgtcgcttta cgtcatcgca 480
aacgaatctg atttgcttaa tgagttgatg tctagtcttc agtattcagg tcttggtgga 540
aagcgttcaa gtggttttgg tcgttttgag ttagatattc aaaatatccc actagaattg 600
tcagatagac tgactaagaa tcattcagat aaagtgatga gtcttacgac agcacttcct 660
gtagatgctg accttgaaga agcaatggaa gatggacatt acttattaac taaatcaagt 720
ggttttgcat ttagtcatgc taccaatgag aattatcgta agcaggatct ttacaaattt 780
gcttctggtt caactttag taaaacattt gaaggtcaga ttgttgatgt gagaccactt 840
gatttccctc atgctgtttt aaattatgct aaaccactct tctttaaatt ggaggtataa 900

<210> SEQ ID NO 487
<211> LENGTH: 1074
<212> TYPE: DNA
<213> ORGANISM: Steptococcus thermophilus

<400> SEQUENCE: 487
atgaaaaatg actatagaac atttaaatta agcctcctga cacttgctcc aattcatatt 60
ggtaatggag agaagtatac ctctagagaa tttatctatg aaaataagaa gttttacttt 120
cctgacatgg ggaaattcta taataaaatg gtggagaaga ggcttgctga aaagtttgaa 180
gcatttctaa ttcaaactcg tccaaatgca cgtaataatc gtcttatttc cttcttaaat 240
gataaccgaa ttgcagagcg ttcttttgga ggttatagta tctctgaaac aggtttagaa 300
tcggacaaaa atcctgattc agccggagct attaacgaag ttaataaatt tattcgagat 360
gcttttggaa atccctacat tcctggtagc tcactaaaag gtgctattcg taccatttta 420
atgaatacta cccctaagtg gaataatgaa aatgctgtaa atgactttgg aagatttccg 480
aaagagaata agaaccttat cccttgggga ccaaaaaagg gaaaagaata cgatgatttg 540
tttaacgcaa ttcgtgtgag tgatagtaag ccttttgata ataagagtct tatcttagtg 600
cagaaatggg attattcagc gaaaacaaat aaagctaaac cacttccctt gtatagagaa 660
tcaatctctc cattaacaaa aattgaattt gagattacaa caaccactga tgaagctgga 720
agattgattg aagaattagg taagagagca caagcgtttt ataaagacta taaggcattt 780
ttcctatctg aatttcctga tgataagatt caagccaatc tacaataccc aatttattta 840
ggtgcgggga gcggtgcttg gacaaagact ctatttaagc aagctgatgg tattttacaa 900
agacgataca gtcgaatgaa aactaaaatg gttaaaaaag gagttcttaa gctcacaaaa 960
gcacctctta aaacagttaa gattccatct ggtaatcatt cattagtcaa gaaccacgag 1020
tccttttatg aaatgggaaa agctaatttc atgattaagg agattgataa atga 1074

<210> SEQ ID NO 488
<211> LENGTH: 5974
<212> TYPE: DNA
<213> ORGANISM: Steptococcus agalactiae

<400> SEQUENCE: 488
atgaataagc catattcaat aggccttgac atcggtacta attccgtcgg atggagcatt 60
attacagatg attataaagt acctgctaag aagatgagag ttttagggaa cactgataaa 120
gaatatatta agaagaatct cataggtgct ctgcttttg atggcgggaa tactgctgca 180
gatagacgct tgaagcgaac tgctcgtcgt cgttatacac gtcgtagaaa tcgtattcta 240
tatttacaag aaatttttgc agaggaaatg agtaaagttg atgatagttt ctttcatcga 300
ttagaggatt cttttctagt tgaggaagat aagagaggga gcaagtatcc tatctttgca 360
acattgcagg aagagaaaga ttatcatgaa aaattttcga caatctatca tttgagaaaa 420
gaattagctg acaagaaaga aaaagcagac cttcgtctta tttatattgc tctagctcat 480
atcattaaat ttagagggca tttcctaatt gaggatgata gctttgatgt caggaataca 540
gacatttcaa aacaatatca agatttttta gaaatcttta atacaacttt tgaaaataat 600
gatttgttat ctcaaaacgt tgacgtagag gcaatactaa cagataagat tagcaagtct 660
gcgaagaaag atcgtatttt agcgcagtat cctaaccaaa aatctactgg catttttgca 720
gaatttttga aattgattgt cggaaatcaa gctgacttca agaaatattt caatttggag 780
gataaaacgc cgcttcaatt cgctaaggat agctacgatg aagatttaga aaatcttctt 840
ggacagattg gtgatgaatt tgcagactta ttctcagcag cgaaaaagtt atatgatagt 900
gtccttttgt ctggcattct tacagtaatc gacctcagta ccaaggcgcc actttcagct 960
tctatgattc agcgttatga tgaacataga gaggacttga aacagttaaa acaattcgta 1020
aaagcttcat tgccggaaaa atatcaagaa atatttgctg attcatcaaa agatggctac 1080
gctggttata ttgaaggtaa aactaatcaa gaagcttttt ataaatacct gtcaaaattg 1140
ttgaccaagc aagaagatag cgagaatttt cttgaaaaaa tcaagaatga agatttcttg 1200
agaaaacaaa ggacctttga taatggctca attccacacc aagtccattt gacagagctg 1260
aaagctatta tccgccgtca atcagaatac tatcccttct tgaaagagaa tcaagatagg 1320
attgaaaaaa tccttacctt tagaattcct tattatatcg ggccactagc acgtgagaag 1380
agtgattttg catggatgac tcgcaaaaca gatgacagta ttcgaccttg gaattttgaa 1440
gacttggttg ataaagaaaa atctgcggaa gcttttatcc atcgtatgac caacaatgat 1500
ttttatcttc ctgaagaaaa agttttacca aagcatagtc ttatttatga aaaatttacg 1560
gtctataatg agttgactaa ggttagatat aaaaatgagc aaggtgagac ttattttttt 1620
gatagcaata ttaaacaaga aatctttgat ggagtattca aggaacatcg taaggtatcc 1680

```
aagaagaagt tgctagattt tctggctaaa gaatatgagg agtttaggat agtagatgtt   1740
attggtctag ataaagaaaa taaagctttc aacgcctcat tgggaactta ccacgatctc   1800
gaaaaaatac tagacaaaga ttttctagat aatccagata atgagtctat tctggaagat   1860
atcgtccaaa ctctaacatt atttgaagac agagaaatga ttaagaagcg tcttgaaaac   1920
tataaagatc tttttacaga gtcacaacta aaaaaactct atcgtcgtca ctatactggc   1980
tggggacgat tgtctgctaa gttaatcaat ggtattcgag ataaagagag tcaaaaaaca   2040
atcttggact atcttattga tgatggtaga tctaatcgca actttatgca gttgataaat   2100
gatgatggtc tatctttcaa atcaattatc agtaaggcac aggctggtag tcattcagat   2160
aatctaaaag aagttgtagg tgagcttgca ggtagccctg ctattaaaaa gggaattcta   2220
caaagtttga aaattgttga tgagcttgtt aaagtcatgg gatacgaacc tgaacaaatt   2280
gtggttgaga tggcgcgtga gaatcaaaca acaaatcaag gtcgtcgtaa ctctcgacaa   2340
cgctataaac ttcttgatga tggcgttaag aatctagcta gtgacttgaa tggcaatatt   2400
ttgaaagaat atcctacgga taatcaagcg ttgcaaaatg aaagactttt cctttactac   2460
ttacaaaacg gaagagatat gtatacaggg gaagctctag atattgacaa tttaagtcaa   2520
tatgatattg accacattat tcctcaagct ttcataaaag atgattctat tgataatcgt   2580
gttttggtat catctgctaa aaatcgtgga aagtcagatg atgttcctag ccttgaaatt   2640
gtaaaagatt gtaaagtttt ctggaaaaaa ttacttgatg ctaagttaat gagtcagcgt   2700
aagtatgata atttgactaa ggcagagcgc ggaggcctaa cttccgatga taaggcaaga   2760
tttatccaac gtcagttggt tgagacacga caaattacca agcatgttgc ccgtatcttg   2820
gatgaacgct ttaataatga gcttgatagt aaaggtagaa ggatccgcaa agttaaaatt   2880
gtaaccttga agtcaaattt ggtttcaaat ttccgaaaag aatttggatt ctataaaatt   2940
cgtgaagtta acaattatca ccatgcacat gatgcctatc ttaatgcagt agttgctaaa   3000
gctattctaa ccaaatatcc tcagttagag ccagaatttg tctacggcga ctatccaaaa   3060
tataatagtt acaaaacgcg taaatccgct acagaaaagc tatttttcta ttcaaatatt   3120
atgaacttct ttaaaactaa ggtaacttta gcggatggaa ccgttgttgt aaaagatgat   3180
attgaagtta ataatgatac gggtgaaatt gtttgggata aaaagaaaca ctttgcgaca   3240
gttagaaaag tcttgtcata ccctcagaac aatatcgtga agaagacaga gattcagaca   3300
ggtggtttct ctaaggaatc aatcttggcg catggtaact cagataagtt gattccaaga   3360
aaaacgaagg atatttattt agatcctaag aaatatggag gttttgatag tccgatagta   3420
gcttactctg ttttagttgt agctgatatc aaaaagggta aagcacaaaa actaaaaaca   3480
gttacggaac ttttaggaat taccatcatg gagaggtcca gatttgagaa aaatccatca   3540
gctttccttg aatcaaaagg ctatttaaat attagggctg ataaactaat tattttgccc   3600
aagtatagtc tgttcgaatt agaaaatggg cgtcgtcgat tacttgctag tgctggtgaa   3660
ttacaaaaag gtaatgagct agccttacca acacaattta tgaagttctt ataccttgca   3720
agtcgttata atgagtcaaa aggtaaacca gaggagattg agaagaaaca agaatttgta   3780
aatcaacatg tctcttattt tgatgacatc cttcaattaa ttaatgattt ttcaaaacga   3840
gttattctag cagatgctaa tttagagaaa atcaataagc tttaccaaga taataaggaa   3900
aatatatcag tagatgaact tgctaataat attatcaatc tatttacttt taccagtcta   3960
ggagctccag cagcttttaa attttttgat aaaatagttg atagaaaacg ctatacatca   4020
```

-continued actaaagaag tacttaattc taccctaatt catcaatcta ttactggact ttatgaaaca 4080
cgtattgatt tgggtaagtt aggagaagat tgatatggca ggttggcgaa ccgttgttgt 4140
aaatacacat tctaagctct cttataaaaa taatcatctg atttttaaag attcttatca 4200
gacggaaatg attcatctat cagagattga cattctaatc atggaaacaa cagatatcgt 4260
tttgtcgacc atgctgatta aacgtttggt tgatgaaaat attttagtta tattttgtga 4320
cgataaacgc ttgccaacag ctatgttaat gccgtactat gccagacatg attcgagttt 4380
acaattatct aggcagatgt catggattga agatgtcaaa gcagatgttt ggacatcaat 4440
tattgcacaa aaaatttga atcagtcttt ttatctcggt gagtgttctt tctttgaaaa 4500
atcccagtct attatgaatc tctaccatga cttagaacct tttgatcctt ctaatcgtga 4560
ggggcatgct gctaggattt atttcaatac actttttgga aatgattttt caagagagca 4620
ggataatcca ataaatgctg gtttagacta cggatattca ttgcttttga gtatgtttgc 4680
gcgtgaagtt gttaagtgtg gttgcatgac acaatttggc ttgaagcatg ctaatcaatt 4740
taatcagttc aacctagcaa gcgatattat ggaaccattt cgcccaatcg ttgataggat 4800
tatttatgaa aataggcaga gtgattttgt caaaatgaaa agagaactct tttctatgtt 4860
ttcagagaca tacagctaca atggtaaaga aatgtatctc tcaaatattg tcagcgacta 4920
taccaaaaaa gttattaagt cgctaaatag tgatgggaat ggaattccgg agtttaggat 4980
atgagttatc ggtatatgcg aatgatttta atgtttgata tgcctactga aacagcagaa 5040
gaacggaagg cgtatcgtaa gtttagaaag tttctcttga gcgaaggctt tatcatgcat 5100
cagttttctg tttatagtaa attattactc aataatacag ctaataatgc tatgataggt 5160
cggcttaaag tgaataatcc taaaaagggt aatatcacac tcttaacagt tacggaaaaa 5220
caatttgcga gaatggttta cctccatgga gaacgcaaca caagtgttgc caactctgat 5280
agtcgcttgg ttttcctagg agattcttat gatcaagatt aattttccaa ttttagatga 5340
accattagtg ttaagtaatg ctacgatttt aacgatagaa gatgtttcag tttattcttc 5400
attggtgaaa catttttatc aatatgacgt agatgaacat ttgaaattat ttgatgataa 5460
gcagaaaagt ctgaaggcaa cagagttaat gctggttaca gatatcttag gatacgatgt 5520
caactcagca cctattctaa agttgataca tggtgactta gaaaatcaat tcaacgaaaa 5580
gccagaagtg aaatcaatgg tagaaaaatt agcagctact attacagaac ttatcgcatt 5640
tgagtgtcta gagaatgagc ttgatttaga atacgatgaa attaagattt tagaactcat 5700
taaggcactg ggagtcaaaa ttgagacaca gagcgacact atctttgaaa aatgttttga 5760
aattatacaa gtttaccatt atttaacgaa aaagaatctc ttggtttttg ttaatagcgg 5820
agcttatctt accaaagatg aagttataaa attatgtgaa tacatcaatt taatgcaaaa 5880
gtcagtactc tttctagaac ctagaagact ctatgattta ccgcaatatg ttattgataa 5940
ggattatttc ttgataggcg aaaatatggt ataa 5974

<210> SEQ ID NO 489
<211> LENGTH: 4113
<212> TYPE: DNA
<213> ORGANISM: Steptococcus agalactiae

<400> SEQUENCE: 489
atgaataagc catattcaat aggccttgac atcggtacta attccgtcgg atggagcatt 60
attacagatg attataaagt acctgctaag aagatgagag ttttagggaa cactgataaa 120
gaatatatta agaagaatct cataggtgct ctgctttttg atggcgggaa tactgctgca 180

```
gatagacgct tgaagcgaac tgctcgtcgt cgttatacac gtcgtagaaa tcgtattcta    240
tatttacaag aaatttttgc agaggaaatg agtaaagttg atgatagttt ctttcatcga    300
ttagaggatt cttttctagt tgaggaagat aagagaggga gcaagtatcc tatctttgca    360
acattgcagg aagagaaaga ttatcatgaa aaattttcga caatctatca tttgagaaaa    420
gaattagctg acaagaaaga aaaagcagac cttcgtctta tttatattgc tctagctcat    480
atcattaaat ttagagggca tttcctaatt gaggatgata gctttgatgt caggaataca    540
gacatttcaa aacaatatca agatttttta gaaatcttta atacaacttt tgaaaataat    600
gatttgttat ctcaaaacgt tgacgtagag gcaatactaa cagataagat tagcaagtct    660
gcgaagaaag atcgtatttt agcgcagtat cctaaccaaa aatctactgg catttttgca    720
gaatttttga aattgattgt cggaaatcaa gctgacttca agaaatattt caatttggag    780
gataaaacgc cgcttcaatt cgctaaggat agctacgatg aagatttaga aaatcttctt    840
ggacagattg gtgatgaatt tgcagactta ttctcagcag cgaaaaagtt atatgatagt    900
gtccttttgt ctggcattct tacagtaatc gacctcagta ccaaggcgcc actttcagct    960
tctatgattc agcgttatga tgaacataga gaggacttga aacagttaaa acaattcgta   1020
aaagcttcat tgccggaaaa atatcaagaa atatttgctg attcatcaaa agatggctac   1080
gctggttata ttgaaggtaa aactaatcaa gaagcttttt ataaatacct gtcaaaattg   1140
ttgaccaagc aagaagatag cgagaatttt cttgaaaaaa tcaagaatga agatttcttg   1200
agaaaacaaa ggacctttga taatggctca attccacacc aagtccattt gacagagctg   1260
aaagctatta tccgccgtca atcagaatac tatcccttct tgaaagagaa tcaagatagg   1320
attgaaaaaa tccttacctt tagaattcct tattatatcg ggccactagc acgtgagaag   1380
agtgattttg catggatgac tcgcaaaaca gatgacagta ttcgaccttg gaattttgaa   1440
gacttggttg ataaagaaaa atctgcggaa gcttttatcc atcgtatgac caacaatgat   1500
ttttatcttc ctgaagaaaa agttttacca aagcatagtc ttatttatga aaaatttacg   1560
gtctataatg agttgactaa ggttagatat aaaaatgagc aaggtgagac ttattttttt   1620
gatagcaata ttaaacaaga aatctttgat ggagtattca aggaacatcg taaggtatcc   1680
aagaagaagt tgctagattt tctggctaaa gaatatgagg agtttaggat agtagatgtt   1740
attggtctag ataaagaaaa taaagctttc aacgcctcat tgggaactta ccacgatctc   1800
gaaaaaatac tagacaaaga ttttctagat aatccagata atgagtctat tctggaagat   1860
atcgtccaaa ctctaacatt atttgaagac agagaaatga ttaagaagcg tcttgaaaac   1920
tataaagatc tttttacaga gtcacaacta aaaaaactct atcgtcgtca ctatactggc   1980
tggggacgat tgtctgctaa gttaatcaat ggtattcgag ataaagagag tcaaaaaaca   2040
atcttggact atcttattga tgatggtaga tctaatcgca actttatgca gttgataaat   2100
gatgatggtc tatctttcaa atcaattatc agtaaggcac aggctggtag tcattcagat   2160
aatctaaaag aagttgtagg tgagcttgca ggtagccctg ctattaaaaa gggaattcta   2220
caaagtttga aaattgttga tgagcttgtt aaagtcatgg gatacgaacc tgaacaaatt   2280
gtggttgaga tggcgcgtga gaatcaaaca acaaatcaag gtcgtcgtaa ctctcgacaa   2340
cgctataaac ttcttgatga tggcgttaag aatctagcta gtgacttgaa tggcaatatt   2400
ttgaaagaat atcctacgga taatcaagcg ttgcaaaatg aaagactttt cctttactac   2460
ttacaaaacg gaagagatat gtatacaggg gaagctctag atattgacaa tttaagtcaa   2520
```

```
tatgatattg accacattat tcctcaagct ttcataaaag atgattctat tgataatcgt   2580
gttttggtat catctgctaa aaatcgtgga aagtcagatg atgttcctag ccttgaaatt   2640
gtaaaagatt gtaaagtttt ctggaaaaaa ttacttgatg ctaagttaat gagtcagcgt   2700
aagtatgata atttgactaa ggcagagcgc ggaggcctaa cttccgatga taaggcaaga   2760
tttatccaac gtcagttggt tgagacacga caaattacca agcatgttgc ccgtatcttg   2820
gatgaacgct ttaataatga gcttgatagt aaaggtagaa ggatccgcaa agttaaaatt   2880
gtaaccttga agtcaaattt ggtttcaaat ttccgaaaag aatttggatt ctataaaatt   2940
cgtgaagtta acaattatca ccatgcacat gatgcctatc ttaatgcagt agttgctaaa   3000
gctattctaa ccaaatatcc tcagttagag ccagaatttg tctacggcga ctatccaaaa   3060
tataatagtt acaaaacgcg taaatccgct acagaaaagc tatttttcta ttcaaatatt   3120
atgaacttct ttaaaactaa ggtaacttta gcggatggaa ccgttgttgt aaaagatgat   3180
attgaagtta ataatgatac gggtgaaatt gtttgggata aaaagaaaca ctttgcgaca   3240
gttagaaaag tcttgtcata ccctcagaac aatatcgtga agaagacaga gattcagaca   3300
ggtggtttct ctaaggaatc aatcttggcg catggtaact cagataagtt gattccaaga   3360
aaaacgaagg atatttattt agatcctaag aaatatggag gttttgatag tccgatagta   3420
gcttactctg ttttagttgt agctgatatc aaaaagggta aagcacaaaa actaaaaaca   3480
gttacggaac ttttaggaat taccatcatg gagaggtcca gatttgagaa aaatccatca   3540
gctttccttg aatcaaaagg ctatttaaat attagggctg ataaactaat tattttgccc   3600
aagtatagtc tgttcgaatt agaaaatggg cgtcgtcgat tacttgctag tgctggtgaa   3660
ttacaaaaag gtaatgagct agccttacca acacaattta tgaagttctt ataccttgca   3720
agtcgttata atgagtcaaa aggtaaacca gaggagattg agaagaaaca agaatttgta   3780
aatcaacatg tctcttattt tgatgacatc cttcaattaa ttaatgattt ttcaaaacga   3840
gttattctag cagatgctaa tttagagaaa atcaataagc tttaccaaga taataaggaa   3900
aatatatcag tagatgaact tgctaataat attatcaatc tatttacttt taccagtcta   3960
ggagctccag cagcttttaa attttttgat aaaatagttg atagaaaacg ctatacatca   4020
actaaagaag tacttaattc taccctaatt catcaatcta ttactggact ttatgaaaca   4080
cgtattgatt tgggtaagtt aggagaagat tga                                4113
```

<210> SEQ ID NO 490
<211> LENGTH: 870
<212> TYPE: DNA
<213> ORGANISM: Steptococcus agalactiae

<400> SEQUENCE: 490

```
atggcaggtt ggcgaaccgt tgttgtaaat acacattcta agctctctta taaaaataat     60
catctgattt ttaaagattc ttatcagacg gaaatgattc atctatcaga gattgacatt    120
ctaatcatgg aaacaacaga tatcgttttg tcgaccatgc tgattaaacg tttggttgat    180
gaaaatattt tagttatatt ttgtgacgat aaacgcttgc caacagctat gttaatgccg    240
tactatgcca gacatgattc gagtttacaa ttatctaggc agatgtcatg gattgaagat    300
gtcaaagcag atgtttggac atcaattatt gcacaaaaaa ttttgaatca gtctttttat    360
ctcggtgagt gttctttctt tgaaaaatcc cagtctatta tgaatctcta ccatgactta    420
gaacctttttg atccttctaa tcgtgagggg catgctgcta ggatttattt caatacactt    480
tttggaaatg atttttcaag agagcaggat aatccaataa atgctggttt agactacgga    540
```

```
tattcattgc ttttgagtat gtttgcgcgt gaagttgtta agtgtggttg catgacacaa    600

tttggcttga agcatgctaa tcaatttaat cagttcaacc tagcaagcga tattatggaa    660

ccatttcgcc caatcgttga taggattatt tatgaaaata ggcagagtga ttttgtcaaa    720

atgaaaagag aactcttttc tatgttttca gagacataca gctacaatgg taaagaaatg    780

tatctctcaa atattgtcag cgactatacc aaaaaagtta ttaagtcgct aaatagtgat    840

gggaatggaa ttccggagtt taggatatga                                     870
```

<210> SEQ ID NO 491
<211> LENGTH: 327
<212> TYPE: DNA
<213> ORGANISM: Steptococcus agalactiae

<400> SEQUENCE: 491

```
atgcgaatga ttttaatgtt tgatatgcct actgaaacag cagaagaacg gaaggcgtat     60

cgtaagttta gaaagtttct cttgagcgaa ggctttatca tgcatcagtt ttctgtttat    120

agtaaattat tactcaataa tacagctaat aatgctatga taggtcggct taaagtgaat    180

aatcctaaaa agggtaatat cacactctta acagttacgg aaaaacaatt tgcgagaatg    240

gtttacctcc atggagaacg caacacaagt gttgccaact ctgatagtcg cttggttttc    300

ctaggagatt cttatgatca agattaa                                         327
```

<210> SEQ ID NO 492
<211> LENGTH: 666
<212> TYPE: DNA
<213> ORGANISM: Steptococcus agalactiae

<400> SEQUENCE: 492

```
atgatcaaga ttaatttcc aattttagat gaaccattag tgttaagtaa tgctacgatt     60

ttaacgatag aagatgtttc agtttattct tcattggtga aacattttta tcaatatgac    120

gtagatgaac atttgaaatt atttgatgat aagcagaaaa gtctgaaggc aacagagtta    180

atgctggtta cagatatctt aggatacgat gtcaactcag cacctattct aaagttgata    240

catggtgact tagaaaatca attcaacgaa aagccagaag tgaaatcaat ggtagaaaaa    300

ttagcagcta ctattacaga acttatcgca tttgagtgtc tagagaatga gcttgattta    360

gaatacgatg aaattaagat tttagaactc attaaggcac tgggagtcaa aattgagaca    420

cagagcgaca ctatctttga aaaatgtttt gaaattatac aagtttacca ttatttaacg    480

aaaaagaatc tcttggtttt tgttaatagc ggagcttatc ttaccaaaga tgaagttata    540

aaattatgtg aatacatcaa tttaatgcaa aagtcagtac tctttctaga acctagaaga    600

ctctatgatt taccgcaata tgttattgat aaggattatt tcttgatagg cgaaaatatg    660

gtataa                                                                666
```

<210> SEQ ID NO 493
<211> LENGTH: 5995
<212> TYPE: DNA
<213> ORGANISM: Steptococcus agalactiae

<400> SEQUENCE: 493

```
atgaataagc catattcaat aggccttgac atcggtacta attccgtcgg atggagcatt     60

attacagatg attataaagt acctgctaag aagatgagag ttttagggaa cactgataaa    120

gaatatatta agaagaatct cataggtgct ctgctttttg atggcgggaa tactgctgca    180
```

```
gatagacgct tgaagcgaac tgctcgtcgt cgttatacac gtcgtagaaa tcgtattcta    240
tatttacaag aaatttttgc agaggaaatg agtaaagttg atgatagttt ctttcatcga    300
ttagaggatt cttttctagt tgaggaagat aagagaggta gcaagtatcc tatctttgca    360
acaatgcagg aggagaaata ttatcatgaa aaatttccga caatctatca tttgagaaaa    420
gaattggctg acaagaaaga aaaagcagac cttcgtcttg tttatctggc tctagctcat    480
atcattaaat tcagagggca tttcctaatt gaggatgata gatttgatgt gaggaatacc    540
gatattcaaa aacaatatca agccttttta gaaatttttg atactacctt tgaaaataat    600
catttgttat ctcaaaatgt agatgtagaa gcaattctaa cagataagat tagcaagtct    660
gcgaagaagg atcgcatctt agcgcagtat cctaaccaaa aatctactgg tatttttgca    720
gaatttttga aattgattgt cggaaatcaa gctgacttca agaaacattt caatttggag    780
gataaaacac cgcttcaatt cgctaaggat agctacgatg aagatttaga aaatcttctt    840
ggacagattg gtgatgaatt tgcagactta ttctcagtag cgaaaaagct atatgatagt    900
gttcttttat ctggcattct tacagtaact gatctcagta ccaaggcgcc actttctgcc    960
tctatgattc agcgttatga tgaacatcat gaggacttaa agcatctaaa acaattcgta   1020
aaagcttcat tacctgaaaa ttatcgggaa gtatttgctg attcatcaaa agatggctac   1080
gctggctata ttgaaggcaa aactaatcaa gaagcttttt ataaatatct gttaaaattg   1140
ttgaccaaac aagaaggtag cgagtatttt cttgagaaaa ttaagaatga agatttttttg   1200
agaaaacaga gaacctttga taatggctca atcccgcatc aagtccattt gacagaattg   1260
agggctatta ttcgacgtca atcagaatac tatccattct tgaaagagaa tcaagatagg   1320
attgaaaaaa tccttacctt tagaattcct tattatgtcg ggccactagc acgtgagaag   1380
agtgattttg catggatgac tcgcaaaaca gatgacagta ttcgaccttg gaattttgaa   1440
gacttggttg ataaagaaaa atctgcggaa gcttttatcc atcgcatgac caacaatgac   1500
ctctatcttc cagaagaaaa agttttacca aagcatagtc ttatttatga aaaatttact   1560
gtttacaatg aattaacgaa ggttagattt ttggcagaag gctttaaaga ttttcaattt   1620
ttaaatagga agcaaaaaga aactatcttt aacagcttgt ttaaggaaaa acgtaaagta   1680
actgaaaagg atattattag tttttttgaat aaagttgatg gatatgaagg aattgcaatc   1740
aaaggaattg agaaacagtt taacgctagc ctttcaacct atcatgatct taaaaaaata   1800
cttggcaagg atttccttga taatacagat aacgagctta ttttggaaga tatcgtccaa   1860
actctaacct tatttgaaga tagagaaatg attaagaagt gtcttgacat ctataaagat   1920
ttttttacag agtcacagct taaaaagctc tatcgccgtc actatactgg ctggggacga   1980
ttgtctgcta agctaataaa tggcatccga aataaagaga atcaaaaaac aatcttggac   2040
tatcttattg atgatggaag tgcaaaccga aacttcatgc agttgataaa tgatgatgat   2100
ctatcattta aaccaattat tgacaaggca cgaactggta gtcattcgga taatctgaaa   2160
gaagttgtag gtgaacttgc tggtagccct gctattaaaa aagggattct acaaagtttg   2220
aaaatagttg atgagctggt taaagtcatg ggctatgaac ctgaacaaat cgtggttgaa   2280
atggcacgtg agaaccaaac gacagcaaaa ggattaagtc gttcacgaca acgcttgaca   2340
accttgagag aatctcttgc taatttgaag agtaatattt tggaagagaa aaagcctaag   2400
tatgtgaaag atcaagttga aaatcatcat ttatctgatg accgtctttt cctttactac   2460
ttacaaaacg gaagagatat gtatacaaaa aaggctctgg atattgataa tttaagtcaa   2520
tatgatattg accacattat tcctcaagct ttcataaaag atgattctat tgataatcgt   2580
```

```
gttttggtat catctgctaa aaatcgtgga aaatcagatg atgttcctag cattgaaatt   2640
gtaaaagctc gcaaaatgtt ctggaaaaat ttactggatg ctaagttaat gagtcagcgt   2700
aagtatgata atttgactaa ggcagagcgc ggaggcctaa cttccgatga taaggcaaga   2760
tttatccaac gtcagttggt tgagactcga caaattacca agcatgtagc tcgtatcttg   2820
gatgaacgct tcaataatga agttgataat ggtaaaaaga tttgcaaggt taaaattgta   2880
accttgaagt caaatttggt ttcaaatttc cgaaaagaat ttggattcta taaaattcgt   2940
gaagttaatg attatcacca tgcacacgat gcttatctta atgcagtagt tgccaaagct   3000
attctaacca aatatccaca gttagagcca gagtttgtct acggaatgta tagacagaaa   3060
aaactttcga aaatcgttca tgaggataag gaagaaaaat atagtgaagc aaccaggaaa   3120
atgtttttct actccaactt gatgaatatg ttcaaaagag ttgtgaggtt agcagatggt   3180
tctattgttg taagaccagt aatagaaact ggtagatata tgagaaaaac tgcatgggat   3240
aaaaagaaac actttgcgac agttagaaaa gtcttgtcat accctcagaa caatatcgtg   3300
aagaagacag agattcagac aggtggtttc tctaaggaat caatcttggc gcatggtaac   3360
tcagataagt tgattccaag aaaaacgaag gatatttatt tagatcctaa gaaatatgga   3420
ggttttgata gtccgatagt agcttactct gttttagttg tagctgatat caaaaaaggt   3480
aaagcacaaa aactaaaaac agttacggaa cttttaggaa ttaccatcat ggagaggtcc   3540
agatttgaga aaaatccatc agctttcctt gaatcaaaag gttatttaaa tattagggac   3600
gataaattaa tgattttacc gaagtatagt ctgttcgaat tagaaaatgg gcgtcgtcga   3660
ttacttgcta gtgctggtga attacaaaaa ggtaacgagc tagccttacc aacacaattt   3720
atgaagttct tataccttgc aagtcgttat aatgagtcaa aaggtaaacc agaggagatt   3780
gagaagaaac aagaatttgt aaatcaacat gtctcttatt ttgatgacat ccttcaatta   3840
attaatgatt tttcaaaacg agttattcta gcagatgcta atttagagaa aatcaataag   3900
ctttaccagg ataataagga aaatatacca gtagatgaac ttgctaataa tattatcaat   3960
ctatttactt ttaccagtct aggagctcca gcagctttta aatttttga taaaatagtt   4020
gatagaaaac gctatacatc aactaaagaa gtacttaatt ctactctaat ccatcaatct   4080
attactggac tttatgaaac acgtattgat ttgggtaaat taggagaaga ttgatatggc   4140
aggttggcga actgttgttg taaatacaca ttctaagctc tcttataaaa ataatcatct   4200
gatttttaaa gattcttatc agacggaaat gattcatctt tcagagattg atattctaat   4260
catggaaacg acagatattg ttttgtcgac tatgctgatt aaacgtttgg ttgatgaaaa   4320
tattttagtc atattttgtg atgataaacg cttgccaaca gctatgttaa tgccgtacta   4380
tgctagacat gattcgagtt tacaattatc taggcagatg tcatggattg aggatgtcaa   4440
agcggatgtt tggacatcaa ttattgcaca aaaaattttg aatcagtcct tttatctcgg   4500
tgagtgttct ttctttgaaa aatcccagtc tattatgaat ctctatcatg atttagaatc   4560
ttttgaccct tccaatcgtg aaggtcatgc agctaggatt tatttcaata cactttttgg   4620
aaatgatttt tcaagagagc aggataatcc aataaatgct ggtttagact atggatattc   4680
tctgattttg agtatgtttg cgcgtgaagt tgttaagtgt ggttgcatga cacaatttgg   4740
cttaaagcat gctaatcaat ttaatcagtt caacctagca agcgatatta tggaaccatt   4800
tcgcccaatc gttgatagga ttatttatga aaataggcag agtgattttg tcaaaatgaa   4860
aagagaactc ttttctatgt tttcagagac atacagctac aacggtaaag aaatgtatct   4920
```

```
ttcaaatatt gtcagcgatt acaccaaaaa agttattaag tcgctaaata gtgatgggaa   4980
tggaattccg gagtttagga tatgagttat cggtatatga gaatgatttt aatgtttgat   5040
atgcctactg aaacagtaga agaacgtaag gcgtatcgta agtttagaaa gtttctgttg   5100
agcgaaggtt ttattatgca tcagttctct gtttatagta aattattgct caataataca   5160
gctaataatg ccatgatagg tcggcttaaa gtgaataatc ctaagaaagg gagtataact   5220
cttttgacag ttaccgagaa gcagtttgca aggatggttt atctacatgg tgaacataat   5280
atgagtgttg ccaactctga tagtcgcttg gttttcctag gagattctta tgatcaagat   5340
taattttcca attttagatg aaccattagt gttaagtaat gctacgattt taacgataga   5400
agatgtttca gtttattctt cattggtgaa acatttttat caatatgacg tagatgaaca   5460
tttgaaatta tttgatgata agcagaaaag tctgaaggca acggagttaa tgttagttac   5520
agatatctta ggatacgatg tcaactcagc acctattcta aagttgatac atggtgactt   5580
agaaaatcaa ttcaacgaaa agccagaagt gaaatcaatg gtagaaaaat tagcagctac   5640
tattacagaa cttatcgcat ttgagtgtct agagaatgag cttgatttag aatacgatga   5700
aattacgatt ttagaactca ttaaggcact gggagtcaaa attgagacac agagcgacac   5760
tatctttgaa aaatgttttg aaattataca agtttaccat tatttaacga aaaagaatct   5820
cttagttttt gttaatagcg gagcttatct taccaaagat gaagttataa aattatgtga   5880
atacatcaat ttaatgcaaa agtcagtact ctttctagaa cctagaagac tctatgattt   5940
accgcaatat gttattgata aggattattt cttgataggc gaaaatatgg tataa         5995
```

<210> SEQ ID NO 494
<211> LENGTH: 4134
<212> TYPE: DNA
<213> ORGANISM: Steptococcus agalactiae

<400> SEQUENCE: 494

```
atgaataagc catattcaat aggccttgac atcggtacta attccgtcgg atggagcatt     60
attacagatg attataaagt acctgctaag aagatgagag ttttagggaa cactgataaa    120
gaatatatta agaagaatct cataggtgct ctgcttttttg atggcgggaa tactgctgca    180
gatagacgct tgaagcgaac tgctcgtcgt cgttatacac gtcgtagaaa tcgtattcta    240
tatttacaag aaatttttgc agaggaaatg agtaaagttg atgatagttt ctttcatcga    300
ttagaggatt cttttctagt tgaggaagat aagagaggta gcaagtatcc tatctttgca    360
acaatgcagg aggagaaata ttatcatgaa aaatttccga caatctatca tttgagaaaa    420
gaattggctg acaagaaaga aaaagcagac cttcgtcttg tttatctggc tctagctcat    480
atcattaaat tcagagggca tttcctaatt gaggatgata gatttgatgt gaggaatacc    540
gatattcaaa aacaatatca agccttttta gaaatttttg atactacctt tgaaaataat    600
catttgttat ctcaaaatgt agatgtagaa gcaattctaa cagataagat tagcaagtct    660
gcgaagaagg atcgcatctt agcgcagtat cctaaccaaa aatctactgg tattttttgca    720
gaatttttga aattgattgt cggaaatcaa gctgacttca agaaacattt caatttggag    780
gataaaacac cgcttcaatt cgctaaggat agctacgatg aagatttaga aaatcttctt    840
ggacagattg gtgatgaatt tgcagactta ttctcagtag cgaaaaagct atatgatagt    900
gttcttttat ctggcattct tacagtaact gatctcagta ccaaggcgcc actttctgcc    960
tctatgattc agcgttatga tgaacatcat gaggacttaa agcatctaaa acaattcgta   1020
aaagcttcat tacctgaaaa ttatcgggaa gtatttgctg attcatcaaa agatggctac   1080
```

```
gctggctata ttgaaggcaa aactaatcaa gaagcttttt ataaatatct gttaaaattg   1140
ttgaccaaac aagaaggtag cgagtatttt cttgagaaaa ttaagaatga agattttttg   1200
agaaaacaga gaacctttga taatggctca atcccgcatc aagtccattt gacagaattg   1260
agggctatta ttcgacgtca atcagaatac tatccattct tgaaagagaa tcaagatagg   1320
attgaaaaaa tccttacctt tagaattcct tattatgtcg ggccactagc acgtgagaag   1380
agtgattttg catggatgac tcgcaaaaca gatgacagta ttcgaccttg gaattttgaa   1440
gacttggttg ataaagaaaa atctgcggaa gcttttatcc atcgcatgac caacaatgac   1500
ctctatcttc cagaagaaaa agttttacca aagcatagtc ttatttatga aaaatttact   1560
gtttacaatg aattaacgaa ggttagattt ttggcagaag gctttaaaga ttttcaattt   1620
ttaaatagga agcaaaaaga aactatcttt aacagcttgt ttaaggaaaa acgtaaagta   1680
actgaaaagg atattattag tttttgaat aaagttgatg gatatgaagg aattgcaatc   1740
aaaggaattg agaaacagtt taacgctagc ctttcaacct atcatgatct taaaaaaata   1800
cttggcaagg atttccttga taatacagat aacgagctta ttttggaaga tatcgtccaa   1860
actctaacct tatttgaaga tagagaaatg attaagaagt gtcttgacat ctataaagat   1920
tttttacag agtcacagct taaaaagctc tatcgccgtc actatactgg ctggggacga   1980
ttgtctgcta agctaataaa tggcatccga aataaagaga atcaaaaaac aatcttggac   2040
tatcttattg atgatggaag tgcaaaccga aacttcatgc agttgataaa tgatgatgat   2100
ctatcattta aaccaattat tgacaaggca cgaactggta gtcattcgga taatctgaaa   2160
gaagttgtag gtgaacttgc tggtagccct gctattaaaa aagggattct acaaagtttg   2220
aaaatagttg atgagctggt taaagtcatg ggctatgaac ctgaacaaat cgtggttgaa   2280
atggcacgtg agaaccaaac gacagcaaaa ggattaagtc gttcacgaca acgcttgaca   2340
accttgagag aatctcttgc taatttgaag agtaatattt tggaagagaa aaagcctaag   2400
tatgtgaaag atcaagttga aaatcatcat ttatctgatg accgtctttt cctttactac   2460
ttacaaaacg gaagagatat gtatacaaaa aaggctctgg atattgataa tttaagtcaa   2520
tatgatattg accacattat tcctcaagct ttcataaaag atgattctat tgataatcgt   2580
gttttggtat catctgctaa aaatcgtgga aaatcagatg atgttcctag cattgaaatt   2640
gtaaaagctc gcaaaatgtt ctggaaaaat ttactggatg ctaagttaat gagtcagcgt   2700
aagtatgata atttgactaa ggcagagcgc ggaggcctaa cttccgatga taaggcaaga   2760
tttatccaac gtcagttggt tgagactcga caaattacca agcatgtagc tcgtatcttg   2820
gatgaacgct tcaataatga agttgataat ggtaaaaaga tttgcaaggt taaaattgta   2880
accttgaagt caaatttggt ttcaaatttc cgaaaagaat ttggattcta taaaattcgt   2940
gaagttaatg attatcacca tgcacacgat gcttatctta atgcagtagt tgccaaagct   3000
attctaacca aatatccaca gttagagcca gagtttgtct acggaatgta tagacagaaa   3060
aaactttcga aaatcgttca tgaggataag gaagaaaaat atagtgaagc aaccaggaaa   3120
atgtttttct actccaactt gatgaatatg ttcaaaagag ttgtgaggtt agcagatggt   3180
tctattgttg taagaccagt aatagaaact ggtagatata tgagaaaaac tgcatgggat   3240
aaaaagaaac actttgcgac agttagaaaa gtcttgtcat accctcagaa caatatcgtg   3300
aagaagacag agattcagac aggtggtttc tctaaggaat caatcttggc gcatggtaac   3360
tcagataagt tgattccaag aaaaacgaag gatatttatt tagatcctaa gaaatatgga   3420
```

```
ggttttgata gtccgatagt agcttactct gttttagttg tagctgatat caaaaaaggt   3480

aaagcacaaa aactaaaaac agttacggaa cttttaggaa ttaccatcat ggagaggtcc   3540

agatttgaga aaaatccatc agctttcctt gaatcaaaag gttatttaaa tattagggac   3600

gataaattaa tgattttacc gaagtatagt ctgttcgaat tagaaaatgg gcgtcgtcga   3660

ttacttgcta gtgctggtga attacaaaaa ggtaacgagc tagccttacc aacacaattt   3720

atgaagttct tataccttgc aagtcgttat aatgagtcaa aaggtaaacc agaggagatt   3780

gagaagaaac aagaatttgt aaatcaacat gtctcttatt ttgatgacat ccttcaatta   3840

attaatgatt tttcaaaacg agttattcta gcagatgcta atttagagaa aatcaataag   3900

ctttaccagg ataataagga aaatatacca gtagatgaac ttgctaataa tattatcaat   3960

ctatttactt ttaccagtct aggagctcca gcagctttta aatttttga taaaatagtt   4020

gatagaaaac gctatacatc aactaaagaa gtacttaatt ctactctaat ccatcaatct   4080

attactggac tttatgaaac acgtattgat ttgggtaaat taggagaaga ttga         4134
```

<210> SEQ ID NO 495
<211> LENGTH: 870
<212> TYPE: DNA
<213> ORGANISM: Steptococcus agalactiae

<400> SEQUENCE: 495

```
atggcaggtt ggcgaactgt tgttgtaaat acacattcta agctctctta taaaaataat     60

catctgattt ttaaagattc ttatcagacg gaaatgattc atctttcaga gattgatatt    120

ctaatcatgg aaacgacaga tattgttttg tcgactatgc tgattaaacg tttggttgat    180

gaaaatattt tagtcatatt ttgtgatgat aaacgcttgc caacagctat gttaatgccg    240

tactatgcta gacatgattc gagtttacaa ttatctaggc agatgtcatg gattgaggat    300

gtcaaagcgg atgtttggac atcaattatt gcacaaaaaa ttttgaatca gtccttttat    360

ctcggtgagt gttctttctt tgaaaaatcc cagtctatta tgaatctcta tcatgattta    420

gaatcttttg acccttccaa tcgtgaaggt catgcagcta ggatttattt caatacactt    480

tttggaaatg atttttcaag agagcaggat aatccaataa atgctggttt agactatgga    540

tattctctga ttttgagtat gtttgcgcgt gaagttgtta agtgtggttg catgacacaa    600

tttggcttaa agcatgctaa tcaatttaat cagttcaacc tagcaagcga tattatggaa    660

ccatttcgcc caatcgttga taggattatt tatgaaaata ggcagagtga ttttgtcaaa    720

atgaaaagag aactcttttc tatgttttca gagacataca gctacaacgg taaagaaatg    780

tatctttcaa atattgtcag cgattacacc aaaaaagtta ttaagtcgct aaatagtgat    840

gggaatggaa ttccggagtt taggatatga                                     870
```

<210> SEQ ID NO 496
<211> LENGTH: 342
<212> TYPE: DNA
<213> ORGANISM: Steptococcus agalactiae

<400> SEQUENCE: 496

```
atgagttatc ggtatatgag aatgatttta atgtttgata tgcctactga aacagtagaa     60

gaacgtaagg cgtatcgtaa gtttagaaag tttctgttga gcgaaggttt tattatgcat    120

cagttctctg tttatagtaa attattgctc aataatacag ctaataatgc catgataggt    180

cggcttaaag tgaataatcc taagaaaggg agtataactc ttttgacagt taccgagaag    240

cagtttgcaa ggatggttta tctacatggt gaacataata tgagtgttgc caactctgat    300
```

agtcgcttgg ttttcctagg agattcttat gatcaagatt aa 342

<210> SEQ ID NO 497
<211> LENGTH: 666
<212> TYPE: DNA
<213> ORGANISM: Steptococcus agalactiae

<400> SEQUENCE: 497
atgatcaaga ttaattttcc aattttagat gaaccattag tgttaagtaa tgctacgatt 60
ttaacgatag aagatgtttc agtttattct tcattggtga aacattttta tcaatatgac 120
gtagatgaac atttgaaatt atttgatgat aagcagaaaa gtctgaaggc aacggagtta 180
atgttagtta cagatatctt aggatacgat gtcaactcag cacctattct aaagttgata 240
catggtgact tagaaaatca attcaacgaa aagccagaag tgaaatcaat ggtagaaaaa 300
ttagcagcta ctattacaga acttatcgca tttgagtgtc tagagaatga gcttgattta 360
gaatacgatg aaattacgat tttagaactc attaaggcac tgggagtcaa aattgagaca 420
cagagcgaca ctatctttga aaaatgtttt gaaattatac aagtttacca ttatttaacg 480
aaaaagaatc tcttagtttt tgttaatagc ggagcttatc ttaccaaaga tgaagttata 540
aaattatgtg aatacatcaa tttaatgcaa aagtcagtac tctttctaga acctagaaga 600
ctctatgatt taccgcaata tgttattgat aaggattatt tcttgatagg cgaaaatatg 660
gtataa 666

<210> SEQ ID NO 498
<211> LENGTH: 6580
<212> TYPE: DNA
<213> ORGANISM: Steptococcus mutans

<400> SEQUENCE: 498
atgaaaaaac cttactctat tggacttgat attggaacca attctgttgg ttgggctgtt 60
gtgacagatg actacaaagt tcctgctaag aagatgaagg ttctgggaaa tacagataaa 120
agtcatatcg agaaaaattt gcttggcgct ttattatttg atagcgggaa tactgcagaa 180
gacagacggt taaagagaac tgctcgccgt cgttacacac gtcgcagaaa tcgtatttta 240
tatttgcaag agatttttc agaagaaatg ggcaaggtag atgatagttt ctttcatcgt 300
ttagaggatt cttttcttgt tactgaggat aaacgaggag agcgccatcc catttttggg 360
aatcttgaag aagaagttaa gtatcatgaa aattttccaa ccatttatca tttgcggcaa 420
tatcttgcgg ataatccaga aaaagttgat ttgcgtttag tttatttggc tttggcacat 480
ataattaagt ttagaggtca ttttttaatt gaaggaaagt ttgatacacg caataatgat 540
gtacaaagac tgtttcaaga atttttagca gtctatgata atacttttga gaatagttcg 600
cttcaggagc aaaatgttca agttgaagaa attctgactg ataaaatcag taaatctgct 660
aagaaagata gagttttgaa actttttcct aatgaaaagt ctaatggccg ctttgcagaa 720
tttctaaaac taattgttgg taatcaagct gattttaaaa agcattttga attagaagag 780
aaagcaccat tgcaattttc taaagatact tatgaagaag agttagaagt actattagct 840
caaattggag ataattacgc agagctcttt ttatcagcaa agaaactgta tgatagtatc 900
cttttatcag ggattttaac agttactgat gttggtacca aagcgccttt atctgcttcg 960
atgattcagc gatataatga acatcagatg gatttagctc agcttaaaca attcattcgt 1020
cagaaattat cagataaata taacgaagtt ttttctgatg tttcaaaaga cggctatgcg 1080
ggttatattg atgggaaaac aaatcaagaa gctttttata aataccttaa aggtctatta 1140
aataagattg agggaagtgg ctatttcctt gataaaattg agcgtgaaga ttttctaaga 1200
aagcaacgta cctttgacaa tggctctatt ccacatcaga ttcatcttca agaaatgcgt 1260
gctatcattc gtagacaggc tgaattttat ccgtttttag cagacaatca agataggatt 1320
gagaaattat tgactttccg tattccctac tatgttggtc cattagcgcg cggaaaaagt 1380
gattttgctt ggttaagtcg gaaatcggct gataaaatta caccatggaa ttttgatgaa 1440
atcgttgata aagaatcctc tgcagaagct tttatcaatc gtatgacaaa ttatgatttg 1500
tacttgccaa atcaaaaagt tcttcctaaa catagtttat tatacgaaaa atttactgtt 1560
tacaatgaat taacaaaggt taaatataaa acagagcaag gaaaaacagc atttttttgat 1620
gccaatatga agcaagaaat ctttgatggc gtatttaagg tttatcgaaa agtaactaaa 1680
gataaattaa tggatttcct tgaaaaagaa tttgatgaat ttcgtattgt tgatttaaca 1740
ggtctggata aagaaaataa agtatttaac gcttcttatg gaacttatca tgatttgtgt 1800
aaaattttag ataaagattt tctcgataat tcaaagaatg aaaagatttt agaagatatt 1860
gtgttgacct taacgttatt tgaagataga gaaatgatta gaaaacgtct agaaaattac 1920
agtgatttat tgaccaaaga acaagtgaaa aagctggaaa gacgtcatta tactggttgg 1980
ggaagattat cagctgagtt aattcatggt attcgcaata aagaaagcag aaaaacaatt 2040
cttgattatc tcattgatga tggcaatagc aatcggaact ttatgcaact gattaacgat 2100
gatgctcttt ctttcaaaga agagattgct aaggcacaag ttattggaga aacagacaat 2160
ctaaatcaag ttgttagtga tattgctggc agccctgcta ttaaaaaagg aattttacaa 2220
agcttgaaga ttgttgatga gcttgtcaaa attatgggac atcaacctga aaatatcgtc 2280
gtggagatgg cgcgtgaaaa ccagtttacc aatcagggac gacgaaattc acagcaacgt 2340
ttgaaaggtt tgacagattc tattaaagaa tttggaagtc aaattcttaa agaacatccg 2400
gttgagaatt cacagttaca aaatgataga ttgtttctat attatttaca aaacggcaga 2460
gatatgtata ctggagaaga attggatatt gattatctaa gccagtatga tatagaccat 2520
attatcccgc aagcttttat aaaggataat tctattgata atagagtatt gactagctca 2580
aaggaaaatc gtggaaaatc ggatgatgta ccaagtaaag atgttgttcg taaaatgaaa 2640
tcctattgga gtaagctact ttcggcaaag cttattacac aacgtaaatt tgataatttg 2700
acaaaagctg aacgaggtgg attgaccgac gatgataaag ctggattcat caagcgtcaa 2760
ttagtagaaa cacgacaaat taccaaacat gtagcacgta ttctggacga acgatttaat 2820
acagaaacag atgaaaacaa caagaaaatt cgtcaagtaa aaattgtgac cttgaaatca 2880
aatcttgttt ccaatttccg taaagagttt gaactctaca aagtgcgtga aattaatgac 2940
tatcatcatg cacatgatgc ctatctcaat gctgtaattg gaaaggcttt actaggtgtt 3000
tacccacaat tggaacctga atttgtttat ggtgattatc ctcattttca tggacataaa 3060
gaaaataaag caactgctaa gaaatttttc tattcaaata ttatgaactt ctttaaaaaa 3120
gatgatgtcc gtactgataa aaatggtgaa attatctgga aaaaagatga gcatatttct 3180
aatattaaaa aagtgctttc ttatccacaa gttaatattg ttaagaaagt agaggagcaa 3240
acgggaggat tttctaaaga atctatcttg ccgaaaggta attctgacaa gcttattcct 3300
cgaaaaacga agaaatttta ttgggatacc aagaaatatg gaggatttga tagcccgatt 3360
gttgcttatt ctattttagt tattgctgat attgaaaaag gtaaatctaa aaaattgaaa 3420
acagtcaaag ccttagttgg tgtcactatt atggaaaaga tgacttttga aagggatcca 3480

```
gttgcttttc ttgagcgaaa aggctatcga aatgttcaag aagaaaatat tataaagtta   3540
ccaaaatata gtttatttaa actagaaaac ggacgaaaaa ggctattggc aagtgctagg   3600
gaacttcaaa agggaaatga aatcgttttg ccaaatcatt taggaacctt gctttatcac   3660
gctaaaaata ttcataaagt tgatgaacca aagcatttgg actatgttga taaacataaa   3720
gatgaattta aggagttgct agatgttgtg tcaaactttt ctaaaaaata tactttagca   3780
gaaggaaatt tagaaaaaat caaagaatta tatgcacaaa ataatggtga agatcttaaa   3840
gaattagcaa gttcatttat caacttatta acatttactg ctataggagc accggctact   3900
tttaaattct ttgataaaaa tattgatcga aaacgatata cttcaactac tgaaattctc   3960
aacgctaccc tcatccacca atccatcacc ggtctttatg aaacgcggat tgatctcaat   4020
aagttaggag gagactaatg ggctggcgga cagtggttgt taatacgcat tccaagttgt   4080
cttataagaa caaccacttg atttttaaag atgcttatca gacagagatg attcatctgt   4140
ctgagattga catcttatta cttgagacaa cagatattgt tttgtcaact atgctaatca   4200
aacgcttggt tgatgagaat attttggtca ttttttgtga tgacaaacgt ctgccaacag   4260
ccatgctcat gccttactat gcgcgtcacg attccagctt gcagctgagt catcagattt   4320
cttggacaga agaagtgaaa tgcgatgtct ggacaacaat catcgctcaa aagattttga   4380
atcagtcatg ttatttggga gaatgttttt attttgaaaa atctcagtca attatggatt   4440
tatatcatga cttagagcct tttgacccta gtaatcgaga aggacattct gcgcggattt   4500
atttcaatac cttatttgga aatgtttttt ccagagaaca agataatgat attaatgcag   4560
gtcttgacta tggttatacg ctgctgttaa gtatgtttgc gcgtgaagtg gttgtatctg   4620
gctgtatgac acaatttggt ctcaagcatg ccaaccaatt caatcagttt aactttgcca   4680
gtgatattat ggagcctttt cgtccaattg ttgaccgtat tgtttatgaa aatcgaaata   4740
actcttttat taaaataaaa cgtgagctat tcagcatgtt ttcagacacc tatctttata   4800
ataataagga gatgtatttg acaaatattg tcagcgatta taccaaaaag gtaatcaagg   4860
cgctgaataa tgatgggaaa ggagttcctg agtttaggat atgagttacc gatatatgcg   4920
aatgatttta atgtttgata tgccaacaga tactgctgag gaacgcaaag cttatcgtaa   4980
atttcggaaa tttttactga gcgaaggttt catcatgcat cagttttcag tatacagcaa   5040
gctgcttttg aataactctg ccaatacagc catgattgcc cgcttgaagg agaataatcc   5100
aaagaagggc aatatcacct tgttgaccgt gactgaaaag cagtttgccc gtatgattta   5160
cctgaatggt gagcgtgata ctagcattgc taattcggat tcacgactgg tctttctagg   5220
ggaggctttt cctgatgaaa cttaattttc ctatattgga tgaaccaata actcttgaaa   5280
aatctacgat tttggtatta gaagatgtgc aagtttttgc tcaaatggtg agaaatcttt   5340
atcaatatga tgaagatagt gaacttaaat tttttaatag aaaatttaag agtctgaaac   5400
catctgagtt aatgcttgtg acagatattt taggttatga tgtcaatgcc ccgtccttgc   5460
tgaagttggt tcacgctgat ttagaaaatc agtttaatga aaaaccagag gttaagtcta   5520
tggttgaaaa actggcaaat accattacgg aattaattgc ttatgaatgt ttagaaaatg   5580
aattggactt agaatatgat gagattacta ttttagagtt aatcaaagct ttaggcgtca   5640
aaattgaaac acaaagtgat accatttttg aaaaaatgtt tgaagtcctt caagtttata   5700
agtatctaaa taaaaagaag cttctcgttt ttatcaatac tttatcctat tttaaaagag   5760
aagaaatcgc gcaaattcta gaatatattc acttatccga tatggttgtt ttatttcttg   5820
```

```
aaccccgtaa aattgatggt tttgctcaat atattttaga tgaagattat ttcttgataa   5880

cagaaagcaa caactaaata cgaataataa gatagtttct aaatcagggg ctgtctttta   5940

ttatggattg acaaatgcgt ataatgcgta taaaataaaa agagaaatgt tatttgccat   6000

taacagggaa agaattagct aaattagcga taaacaatgg atgggaagaa gttcgggtga   6060

gaggaagtca tcatcatttc aagaaagatg gagtatctta tattgtgacg attcctattc   6120

atggaaataa agtgcttaaa attggtcttg aaaagaaact cttaagggat ttaaatttat   6180

tatgatagag gaggaagtcg tcatgttaaa atcatatcct gtaatttttc ataaggaaga   6240

ggaagggtat tgggttgaat ttcctgaatt tggcggtggt acgcaagggg aagatttgga   6300

agaagccatg aagaacgctc gtcagatgtt agaaagtgtg ttggcatctt atcttgatga   6360

agggttggtt ctacccattt caagcgatat tcagaaaata tctgttgaag atggttttgc   6420

gaccatgatt caagctgatc ctagtcctta tctcaaaaat aacaaagcta ttcggaaaaa   6480

tgttaccgtg cctgagtggt tgatacgatt agcagaccgt gaccgagtaa attattctga   6540

agtattaaca aaggctttgg aaaagaaact acaattataa                         6580
```

<210> SEQ ID NO 499
<211> LENGTH: 4038
<212> TYPE: DNA
<213> ORGANISM: Steptococcus mutans

<400> SEQUENCE: 499

```
atgaaaaaac cttactctat tggacttgat attggaacca attctgttgg ttgggctgtt     60

gtgacagatg actacaaagt tcctgctaag aagatgaagg ttctgggaaa tacagataaa    120

agtcatatcg agaaaaattt gcttggcgct ttattatttg atagcgggaa tactgcagaa    180

gacagacggt taaagagaac tgctcgccgt cgttacacac gtcgcagaaa tcgtatttta    240

tatttgcaag agatttttc agaagaaatg ggcaaggtag atgatagttt ctttcatcgt     300

ttagaggatt cttttcttgt tactgaggat aaacgaggag agcgccatcc catttttggg    360

aatcttgaag aagaagttaa gtatcatgaa aattttccaa ccatttatca tttgcggcaa    420

tatcttgcgg ataatccaga aaaagttgat ttgcgtttag tttatttggc tttggcacat    480

ataattaagt ttagaggtca ttttttaatt gaaggaaagt ttgatacacg caataatgat    540

gtacaaagac tgtttcaaga atttttagca gtctatgata atacttttga gaatagttcg    600

cttcaggagc aaaatgttca agttgaagaa attctgactg ataaaatcag taaatctgct    660

aagaaagata gagttttgaa acttttttcct aatgaaaagt ctaatggccg ctttgcagaa   720

tttctaaaac taattgttgg taatcaagct gattttaaaa agcattttga attagaagag    780

aaagcaccat tgcaattttc taaagatact tatgaagaag agttagaagt actattagct    840

caaattggag ataattacgc agagctcttt ttatcagcaa agaaactgta tgatagtatc    900

cttttatcag ggattttaac agttactgat gttggtacca aagcgccttt atctgcttcg    960

atgattcagc gatataatga acatcagatg gatttagctc agcttaaaca attcattcgt   1020

cagaaattat cagataaata taacgaagtt ttttctgatg tttcaaaaga cggctatgcg   1080

ggttatattg atgggaaaac aaatcaagaa gctttttata aataccttaa aggtctatta   1140

aataagattg agggaagtgg ctatttcctt gataaaattg agcgtgaaga ttttctaaga   1200

aagcaacgta cctttgacaa tggctctatt ccacatcaga ttcatcttca agaaatgcgt   1260

gctatcattc gtagacaggc tgaattttat ccgtttttag cagacaatca agataggatt   1320

gagaaattat tgactttccg tattccctac tatgttggtc cattagcgcg cggaaaaagt   1380
```

```
gattttgctt ggttaagtcg gaaatcggct gataaaatta caccatggaa ttttgatgaa   1440
atcgttgata aagaatcctc tgcagaagct tttatcaatc gtatgacaaa ttatgatttg   1500
tacttgccaa atcaaaaagt tcttcctaaa catagtttat tatacgaaaa atttactgtt   1560
tacaatgaat taacaaaggt taaatataaa acagagcaag gaaaaacagc atttttgat    1620
gccaatatga agcaagaaat ctttgatggc gtatttaagg tttatcgaaa agtaactaaa   1680
gataaattaa tggatttcct tgaaaaagaa tttgatgaat ttcgtattgt tgatttaaca   1740
ggtctggata aagaaaataa agtatttaac gcttcttatg gaacttatca tgatttgtgt   1800
aaaattttag ataaagattt tctcgataat tcaaagaatg aaaagatttt agaagatatt   1860
gtgttgacct taacgttatt tgaagataga gaaatgatta gaaaacgtct agaaaattac   1920
agtgatttat tgaccaaaga acaagtgaaa aagctggaaa gacgtcatta tactggttgg   1980
ggaagattat cagctgagtt aattcatggt attcgcaata aagaaagcag aaaaacaatt   2040
cttgattatc tcattgatga tggcaatagc aatcggaact ttatgcaact gattaacgat   2100
gatgctcttt ctttcaaaga agagattgct aaggcacaag ttattggaga aacagacaat   2160
ctaaatcaag ttgttagtga tattgctggc agccctgcta ttaaaaaagg aattttacaa   2220
agcttgaaga ttgttgatga gcttgtcaaa attatgggac atcaacctga aaatatcgtc   2280
gtggagatgg cgcgtgaaaa ccagtttacc aatcagggac gacgaaattc acagcaacgt   2340
ttgaaaggtt tgacagattc tattaaagaa tttggaagtc aaattcttaa agaacatccg   2400
gttgagaatt cacagttaca aaatgataga ttgtttctat attatttaca aaacggcaga   2460
gatatgtata ctggagaaga attggatatt gattatctaa gccagtatga tatagaccat   2520
attatcccgc aagcttttat aaaggataat tctattgata atagagtatt gactagctca   2580
aaggaaaatc gtggaaaatc ggatgatgta ccaagtaaag atgttgttcg taaaatgaaa   2640
tcctattgga gtaagctact ttcggcaaag cttattacac aacgtaaatt tgataatttg   2700
acaaaagctg aacgaggtgg attgaccgac gatgataaag ctggattcat caagcgtcaa   2760
ttagtagaaa cacgacaaat taccaaacat gtagcacgta ttctggacga acgatttaat   2820
acagaaacag atgaaaacaa caagaaaatt cgtcaagtaa aaattgtgac cttgaaatca   2880
aatcttgttt ccaatttccg taaagagttt gaactctaca aagtgcgtga aattaatgac   2940
tatcatcatg cacatgatgc ctatctcaat gctgtaattg gaaaggcttt actaggtgtt   3000
tacccacaat tggaacctga atttgtttat ggtgattatc ctcattttca tggacataaa   3060
gaaaataaag caactgctaa gaaatttttc tattcaaata ttatgaactt ctttaaaaaa   3120
gatgatgtcc gtactgataa aaatggtgaa attatctgga aaaaagatga gcatatttct   3180
aatattaaaa aagtgctttc ttatccacaa gttaatattg ttaagaaagt agaggagcaa   3240
acgggaggat tttctaaaga atctatcttg ccgaaaggta attctgacaa gcttattcct   3300
cgaaaaacga agaaatttta ttgggatacc aagaaatatg gaggatttga tagcccgatt   3360
gttgcttatt ctattttagt tattgctgat attgaaaaag gtaaatctaa aaaattgaaa   3420
acagtcaaag ccttagttgg tgtcactatt atggaaaaga tgacttttga aagggatcca   3480
gttgcttttc ttgagcgaaa aggctatcga aatgttcaag aagaaaatat tataaagtta   3540
ccaaaatata gtttatttaa actagaaaac ggacgaaaaa ggctattggc aagtgctagg   3600
gaacttcaaa agggaaatga aatcgttttg ccaaatcatt taggaacctt gctttatcac   3660
gctaaaaata ttcataaagt tgatgaacca aagcatttgg actatgttga taaacataaa   3720
```

-continued gatgaattta aggagttgct agatgttgtg tcaaactttt ctaaaaaata tactttagca 3780
gaaggaaatt tagaaaaaat caaagaatta tatgcacaaa ataatggtga agatcttaaa 3840
gaattagcaa gttcatttat caacttatta acatttactg ctataggagc accggctact 3900
tttaaattct ttgataaaaa tattgatcga aaacgatata cttcaactac tgaaattctc 3960
aacgctaccc tcatccacca atccatcacc ggtctttatg aaacgcggat tgatctcaat 4020
aagttaggag gagactaa 4038

<210> SEQ ID NO 500
<211> LENGTH: 867
<212> TYPE: DNA
<213> ORGANISM: Steptococcus mutans

<400> SEQUENCE: 500
atgggctggc ggacagtggt tgttaatacg cattccaagt tgtcttataa gaacaaccac 60
ttgattttta aagatgctta tcagacagag atgattcatc tgtctgagat tgacatctta 120
ttacttgaga caacagatat tgttttgtca actatgctaa tcaaacgctt ggttgatgag 180
aatattttgg tcattttttg tgatgacaaa cgtctgccaa cagccatgct catgccttac 240
tatgcgcgtc acgattccag cttgcagctg agtcatcaga tttcttggac agaagaagtg 300
aaatgcgatg tctggacaac aatcatcgct caaaagattt tgaatcagtc atgttatttg 360
ggagaatgtt tttattttga aaaatctcag tcaattatgg atttatatca tgacttagag 420
ccttttgacc ctagtaatcg agaaggacat tctgcgcgga tttatttcaa taccttattt 480
ggaaatgttt tttccagaga acaagataat gatattaatg caggtcttga ctatggttat 540
acgctgctgt taagtatgtt tgcgcgtgaa gtggttgtat ctggctgtat gacacaattt 600
ggtctcaagc atgccaacca attcaatcag tttaactttg ccagtgatat tatggagcct 660
tttcgtccaa ttgttgaccg tattgtttat gaaaatcgaa ataactcttt tattaaaata 720
aaacgtgagc tattcagcat gttttcagac acctatcttt ataataataa ggagatgtat 780
ttgacaaata ttgtcagcga ttataccaaa aaggtaatca aggcgctgaa taatgatggg 840
aaaggagttc ctgagtttag gatatga 867

<210> SEQ ID NO 501
<211> LENGTH: 330
<212> TYPE: DNA
<213> ORGANISM: Steptococcus mutans

<400> SEQUENCE: 501
atgcgaatga ttttaatgtt tgatatgcca acagatactg ctgaggaacg caaagcttat 60
cgtaaatttc ggaaattttt actgagcgaa ggtttcatca tgcatcagtt ttcagtatac 120
agcaagctgc ttttgaataa ctctgccaat acagccatga ttgcccgctt gaaggagaat 180
aatccaaaga agggcaatat caccttgttg accgtgactg aaaagcagtt tgcccgtatg 240
atttacctga atggtgagcg tgatactagc attgctaatt cggattcacg actggtcttt 300
ctaggggagg cttttcctga tgaaacttaa 330

<210> SEQ ID NO 502
<211> LENGTH: 573
<212> TYPE: DNA
<213> ORGANISM: Steptococcus mutans

<400> SEQUENCE: 502
atggtgagaa atctttatca atatgatgaa gatagtgaac ttaaattttt taatagaaaa 60

```
tttaagagtc tgaaaccatc tgagttaatg cttgtgacag atattttagg ttatgatgtc    120

aatgccccgt ccttgctgaa gttggttcac gctgatttag aaaatcagtt taatgaaaaa    180

ccagaggtta agtctatggt tgaaaaactg gcaaatacca ttacggaatt aattgcttat    240

gaatgtttag aaaatgaatt ggacttagaa tatgatgaga ttactatttt agagttaatc    300

aaagctttag gcgtcaaaat tgaaacacaa agtgatacca tttttgaaaa aatgtttgaa    360

gtccttcaag tttataagta tctaaataaa aagaagcttc tcgtttttat caatacttta    420

tcctatttta aaagagaaga aatcgcgcaa attctagaat atattcactt atccgatatg    480

gttgttttat ttcttgaacc ccgtaaaatt gatggttttg ctcaatatat tttagatgaa    540

gattatttct tgataacaga aagcaacaac taa                                  573
```

```
<210> SEQ ID NO 503
<211> LENGTH: 378
<212> TYPE: DNA
<213> ORGANISM: Steptococcus mutans

<400> SEQUENCE: 503

atgttaaaat catatcctgt aatttttcat aaggaagagg aagggtattg ggttgaattt     60

cctgaatttg gcggtggtac gcaaggggaa gatttggaag aagccatgaa gaacgctcgt    120

cagatgttag aaagtgtgtt ggcatcttat cttgatgaag ggttggttct acccatttca    180

agcgatattc agaaaatatc tgttgaagat ggttttgcga ccatgattca agctgatcct    240

agtccttatc tcaaaaataa caaagctatt cggaaaaatg ttaccgtgcc tgagtggttg    300

atacgattag cagaccgtga ccgagtaaat tattctgaag tattaacaaa ggctttggaa    360

aagaaactac aattataa                                                  378
```

```
<210> SEQ ID NO 504
<211> LENGTH: 5966
<212> TYPE: DNA
<213> ORGANISM: Steptococcus pyogenes

<400> SEQUENCE: 504

atggataaga aatactcaat aggcttagat atcggcacaa atagcgtcgg atgggcggtg     60

atcactgatg aatataaggt tccgtctaaa aagttcaagg ttctgggaaa tacagaccgc    120

cacagtatca aaaaaaatct tataggggct cttttatttg acagtggaga gacagcggaa    180

gcgactcgtc tcaaacggac agctcgtaga aggtatacac gtcggaagaa tcgtatttgt    240

tatctacagg agatttttc aaatgagatg gcgaaagtag atgatagttt ctttcatcga    300

cttgaagagt cttttttggt ggaagaagac aagaagcatg aacgtcatcc tatttttgga    360

aatatagtag atgaagttgc ttatcatgag aaatatccaa ctatctatca tctgcgaaaa    420

aaattggtag attctactga taaagcggat ttgcgcttaa tctatttggc cttagcgcat    480

atgattaagt ttcgtggtca tttttgatt gagggagatt taaatcctga taatagtgat    540

gtggacaaac tatttatcca gttggtacaa acctacaatc aattatttga agaaaaccct    600

attaacgcaa gtggagtaga tgctaaagcg attctttctg cacgattgag taaatcaaga    660

cgattagaaa atctcattgc tcagctcccc ggtgagaaga aaaatggctt atttgggaat    720

ctcattgctt tgtcattggg tttgacccct aattttaaat caaattttga tttggcagaa    780

gatgctaaat tacagctttc aaaagatact tacgatgatg atttagataa tttattggcg    840

caaattggag atcaatatgc tgatttgttt ttggcagcta agaatttatc agatgctatt    900
```

-continued

```
ttactttcag atatcctaag agtaaatact gaaataacta aggctcccct atcagcttca    960
atgattaaac gctacgatga acatcatcaa gacttgactc ttttaaaagc tttagttcga   1020
caacaacttc cagaaaagta taaagaaatc tttttttgatc aatcaaaaaa cggatatgca   1080
ggttatattg atgggggagc tagccaagaa gaattttata aatttatcaa accaatttta   1140
gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctattttga gaagacaaga agacttttat ccatttttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggtacct accatgattt gctaaaaatt   1800
attaaagata aagatttttt ggataatgaa gaaaatgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttga aatcagatgg ttttgccaat cgcaatttta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta aagtgattac cttaaaatct   2880
aaattagttt ctgacttccg aaaagatttc caattctata aagtacgtga gattaacaat   2940
taccatcatg cccatgatgc gtatctaaat gccgtcgttg gaactgcttt gattaagaaa   3000
tatccaaaac ttgaatcgga gtttgtctat ggtgattata aagtttatga tgttcgtaaa   3060
atgattgcta agtctgagca agaaataggc aaagcaaccg caaaatattt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
```

cagacaggcg gattctccaa ggagtcaatt ttaccaaaaa gaaattcgga caagcttatt 3360
gctcgtaaaa aagactggga tccaaaaaaa tatggtggtt ttgatagtcc aacggtagct 3420
tattcagtcc tagtggttgc taaggtggaa aaagggaaat cgaagaagtt aaaatccgtt 3480
aaagagttac tagggatcac aattatggaa agaagttcct ttgaaaaaaa tccgattgac 3540
tttttagaag ctaaaggata taaggaagtt aaaaaagact taatcattaa actacctaaa 3600
tatagtcttt ttgagttaga aaacggtcgt aaacggatgc tggctagtgc cggagaatta 3660
caaaaaggaa atgagctggc tctgccaagc aaatatgtga atttttata tttagctagt 3720 cattatgaaa agttgaaggg tagtccagaa gataacgaac aaaaacaatt gtttgtggag 3780
cagcataagc attatttaga tgagattatt gagcaaatca gtgaattttc taagcgtgtt 3840
attttagcag atgccaattt agataaagtt cttagtgcat ataacaaaca tagagacaaa 3900
ccaatacgtg aacaagcaga aaatattatt catttattta cgttgacgaa tcttggagct 3960
cccgctgctt ttaaatattt tgatacaaca attgatcgta aacgatatac gtctacaaaa 4020
gaagttttag atgccactct tatccatcaa tccatcactg gtctttatga aacacgcatt 4080
gatttgagtc agctaggagg tgactgatgg ctggttggcg tactgttgtg gtaaataccc 4140
actcgaaatt atcctataag aataatcatc tgatttttaa ggatgcctat aaaacggagc 4200
tgatccattt atcagaaatt gatattttgt tattagaaac gaccgatatt gtcttgtcca 4260
ctatgctggt aaaacggcta gtggatgaga atgtccttgt catattctgt gatgataaac 4320
gattaccaac agctatgctg atgccttttt atggtcgtca tgattcgagt ttacagcttg 4380
ggaaacaaat gtcctggtca gaaacagtca aatcgcaggt ttggacgacg attattgctc 4440
aaaagatttt gaatcaatct tgctatctag gagcatgctc ctattttgaa aaatcccaat 4500
ctattatgga tttatatcat ggtttggaaa attttgatcc gagtaatcga gaagggcatg 4560
cagcgagaat ttattttaat acactttttg ggaacgattt ctcaagagat ttggagcatc 4620
caatcaatgc aggtctggat tatggttata ctttattatt gagtatgttt gcgcgtgaag 4680
tggttgtgtc tggatgtatg actcagtttg ggcttaaaca cgctaatcag tttaatcagt 4740
tcaattttgc tagcgatatt atggaaccat ttaggccttt agtggataag attgtttatg 4800
aaaatcgaaa tcagcctttt cccaaaataa agagagagtt atttactttg ttttcagata 4860
cattttcata taatggtaaa gagatgtatc tcacgaatat tattagcgat tatactaaaa 4920
aagttgtcaa agctctgaat aatgaaggga aaggagttcc tgaatttagg atatgagtta 4980
tagatatatg agaatgatac ttatgtttga tatgccgacg gacaccgctg aggaacgaaa 5040
agcctatcga aaatttcgga aatttttact tagtgaaggg tttatcatgc atcaattttc 5100
tatttatagt aagttgctgt tgaataatac agctaacaat gccatgattg gtcggctgag 5160
ggagcataat cctaataaag gaaatattac attactaacg gtcacggaaa aacagtttgc 5220
acgaatgatt tatttacatg gtgaaagaaa taattgtatt gcaaactccg atgaaagact 5280
tgtatttctt ggggaggctt ttgatgaatc ttaatttttc cttactagat gaaccgattc 5340
cattaagagg cggtacaatt cttgtgctcg aagatgtctg tgtattttca aaaatagtgc 5400
aatattgtta ccaatatgag gaagattctg aacttaaatt ttttgatcac aagatgaaaa 5460
caatcaaaga atcagaaatc atgcttgtaa cagatatttt aggatttgat gttaactcct 5520
caaccatttt aaaattgatt catgcagatt tagaatctca atttaatgag aaacccgaag 5580
tgaaatcgat gattgacaaa ttggttgcta cgattacaga actgattgtc tttgaatgct 5640
tagaaaatga attagattta gagtatgatg aaatcacaat cctggaattg attaagtcct 5700
taggagtaaa agtagaaacg caaagtgata ctatttttga aaaatgtcta gagatacttc 5760
aaattttcaa atatctcact aagaaaaagt tgcttatttt tgtcaatagc ggagcttttc 5820
taacaaagga tgaagtggct agtttacaag agtatatatc attgacaaat ttaacagttc 5880
tctttttaga accacgtgaa ctatatgatt ttccgcagta tattttagat gaagattatt 5940
tcttaataac taaaaatatg gtataa 5966

<210> SEQ ID NO 505
<211> LENGTH: 4107
<212> TYPE: DNA
<213> ORGANISM: Steptococcus pyogenes

<400> SEQUENCE: 505
atggataaga aatactcaat aggcttagat atcggcacaa atagcgtcgg atgggcggtg 60
atcactgatg aatataaggt tccgtctaaa aagttcaagg ttctgggaaa tacagaccgc 120
cacagtatca aaaaaaatct tataggggct cttttatttg acagtggaga gacagcggaa 180
gcgactcgtc tcaaacggac agctcgtaga aggtatacac gtcggaagaa tcgtatttgt 240
tatctacagg agattttttc aaatgagatg gcgaaagtag atgatagttt ctttcatcga 300
cttgaagagt cttttttggt ggaagaagac aagaagcatg aacgtcatcc tatttttgga 360
aatatagtag atgaagttgc ttatcatgag aaatatccaa ctatctatca tctgcgaaaa 420
aaattggtag attctactga taaagcggat ttgcgcttaa tctatttggc cttagcgcat 480
atgattaagt ttcgtggtca tttttttgatt gagggagatt taaatcctga taatagtgat 540
gtggacaaac tatttatcca gttggtacaa acctacaatc aattatttga agaaaaccct 600
attaacgcaa gtggagtaga tgctaaagcg attctttctg cacgattgag taaatcaaga 660
cgattagaaa atctcattgc tcagctcccc ggtgagaaga aaaatggctt atttgggaat 720
ctcattgctt tgtcattggg tttgacccct aattttaaat caaattttga tttggcagaa 780
gatgctaaat tacagctttc aaaagatact tacgatgatg atttagataa tttattggcg 840
caaattggag atcaatatgc tgatttgttt ttggcagcta agaatttatc agatgctatt 900
ttactttcag atatcctaag agtaaatact gaaataacta aggctcccct atcagcttca 960
atgattaaac gctacgatga acatcatcaa gacttgactc ttttaaaagc tttagttcga 1020
caacaacttc cagaaaagta taaagaaatc ttttttgatc aatcaaaaaa cggatatgca 1080
ggttatattg atgggggagc tagccaagaa gaattttata aatttatcaa accaatttta 1140
gaaaaaatgg atggtactga ggaattattg gtgaaactaa atcgtgaaga tttgctgcgc 1200
aagcaacgga cctttgacaa cggctctatt ccccatcaaa ttcacttggg tgagctgcat 1260
gctattttga gaagacaaga agacttttat ccatttttaa aagacaatcg tgagaagatt 1320
gaaaaaatct tgacttttcg aattccttat tatgttggtc cattggcgcg tggcaatagt 1380
cgttttgcat ggatgactcg gaagtctgaa gaaacaatta ccccatggaa ttttgaagaa 1440
gttgtcgata aaggtgcttc agctcaatca tttattgaac gcatgacaaa ctttgataaa 1500
aatcttccaa atgaaaaagt actaccaaaa catagtttgc tttatgagta ttttacggtt 1560
tataacgaat tgacaaaggt caaatatgtt actgaaggaa tgcgaaaacc agcatttctt 1620
tcaggtgaac agaagaaagc cattgttgat ttactcttca aaacaaatcg aaaagtaacc 1680
gttaagcaat taaaagaaga ttatttcaaa aaaatagaat gttttgatag tgttgaaatt 1740
tcaggagttg aagatagatt taatgcttca ttaggtacct accatgattt gctaaaaatt 1800

```
attaaagata aagatttttt ggataatgaa gaaaatgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttga aatcagatgg ttttgccaat cgcaatttta tgcagctgat ccatgatgat    2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta aagtgattac cttaaaatct   2880
aaattagttt ctgacttccg aaaagatttc caattctata aagtacgtga gattaacaat   2940
taccatcatg cccatgatgc gtatctaaat gccgtcgttg gaactgcttt gattaagaaa   3000
tatccaaaac ttgaatcgga gtttgtctat ggtgattata aagtttatga tgttcgtaaa   3060
atgattgcta agtctgagca agaaataggc aaagcaaccg caaaatattt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
aaagagttac tagggatcac aattatggaa agaagttcct ttgaaaaaaa tccgattgac   3540
tttttagaag ctaaaggata taaggaagtt aaaaaagact taatcattaa actacctaaa   3600
tatagtcttt ttgagttaga aaacggtcgt aaacggatgc tggctagtgc cggagaatta   3660
caaaaaggaa atgagctggc tctgccaagc aaatatgtga atttttata tttagctagt    3720
cattatgaaa agttgaaggg tagtccagaa gataacgaac aaaaacaatt gtttgtggag   3780
cagcataagc attatttaga tgagattatt gagcaaatca gtgaattttc taagcgtgtt   3840
attttagcag atgccaattt agataaagtt cttagtgcat ataacaaaca tagagacaaa   3900
ccaatacgtg aacaagcaga aaatattatt catttattta cgttgacgaa tcttggagct   3960
cccgctgctt ttaaatattt tgatacaaca attgatcgta aacgatatac gtctacaaaa   4020
gaagttttag atgccactct tatccatcaa tccatcactg gtctttatga aacacgcatt   4080
gatttgagtc agctaggagg tgactga                                       4107
```

<210> SEQ ID NO 506
<211> LENGTH: 870
<212> TYPE: DNA
<213> ORGANISM: Steptococcus pyogenes

<400> SEQUENCE: 506
atggctggtt ggcgtactgt tgtggtaaat acccactcga aattatccta taagaataat 60
catctgattt ttaaggatgc ctataaaacg gagctgatcc atttatcaga aattgatatt 120
ttgttattag aaacgaccga tattgtcttg tccactatgc tggtaaaacg gctagtggat 180
gagaatgtcc ttgtcatatt ctgtgatgat aaacgattac caacagctat gctgatgcct 240
ttttatggtc gtcatgattc gagtttacag cttgggaaac aaatgtcctg gtcagaaaca 300
gtcaaatcgc aggtttggac gacgattatt gctcaaaaga ttttgaatca atcttgctat 360
ctaggagcat gctcctattt tgaaaaatcc caatctatta tggatttata tcatggtttg 420
gaaaattttg atccgagtaa tcgagaaggg catgcagcga gaatttattt taatacactt 480
tttgggaacg atttctcaag agatttggag catccaatca atgcaggtct ggattatggt 540
tatactttat tattgagtat gtttgcgcgt gaagtggttg tgtctggatg tatgactcag 600
tttgggctta aacacgctaa tcagtttaat cagttcaatt ttgctagcga tattatggaa 660
ccatttaggc ctttagtgga taagattgtt tatgaaaatc gaaatcagcc ttttcccaaa 720
ataaagagag agttatttac tttgttttca gatacatttt catataatgg taaagagatg 780
tatctcacga atattattag cgattatact aaaaaagttg tcaaagctct gaataatgaa 840
gggaaaggag ttcctgaatt taggatatga 870

<210> SEQ ID NO 507
<211> LENGTH: 342
<212> TYPE: DNA
<213> ORGANISM: Steptococcus pyogenes

<400> SEQUENCE: 507
atgagttata gatatatgag aatgatactt atgtttgata tgccgacgga caccgctgag 60
gaacgaaaag cctatcgaaa atttcggaaa tttttactta gtgaagggtt tatcatgcat 120
caattttcta tttatagtaa gttgctgttg aataatacag ctaacaatgc catgattggt 180
cggctgaggg agcataatcc taataaagga aatattacat tactaacggt cacggaaaaa 240
cagtttgcac gaatgattta tttacatggt gaaagaaata attgtattgc aaactccgat 300
gaaagacttg tatttcttgg ggaggctttt gatgaatctt aa 342

<210> SEQ ID NO 508
<211> LENGTH: 663
<212> TYPE: DNA
<213> ORGANISM: Steptococcus pyogenes

<400> SEQUENCE: 508
atgaatctta atttttcctt actagatgaa ccgattccat taagaggcgg tacaattctt 60
gtgctcgaag atgtctgtgt attttcaaaa atagtgcaat attgttacca atatgaggaa 120
gattctgaac ttaaattttt tgatcacaag atgaaaacaa tcaaagaatc agaaatcatg 180
cttgtaacag atattttagg atttgatgtt aactcctcaa ccattttaaa attgattcat 240
gcagatttag aatctcaatt taatgagaaa cccgaagtga aatcgatgat tgacaaattg 300
gttgctacga ttacagaact gattgtcttt gaatgcttag aaaatgaatt agatttagag 360
tatgatgaaa tcacaatcct ggaattgatt aagtccttag gagtaaaagt agaaacgcaa 420
agtgatacta tttttgaaaa atgtctagag atacttcaaa ttttcaaata tctcactaag 480
aaaaagttgc ttatttttgt caatagcgga gcttttctaa caaaggatga agtggctagt 540
ttacaagagt atatatcatt gacaaattta acagttctct tttagaacc acgtgaacta 600 tatgattttc cgcagtatat tttagatgaa gattatttct taataactaa aaatatggta 660
taa 663

<210> SEQ ID NO 509
<211> LENGTH: 8020
<212> TYPE: DNA
<213> ORGANISM: Steptococcus pyogenes

<400> SEQUENCE: 509
atgagaatga ttttagcaca ctatgactgt aaaaaagata aaaagcaatc tttagatgag 60
catttatggc atgtggcctg ttctagtcga caggaagcat ctataattgg tcaaggagat 120
gtgctttttt taattggtct ttaccacgac ctgggcaaag ctgatcgaac ctttcaagat 180
aaattattaa ataatccaaa tcggcatgtt gatcactctt atgcaggggc aaaatactta 240
tgttctatta ttgggcctca tctaaaaaac cgaggggttg ataaaaatga gagaatgaca 300
ttcaacgaaa tggtggggta tgtcatctct gctcatcatg ggatgtatga tttatgctac 360
tattttgacg atgctgaata ttatggcttt aataagttta aaaatcgtat caatagagac 420
ttagatggtt atcactatca tgaagatatt aaagggtacg ctctaaaatt agaaaaaaaa 480
ttatgtgatt atggctacaa agatttaagg gagcttattg ataaagcttt tgataattac 540
caacaagcca tgtcttcctt aaactggcaa gataagagtg agtgggatta ttatcagtct 600
tgtatggtga gactttactt gtcactctta aaaaacgctg atattttgga cacagtaaat 660
gcctatggcc ttaagataag tcctatggat aaaacagagc gatcctttct aaaacactcc 720
tatttagcgg ccattgaaca aaaatatgct agctttggac agccaaacaa tcagttgaac 780
actattcgga cagaaatcgc tgagcgtgtt aaagaaagag gtaaacgaga ttccaagggg 840
atttatcgct tagatttacc gacaggagct ggcaagacta atcttagtat gcgttatgcg 900
tttcaccaat tagttcatca cgacaaatca aggttttttt acataactcc ctttctttcg 960
gttcttgagc aaaatgcttc cgaaattaga aaagttacag gtgaccttgg cgttctagaa 1020
caccattcca atgtggtgaa acaggctaat gaagatgatg atgataagga cagtttattg 1080
tcagcttatc ttagtgatag ctgggacagt caagtagtct tgacttctat ggttcaattt 1140
ttccaaacac ttttcaaaac aaaatcagct aatctgagac gtttttcaag tttgattaat 1200
agtgttgtga ttctagatga agttcaatcc ctgcctattg aagtcaccac tttgtttaat 1260
ttaacgatga attttttaaa taaagttatg gatacaacca tcgttctttg cacagcgaca 1320
caacctgctt atgattcttc agagattgac catcgtatct gttatggagg gaacttggga 1380
gaattagctg aaatagttga gttaacgatt gaagaaaaac agattttttc aaggacagag 1440
cttagaaaat ttgatgatag tgatcagaaa gttcacttga ctgatgttat taaccttatt 1500
ctaggtgagg aaaactcagt tcttgctatt tttaatacga aaaaaacggt tcataactgc 1560
tatactatgc taaaagacat gactgataga ccggtctatc agctttcgac aaatatgtgt 1620
gcgcagcata gacttgactt gattgctaag atcaaaacgg agttacaaaa taatatccct 1680
attatttgta ttagcacgca attaattgaa gcaggtgtag atgttgattt tcatcgcgtc 1740
attcgttcct actcagggat tgattctatt gttcaggctg ctggacggtg taaccgagaa 1800

```
ggcaaacgag ataaagggca agtcactctt gtcaatctga ccaatgaaga ggaaaatatt   1860
tctaggctga cagaaataaa aactaaaaaa gaagccacag aatctattct tcataagatt   1920
gggtctccaa ttgatatctc aactttaaac cgtgactttt ttgagtatta ttatgccaat   1980
aatcagggac tgatggatta tcctttggaa gacaacctat caatctacga ctatttaagc   2040
cttaatattt atcagacggc aaataaaaag ttcaaaggta agttaaaaca agcttttaaa   2100
acagcaggag ccaaaatgaa cctcatcaat aatgatatga taggaattct cgtaccttat   2160
ggcgaagctg agaaaaaatt ggcttattta gaagaattag gtgtgtcaca tttttatca   2220
gcaaaagatt atcaaacgat aaaatcatta ctaaaagagt tacaaccttt tacggttaat   2280
gtccgcgaga acgatcctct ctttgagaca acaaaatctt atctaaatgg tcagattctg   2340
gttttgacgt cggagtatta tgacacggaa agaggagtta aatacgattc agctagcttt   2400
tacttctaac tcaaaacgaa agaagattaa caaaaggttg ttagaggacc ttgttaacct   2460
gccaatcatc attagtaatt attatcaatt tagactattt aataaaatta gattacaaaa   2520
aaacagaagg aggaaagtag cttgtacaga tctagagact tctacgtgag agtaagtggt   2580
cagcgagctc tttttacaaa tccagccaca aaagggggat cggaacgctc atcctattcg   2640
gttccgacta gacaggcact gaatggtatc gttgatgcca tctattataa gccgaccttt   2700
actaatatcg tcacagaggt taaggttatt aaccagattc aaaccgaatt acagggtgtc   2760
agggctctgt tacatgatta tagtgcagat ttaagttatg tatcctattt gagtgatgtt   2820
gtttatctga tcaagtttca ttttgtttgg aatgaagata gaaaagattt gaactcagat   2880
agacttccag ctaaacatga agccattatg gagcgttcta ttcgtaaagg gggacgtcga   2940
gatgtgtttt tgggtacaag agaatgttta gggcttgtag atgatatcag ccaagaagag   3000
tatgagacta ctgtgtcgta ttataatggt gtcaatatcg acttgggaat catgttccat   3060
tcctttgcct atccgaagga caaaaagaca ccattaaaat catactttac aaagactgtg   3120
atgaaaaatg gagtcattac gtttaaagca cagtctgaat gcgatattgt taacacgctt   3180
tctagttatg cttttaaagc accagaggag ataaaatcgg ttaacgatga atgcatggag   3240
tatgatgcca tggagaaagg agaaaactga tggatttttt tacttctctc ttgaagactt   3300
atgaaaaagc agagctagca gacttggttg atcatcaaaa aagaaataat gagccggttt   3360
tactgccgat ttatcatacg agtttaaagt caaatggtaa aaatatcatt tcagtgaaac   3420
ttgacaaaga tggccagttt cacaaggcag aatttatggc agataagcaa atgattattt   3480
ttcctgtaac ggctgattct gttgctaggt caggtagtca tcctgcaccg catcccctag   3540
tcgataaatt tgcttattat agtgctgaaa tggggcagat tcagtatgat tcttttcata   3600
agcaactgaa taactggatt gattattgtg aggagggtga tgtcaagaaa tttttaacct   3660
ttgttcagca gttcattttg aagccagaat ttctaacatt gattcttgat tctttaattg   3720
gtcctgatta tcaacataat caattaaaag tcacattttg tgatgccact ggaaaagaaa   3780
aattaattga tttatcagct tgctttttag aattttcaat tgatcagttc cagggcttta   3840
aaaatgaatc ggtttcgaca tttaaagcct tacaccaatc ctatatttct tttgttgaag   3900
ccaatcgtga aaatctcggt atttgtaata ttagtggacg agaggaacag cttaccgata   3960
agcatagagg tttgatgggg aatgctaaaa tcatctctgt tagtaataaa agagaagctt   4020
ataaaggacg ttttagagaa cgcgaagacg tttttagtgt tggctatgaa acttccgaaa   4080
agattcattt aatgctcaag tacctttttag aaaataaaaa taccagtact tggttagggt   4140
cttctcaata tttaatcaac tggttcagcg atgatttaac aaatgatagt cggttggata   4200
```

-continued

```
ttgtatcacc aatctttgat gatggacttg aagaagatga tgatgacgat acgcctcctg   4260
ttataacatt agcaactgaa gacaataaaa gaattggtaa atcattcatc aagggacaaa   4320
aattatttgc taatgatgcc acttactacg ttgctatttt gaataaaacc agcaatgggc   4380
ggattgcttt aaaatatttt cgtcagcttc aagcgtccca attactcacc aatcttaaca   4440
agtggcagga aacatacagt tgggagtcgc gatctaagtt tgggaaaagt cgcttaagaa   4500
cccctacttt tcatgacatc cttaatgtgt cctacggggt tgatagggat cgcttccttg   4560
aattagataa tgataacttc aaaagtgatc aaattcaaaa gttagtggca agtttgattg   4620
atggtaaacc gatgccacag tccattgtca aaaagttagg taacaatgtt aaagaacgac   4680
atcgttaccg taagcactgg tatcaagttg agcaggtctg cttagcaatt ttacacaaac   4740
aaaatgggga ggaattttca ccgatgctag atcataccaa tcaaaatcgt tcctatcttt   4800
ttggacgatt attagcaatt tttgaattaa tcgagacctt gcgttatggc ttggatggaa   4860
acaataacga ccgtattacc aatgctgaac gttattggac agcctatact ggacaaccaa   4920
caaaattgat gatgttattg gaaaataaaa ttaagcctta cgaagaacca ttgaaattaa   4980
atcgtcgtgg cagttggatg aaattagaaa aagaaaaaga agagatttta gaactgttaa   5040
atcctctgtt agaaacagaa acaatggaaa aacccttaga ttaccgcttt atttttgggt   5100
attatgctga gaaaaactat tactatacaa aacaaaacac ggaagtaaca gaaagtgagg   5160
agtaaaaaga tgttggaaca caaaattgat tttatggtaa ctcttgaagt gaaagaagca   5220
aatgcaaatg gtgatccctt aaatggaaac atgcctcgta cagatgccaa aggatatggt   5280
gtgatgagtg atgtctccat taaacgtaag attcgtaatc gtttgcaaga tatggggaag   5340
tctatttttg tgcaagctaa tgagcgtatt gaagatgatt ttcgttcact ggaaaaacgc   5400
ttttcgcaac attttacagc taagacacct gacaaagaaa ttgaagaaaa agcaaatgca   5460
ttatggtttg atgttcgtgc ttttggacaa gtttttactt atctgaaaaa atcaattggg   5520
gtgcgtggac cagtttccat cagtatggct aagtccttgg agccaattgt catttccagc   5580
cttcaaatta cgcgtagtac caatggtatg gaagctaaga ataatagtgg ccgctcttct   5640
gatacgatgg ggacaaaaca ttttgtagat tatggtgtgt atgtacttaa aggttctatc   5700
aatgcttatt ttgctgaaaa gactggtttt tctcaggaag atgctgaggc tattaaagaa   5760
gttttggtta gcttgtttga aaatgatgcg tcgtctgcac gtccggaagg ctctatgcga   5820
gtttgtgaag tcttttggtt tacgcattca agcaaattgg gaaatgtttc aagtgcgcgt   5880
gtctttgact tgttagagta tcatcaatca atagaagaaa aaagcactta tgacgcttat   5940
cagattcatc taaatcaaga aaaattggct aaatatgaag cgaaagggtt aacgcttgaa   6000
atcctagaag gactctagta tggtctatgc cgaagatgat tatttaatgc tgtcaggtat   6060
tcagcatttc caattttgta aacgtcaatg ggcgttgatc catattgagc aacaatggct   6120
tgataatgaa gcgacagcgc atggacaggt tttacatact aaagcagata acccttacat   6180
taaagaaaaa cgaaaagagc ttttggtctc acgtgctatg cccatttctt ctgcagaact   6240
tggactttca ggaattatgg atgttgtgga attttataaa gatgatcaag gtgtgtcttt   6300
gaggggaaaa cgtgggaaat ggttaccaaa agttgtggaa tacaagcgcg gaaaacctaa   6360
aaaagatacc agagatattg tccagttggt ggctcagacc atgtgtttag aagaaacgct   6420
agactgcgac attaacgaag gttgtcttta ttaccatagt gtcaatcaaa gagtgattgt   6480
tcctatgaca tcagctttgc gtcaagaagt gaaggaatta gccgcagaga tgcatgaggt   6540
```

-continued

```
ttatcagagt caaatgctac ctaaagcagc ttattttaaa aactgtcagc tttgttcttt   6600
agtcgatatt tgtaagccca ggttgagtaa aaaaacaagg agtgtgtcgc gttacatcaa   6660
tgaggctatg accagtgagg agatggacct atgaagaagt tgctaaatac cttgtatttg   6720
acgcaagaag atttttatgt cactaaagag ggcgataaca ttgttatcaa gcaagaaggt   6780
aaggttctca aacggtttcc gtttcggatt attgacggta ttgtctgttt ttcttatttg   6840
ggtgtgtcgt ctgctttggt gaagttatgt acggagaatc agattaattt atcgtttcat   6900
acaccacaag ggcgtttttg tggtcgctat attggttcaa ccaatgggaa tgtgttgttg   6960
cgtagagaac attatcgttt atctgatcgt gaggaatctt tggaatacgc aaagcggttt   7020
attttggcta aaatttccaa ctcaaggaaa tacttgctac gctttaaacg agatcatcgt   7080
caacagattg ataccaagct tttgaggct gttaatgacg aattgatatg ggctttagag   7140
atggttcagg cagcagataa taaagactct ttaagaggga ttgaaggcca agctgctaat   7200
cagtattttc gcatatttaa tgacctggtg ttgacggaca aaaaaacgtt ttacttccaa   7260
ggtcggagta aacgaccacc cttagattgt gttaatgccc tcttgtcttt tggttacagt   7320
ttactgacct ttgaatgtca atctgccttg gaagctgtcg gattagacag ttacgttggt   7380
ttctttcaca cggatcgtcc tgggcgtgct agtttagcgc ttgatttagt tgaagagttc   7440
cgctcatata ttgtagatcg ttttgtcttt tcattaatta ataaaggaca acttcagaaa   7500
aaacactttg aggttaaaga aaatggtagt attttattga cggaaaatgg cagagctatt   7560
tttattgatt tgtggcagaa gcgtaagcat actgaggtag aacatccttt tacaaaagag   7620
aaagtaaaac ttatgttatt accctatgta caagcgcagc ttttagctaa ggctatacga   7680
ggagatttag aaagctatcc acctttatg gtttaggaga tgttatatga tggttttagt   7740
cacttatgat gtaaatacgg aaacacctgc tggtagaaaa agattgcgtc atgttgccaa   7800
actctgtgtg gactatgggc aacgtgttca aaattctgtt tttgaatgtt ctgtgacacc   7860
cgcagaattt gtggatataa agcaccgctt aacacaaatc attgatgaga aaactgatag   7920
tattcgcttt tatttattgg ggaaaaattg gcagaggcgt gtggaaacac ttggtcgctc   7980
agacagctat gacccagata aaggtgtctt attattgtaa                         8020
```

<210> SEQ ID NO 510
<211> LENGTH: 2409
<212> TYPE: DNA
<213> ORGANISM: Steptococcus pyogenes

<400> SEQUENCE: 510

```
atgagaatga ttttagcaca ctatgactgt aaaaaagata aaaagcaatc tttagatgag     60
catttatggc atgtggcctg ttctagtcga caggaagcat ctataattgg tcaaggagat    120
gtgctttttt taattggtct ttaccacgac ctgggcaaag ctgatcgaac ctttcaagat    180
aaattattaa ataatccaaa tcggcatgtt gatcactctt atgcaggggc aaaatactta    240
tgttctatta ttgggcctca tctaaaaaac cgaggggttg ataaaaatga gagaatgaca    300
ttcaacgaaa tggtggggta tgtcatctct gctcatcatg ggatgtatga tttatgctac    360
tattttgacg atgctgaata ttatggcttt aataagttta aaaatcgtat caatagagac    420
ttagatggtt atcactatca tgaagatatt aaagggtacg ctctaaaatt agaaaaaaaa    480
ttatgtgatt atggctacaa agatttaagg gagcttattg ataaagcttt tgataattac    540
caacaagcca tgtcttcctt aaactggcaa gataagagtg agtgggatta ttatcagtct    600
tgtatggtga gactttactt gtcactctta aaaaacgctg atattttgga cacagtaaat    660
```

```
gcctatggcc ttaagataag tcctatggat aaaacagagc gatcctttct aaaacactcc    720
tatttagcgg ccattgaaca aaaatatgct agctttggac agccaaacaa tcagttgaac    780
actattcgga cagaaatcgc tgagcgtgtt aaagaaagag gtaaacgaga ttccaagggg    840
atttatcgct tagatttacc gacaggagct ggcaagacta atcttagtat gcgttatgcg    900
tttcaccaat tagttcatca cgacaaatca aggttttttt acataactcc ctttctttcg    960
gttcttgagc aaaatgcttc cgaaattaga aaagttacag gtgaccttgg cgttctagaa   1020
caccattcca atgtggtgaa acaggctaat gaagatgatg atgataagga cagtttattg   1080
tcagcttatc ttagtgatag ctgggacagt caagtagtct tgacttctat ggttcaattt   1140
ttccaaacac ttttcaaaac aaaatcagct aatctgagac gtttttcaag tttgattaat   1200
agtgttgtga ttctagatga agttcaatcc ctgcctattg aagtcaccac tttgtttaat   1260
ttaacgatga attttttaaa taaagttatg gatacaacca tcgttctttg cacagcgaca   1320
caacctgctt atgattcttc agagattgac catcgtatct gttatggagg gaacttggga   1380
gaattagctg aaatagttga gttaacgatt gaagaaaaac agattttttc aaggacagag   1440
cttagaaaat ttgatgatag tgatcagaaa gttcacttga ctgatgttat taaccttatt   1500
ctaggtgagg aaaactcagt tcttgctatt tttaatacga aaaaaacggt tcataactgc   1560
tatactatgc taaaagacat gactgataga ccggtctatc agctttcgac aaatatgtgt   1620
gcgcagcata gacttgactt gattgctaag atcaaaacgg agttacaaaa taatatccct   1680
attatttgta ttagcacgca attaattgaa gcaggtgtag atgttgattt tcatcgcgtc   1740
attcgttcct actcagggat tgattctatt gttcaggctg ctggacggtg taaccgagaa   1800
ggcaaacgag ataaagggca agtcactctt gtcaatctga ccaatgaaga ggaaaatatt   1860
tctaggctga cagaaataaa aactaaaaaa gaagccacag aatctattct tcataagatt   1920
gggtctccaa ttgatatctc aactttaaac cgtgactttt ttgagtatta ttatgccaat   1980
aatcagggac tgatggatta tcctttggaa gacaacctat caatctacga ctatttaagc   2040
cttaatattt atcagacggc aaataaaaag ttcaaaggta agttaaaaca agcttttaaa   2100
acagcaggag ccaaaatgaa cctcatcaat aatgatatga taggaattct cgtaccttat   2160
ggcgaagctg agaaaaaatt ggcttattta gaagaattag gtgtgtcaca tttttttatca   2220
gcaaaagatt atcaaacgat aaaatcatta ctaaaagagt tacaaccttt tacggttaat   2280
gtccgcgaga acgatcctct ctttgagaca acaaaatctt atctaaatgg tcagattctg   2340
gttttgacgt cggagtatta tgacacggaa agaggagtta aatacgattc agctagcttt   2400
tacttctaa                                                           2409
```

<210> SEQ ID NO 511
<211> LENGTH: 729
<212> TYPE: DNA
<213> ORGANISM: Steptococcus pyogenes

<400> SEQUENCE: 511

```
ttgtacagat ctagagactt ctacgtgaga gtaagtggtc agcgagctct ttttacaaat     60
ccagccacaa aagggggatc ggaacgctca tcctattcgg ttccgactag acaggcactg    120
aatggtatcg ttgatgccat ctattataag ccgaccttta ctaatatcgt cacagaggtt    180
aaggttatta accagattca aaccgaatta cagggtgtca gggctctgtt acatgattat    240
agtgcagatt taagttatgt atcctatttg agtgatgttg tttatctgat caagtttcat    300
```

-continued

```
tttgtttgga atgaagatag aaaagatttg aactcagata gacttccagc taaacatgaa    360

gccattatgg agcgttctat tcgtaaaggg ggacgtcgag atgtgttttt gggtacaaga    420

gaatgtttag ggcttgtaga tgatatcagc caagaagagt atgagactac tgtgtcgtat    480

tataatggtg tcaatatcga cttgggaatc atgttccatt cctttgccta tccgaaggac    540

aaaaagacac cattaaaatc atactttaca aagactgtga tgaaaaatgg agtcattacg    600

tttaaagcac agtctgaatg cgatattgtt aacacgcttt ctagttatgc ttttaaagca    660

ccagaggaga taaaatcggt taacgatgaa tgcatggagt atgatgccat ggagaaagga    720

gaaaactga                                                            729
```

<210> SEQ ID NO 512
<211> LENGTH: 1896
<212> TYPE: DNA
<213> ORGANISM: Steptococcus pyogenes

<400> SEQUENCE: 512

```
atggattttt ttacttctct cttgaagact tatgaaaaag cagagctagc agacttggtt     60

gatcatcaaa aaagaaataa tgagccggtt ttactgccga tttatcatac gagtttaaag    120

tcaaatggta aaaatatcat ttcagtgaaa cttgacaaag atggccagtt tcacaaggca    180

gaatttatgg cagataagca aatgattatt tttcctgtaa cggctgattc tgttgctagg    240

tcaggtagtc atcctgcacc gcatccccta gtcgataaat ttgcttatta tagtgctgaa    300

atggggcaga ttcagtatga ttcttttcat aagcaactga ataactggat tgattattgt    360

gaggagggtg atgtcaagaa atttttaacc tttgttcagc agttcatttt gaagccagaa    420

tttctaacat tgattcttga ttctttaatt ggtcctgatt atcaacataa tcaattaaaa    480

gtcacatttt gtgatgccac tggaaaagaa aaattaattg atttatcagc ttgcttttta    540

gaattttcaa ttgatcagtt ccagggcttt aaaaatgaat cggtttcgac atttaaagcc    600

ttacaccaat cctatatttc ttttgttgaa gccaatcgtg aaaatctcgg tatttgtaat    660

attagtggac gagaggaaca gcttaccgat aagcatagag gtttgatggg gaatgctaaa    720

atcatctctg ttagtaataa aagagaagct tataaaggac gttttagaga acgcgaagac    780

gtttttagtg ttggctatga aacttccgaa aagattcatt taatgctcaa gtacctttta    840

gaaaataaaa ataccagtac ttggttaggg tcttctcaat atttaatcaa ctggttcagc    900

gatgatttaa caaatgatag tcggttggat attgtatcac caatctttga tgatggactt    960

gaagaagatg atgatgacga tacgcctcct gttataacat tagcaactga agacaataaa   1020

agaattggta aatcattcat caagggacaa aaattatttg ctaatgatgc cacttactac   1080

gttgctattt tgaataaaac cagcaatggg cggattgctt taaaatattt tcgtcagctt   1140

caagcgtccc aattactcac caatcttaac aagtggcagg aaacatacag ttgggagtcg   1200

cgatctaagt ttgggaaaag tcgcttaaga acccctactt ttcatgacat ccttaatgtg   1260

tcctacgggg ttgataggga tcgcttcctt gaattagata atgataactt caaaagtgat   1320

caaattcaaa agttagtggc aagtttgatt gatggtaaac cgatgccaca gtccattgtc   1380

aaaaagttag gtaacaatgt taaagaacga catcgttacc gtaagcactg gtatcaagtt   1440

gagcaggtct gcttagcaat tttacacaaa caaaatgggg aggaattttc accgatgcta   1500

gatcatacca atcaaaatcg ttcctatctt tttggacgat tattagcaat ttttgaatta   1560

atcgagacct tgcgttatgg cttggatgga aacaataacg accgtattac caatgctgaa   1620

cgttattgga cagcctatac tggacaacca acaaaattga tgatgttatt ggaaaataaa   1680
```

attaagcctt acgaagaacc attgaaatta aatcgtcgtg gcagttggat gaaattagaa 1740
aaagaaaaag aagagatttt agaactgtta aatcctctgt tagaaacaga aacaatggaa 1800
aaacccttag attaccgctt tatttttggg tattatgctg agaaaaacta ttactataca 1860
aaacaaaaca cggaagtaac agaaagtgag gagtaa 1896

<210> SEQ ID NO 513
<211> LENGTH: 849
<212> TYPE: DNA
<213> ORGANISM: Steptococcus pyogenes

<400> SEQUENCE: 513
atgttggaac acaaaattga ttttatggta actcttgaag tgaaagaagc aaatgcaaat 60
ggtgatccct taaatggaaa catgcctcgt acagatgcca aaggatatgg tgtgatgagt 120
gatgtctcca ttaaacgtaa gattcgtaat cgtttgcaag atatggggaa gtctattttt 180
gtgcaagcta atgagcgtat tgaagatgat tttcgttcac tggaaaaacg cttttcgcaa 240
cattttacag ctaagacacc tgacaaagaa attgaagaaa aagcaaatgc attatggttt 300
gatgttcgtg cttttggaca agtttttact tatctgaaaa aatcaattgg ggtgcgtgga 360
ccagtttcca tcagtatggc taagtccttg gagccaattg tcatttccag ccttcaaatt 420
acgcgtagta ccaatggtat ggaagctaag aataatagtg gccgctcttc tgatacgatg 480
gggacaaaac attttgtaga ttatggtgtg tatgtactta aaggttctat caatgcttat 540
tttgctgaaa agactggttt ttctcaggaa gatgctgagg ctattaaaga agttttggtt 600
agcttgtttg aaaatgatgc gtcgtctgca cgtccggaag gctctatgcg agtttgtgaa 660
gtcttttggt ttacgcattc aagcaaattg ggaaatgttt caagtgcgcg tgtctttgac 720
ttgttagagt atcatcaatc aatagaagaa aaaagcactt atgacgctta tcagattcat 780
ctaaatcaag aaaaattggc taaatatgaa gcgaaagggt taacgcttga aatcctagaa 840
ggactctag 849

<210> SEQ ID NO 514
<211> LENGTH: 675
<212> TYPE: DNA
<213> ORGANISM: Steptococcus pyogenes

<400> SEQUENCE: 514
atggtctatg ccgaagatga ttatttaatg ctgtcaggta ttcagcattt ccaattttgt 60
aaacgtcaat gggcgttgat ccatattgag caacaatggc ttgataatga agcgacagcg 120
catggacagg ttttacatac taaagcagat aacccttaca ttaaagaaaa acgaaaagag 180
cttttggtct cacgtgctat gcccatttct tctgcagaac ttggactttc aggaattatg 240
gatgttgtgg aattttataa agatgatcaa ggtgtgtctt tgaggggaaa acgtgggaaa 300
tggttaccaa aagttgtgga atacaagcgc ggaaaaccta aaaaagatac cagagatatt 360
gtccagttgg tggctcagac catgtgttta gaagaaacgc tagactgcga cattaacgaa 420
ggttgtcttt attaccatag tgtcaatcaa agagtgattg ttcctatgac atcagctttg 480
cgtcaagaag tgaaggaatt agccgcagag atgcatgagg tttatcagag tcaaatgcta 540
cctaaagcag cttattttaa aaactgtcag ctttgttctt tagtcgatat ttgtaagccc 600
aggttgagta aaaaaacaag gagtgtgtcg cgttacatca atgaggctat gaccagtgag 660
gagatggacc tatga 675

<210> SEQ ID NO 515
<211> LENGTH: 1026
<212> TYPE: DNA
<213> ORGANISM: Steptococcus pyogenes

<400> SEQUENCE: 515
atgaagaagt tgctaaatac cttgtatttg acgcaagaag atttttatgt cactaaagag 60
ggcgataaca ttgttatcaa gcaagaaggt aaggttctca aacggtttcc gtttcggatt 120
attgacggta ttgtctgttt ttcttatttg ggtgtgtcgt ctgctttggt gaagttatgt 180
acggagaatc agattaattt atcgtttcat acaccacaag ggcgtttttg tggtcgctat 240
attggttcaa ccaatgggaa tgtgttgttg cgtagagaac attatcgttt atctgatcgt 300
gaggaatctt tggaatacgc aaagcggttt attttggcta aaatttccaa ctcaaggaaa 360
tacttgctac gctttaaacg agatcatcgt caacagattg ataccaagct ttttgaggct 420
gttaatgacg aattgatatg ggctttagag atggttcagg cagcagataa taaagactct 480
ttaagaggga ttgaaggcca agctgctaat cagtattttc gcatatttaa tgacctggtg 540
ttgacggaca aaaaaacgtt ttacttccaa ggtcggagta aacgaccacc cttagattgt 600
gttaatgccc tcttgtcttt tggttacagt ttactgacct ttgaatgtca atctgccttg 660
gaagctgtcg gattagacag ttacgttggt ttctttcaca cggatcgtcc tgggcgtgct 720
agtttagcgc ttgatttagt tgaagagttc cgctcatata ttgtagatcg ttttgtcttt 780
tcattaatta ataaaggaca acttcagaaa aaacactttg aggttaaaga aaatggtagt 840
attttattga cggaaaatgg cagagctatt tttattgatt tgtggcagaa gcgtaagcat 900
actgaggtag aacatccttt tacaaaagag aaagtaaaac ttatgttatt accctatgta 960
caagcgcagc ttttagctaa ggctatacga ggagatttag aaagctatcc accttttatg 1020
gtttag 1026

<210> SEQ ID NO 516
<211> LENGTH: 294
<212> TYPE: DNA
<213> ORGANISM: Steptococcus pyogenes

<400> SEQUENCE: 516
atgatggttt tagtcactta tgatgtaaat acggaaacac ctgctggtag aaaaagattg 60
cgtcatgttg ccaaactctg tgtggactat gggcaacgtg ttcaaaattc tgtttttgaa 120
tgttctgtga cacccgcaga atttgtggat ataaagcacc gcttaacaca aatcattgat 180
gagaaaactg atagtattcg cttttattta ttggggaaaa attggcagag gcgtgtggaa 240
acacttggtc gctcagacag ctatgaccca gataaaggtg tcttattatt gtaa 294

<210> SEQ ID NO 517
<211> LENGTH: 5966
<212> TYPE: DNA
<213> ORGANISM: Steptococcus pyogenes

<400> SEQUENCE: 517
atggataaga aatactcaat aggcttagat atcggcacaa atagcgtcgg atgggcggtg 60
atcactgatg attataaggt tccgtctaaa aagctcaagg gtctgggaaa tacagaccgc 120
cacggtatca aaaaaaatct tataggggct cttttatttg acagtggaga gacagcggaa 180
gcgactcgtc tcaaacggac agctcgtaga aggtatacac gtcggaagaa tcgtatttgt 240
tatctacagg agatttttc aaatgagatg gcgaaagtag atgatagttt ctttcatcga 300

```
cttgaagagt ctttttggt ggaagaagac aagaagcatg aacgtcatcc tatttttgga    360
aatatagtag atgaagttgc ttatcatgag aaatatccaa ctatctatca tctgcgaaaa    420
aaattggcag attctactga taaagtggat ttgcgcttaa tctatttggc cttagcgcat    480
atgattaagt ttcgtggtca ttttttgatt gagggagatt taaatcctga taatagtgat    540
gtggacaaac tatttatcca gttggtacaa acctacaatc aattatttga agaaaaccct    600
attaacgcaa gtagagtaga tgctaaagcg attctttctg cacgattgag taaatcaaga    660
cgattagaaa atctcattgc tcagctcccc ggtgagaaga aaaatggatt gtttgggaat    720
ctcattgctt tgtcattggg attgacccct aattttaaat caaattttga tttggcagaa    780
gatgctaaat tacagctttc aaaagatact tacgatgatg atttagataa tttattggcg    840
caaattggag atcaatatgc tgatttgttt ttggcagcta agaatttatc agatgctact    900
ttactttcag atatcctaag agtaaatagt gaaataacta aggctcccct atcagcttca    960
atgattaagc gctacgatga acatcatcaa gacttgactc ttttaaaagc tttagttcga   1020
caacaacttc cagaaaagta taaagaaatc ttttttgatc aatcaaaaaa cggatatgca   1080
ggttatattg atgggggagc tagccaagaa gaattttata aatttatcaa accaatttta   1140
gaaaaaatgg atggtactga ggaattattg gcgaaactaa atcgtgaaga tttgctgcgc   1200
aagcaacgga cctttgacaa cggctctatt ccctatcaaa ttcacttggg tgagctgcat   1260
gctattttga gaagacaaga agacttttat ccatttttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaagt caaatatgtt actgagggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggtacct accatgattt gctaaaaatt   1800
attaaagata aagatttttt ggataatgaa gaaaacgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttga aatcagatgg ttttgccaat cgcaatttta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgtgagcgt   2340
atgaaacgta ttgaagaagg aataaaagaa ctaggaagtg atattctaaa ggagtatcct   2400
gttgaaaaca ctcaattaca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
```

-continued

```
aactattgga gacaacttct aaacgccaag ttaatcactc aacgtaagtt tgataattta   2700
acaaaagctg aacgtggagg tttgagtgaa cttgataaag ttggttttat caaacgccaa   2760
ttggttgaaa ctcgccaaat cactaagcat gtggcacaaa ttttggatag tcgcatgaat   2820
actaaatacg atgaaaatga taaacttatt cgagaggtta gagtgattac cttaaaatct   2880
aaattagttt ctgacttccg aaaagatttc caattctata aagtacgtga gattaacaat   2940
taccatcatg cccatgatgc gtatcttaat gccgtcgttg gaactgcttt gattaagaaa   3000
tatccaaaac ttgaatcgga gtttgtctat ggtgattata aagtttatga tgttcgtaaa   3060
atgattgcta agtctgagca ggaaataggc aaagcaaccg caaaatattt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
aaagagttac tagggatcac aataatggaa agaagctctt ttgaaaaaga tccgattgac   3540
tttttagaag ctaaaggata taaggaagtt agaaaagact taatcattaa actacctaaa   3600
tatagtcttt ttgagttaga aaacggtcgt aaacggatgc tggctagtgc cggagaattg   3660
caaaaaggaa atgagctagc tctgccaagc aaatatgtga atttttttata tttagctagt   3720
cattatgaaa agttgaaggg tagtccagaa gataacgaac aaaaacaatt gtttgtggag   3780
cagcataagc attatttaga tgagattatt gagcaaatca gtgaattttc taagcgtgtt   3840
attttagcag atgccaattt agataaagtt cttagtgcat ataacaaaca tagagacaaa   3900
ccaatacgtg aacaagcaga aaatattatt catttattta cgttgacgaa tcttggagct   3960
cccgctgctt ttaaatattt tgatacaaca attgatcgta aacgatatac gtctacaaaa   4020
gaagttttag atgccactct tatccatcaa tccatcactg gtctttatga aacacgcatt   4080
gatttgagtc agctaggagg tgactgatgg ctggttggcg tactgttgtg gtaaataccc   4140
actcgaaatt atcctataag aataatcatc tgatttttaa ggatgcctat aaaacggagc   4200
tgatccattt atcagaaatt gatattttgt tattagaaac gaccgatatt gtcttgtcca   4260
ctatgctggt aaaacggcta gtggatgaga atgtccttgt catattctgt gatgataaac   4320
gattaccaac agctatgctg atgccttttt atggtcgtca tgattcgagt ttacagcttg   4380
ggaaacaaat gtcctggtca gaaacagtca aatcgcaggt ttggacgacg attattgctc   4440
aaaagatttt gaatcaatct tgctatctag gagcatgctc ctattttgaa aaatcccaat   4500
ctattatgga tttatatcat ggtttggaaa attttgatcc gagtaatcga gaagggcatg   4560
cagcgagaat ttattttaat acactttttg ggaacgattt ctcaagagat ttggagcatc   4620
caatcaatgc aggtctggat tatggttata ctttattatt gagtatgttt gcgcgtgaag   4680
tggttgtgtc tggatgtatg actcaatttg gactcaaaca cgccaatcag tttaatcagt   4740
tcaattttgc tagcgatatt atggaaccat ttaggccttt ggtggataag attgtttatg   4800
aaaatcgaaa tcagcctttt cccaaaataa agagagagtt atttactttg ttttcagata   4860
cattttcata taatggtaaa gagatgtatc tcacgaatat tattagcgat tatactaaaa   4920
aagttgtcaa agctctgaat aatgaaggga aaggagttcc tgaatttagg atatgagtta   4980
tagatatatg agaatgatac ttatgtttga tatgccgacg gacactgctg aggaacgaaa   5040
```

agcttatcga aaatttcgga aatttttact tagtgaaggg tttatcatgc atcaattttc 5100
tatttatagt aagttactgt tgaataatac agctaacaac gccatgattg gtcggctgag 5160
ggagcataat cctcataaag gaaatattac attactaaca gtcacagaaa aacagtttgc 5220
acgaatgatt tatttacatg gtgaaagaaa taattgtatt gcaaactccg atgagagact 5280
tgtatttctt ggggaggctt ttgatgaatc ttaattttcc cttattagat gaaccgattc 5340
cattaagagg cggtacaatt cttgtgctcg aagatgtctg tgtattttca aaaatagtgc 5400
aatattgtta caaatatgag gaagattctg aacttaaatt ttttgatcac aagatgaaaa 5460
ccatcaaaga atcagaaatc atgcttgtaa cagatatttt aggatttgat gttaactcct 5520
caaccatttt aaaattgatt catgcagatt tagaatctca atttaatgag aaacccgaag 5580
tgaaatcgat gattgacaaa ttggttgcta cgattacaga actgattgtc tttgaatgct 5640
tagaaaatga attagattta gagtatgatg aaatcacaat cctggaattg attaagtcct 5700
taggagtaaa agtagaaacg caaagtgata ctatttttga aaaatgtcta gagatacttc 5760
aaattttcaa atatctcact aagaaaaagt tgcttatttt tgtcaatagc ggagcttttc 5820
taacaaagga tgaagtggct agtttacaag agtatatatc attgacaaat ttaacagttc 5880
tctttttaga accacgtgaa ctatatgatt ttccgcagta tattttagat gaagattatt 5940
tcttaataac taaaaatatg gtataa 5966

<210> SEQ ID NO 518
<211> LENGTH: 4107
<212> TYPE: DNA
<213> ORGANISM: Steptococcus pyogenes

<400> SEQUENCE: 518
atggataaga aatactcaat aggcttagat atcggcacaa atagcgtcgg atgggcggtg 60
atcactgatg attataaggt tccgtctaaa aagctcaagg gtctgggaaa tacagaccgc 120
cacggtatca aaaaaaatct tataggggct cttttatttg acagtggaga gacagcggaa 180
gcgactcgtc tcaaacggac agctcgtaga aggtatacac gtcggaagaa tcgtatttgt 240
tatctacagg agatttttc aaatgagatg gcgaaagtag atgatagttt ctttcatcga 300
cttgaagagt cttttttggt ggaagaagac aagaagcatg aacgtcatcc tatttttgga 360
aatatagtag atgaagttgc ttatcatgag aaatatccaa ctatctatca tctgcgaaaa 420
aaattggcag attctactga taaagtggat ttgcgcttaa tctatttggc cttagcgcat 480
atgattaagt ttcgtggtca tttttgatt gagggagatt taaatcctga taatagtgat 540
gtggacaaac tatttatcca gttggtacaa acctacaatc aattatttga agaaaaccct 600
attaacgcaa gtagagtaga tgctaaagcg attctttctg cacgattgag taaatcaaga 660
cgattagaaa atctcattgc tcagctcccc ggtgagaaga aaaatggatt gtttgggaat 720
ctcattgctt tgtcattggg attgacccct aattttaaat caaattttga tttggcagaa 780
gatgctaaat tacagctttc aaaagatact tacgatgatg atttagataa tttattggcg 840
caaattggag atcaatatgc tgatttgttt ttggcagcta agaatttatc agatgctact 900
ttactttcag atatcctaag agtaaatagt gaaataacta aggctcccct atcagcttca 960
atgattaagc gctacgatga acatcatcaa gacttgactc ttttaaaagc tttagttcga 1020
caacaacttc cagaaaagta taaagaaatc ttttttgatc aatcaaaaaa cggatatgca 1080
ggttatattg atgggggagc tagccaagaa gaattttata aatttatcaa accaatttta 1140

```
gaaaaaatgg atggtactga ggaattattg gcgaaactaa atcgtgaaga tttgctgcgc   1200
aagcaacgga cctttgacaa cggctctatt ccctatcaaa ttcacttggg tgagctgcat   1260
gctattttga gaagacaaga agacttttat ccatttttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaagt caaatatgtt actgagggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggtacct accatgattt gctaaaaatt   1800
attaaagata aagatttttt ggataatgaa gaaaacgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttga aatcagatgg ttttgccaat cgcaatttta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgtgagcgt   2340
atgaaacgta ttgaagaagg aataaaagaa ctaggaagtg atattctaaa ggagtatcct   2400
gttgaaaaca ctcaattaca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acaaaagctg aacgtggagg tttgagtgaa cttgataaag ttggttttat caaacgccaa   2760
ttggttgaaa ctcgccaaat cactaagcat gtggcacaaa ttttggatag tcgcatgaat   2820
actaaatacg atgaaaatga taaacttatt cgagaggtta gagtgattac cttaaaatct   2880
aaattagttt ctgacttccg aaaagatttc caattctata aagtacgtga gattaacaat   2940
taccatcatg cccatgatgc gtatcttaat gccgtcgttg gaactgcttt gattaagaaa   3000
tatccaaaac ttgaatcgga gtttgtctat ggtgattata aagtttatga tgttcgtaaa   3060
atgattgcta agtctgagca ggaaataggc aaagcaaccg caaaatattt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
aaagagttac tagggatcac aataatggaa agaagctctt ttgaaaaaga tccgattgac   3540
```

tttttagaag ctaaaggata taaggaagtt agaaaagact taatcattaa actacctaaa 3600
tatagtcttt ttgagttaga aaacggtcgt aaacggatgc tggctagtgc cggagaattg 3660
caaaaaggaa atgagctagc tctgccaagc aaatatgtga attttttata tttagctagt 3720
cattatgaaa agttgaaggg tagtccagaa gataacgaac aaaaacaatt gtttgtggag 3780
cagcataagc attatttaga tgagattatt gagcaaatca gtgaattttc taagcgtgtt 3840
attttagcag atgccaattt agataaagtt cttagtgcat ataacaaaca tagagacaaa 3900
ccaatacgtg aacaagcaga aaatattatt catttattta cgttgacgaa tcttggagct 3960
cccgctgctt ttaaatattt tgatacaaca attgatcgta aacgatatac gtctacaaaa 4020
gaagttttag atgccactct tatccatcaa tccatcactg gtctttatga aacacgcatt 4080
gatttgagtc agctaggagg tgactga 4107

<210> SEQ ID NO 519
<211> LENGTH: 870
<212> TYPE: DNA
<213> ORGANISM: Steptococcus pyogenes

<400> SEQUENCE: 519
atggctggtt ggcgtactgt tgtggtaaat acccactcga aattatccta taagaataat 60
catctgattt ttaaggatgc ctataaaacg gagctgatcc atttatcaga aattgatatt 120
ttgttattag aaacgaccga tattgtcttg tccactatgc tggtaaaacg gctagtggat 180
gagaatgtcc ttgtcatatt ctgtgatgat aaacgattac caacagctat gctgatgcct 240
ttttatggtc gtcatgattc gagtttacag cttgggaaac aaatgtcctg gtcagaaaca 300
gtcaaatcgc aggtttggac gacgattatt gctcaaaaga ttttgaatca atcttgctat 360
ctaggagcat gctcctattt tgaaaaatcc caatctatta tggatttata tcatggtttg 420
gaaaattttg atccgagtaa tcgagaaggg catgcagcga gaatttattt taatacactt 480
tttgggaacg atttctcaag agatttggag catccaatca atgcaggtct ggattatggt 540
tatactttat tattgagtat gtttgcgcgt gaagtggttg tgtctggatg tatgactcaa 600
tttggactca aacacgccaa tcagtttaat cagttcaatt ttgctagcga tattatggaa 660
ccatttaggc ctttggtgga taagattgtt tatgaaaatc gaaatcagcc ttttcccaaa 720
ataaagagag agttatttac tttgttttca gatacatttt catataatgg taaagagatg 780
tatctcacga atattattag cgattatact aaaaaagttg tcaaagctct gaataatgaa 840
gggaaaggag ttcctgaatt taggatatga 870

<210> SEQ ID NO 520
<211> LENGTH: 327
<212> TYPE: DNA
<213> ORGANISM: Steptococcus pyogenes

<400> SEQUENCE: 520
atgagaatga tacttatgtt tgatatgccg acggacactg ctgaggaacg aaaagcttat 60
cgaaaatttc ggaaattttt acttagtgaa gggtttatca tgcatcaatt ttctatttat 120
agtaagttac tgttgaataa tacagctaac aacgccatga ttggtcggct gagggagcat 180
aatcctcata aaggaaatat tacattacta acagtcacag aaaaacagtt tgcacgaatg 240
atttatttac atggtgaaag aaataattgt attgcaaact ccgatgagag acttgtattt 300
cttggggagg cttttgatga atcttaa 327

<210> SEQ ID NO 521
<211> LENGTH: 663
<212> TYPE: DNA
<213> ORGANISM: Steptococcus pyogenes

<400> SEQUENCE: 521
atgaatctta attttccctt attagatgaa ccgattccat taagaggcgg tacaattctt 60
gtgctcgaag atgtctgtgt attttcaaaa atagtgcaat attgttacaa atatgaggaa 120
gattctgaac ttaaattttt tgatcacaag atgaaaacca tcaaagaatc agaaatcatg 180
cttgtaacag atattttagg atttgatgtt aactcctcaa ccattttaaa attgattcat 240
gcagatttag aatctcaatt taatgagaaa cccgaagtga aatcgatgat tgacaaattg 300
gttgctacga ttacagaact gattgtcttt gaatgcttag aaaatgaatt agatttagag 360
tatgatgaaa tcacaatcct ggaattgatt aagtccttag gagtaaaagt agaaacgcaa 420
agtgatacta tttttgaaaa atgtctagag atacttcaaa ttttcaaata tctcactaag 480
aaaaagttgc ttatttttgt caatagcgga gcttttctaa caaaggatga agtggctagt 540
ttacaagagt atatatcatt gacaaattta acagttctct ttttagaacc acgtgaacta 600
tatgattttc cgcagtatat tttagatgaa gattatttct taataactaa aaatatggta 660
taa 663

<210> SEQ ID NO 522
<211> LENGTH: 30
<212> TYPE: DNA
<213> ORGANISM: Steptococcus thermophilus

<400> SEQUENCE: 522
caacacattc aacagattaa tgaagaatac 30

<210> SEQ ID NO 523
<211> LENGTH: 30
<212> TYPE: DNA
<213> ORGANISM: Steptococcus thermophilus

<400> SEQUENCE: 523
tccactcacg tacaaatagt gagtgtactc 30

<210> SEQ ID NO 524
<211> LENGTH: 30
<212> TYPE: DNA
<213> ORGANISM: Steptococcus thermophilus

<400> SEQUENCE: 524
gcccttctaa ttggattacc ttccgaggtg 30

<210> SEQ ID NO 525
<211> LENGTH: 30
<212> TYPE: DNA
<213> ORGANISM: Steptococcus thermophilus

<400> SEQUENCE: 525
ctcagtcgtt actggtgaac cagtttcaat 30

<210> SEQ ID NO 526
<211> LENGTH: 30
<212> TYPE: DNA
<213> ORGANISM: Steptococcus thermophilus

<400> SEQUENCE: 526
attgtctatt acgacaacat ggaagatgat 30

<210> SEQ ID NO 527
<211> LENGTH: 31
<212> TYPE: DNA
<213> ORGANISM: Steptococcus thermophilus

<400> SEQUENCE: 527
gagtttcttt gtcagactct aacacagccg c 31

<210> SEQ ID NO 528
<211> LENGTH: 30
<212> TYPE: DNA
<213> ORGANISM: Steptococcus thermophilus

<400> SEQUENCE: 528
ttactagagc gtgtcgttaa ccactttaaa 30

<210> SEQ ID NO 529
<211> LENGTH: 30
<212> TYPE: DNA
<213> ORGANISM: Steptococcus thermophilus

<400> SEQUENCE: 529
ttcgttaaag tcacctcgtg ctagcgttgc 30

<210> SEQ ID NO 530
<211> LENGTH: 30
<212> TYPE: DNA
<213> ORGANISM: Steptococcus thermophilus

<400> SEQUENCE: 530
ataacggtag caaatataaa cctgttactg 30

<210> SEQ ID NO 531
<211> LENGTH: 30
<212> TYPE: DNA
<213> ORGANISM: Steptococcus thermophilus

<400> SEQUENCE: 531
gaagtagcca tacaagaaga tggatcagca 30

<210> SEQ ID NO 532
<211> LENGTH: 29
<212> TYPE: DNA
<213> ORGANISM: Steptococcus thermophilus

<400> SEQUENCE: 532
atgtcactga gtgtctaagc attgcgtac 29

<210> SEQ ID NO 533
<211> LENGTH: 30
<212> TYPE: DNA
<213> ORGANISM: Steptococcus thermophilus

<400> SEQUENCE: 533
tgaataagca gttcttgacg accaaccgac 30

<210> SEQ ID NO 534
<211> LENGTH: 30
<212> TYPE: DNA
<213> ORGANISM: Steptococcus thermophilus

<400> SEQUENCE: 534
tcaacaattg caacatctta taacccactt 30

<210> SEQ ID NO 535
<211> LENGTH: 30
<212> TYPE: DNA
<213> ORGANISM: Steptococcus thermophilus

<400> SEQUENCE: 535
ttacgtttga aaagaatatc aaatcaatga 30

<210> SEQ ID NO 536
<211> LENGTH: 30
<212> TYPE: DNA
<213> ORGANISM: Steptococcus thermophilus

<400> SEQUENCE: 536
gctctacgac ttcttccacg agttcctgcc 30

<210> SEQ ID NO 537
<211> LENGTH: 30
<212> TYPE: DNA
<213> ORGANISM: Steptococcus thermophilus

<400> SEQUENCE: 537
aacacagcaa gacaagagga tgatgctatg 30

<210> SEQ ID NO 538
<211> LENGTH: 30
<212> TYPE: DNA
<213> ORGANISM: Steptococcus thermophilus

<400> SEQUENCE: 538
aagtagttga tgacctctac aatggtttat 30

<210> SEQ ID NO 539
<211> LENGTH: 30
<212> TYPE: DNA
<213> ORGANISM: Steptococcus thermophilus

<400> SEQUENCE: 539
aataatttat ggtatagctt aatatcattg 30

<210> SEQ ID NO 540
<211> LENGTH: 30
<212> TYPE: DNA
<213> ORGANISM: Steptococcus thermophilus

<400> SEQUENCE: 540
aatcaatacg acaagagtta aaatggtctt 30

<210> SEQ ID NO 541
<211> LENGTH: 30
<212> TYPE: DNA
<213> ORGANISM: Steptococcus thermophilus

<400> SEQUENCE: 541
aatcgttcaa attctgtttt aggtacattt 30

<210> SEQ ID NO 542
<211> LENGTH: 30
<212> TYPE: DNA
<213> ORGANISM: Steptococcus thermophilus

<400> SEQUENCE: 542
aatgacgagg agctattggc acaacttaca 30

<210> SEQ ID NO 543
<211> LENGTH: 30
<212> TYPE: DNA
<213> ORGANISM: Steptococcus thermophilus

<400> SEQUENCE: 543
aattaagggc atagaaaggg agacaacatg 30

<210> SEQ ID NO 544
<211> LENGTH: 30
<212> TYPE: DNA
<213> ORGANISM: Steptococcus thermophilus

<400> SEQUENCE: 544
acaattcttc atccggtaac tgctcaagtg 30

<210> SEQ ID NO 545
<211> LENGTH: 30
<212> TYPE: DNA
<213> ORGANISM: Steptococcus thermophilus

<400> SEQUENCE: 545
acacttggca ggcttattac tcaacagcga 30

<210> SEQ ID NO 546
<211> LENGTH: 30
<212> TYPE: DNA
<213> ORGANISM: Steptococcus thermophilus

<400> SEQUENCE: 546
ataaactatg aaattttata atttttaaga 30

<210> SEQ ID NO 547
<211> LENGTH: 30
<212> TYPE: DNA
<213> ORGANISM: Steptococcus thermophilus

<400> SEQUENCE: 547
ataactgaag gataggagct tgtaaagtct 30

<210> SEQ ID NO 548
<211> LENGTH: 29
<212> TYPE: DNA
<213> ORGANISM: Steptococcus thermophilus

<400> SEQUENCE: 548
ataatgccgt tgaattacac ggcaagtca 29

<210> SEQ ID NO 549
<211> LENGTH: 30
<212> TYPE: DNA
<213> ORGANISM: Steptococcus thermophilus

<400> SEQUENCE: 549
caaccaacgg taacagctac tttttacagt 30

<210> SEQ ID NO 550
<211> LENGTH: 30
<212> TYPE: DNA

<213> ORGANISM: Steptococcus thermophilus

<400> SEQUENCE: 550
catagagtgg aaaactagaa acagattcaa 30

<210> SEQ ID NO 551
<211> LENGTH: 29
<212> TYPE: DNA
<213> ORGANISM: Steptococcus thermophilus

<400> SEQUENCE: 551
cgacacaaga acgtatgcaa gagttcaag 29

<210> SEQ ID NO 552
<211> LENGTH: 30
<212> TYPE: DNA
<213> ORGANISM: Steptococcus thermophilus

<400> SEQUENCE: 552
cgatatttaa aatcattttc ataacttcat 30

<210> SEQ ID NO 553
<211> LENGTH: 30
<212> TYPE: DNA
<213> ORGANISM: Steptococcus thermophilus

<400> SEQUENCE: 553
cgatttgaca atctgctgac cactgttatc 30

<210> SEQ ID NO 554
<211> LENGTH: 30
<212> TYPE: DNA
<213> ORGANISM: Steptococcus thermophilus

<400> SEQUENCE: 554
ctgttccttg ttcttttgtt gtatcttttc 30

<210> SEQ ID NO 555
<211> LENGTH: 30
<212> TYPE: DNA
<213> ORGANISM: Steptococcus thermophilus

<400> SEQUENCE: 555
gagcgagctc gaaataatct taattacaag 30

<210> SEQ ID NO 556
<211> LENGTH: 30
<212> TYPE: DNA
<213> ORGANISM: Steptococcus thermophilus

<400> SEQUENCE: 556
gcagtatcag caagcaagct gttagttact 30

<210> SEQ ID NO 557
<211> LENGTH: 30
<212> TYPE: DNA
<213> ORGANISM: Steptococcus thermophilus

<400> SEQUENCE: 557
gctggcgagg aaacgaacaa ggcctcaaca 30

<210> SEQ ID NO 558
<211> LENGTH: 30

<212> TYPE: DNA
<213> ORGANISM: Steptococcus thermophilus

<400> SEQUENCE: 558
gcttagctgt ccaatccacg aacgtggatg 30

<210> SEQ ID NO 559
<211> LENGTH: 30
<212> TYPE: DNA
<213> ORGANISM: Steptococcus thermophilus

<400> SEQUENCE: 559
ggcgtcccaa tcctgattaa tacttactcg 30

<210> SEQ ID NO 560
<211> LENGTH: 30
<212> TYPE: DNA
<213> ORGANISM: Steptococcus thermophilus

<400> SEQUENCE: 560
gttcgctagc gtcatgtggt aacgtattta 30

<210> SEQ ID NO 561
<211> LENGTH: 30
<212> TYPE: DNA
<213> ORGANISM: Steptococcus thermophilus

<400> SEQUENCE: 561
tctatatcga ggtcaactaa caattatgct 30

<210> SEQ ID NO 562
<211> LENGTH: 30
<212> TYPE: DNA
<213> ORGANISM: Steptococcus thermophilus

<400> SEQUENCE: 562
tgcatcgagc acgttcgagt ttaccgtttc 30

<210> SEQ ID NO 563
<211> LENGTH: 30
<212> TYPE: DNA
<213> ORGANISM: Steptococcus thermophilus

<400> SEQUENCE: 563
tgtttgacag caaatcaaga ttcgaattgt 30

<210> SEQ ID NO 564
<211> LENGTH: 30
<212> TYPE: DNA
<213> ORGANISM: Steptococcus thermophilus

<400> SEQUENCE: 564
ttcattcttc cgtttttgtt tgcgaatcct 30

<210> SEQ ID NO 565
<211> LENGTH: 30
<212> TYPE: DNA
<213> ORGANISM: Steptococcus thermophilus

<400> SEQUENCE: 565
tgacttagcg aatttaatcg ctaagatatc 30

<210> SEQ ID NO 566

<211> LENGTH: 30
<212> TYPE: DNA
<213> ORGANISM: Steptococcus thermophilus

<400> SEQUENCE: 566
tttatacttt atctttttaa agaatgtatt 30

<210> SEQ ID NO 567
<211> LENGTH: 30
<212> TYPE: DNA
<213> ORGANISM: Steptococcus thermophilus

<400> SEQUENCE: 567
cctaaaatca ttttcaacga gttgcgatac 30

<210> SEQ ID NO 568
<211> LENGTH: 30
<212> TYPE: DNA
<213> ORGANISM: Steptococcus thermophilus

<400> SEQUENCE: 568
aataaattgc tatgatacag cgtaccgata 30

<210> SEQ ID NO 569
<211> LENGTH: 30
<212> TYPE: DNA
<213> ORGANISM: Steptococcus thermophilus

<400> SEQUENCE: 569
tgctctctat gcgattggac gtctgtctaa 30

<210> SEQ ID NO 570
<211> LENGTH: 30
<212> TYPE: DNA
<213> ORGANISM: Steptococcus thermophilus

<400> SEQUENCE: 570
aagaaagata agaaaaaagt aacactactt 30

<210> SEQ ID NO 571
<211> LENGTH: 30
<212> TYPE: DNA
<213> ORGANISM: Steptococcus thermophilus

<400> SEQUENCE: 571
tctctttcca tcggtactgg tatatctcat 30

<210> SEQ ID NO 572
<211> LENGTH: 30
<212> TYPE: DNA
<213> ORGANISM: Steptococcus thermophilus

<400> SEQUENCE: 572
attggtagcc aagtaaatat caccattgat 30

<210> SEQ ID NO 573
<211> LENGTH: 30
<212> TYPE: DNA
<213> ORGANISM: Steptococcus thermophilus

<400> SEQUENCE: 573
ttcttcaaat tcaccgactg caaaattaca 30

<210> SEQ ID NO 574
<211> LENGTH: 30
<212> TYPE: DNA
<213> ORGANISM: Steptococcus thermophilus

<400> SEQUENCE: 574
gcttcctaag tgcatgaaaa tcgcaaacgg 30

<210> SEQ ID NO 575
<211> LENGTH: 30
<212> TYPE: DNA
<213> ORGANISM: Steptococcus thermophilus

<400> SEQUENCE: 575
tatacctgtc tatgtaaggg aatttaactc 30

<210> SEQ ID NO 576
<211> LENGTH: 30
<212> TYPE: DNA
<213> ORGANISM: Steptococcus thermophilus

<400> SEQUENCE: 576
ggtgtaggtg ctgttggtaa gttgtttaat 30

<210> SEQ ID NO 577
<211> LENGTH: 30
<212> TYPE: DNA
<213> ORGANISM: Steptococcus thermophilus

<400> SEQUENCE: 577
gtgaaacagg ttatcaaaaa acgtatattg 30

<210> SEQ ID NO 578
<211> LENGTH: 30
<212> TYPE: DNA
<213> ORGANISM: Steptococcus thermophilus

<400> SEQUENCE: 578
ttattcttgg aattattaca gaccctacta 30

<210> SEQ ID NO 579
<211> LENGTH: 30
<212> TYPE: DNA
<213> ORGANISM: Steptococcus thermophilus

<400> SEQUENCE: 579
gctttcatta tatcacttac tcataaatct 30

<210> SEQ ID NO 580
<211> LENGTH: 30
<212> TYPE: DNA
<213> ORGANISM: Steptococcus thermophilus

<400> SEQUENCE: 580
taatcacccc tttttctagc tcttgattga 30

<210> SEQ ID NO 581
<211> LENGTH: 30
<212> TYPE: DNA
<213> ORGANISM: Steptococcus thermophilus

<400> SEQUENCE: 581
caagcagtgt aaaggtggtt taaatgttaa 30

<210> SEQ ID NO 582
<211> LENGTH: 30
<212> TYPE: DNA
<213> ORGANISM: Steptococcus thermophilus

<400> SEQUENCE: 582
aacccgcgtg gttatgggct tgaggagtgt 30

<210> SEQ ID NO 583
<211> LENGTH: 30
<212> TYPE: DNA
<213> ORGANISM: Steptococcus thermophilus

<400> SEQUENCE: 583
atattaatag cgattctatg ctacaacgtg 30

<210> SEQ ID NO 584
<211> LENGTH: 30
<212> TYPE: DNA
<213> ORGANISM: Steptococcus thermophilus

<400> SEQUENCE: 584
tcatcttcta agtaaatacc actgtcaggg 30

<210> SEQ ID NO 585
<211> LENGTH: 29
<212> TYPE: DNA
<213> ORGANISM: Steptococcus thermophilus

<400> SEQUENCE: 585
ttttcgcaaa gtaagcgaag ctctacgtg 29

<210> SEQ ID NO 586
<211> LENGTH: 30
<212> TYPE: DNA
<213> ORGANISM: Steptococcus thermophilus

<400> SEQUENCE: 586
ttctgtagcc actccgtgga tgccttcagc 30

<210> SEQ ID NO 587
<211> LENGTH: 30
<212> TYPE: DNA
<213> ORGANISM: Steptococcus thermophilus

<400> SEQUENCE: 587
ttctttagtt cggacaccct caacacctat 30

<210> SEQ ID NO 588
<211> LENGTH: 30
<212> TYPE: DNA
<213> ORGANISM: Steptococcus thermophilus

<400> SEQUENCE: 588
gctttgattg gacggaaaat ggtatccctg 30

<210> SEQ ID NO 589
<211> LENGTH: 31
<212> TYPE: DNA
<213> ORGANISM: Steptococcus thermophilus

<400> SEQUENCE: 589
ttcctcatct ttctccgctt ttgctagact t 31

<210> SEQ ID NO 590
<211> LENGTH: 30
<212> TYPE: DNA
<213> ORGANISM: Steptococcus thermophilus

<400> SEQUENCE: 590
ttagaccaga tggacagata ttcttcatcg 30

<210> SEQ ID NO 591
<211> LENGTH: 31
<212> TYPE: DNA
<213> ORGANISM: Steptococcus thermophilus

<400> SEQUENCE: 591
tcatcagagt caacaatcac gggaaagacc t 31

<210> SEQ ID NO 592
<211> LENGTH: 30
<212> TYPE: DNA
<213> ORGANISM: Steptococcus thermophilus

<400> SEQUENCE: 592
acactcatcc ttatcctgta gttcaaaaca 30

<210> SEQ ID NO 593
<211> LENGTH: 30
<212> TYPE: DNA
<213> ORGANISM: Steptococcus thermophilus

<400> SEQUENCE: 593
cagcactagc cgcaagccct tgtatattaa 30

<210> SEQ ID NO 594
<211> LENGTH: 30
<212> TYPE: DNA
<213> ORGANISM: Steptococcus thermophilus

<400> SEQUENCE: 594
tagaaatcaa ggaacttgga tgaaaagtaa 30

<210> SEQ ID NO 595
<211> LENGTH: 30
<212> TYPE: DNA
<213> ORGANISM: Steptococcus thermophilus

<400> SEQUENCE: 595
atatgaaagg gaaatgatat gaagaatgaa 30

<210> SEQ ID NO 596
<211> LENGTH: 31
<212> TYPE: DNA
<213> ORGANISM: Steptococcus thermophilus

<400> SEQUENCE: 596
ttttgggata caacacgcag tcgttgactt g 31

<210> SEQ ID NO 597
<211> LENGTH: 30
<212> TYPE: DNA
<213> ORGANISM: Steptococcus thermophilus

<400> SEQUENCE: 597
gtttgagatg ccaatgtttt tcaatccttg 30

<210> SEQ ID NO 598
<211> LENGTH: 30
<212> TYPE: DNA
<213> ORGANISM: Steptococcus thermophilus

<400> SEQUENCE: 598
gtatcaaaag acgcattcat gaagcgagct 30

<210> SEQ ID NO 599
<211> LENGTH: 30
<212> TYPE: DNA
<213> ORGANISM: Steptococcus thermophilus

<400> SEQUENCE: 599
aaaaacaatt gaaattcata atcagcgctt 30

<210> SEQ ID NO 600
<211> LENGTH: 29
<212> TYPE: DNA
<213> ORGANISM: Steptococcus thermophilus

<400> SEQUENCE: 600
gcttttaacg ttttaagaga ataccctct 29

<210> SEQ ID NO 601
<211> LENGTH: 30
<212> TYPE: DNA
<213> ORGANISM: Steptococcus thermophilus

<400> SEQUENCE: 601
gtgacgctgc aatgacttgc catagtaatt 30

<210> SEQ ID NO 602
<211> LENGTH: 30
<212> TYPE: DNA
<213> ORGANISM: Steptococcus thermophilus

<400> SEQUENCE: 602
atactggtat atagtaattc atacttcatc 30

<210> SEQ ID NO 603
<211> LENGTH: 30
<212> TYPE: DNA
<213> ORGANISM: Steptococcus thermophilus

<400> SEQUENCE: 603
ttggtttcat atttactcct ttgtgttttg 30

<210> SEQ ID NO 604
<211> LENGTH: 30
<212> TYPE: DNA
<213> ORGANISM: Steptococcus thermophilus

<400> SEQUENCE: 604
ctgatttggt cttgttcttt tgtccctttt 30

<210> SEQ ID NO 605
<211> LENGTH: 30
<212> TYPE: DNA
<213> ORGANISM: Steptococcus thermophilus

<400> SEQUENCE: 605
gcagcagttg agaactttag cgtccagtgg 30

<210> SEQ ID NO 606
<211> LENGTH: 30
<212> TYPE: DNA
<213> ORGANISM: Steptococcus thermophilus

<400> SEQUENCE: 606
tgctactatg aaggacgctg ttgatacttt 30

<210> SEQ ID NO 607
<211> LENGTH: 30
<212> TYPE: DNA
<213> ORGANISM: Steptococcus thermophilus

<400> SEQUENCE: 607
tcttctttaa tcttttttaa cgtcaacgtt 30

<210> SEQ ID NO 608
<211> LENGTH: 30
<212> TYPE: DNA
<213> ORGANISM: Steptococcus thermophilus

<400> SEQUENCE: 608
gtatccatta atatagtagc atttctatca 30

<210> SEQ ID NO 609
<211> LENGTH: 30
<212> TYPE: DNA
<213> ORGANISM: Steptococcus thermophilus

<400> SEQUENCE: 609
attcattaat atctgcaagg atgtcttgtt 30

<210> SEQ ID NO 610
<211> LENGTH: 30
<212> TYPE: DNA
<213> ORGANISM: Steptococcus thermophilus

<400> SEQUENCE: 610
gagaaagtag cccattcggc ccattcgggg 30

<210> SEQ ID NO 611
<211> LENGTH: 30
<212> TYPE: DNA
<213> ORGANISM: Steptococcus thermophilus

<400> SEQUENCE: 611
tacttgagtt agctctggaa gtcatttatc 30

<210> SEQ ID NO 612
<211> LENGTH: 30
<212> TYPE: DNA
<213> ORGANISM: Steptococcus thermophilus

<400> SEQUENCE: 612
ctgcatttgt aaccatgact tcttcgtcgt 30

<210> SEQ ID NO 613
<211> LENGTH: 30
<212> TYPE: DNA
<213> ORGANISM: Steptococcus thermophilus

<400> SEQUENCE: 613
aatttgtcat cgacatctac caacgcccag 30

<210> SEQ ID NO 614
<211> LENGTH: 30
<212> TYPE: DNA
<213> ORGANISM: Steptococcus thermophilus

<400> SEQUENCE: 614
ataaaattat gccacgtttt ggcactagat 30

<210> SEQ ID NO 615
<211> LENGTH: 30
<212> TYPE: DNA
<213> ORGANISM: Steptococcus thermophilus

<400> SEQUENCE: 615
atgtctctga ggctgtagta atttacttgt 30

<210> SEQ ID NO 616
<211> LENGTH: 30
<212> TYPE: DNA
<213> ORGANISM: Steptococcus thermophilus

<400> SEQUENCE: 616
ctttaaagag ttgattaagt gcgttactgt 30

<210> SEQ ID NO 617
<211> LENGTH: 30
<212> TYPE: DNA
<213> ORGANISM: Steptococcus thermophilus

<400> SEQUENCE: 617
aaatgggtta tgctgttcaa tatgcgtccc 30

<210> SEQ ID NO 618
<211> LENGTH: 30
<212> TYPE: DNA
<213> ORGANISM: Steptococcus thermophilus

<400> SEQUENCE: 618
aaactgaaaa caacacagac aattcaacaa 30

<210> SEQ ID NO 619
<211> LENGTH: 30
<212> TYPE: DNA
<213> ORGANISM: Steptococcus thermophilus

<400> SEQUENCE: 619
gcccaaaatg ctagacgttt gaatgacggc 30

<210> SEQ ID NO 620
<211> LENGTH: 30
<212> TYPE: DNA
<213> ORGANISM: Steptococcus thermophilus

<400> SEQUENCE: 620
atgaagaacg tgattcacct acggtatgct 30

<210> SEQ ID NO 621
<211> LENGTH: 31
<212> TYPE: DNA
<213> ORGANISM: Steptococcus thermophilus

<400> SEQUENCE: 621
gcttttgcag aattgtctcc agtgccgatt t 31

<210> SEQ ID NO 622
<211> LENGTH: 30
<212> TYPE: DNA
<213> ORGANISM: Steptococcus thermophilus

<400> SEQUENCE: 622
tgtactctat tgattgcttc atctttatta 30

<210> SEQ ID NO 623
<211> LENGTH: 31
<212> TYPE: DNA
<213> ORGANISM: Steptococcus thermophilus

<400> SEQUENCE: 623
ctttcaagat actcatcaac cattgatgtc a 31

<210> SEQ ID NO 624
<211> LENGTH: 30
<212> TYPE: DNA
<213> ORGANISM: Steptococcus thermophilus

<400> SEQUENCE: 624
ctatgtcttt actgttcttc caaaaccacc 30

<210> SEQ ID NO 625
<211> LENGTH: 30
<212> TYPE: DNA
<213> ORGANISM: Steptococcus thermophilus

<400> SEQUENCE: 625
tgctacgtgc tctgtacggg cgctatcagc 30

<210> SEQ ID NO 626
<211> LENGTH: 30
<212> TYPE: DNA
<213> ORGANISM: Steptococcus thermophilus

<400> SEQUENCE: 626
cgtggcagcg tggtcgggtt taatagcccg 30

<210> SEQ ID NO 627
<211> LENGTH: 29
<212> TYPE: DNA
<213> ORGANISM: Steptococcus thermophilus

<400> SEQUENCE: 627
aagcccaagt cagagcatcc gtccaagcc 29

<210> SEQ ID NO 628
<211> LENGTH: 30
<212> TYPE: DNA
<213> ORGANISM: Steptococcus thermophilus

<400> SEQUENCE: 628
attgggtttc ggtaagaact aaacatacca 30

<210> SEQ ID NO 629
<211> LENGTH: 30
<212> TYPE: DNA

<213> ORGANISM: Steptococcus thermophilus

<400> SEQUENCE: 629
cacaaaataa ttcggtagtt tttactaact 30

<210> SEQ ID NO 630
<211> LENGTH: 29
<212> TYPE: DNA
<213> ORGANISM: Steptococcus thermophilus

<400> SEQUENCE: 630
tttgaccgtt tatttagacg tgctaaagt 29

<210> SEQ ID NO 631
<211> LENGTH: 30
<212> TYPE: DNA
<213> ORGANISM: Steptococcus thermophilus

<400> SEQUENCE: 631
cttcacctca aatcttagag ctggactaaa 30

<210> SEQ ID NO 632
<211> LENGTH: 30
<212> TYPE: DNA
<213> ORGANISM: Steptococcus thermophilus

<400> SEQUENCE: 632
atgtctgaaa aataaccgac catcattact 30

<210> SEQ ID NO 633
<211> LENGTH: 30
<212> TYPE: DNA
<213> ORGANISM: Steptococcus thermophilus

<400> SEQUENCE: 633
gaagctcatc atgttaaggc taaaacctat 30

<210> SEQ ID NO 634
<211> LENGTH: 30
<212> TYPE: DNA
<213> ORGANISM: Steptococcus thermophilus

<400> SEQUENCE: 634
tagtctaaat agatttcttg caccattgta 30

<210> SEQ ID NO 635
<211> LENGTH: 30
<212> TYPE: DNA
<213> ORGANISM: Steptococcus thermophilus

<400> SEQUENCE: 635
attcgtgaaa aaatatcgtg aaataggcaa 30

<210> SEQ ID NO 636
<211> LENGTH: 30
<212> TYPE: DNA
<213> ORGANISM: Steptococcus thermophilus

<400> SEQUENCE: 636
tctaggctca tctaaagata aatcagtagc 30

<210> SEQ ID NO 637
<211> LENGTH: 31

<212> TYPE: DNA
<213> ORGANISM: Steptococcus thermophilus

<400> SEQUENCE: 637
taaaaacatg gggcggcggt aatagtgtaa g 31

<210> SEQ ID NO 638
<211> LENGTH: 30
<212> TYPE: DNA
<213> ORGANISM: Steptococcus thermophilus

<400> SEQUENCE: 638
acaaccagca aagagagcgc cgacaacatt 30

<210> SEQ ID NO 639
<211> LENGTH: 30
<212> TYPE: DNA
<213> ORGANISM: Steptococcus thermophilus

<400> SEQUENCE: 639
tataacacag gtttagagga tgttatactt 30

<210> SEQ ID NO 640
<211> LENGTH: 31
<212> TYPE: DNA
<213> ORGANISM: Steptococcus thermophilus

<400> SEQUENCE: 640
ctagaagctc aagcggtaaa agttgatggc g 31

<210> SEQ ID NO 641
<211> LENGTH: 30
<212> TYPE: DNA
<213> ORGANISM: Steptococcus thermophilus

<400> SEQUENCE: 641
ctttgagggc aagccctcgc cgttccattt 30

<210> SEQ ID NO 642
<211> LENGTH: 30
<212> TYPE: DNA
<213> ORGANISM: Steptococcus thermophilus

<400> SEQUENCE: 642
aactaccaag caaatcagca atcaataagt 30

<210> SEQ ID NO 643
<211> LENGTH: 30
<212> TYPE: DNA
<213> ORGANISM: Steptococcus thermophilus

<400> SEQUENCE: 643
ctataagtga caatcagcgt agggaatacg 30

<210> SEQ ID NO 644
<211> LENGTH: 30
<212> TYPE: DNA
<213> ORGANISM: Steptococcus thermophilus

<400> SEQUENCE: 644
atcagtgcgg tatatttacc ctagacgcta 30

<210> SEQ ID NO 645

<211> LENGTH: 30
<212> TYPE: DNA
<213> ORGANISM: Steptococcus thermophilus

<400> SEQUENCE: 645
aacagttact attaatcacg attccaacgg 30

<210> SEQ ID NO 646
<211> LENGTH: 30
<212> TYPE: DNA
<213> ORGANISM: Steptococcus thermophilus

<400> SEQUENCE: 646
aattagggcg tcttccttta ttccgtggtt 30

<210> SEQ ID NO 647
<211> LENGTH: 30
<212> TYPE: DNA
<213> ORGANISM: Steptococcus thermophilus

<400> SEQUENCE: 647
atagcttcat tgcgcttttt aatttgacct 30

<210> SEQ ID NO 648
<211> LENGTH: 30
<212> TYPE: DNA
<213> ORGANISM: Steptococcus thermophilus

<400> SEQUENCE: 648
aacaacaaag caaatacaac agtaacaacc 30

<210> SEQ ID NO 649
<211> LENGTH: 30
<212> TYPE: DNA
<213> ORGANISM: Steptococcus thermophilus

<400> SEQUENCE: 649
ctaaactacg tttgaaggtc tcaactccgt 30

<210> SEQ ID NO 650
<211> LENGTH: 30
<212> TYPE: DNA
<213> ORGANISM: Steptococcus thermophilus

<400> SEQUENCE: 650
gaggttgaat agtgagtgca ccatgtttgt 30

<210> SEQ ID NO 651
<211> LENGTH: 30
<212> TYPE: DNA
<213> ORGANISM: Steptococcus thermophilus

<400> SEQUENCE: 651
agtagagaga ccagcacact actgtactac 30

<210> SEQ ID NO 652
<211> LENGTH: 30
<212> TYPE: DNA
<213> ORGANISM: Steptococcus thermophilus

<400> SEQUENCE: 652
cttcgcacga aagtttatta gacaactcgc 30

<210> SEQ ID NO 653
<211> LENGTH: 30
<212> TYPE: DNA
<213> ORGANISM: Steptococcus thermophilus

<400> SEQUENCE: 653
tgatagagct agaattgtct tttttaccga 30

<210> SEQ ID NO 654
<211> LENGTH: 30
<212> TYPE: DNA
<213> ORGANISM: Steptococcus thermophilus

<400> SEQUENCE: 654
agatactctt gctcgcctct gaacaaccag 30

<210> SEQ ID NO 655
<211> LENGTH: 30
<212> TYPE: DNA
<213> ORGANISM: Steptococcus thermophilus

<400> SEQUENCE: 655
ggtgaaaaag gttcactgta cgagtactta 30

<210> SEQ ID NO 656
<211> LENGTH: 30
<212> TYPE: DNA
<213> ORGANISM: Steptococcus thermophilus

<400> SEQUENCE: 656
tcaatgagtg gtatccaaga cgaaaactta 30

<210> SEQ ID NO 657
<211> LENGTH: 30
<212> TYPE: DNA
<213> ORGANISM: Steptococcus thermophilus

<400> SEQUENCE: 657
ccttgtcgtg gctctccata cgcccatata 30

<210> SEQ ID NO 658
<211> LENGTH: 30
<212> TYPE: DNA
<213> ORGANISM: Steptococcus thermophilus

<400> SEQUENCE: 658
tgtttgggaa accgcagtag ccatgattaa 30

<210> SEQ ID NO 659
<211> LENGTH: 32
<212> TYPE: DNA
<213> ORGANISM: Steptococcus thermophilus

<400> SEQUENCE: 659
acagagtaca atattgtcct cattggagac ac 32

<210> SEQ ID NO 660
<211> LENGTH: 30
<212> TYPE: DNA
<213> ORGANISM: Steptococcus thermophilus

<400> SEQUENCE: 660
ctcatattcg ttagttgctt ttgtcataaa 30

<210> SEQ ID NO 661
<211> LENGTH: 30
<212> TYPE: DNA
<213> ORGANISM: Steptococcus thermophilus

<400> SEQUENCE: 661
agaactttat caagataaaa ctactttaaa 30

<210> SEQ ID NO 662
<211> LENGTH: 30
<212> TYPE: DNA
<213> ORGANISM: Steptococcus thermophilus

<400> SEQUENCE: 662
atagtattaa tttcattgaa aaataattgt 30

<210> SEQ ID NO 663
<211> LENGTH: 36
<212> TYPE: DNA
<213> ORGANISM: Steptococcus thermophilus

<400> SEQUENCE: 663
gctttctagc tcgctataat tacccattcc tagaaa 36

<210> SEQ ID NO 664
<211> LENGTH: 40
<212> TYPE: DNA
<213> ORGANISM: Steptococcus thermophilus

<400> SEQUENCE: 664
tcaaaatatg ttattacctt gtatttcata attcaattaa 40

<210> SEQ ID NO 665
<211> LENGTH: 39
<212> TYPE: DNA
<213> ORGANISM: Steptococcus thermophilus

<400> SEQUENCE: 665
ccacttgctg tgtacatcct accagttccg cctatgatg 39

<210> SEQ ID NO 666
<211> LENGTH: 63
<212> TYPE: DNA
<213> ORGANISM: Steptococcus thermophilus

<400> SEQUENCE: 666
caaggacagt tattgatttt ataatcacta tgtgggtata aaaacgtcaa aatttcattt 60
gag 63

<210> SEQ ID NO 667
<211> LENGTH: 41
<212> TYPE: DNA
<213> ORGANISM: Steptococcus thermophilus

<400> SEQUENCE: 667
ttgattcaac ataaaaagcc agttcaattg aacttggctt t 41

<210> SEQ ID NO 668
<211> LENGTH: 2317
<212> TYPE: DNA
<213> ORGANISM: Steptococcus thermophilus

<400> SEQUENCE: 668

```
caaggacagt tattgatttt ataatcacta tgtgggtata aaaacgtcaa aatttcattt     60
gaggtttttg tactctcaag atttaagtaa ctgtacaact caacaattgc aacatcttat    120
aacccacttg tttttgtact ctcaagattt aagtaactgt acaactgttt gacagcaaat    180
caagattcga attgtgtttt tgtactctca agatttaagt aactgtacaa caatgacgag    240
gagctattgg cacaacttac agtttttgta ctctcaagat ttaagtaact gtacaaccga    300
tttgacaatc tgctgaccac tgttatcgtt tttgtactct caagatttaa gtaactgtac    360
aacacacttg gcaggcttat tactcaacag cgagtttttg tactctcaag atttaagtaa    420
ctgtacaacc tgttccttgt tcttttgttg tatcttttcg tttttgtact ctcaagattt    480
aagtaactgt acaacttcat tcttccgttt ttgtttgcga atcctgtttt tgtactctca    540
agatttaagt aactgtacaa cgctggcgag gaaacgaaca aggcctcaac agtttttgta    600
ctctcaagat ttaagtaact gtacaaccat agagtggaaa actagaaaca gattcaagtt    660
tttgtactct caagatttaa gtaactgtac aacataatgc cgttgaatta cacggcaagg    720
tcagtttttg tactctcaag atttaagtaa ctgtacaacg agcgagctcg aaataatctt    780
aattacaagg tttttgtact ctcaagattt aagtaactgt acaacgttcg ctagcgtcat    840
gtggtaacgt atttagtttt tgtactctca agatttaagt aactgtacaa cggcgtccca    900
atcctgatta atacttactc ggtttttgta ctctcaagat ttaagtaact gtacaacaac    960
acagcaagac aagaggatga tgctatggtt tttgtactct caagatttaa gtaactgtac   1020
aaccgacaca agaacgtatg caagagttca aggtttttgt actctcaaga tttaagtaac   1080
tgtacaacac aattcttcat ccggtaactg ctcaagtggt tttgtactc tcaagattta   1140
agtaactgta caacaattaa gggcatagaa agggagacaa catggttttt gtactctcaa   1200
gatttaagta actgtacaac cgatatttaa aatcattttc ataacttcat gtttttgtac   1260
tctcaagatt taagtaactg tacaacgcag tatcagcaag caagctgtta gttactgttt   1320
ttgtactctc aagatttaag taactgtaca acataaacta tgaaatttta taatttttaa   1380
gagtttttgt actctcaaga tttaagtaac tgtacaacaa taatttatgg tatagcttaa   1440
tatcattggt tttgtactc tcaagattta agtaactgta caactgcatc gagcacgttc   1500
gagtttaccg tttcgttttt gtactctcaa gatttaagta actgtacaac tctatatcga   1560
ggtcaactaa caattatgct gtttttgtac tctcaagatt taagtaactg tacaacaatc   1620
gttcaaattc tgttttaggt acatttgttt ttgtactctc aagatttaag taactgtaca   1680
acaatcaata cgacaagagt taaaatggtc ttgtttttgt actctcaaga tttaagtaac   1740
tgtacaacgc ttagctgtcc aatccacgaa cgtggatggt tttgtactc tcaagattta   1800
agtaactgta caaccaacca acggtaacag ctacttttta cagtgttttt gtactctcaa   1860
gatttaagta actgtacaac ataactgaag gataggagct tgtaaagtct gtttttgtac   1920
tctcaagatt taagtaactg tacaactaat gctacatctc aaaggatgat cccagagttt   1980
ttgtactctc aagatttaag taactgtaca acaagtagtt gatgacctct acaatggttt   2040
atgtttttgt actctcaaga tttaagtaac tgtacaacac ctagaagcat ttgagcgtat   2100
attgattggt tttgtactc tcaagattta agtaactgta caacaatttt gccccttctt   2160
tgccccttga ctaggttttt gtactctcaa gatttaagta actgtacaac accattagca   2220
atcatttgtg cccattgagt gtttttgtac tctcaagatt taagtaactg tacagtttga   2280
ttcaacataa aaagccagtt caattgaact tggcttt                            2317
```

<210> SEQ ID NO 669
<211> LENGTH: 30
<212> TYPE: DNA
<213> ORGANISM: Steptococcus thermophilus

<400> SEQUENCE: 669
tcaacaattg caacatctta taacccactt 30

<210> SEQ ID NO 670
<211> LENGTH: 2317
<212> TYPE: DNA
<213> ORGANISM: Steptococcus thermophilus

<400> SEQUENCE: 670
caaggacagt tattgatttt ataatcacta tgtgggtata aaaacgtcaa aatttcattt 60
gaggtttttg tactctcaag atttaagtaa ctgtacaact tacgtttgaa aagaatatca 120
aatcaatgag tttttgtact ctcaagattt aagtaactgt acaactgttt gacagcaaat 180
caagattcga attgtgtttt tgtactctca agatttaagt aactgtacaa caatgacgag 240
gagctattgg cacaacttac agtttttgta ctctcaagat ttaagtaact gtacaaccga 300
tttgacaatc tgctgaccac tgttatcgtt tttgtactct caagatttaa gtaactgtac 360
aacacacttg gcaggcttat tactcaacag cgagtttttg tactctcaag atttaagtaa 420
ctgtacaacc tgttccttgt tcttttgttg tatcttttcg tttttgtact ctcaagattt 480
aagtaactgt acaacttcat tcttccgttt ttgtttgcga atcctgtttt tgtactctca 540
agatttaagt aactgtacaa cgctggcgag gaaacgaaca aggcctcaac agtttttgta 600
ctctcaagat ttaagtaact gtacaaccat agagtggaaa actagaaaca gattcaagtt 660
tttgtactct caagatttaa gtaactgtac aacataatgc cgttgaatta cacggcaagg 720
tcagtttttg tactctcaag atttaagtaa ctgtacaacg agcgagctcg aaataatctt 780
aattacaagg tttttgtact ctcaagattt aagtaactgt acaacgttcg ctagcgtcat 840
gtggtaacgt atttagtttt tgtactctca agatttaagt aactgtacaa cggcgtccca 900
atcctgatta atacttactc ggtttttgta ctctcaagat ttaagtaact gtacaacaac 960
acagcaagac aagaggatga tgctatggtt tttgtactct caagatttaa gtaactgtac 1020
aaccgacaca agaacgtatg caagagttca aggtttttgt actctcaaga tttaagtaac 1080
tgtacaacac aattcttcat ccggtaactg ctcaagtggt tttgtactc tcaagattta 1140 agtaactgta caacaattaa gggcatagaa agggagacaa catggttttt gtactctcaa 1200
gatttaagta actgtacaac cgatatttaa aatcattttc ataacttcat gtttttgtac 1260
tctcaagatt taagtaactg tacaacgcag tatcagcaag caagctgtta gttactgttt 1320
ttgtactctc aagatttaag taactgtaca acataaacta tgaaatttta taatttttaa 1380
gagtttttgt actctcaaga tttaagtaac tgtacaacaa taatttatgg tatagcttaa 1440
tatcattggt tttgtactc tcaagattta agtaactgta caactgcatc gagcacgttc 1500
gagtttaccg tttcgttttt gtactctcaa gatttaagta actgtacaac tctatatcga 1560
ggtcaactaa caattatgct gtttttgtac tctcaagatt taagtaactg tacaacaatc 1620
gttcaaattc tgttttaggt acatttgttt ttgtactctc aagatttaag taactgtaca 1680
acaatcaata cgacaagagt taaaatggtc ttgtttttgt actctcaaga tttaagtaac 1740
tgtacaacgc ttagctgtcc aatccacgaa cgtggatggt tttgtactc tcaagattta 1800 agtaactgta caaccaacca acggtaacag ctacttttta cagtgttttt gtactctcaa 1860
gatttaagta actgtacaac ataactgaag gataggagct tgtaaagtct gtttttgtac 1920
tctcaagatt taagtaactg tacaactaat gctacatctc aaaggatgat cccagagttt 1980
ttgtactctc aagatttaag taactgtaca acaagtagtt gatgacctct acaatggttt 2040
atgtttttgt actctcaaga tttaagtaac tgtacaacac ctagaagcat ttgagcgtat 2100
attgattggt ttttgtactc tcaagattta agtaactgta caacaatttt gccccttctt 2160
tgccccttga ctaggttttt gtactctcaa gatttaagta actgtacaac accattagca 2220
atcatttgtg cccattgagt gtttttgtac tctcaagatt taagtaactg tacagtttga 2280
ttcaacataa aaagccagtt caattgaact tggcttt 2317

<210> SEQ ID NO 671
<211> LENGTH: 30
<212> TYPE: DNA
<213> ORGANISM: Steptococcus thermophilus

<400> SEQUENCE: 671
ttacgtttga aaagaatatc aaatcaatga 30

<210> SEQ ID NO 672
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 672
caaatggata gagaaacgc 19

<210> SEQ ID NO 673
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 673
ctgataaggt gttcgttgtc c 21

<210> SEQ ID NO 674
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 674
ggagcagatg gaatacaaga aagg 24

<210> SEQ ID NO 675
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 675
gagagactag gttgtctcag ca 22

<210> SEQ ID NO 676
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 676
acaaacaaca gagaagtatc tcattg 26

<210> SEQ ID NO 677
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 677
aacgagtaca ctcactattt gtacg 25

<210> SEQ ID NO 678
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 678
ctttccttca tcctcgcttt ggtt 24

<210> SEQ ID NO 679
<211> LENGTH: 30
<212> TYPE: DNA
<213> ORGANISM: Steptococcus thermophilus

<400> SEQUENCE: 679
ttctggtagt ggttttagtc aaacagatgt 30

<210> SEQ ID NO 680
<211> LENGTH: 30
<212> TYPE: DNA
<213> ORGANISM: Steptococcus thermophilus

<400> SEQUENCE: 680
ttctggtagt ggttttagtc aaacagatgt 30

<210> SEQ ID NO 681
<211> LENGTH: 30
<212> TYPE: DNA
<213> ORGANISM: Steptococcus thermophilus

<400> SEQUENCE: 681
ttctggtagt ggatttagtc aaacagatgt 30

<210> SEQ ID NO 682
<211> LENGTH: 30
<212> TYPE: DNA
<213> ORGANISM: Steptococcus thermophilus

<400> SEQUENCE: 682
ttctggtagt ggttttagtc aaacagatgt 30

<210> SEQ ID NO 683
<211> LENGTH: 30
<212> TYPE: DNA
<213> ORGANISM: Steptococcus thermophilus

<400> SEQUENCE: 683
ttctggtagt ggttttagtc aaacagatgt 30

<210> SEQ ID NO 684
<211> LENGTH: 23
<212> TYPE: DNA
<213> ORGANISM: Steptococcus thermophilus

<400> SEQUENCE: 684
tctggtagtg gatttagtca aac 23

<210> SEQ ID NO 685
<211> LENGTH: 23
<212> TYPE: DNA
<213> ORGANISM: Steptococcus thermophilus

<400> SEQUENCE: 685
tctggtagtg gatttagtca aac 23

<210> SEQ ID NO 686
<211> LENGTH: 26
<212> TYPE: DNA
<213> ORGANISM: Steptococcus thermophilus

<400> SEQUENCE: 686
ggtagtggat ttagtcaaac agatgt 26

<210> SEQ ID NO 687
<211> LENGTH: 26
<212> TYPE: DNA
<213> ORGANISM: Steptococcus thermophilus

<400> SEQUENCE: 687
ggtagtggct ttagtcaaac agatgt 26

<210> SEQ ID NO 688
<211> LENGTH: 28
<212> TYPE: DNA
<213> ORGANISM: Steptococcus thermophilus

<400> SEQUENCE: 688
ttctggtagt ggatttagtc aaacagat 28

<210> SEQ ID NO 689
<211> LENGTH: 28
<212> TYPE: DNA
<213> ORGANISM: Steptococcus thermophilus

<400> SEQUENCE: 689
ttctggcagt ggttttagtc aaacagat 28

<210> SEQ ID NO 690
<211> LENGTH: 36
<212> TYPE: RNA
<213> ORGANISM: Steptococcus thermophilus

<400> SEQUENCE: 690
guuuuagagc uguguuguuu cgaaugguuc caaaac 36

<210> SEQ ID NO 691
<211> LENGTH: 222
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 691
caggaaacag ctatgaccat gattacgcca agcttggtac cgagctcgga tccactagta 60
acggccgcca gtgtgctgga attcgccctt aagggcgaat tctgcagata tccatcacac 120
tggcggccgc tcgagcatgc atctagaggg cccaattcgc cctatagtga gtcgtattac 180
aattcactgg ccgtcgtttt acaacgtcgt gactgggaaa ac 222

<210> SEQ ID NO 692
<211> LENGTH: 84
<212> TYPE: DNA
<213> ORGANISM: Artificial Sequence
<220> FEATURE:
<223> OTHER INFORMATION: Description of Artificial Sequence: Synthetic primer

<400> SEQUENCE: 692
tccactcacg tacaaatagt gagtgtactc gtttttgtat tctcaagatt taagtaactg 60
tacagtttga ttcaacataa aaag 84

<210> SEQ ID NO 693
<211> LENGTH: 8
<212> TYPE: PRT
<213> ORGANISM: Steptococcus thermophilus

<400> SEQUENCE: 693

Asp Cys Phe Cys Thr Leu Lys Ile
1 5

<210> SEQ ID NO 694
<211> LENGTH: 21
<212> TYPE: PRT
<213> ORGANISM: Steptococcus thermophilus

<400> SEQUENCE: 694

Val Thr Val Gln Leu Leu Thr Ser Ser Val His Arg Leu Lys Cys Phe
1 5 10 15

Cys Thr Leu Lys Ile
20

<210> SEQ ID NO 695
<211> LENGTH: 16
<212> TYPE: PRT
<213> ORGANISM: Steptococcus thermophilus

<400> SEQUENCE: 695

Val Thr Val Gln Pro Pro Leu Ser Met Glu Arg Tyr Pro Ser Ser Phe
1 5 10 15

<210> SEQ ID NO 696
<211> LENGTH: 10
<212> TYPE: PRT
<213> ORGANISM: Steptococcus thermophilus

<400> SEQUENCE: 696

Lys Ile Val Phe Val Leu Ser Arg Phe Lys
1 5 10

<210> SEQ ID NO 697
<211> LENGTH: 4
<212> TYPE: PRT
<213> ORGANISM: Steptococcus thermophilus

<400> SEQUENCE: 697

Leu Tyr Asn Phe
1

<210> SEQ ID NO 698
<211> LENGTH: 16
<212> TYPE: PRT
<213> ORGANISM: Steptococcus thermophilus

<400> SEQUENCE: 698

Arg His Gln Ser Thr Ala Leu Asn Val Phe Val Leu Ser Arg Phe Lys
1 5 10 15

<210> SEQ ID NO 699
<211> LENGTH: 15
<212> TYPE: PRT
<213> ORGANISM: Steptococcus thermophilus

<400> SEQUENCE: 699

Leu Tyr Asn His Leu Phe Arg Trp Lys Gly Ile Leu Leu Val Phe
1 5 10 15

<210> SEQ ID NO 700
<211> LENGTH: 22
<212> TYPE: PRT
<213> ORGANISM: Steptococcus thermophilus

<400> SEQUENCE: 700

Arg Leu Phe Leu Tyr Ser Gln Asp Leu Ser Asn Cys Thr Thr Phe Asn
1 5 10 15

Val Ile Ser Pro Pro Pro
20

<210> SEQ ID NO 701
<211> LENGTH: 22
<212> TYPE: PRT
<213> ORGANISM: Steptococcus thermophilus

<400> SEQUENCE: 701

Met Phe Leu Tyr Ser Gln Asp Leu Ser Asn Cys Thr Thr Thr Ser Phe
1 5 10 15

Asp Gly Lys Val Ser Phe
20

<210> SEQ ID NO 702
<211> LENGTH: 143
<212> TYPE: DNA
<213> ORGANISM: Steptococcus thermophilus

<400> SEQUENCE: 702
agattgtttt tgtactctca agatttaagt aactgtacaa cttttaacgt catcagtcca 60
ccgccttaaa tgtttttgta ctctcaagat ttaagtaact gtacaaccac ctctttcgat 120
ggaaaggtat ccttctagtt ttt 143

<210> SEQ ID NO 703
<211> LENGTH: 143
<212> TYPE: DNA
<213> ORGANISM: Steptococcus thermophilus

<400> SEQUENCE: 703
tctaacaaaa acatgagagt tctaaattca ttgacatgtt gaaaattgca gtagtcaggt 60
ggcggaattt acaaaaacat gagagttcta aattcattga catgttggtg gagaaagcta 120
cctttccata ggaagatcaa aaa 143

<210> SEQ ID NO 704
<211> LENGTH: 6
<212> TYPE: PRT
<213> ORGANISM: Steptococcus thermophilus

<400> SEQUENCE: 704

Leu Asn Asn Lys Tyr Glu
1 5

<210> SEQ ID NO 705
<211> LENGTH: 15
<212> TYPE: PRT
<213> ORGANISM: Steptococcus thermophilus

<400> SEQUENCE: 705

Ser Lys Leu Leu Gln Val Val Lys Leu Thr Met Leu Gly Gly Gly
1 5 10 15

<210> SEQ ID NO 706
<211> LENGTH: 5
<212> TYPE: PRT
<213> ORGANISM: Steptococcus thermophilus

<400> SEQUENCE: 706

Ile Asn Lys Tyr Glu
1 5

<210> SEQ ID NO 707
<211> LENGTH: 16
<212> TYPE: PRT
<213> ORGANISM: Steptococcus thermophilus

<400> SEQUENCE: 707

Ser Lys Leu Leu Gln Val Val Val Glu Lys Ser Pro Phe Thr Asp Lys
1 5 10 15

<210> SEQ ID NO 708
<211> LENGTH: 8
<212> TYPE: PRT
<213> ORGANISM: Steptococcus thermophilus

<400> SEQUENCE: 708

Ser Gln Lys Gln Val Arg Leu Ile
1 5

<210> SEQ ID NO 709
<211> LENGTH: 21
<212> TYPE: PRT
<213> ORGANISM: Steptococcus thermophilus

<400> SEQUENCE: 709

Thr Val Thr Cys Ser Lys Val Asp Asp Thr Trp Arg Arg Leu His Lys
1 5 10 15

-continued

```
Gln Val Arg Leu Ile
            20


<210> SEQ ID NO 710
<211> LENGTH: 17
<212> TYPE: PRT
<213> ORGANISM: Steptococcus thermophilus

<400> SEQUENCE: 710

Thr Val Thr Cys Gly Gly Arg Glu Ile Ser Leu Tyr Gly Glu Leu Lys
1               5                   10                  15

Gln


<210> SEQ ID NO 711
<211> LENGTH: 14
<212> TYPE: PRT
<213> ORGANISM: Steptococcus thermophilus

<400> SEQUENCE: 711

Ile Thr Lys Thr Ser Glu Leu Asn Leu Tyr Ser Tyr Leu Lys
1               5                   10


<210> SEQ ID NO 712
<211> LENGTH: 29
<212> TYPE: PRT
<213> ORGANISM: Steptococcus thermophilus

<400> SEQUENCE: 712

Asp Val Ala Lys Phe Thr Lys Thr Ser Glu Leu Asn Leu Tyr Ser Tyr
1               5                   10                  15

Leu Trp Arg Lys Arg His Phe Pro Ile Arg Arg Thr Lys
            20                  25
```

METHOD OF MODULATING CELL RESISTANCE

CLAIM OF PRIORITY

This continuation application claims priority under U.S. application Ser. No. 11/990,885, filed on Mar. 5, 2009, issued as U.S. Pat. No. 10,066,233, which claims priority under 35 USC 371 to International Application No. PCT/US2006/33167, filed Aug. 25, 2006, which claims priority to U.S. Provisional Application No. 60/711,396, filed Aug. 26, 2005 and U.S. Provisional Application No. 60/747,683, filed May 19, 2006, each of which is incorporated by reference in its entirety.

FIELD OF INVENTION

The present invention relates to inter alia modulating the resistance of a cell against a target nucleic acid or a transcription product thereof. In particular, the present invention relates, in one aspect, to the use of one or more cas genes or proteins for modulating the resistance of a cell against a target nucleic acid or a transcription product thereof.

BACKGROUND TO THE INVENTION

Cultures—such as starter cultures—are used extensively in the food industry in the manufacture of fermented products including milk products (such as yoghurt, butter and cheese), meat products, bakery products, wine and vegetable products. The preparation of cultures is labour intensive, occupying much space and equipment, and there is a considerable risk of contamination with spoilage bacteria and/or phages during the step of propagation. The failure of bacterial cultures by bacteriophage (phage) infection and multiplication is a major problem with the industrial use of bacterial cultures. There are many different types of phages with varying mechanisms to attack bacteria. Moreover, new strains of bacteriophages appear.

Strategies used in industry to minimise bacteriophage infection, and thus failure of a bacterial culture, include the use of: (i) mixed starter cultures; and (ii) the alternate use of strains having different phage susceptibility profiles (strain rotation).

(i) Traditionally, starter cultures in the dairy industry are mixtures of lactic acid bacterial strains. The complex composition of mixed starter cultures ensures that a certain level of resistance to phage attack is present. However, repeated sub-culturing of mixed strain cultures leads to unpredictable changes in the distribution of individual strains and eventually undesired strain dominance. This in turn may lead to increased susceptibility to phage attack and risk of fermentation failures.

(ii) The rotation of selected bacterial strains which are sensitive to different phages is another approach to limit phage development. However, it is difficult and cumbersome to identify and select a sufficient number of strains having different phage type profiles to provide an efficient and reliable rotation program. In addition, the continuous use of strains requires careful monitoring for new infectious phages and the need to quickly substitute a strain which is infected by the new bacteriophage by a resistant strain. In manufacturing plants where large quantities of bulk starter cultures are made ahead of time, such a quick response is usually not possible.

Several attempts have been made to improve the resistance of cultures for use in industry.

Pedersen et at ($7^{th}$ symposium on lactic acid bacteria: genetics, metabolism and applications, Sep. 1-5, 2002, Egmond aan Zee, The Netherlands) teach a phage resistant *Lactococcus lactis* strain, which has no thymidylate synthase activity and which requires thymidine for DNA replication.

WO 01/14520 discloses a lactic acid bacterium which have a reduced susceptibility towards attack by at least one type of bacteriophage. Said lactic acid bacteria comprise a mutated gene involved in pyrimidine metabolism, namely pyrG which results in a defect in CTP-synthetase.

Kosuge et al (1998—*Appl. Environ. Microbiol.*, Volume: 64, Issue: 11, Page(s): 4328-4332) and Kosuge et al (1994—*FEMS Microbiology Letters,* 123 (1/2) 55-62) teach a *Thermus thermophilus* HB27 bacterium which is mutated in the proB gene and is unable to utilise proline for growth.

However, there is a continuing need to improve cultures for use in industry.

SUMMARY OF THE INVENTION

There is described herein the use of CRISPR loci or a component thereof for modulating the resistance of a cell against a target nucleic acid or a transcription product thereof.

CRISPRs (Clustered Regularly Interspaced Short Palindromic Repeats) (also known as SPIDRs—SPacer Interspersed Direct Repeats) constitute a family of recently described DNA loci. CRISPR loci consist of short and highly conserved DNA repeats (typically 24 to 40 bp, repeated from 1 to 140 times) which are partially palindromic. The repeated sequences (usually specific to a species) are interspaced by variable sequences of constant length (typically 20 to 58 bp depending on the CRISPR). Up to 20 distinct CRISPR loci have been found within a single chromosome.

Although the biological function of CRISPR loci is unknown some hypotheses have been proposed. For example, it has been proposed that they may be involved in the attachment of the chromosome to a cellular structure, or in the chromosome replication and replicon partitioning (Jansen et al., 2002; Pourcel et al., 2005). Moreover, Mojica et al. 2005 hypothesis that CRISPR could be involved in conferring specific immunity against foreign DNA and Pourcel et al. (2005) hypothesise that CRISPRs are structures that are able to take up pieces of foreign DNA as part of a defence mechanism. Bolotin et al. (2005) suggest that the CRISPR spacer elements are the traces of past invasions by extrachromosomal elements, and hypothesise that they provide a cell with immunity against phage infection, and more generally foreign DNA expression, by coding an anti-sense RNA. Bolotin et al. (2005) also suggest that cas genes are necessary for CRISPR formation.

In contrast to the teachings of the prior art which hypothesise that CRISPR or CRISPR spacers could be involved in conferring specific immunity, the present invention is based, in part, on the surprising finding that cas genes or proteins are required for immunity against a target nucleic acid or a transcription product thereof.

Even more surprisingly, the inventors have discovered that one or more cas genes or proteins are associated with two or more CRISPR repeats within CRISPR loci. In other words, cas genes or proteins seem to be specific for a given DNA CRISPR repeat, meaning that cas genes or proteins and the repeated sequence form a functional pair. Accordingly, one or more CRISPR spacers may be used together with one or more of these functional pairs (i.e. CRISPR repeats and cas genes) in order to modulate the resistance of a cell against a target nucleic acid or a transcription product thereof.

In one embodiment, for one or more CRISPR spacers to confer immunity to the cell, the CRISPR repeat(s) and the cas gene(s) or proteins form a functional combination ie. the CRISPR repeat(s) and the cas gene(s) or proteins are compatible.

Accordingly, we suggest here for the first time that a cas gene or protein influences resistance—such as the resistance of a bacteria to one or more bacteriophages. In particular, the knowledge of two or more CRISPR repeats and/or one or more cas genes or proteins for a given cell will be an advantage to predict, determine and modify its resistance, for example, its lysotype, which defines the resistance/sensitivity of a given bacterium to various bacteriophages. Consequently, identification and detection of CRISPR loci in, for example, cells and bacteriophages could help to determine, predict and modify the resistance profile of a cell or phage-host interactions.

Advantageously, the application of one or more CRISPR loci, two or more CRISPR repeats, one or more cas genes or proteins and/or one or more CRISPR spacers in genetic engineering could lead to resistant or sensitive variants of cells for use within a wide variety of applications in the biotechnology industry.

SUMMARY ASPECTS OF THE PRESENT INVENTION

In one aspect there is provided the use of one or more cas genes or proteins for modulating resistance in a cell against a target nucleic acid or a transcription product thereof.

In a second aspect there is provided the use of a recombinant nucleic acid sequence comprising at least one cas gene and at least two CRISPR repeats together with at least one CRISPR spacer, wherein at least one CRISPR spacer is heterologous to at least one cas gene and/or at least two CRISPR repeats to modulate resistance against a target nucleic acid or transcription product thereof.

In a third aspect there is provided a nucleic acid sequence consisting essentially of at least one cas gene.

In a fourth aspect there is provided a nucleic acid sequence consisting essentially of at least one cas gene and at least two CRISPR repeats.

In a fifth aspect there is provided a nucleic acid sequence consisting essentially of at least one cas gene and at least one CRISPR spacer.

In a sixth aspect there is provided a nucleic acid sequence consisting essentially of at least one cas gene, at least one CRISPR spacer and at least two CRISPR repeats.

In a seventh aspect there is provided a recombinant nucleic acid sequence comprising at least one cas gene and at least two CRISPR repeats together with at least one CRISPR spacer, wherein the CRISPR spacer is heterologous to the at least one cas gene and/or the at least two CRISPR repeats.

In an eight aspect there is provided a construct comprising one or more of the nucleic acid sequences described herein In a ninth aspect there is provided a vector comprising one or more of the nucleic acid sequences or one or more of the constructs described herein.

In an tenth aspect there is provided a cell comprising the nucleic acid sequence or the construct or the vector described herein.

In an eleventh aspect there is provided a method for modulating (e.g. conferring or increasing) the resistance of a cell against a target nucleic acid or a transcription product thereof comprising the steps of: (i) identifying a sequence (eg. a conserved sequence) in an organism (preferably, a sequence essential to the function or survival of the organism); (ii) preparing a CRISPR spacer which is homologous to the identified sequence; (iii) preparing a nucleic acid (eg. a recombinant nucleic acid) comprising at least one cas gene and at least two CRISPR repeats together with the CRISPR spacer; and (iv) introducing said nucleic acid into a cell thus to render the cell resistant to said target nucleic acid or transcription product thereof.

In a twelfth aspect there is provided a method for modulating (eg. conferring or increasing) the resistance of a cell against a target nucleic acid or a transcription product thereof comprising the steps of: (i) identifying one or more CRISPR spacers or pseudo CRISPR spacers in an organism resistant to the target nucleic acid or transcription product thereof; (ii) preparing a recombinant nucleic acid comprising at least one cas gene or protein and at least two CRISPR repeats together with said identified one or more spacers; and (iii) introducing said recombinant nucleic acid into a cell thus to render the cell resistant to said target nucleic acid or transcription product thereof.

In a thirteenth aspect there is provided a method for modulating (eg. conferring or increasing) the resistance of a cell comprising at least one or more cas genes or proteins and two or more CRISPR repeats against a target nucleic acid or a transcription product thereof comprising the steps of: (i) identifying one or more CRISPR spacers in an organism resistant to the target nucleic acid or transcription product thereof; and (ii) modifying the sequence of one or more CRISPR spacer(s) in the cell such that the CRISPR spacer(s) has homology to the CRISPR spacer(s) in the organism.

In a fourteenth aspect there is provided a method for modulating (eg. reducing or decreasing) the resistance of a cell comprising at least one or more cas genes or proteins and two or more CRISPR repeats against a target nucleic acid or a transcription product thereof comprising the steps of: (i) identifying one or more CRISPR spacers in an organism that is substantially resistant to the target nucleic acid or transcription product thereof; and (ii) modifying the sequence of at least one or more CRISPR spacer(s) in the cell such that the CRISPR spacer(s) has a reduced degree of homology to the spacer(s) in the organism.

In a fifteenth aspect there is provided a method for modulating (eg. reducing or decreasing) the resistance of a cell comprising at least one or more cas genes or proteins and two or more CRISPR repeats against a target nucleic acid or a transcription product thereof comprising modifying the one or more cas genes or proteins and/or two or more CRISPR repeats in the cell.

In a sixteenth aspect there is provided a method for identifying a CRISPR spacer or pseudo CRISPR spacer for use in modulating the resistance of a cell against a target nucleic acid or a transcription product thereof comprising the steps of: (i) preparing a cell comprising at least two CRISPR repeats and at least one cas gene or protein; (ii) identifying at least one CRISPR spacer or pseudo CRISPR spacers in an organism that is substantially resistant to the target nucleic acid or transcription product thereof; (iii) modifying the sequence of the CRISPR spacer in the cell such that the CRISPR spacer has homology to the spacer of the organism; and (iv) determining if the cell modulates resistance against the target nucleic acid or transcription product thereof, wherein modulation of the resistance of the cell against the target nucleic acid or transcription product thereof is indicative that the CRISPR spacer modulates the resistance of the cell.

In a seventeenth aspect there is provided a method for identifying a cas gene for use in modulating the resistance of a cell against a target nucleic acid or transcription product thereof comprising the steps of: (i) preparing a cell comprising at least one CRISPR spacer and at least two CRISPR repeats; (ii) engineering the cell such that it comprises at least one cas gene; and (iii) determining if the cell modulates resistance against the target nucleic acid or transcription product thereof, wherein modulation of the resistance of the cell against the target nucleic acid or transcription product thereof is indicative that the cas gene can be used to modulate the resistance of the cell.

In an eighteenth aspect there is provided a method for identifying a CRISPR repeat for use in modulating the resistance of a cell against a target nucleic acid or transcription product thereof comprising the steps of: (i) preparing a cell comprising at least one CRISPR spacer and at least one cas gene; (ii) engineering the cell such that it contains the CRISPR repeat; and (iii) determining if the cell modulates resistance against the target nucleic acid or transcription product thereof, wherein modulation of the resistance of the cell against the target nucleic acid or transcription product thereof is indicative that the CRISPR repeat can be used to modulate resistance.

In a nineteenth aspect there is provided a method for identifying a functional combination of a cas gene and a CRISPR repeat comprising the steps of: (a) determining the sequences of the cas gene and the CRISPR repeat; (b) identifying one or more clusters of cas genes as determined by sequence comparison analysis; (c) identifying one or more clusters of CRISPR repeats; and (d) combining those cas gene and CRISPR repeat sequences that fall within the same cluster, wherein the combination of the cas gene and CRISPR repeat sequences within the same cluster is indicative that the combination is a functional combination.

In a twentieth aspect there is provided a method for modulating the lysotype of a bacterial cell comprising one or more cas genes or proteins and two or more CRISPR repeats comprising the steps of: (i) identifying one or more pseudo CRISPR spacers in the genomic sequence of a bacteriophage against which resistance is to be modulated; and (ii) modifying the sequence of one or more CRISPR spacers of the bacterial cell such that the CRISPR spacer(s) of the bacterial cell has homology to the pseudo CRISPR spacer(s) of the bacteriophage against which resistance is to be modulated.

In a twenty-first aspect there is provided a method for modulating (eg. conferring or increasing) the resistance of a bacterial cell against a bacteriophage comprising the steps of: (i) identifying a sequence (eg. a conserved sequence) in a bacteriophage (preferably, a sequence essential to the function or survival of the bacteriophage); (ii) preparing a CRISPR spacer which is homologous to the identified sequence; (iii) preparing a nucleic acid comprising at least one cas gene and at least two CRISPR repeats together with the CRISPR spacer; and (iv) introducing said nucleic acid into the bacterial cell thus to render the bacterial cell resistant to said target nucleic acid or transcription product thereof.

In a twenty-second aspect there is provided a method for modulating (eg. conferring or increasing) the resistance of a bacterial cell against a target nucleic acid or transcription product in a bacteriophage thereof comprising the steps of: (i) identifying one or more pseudo CRISPR spacers in a bacteriophage genome that is capable of providing resistance to the target nucleic acid or transcription product thereof; (ii) preparing a recombinant nucleic acid comprising at least one cas gene and at least two CRISPR repeats together with said identified one or more pseudo CRISPR spacers; and (iii) introducing said recombinant nucleic acid into said bacterial cell thus to render the bacterial cell resistant to said target nucleic acid or transcription product thereof.

In a twenty-third aspect there is provided a method for modulating the resistance of a bacterial cell comprising one or more cas genes or proteins and two or more CRISPR repeats against a target nucleic acid or transcription product thereof in a bacteriophage comprising the steps of: (i) identifying one or more pseudo CRISPR spacers in a bacteriophage that is capable of providing resistance to a target nucleic acid or transcription product thereof; (ii) identifying one or more CRISPR spacers in a bacterial cell in which resistance is to be modulated; and (iii) modifying the sequence of the CRISPR spacer(s) in the bacterial cell in which resistance is to be modulated such that the CRISPR spacer(s) has a higher degree of homology to the pseudo CRISPR spacer(s) of the bacteriophage against which resistance is to be modulated.

In a twenty-fourth aspect there is provided a method for determining the resistance of a cell against a target nucleic acid or a transcription product thereof comprising identifying one or more functional CRISPR repeat-cas combinations and one or more CRISPR spacers in the cell.

In a twenty-fifth aspect there is provided a cell obtained or obtainable by the method(s) described herein.

In a twenty-sixth aspect there is provided a CRISPR spacer or pseudo CRISPR spacer obtained or obtainable by the method(s) described herein.

In a twenty-seventh aspect there is provided a cas gene obtained or obtainable by the method(s) described herein.

In a twenty-eighth aspect there is provided a CRISPR repeat obtained or obtainable by the method(s) described herein.

In a twenty-ninth aspect there is provided a functional combination obtained or obtainable by the method(s) described herein.

In a thirtieth aspect there is provided a recombinant CRISPR locus comprising a CRISPR spacer or pseudo CRISPR spacer, and/or a cas gene, and/or a CRISPR repeat and/or a functional combination.

In a thirty-first aspect there is provided the use of a cell, a CRISPR spacer or pseudo CRISPR spacer, a cas gene, a CRISPR repeat or a functional combination for modulating the resistance of a cell against a target nucleic acid or a transcription product thereof.

In a thirty-second aspect there is provided a cell culture comprising a cell, a CRISPR spacer or pseudo CRISPR spacer, a cas gene, a CRISPR repeat or a functional combination for modulating the resistance of a cell against a target nucleic acid or a transcription product thereof.

In a thirty-third aspect there is provided a food product or feed comprising the culture described herein.

In a thirty-fourth aspect there is provided a process for preparing a food product or feed comprising the use of the culture described herein.

In a thirty-fifth aspect there is provided a food product of feed obtained or obtainable by the process described herein.

In a thirty-sixth aspect there is provided the use of the culture described herein for preparing a food product.

In a thirty-seventh aspect there is provided a nucleotide sequence comprising or consisting of the sequence set forth in any of SEQ ID Nos. 7-10 and SEQ ID Nos. 359-405 or a variant, fragment, homologue or derivative thereof.

In a thirty-eight aspect there is provided an amino acid sequence encoded by the nucleotide sequence described herein.

In a thirty-ninth aspect there is provided a construct or vector comprising one or more of the nucleotide sequences described herein.

In a fortieth aspect there is provided a host cell into which has been incorporated one or more of the nucleotide sequences described herein or the construct or vector described herein.

PREFERRED EMBODIMENTS

In some embodiments, the one or more cas genes or proteins are used in combination with two or more CRISPR repeats.

In some embodiments, the one or more cas genes or proteins and/or the two or more CRISPR repeats are or are derivable (preferably, derived) from the same cell.

In some embodiments, the one or more cas genes or proteins and the two or more CRISPR repeats naturally co-occur in the same cell.

In some embodiments, the one or more cas genes or proteins are used in combination with one or more CRISPR spacers.

In some embodiments, the CRISPR spacer(s) is or is derivable (preferably, derived) from an organism that is different to the cell from which the one or more cas genes or proteins and/or the two or more CRISPR repeats are or are derivable (preferably, derived).

In some embodiments, the spacer is obtained from a cell which is resistant to a target nucleic acid.

In some embodiments, the CRISPR spacer is a synthetic nucleic acid sequence.

In some embodiments, the CRISPR spacer(s) have homology to the target nucleic acid.

In some embodiments, the CRISPR spacer(s) have 100% identity to the target nucleic acid over at least the length of the CRISPR spacer core.

In some embodiments, the one or more cas genes or proteins are used in combination with at least one or more CRISPR spacers and at least two or more CRISPR repeats.

In some embodiments, the target nucleic acid or transcription product thereof is or is derivable (preferably, derived) from bacteriophage DNA.

In some embodiments, the target nucleic acid or transcription product thereof is or is derivable (preferably, derived) from plasmid DNA.

In some embodiments, the target nucleic acid or transcription product thereof is or is derivable (preferably, derived) from a mobile genetic element.

In some embodiments, the target nucleic acid or transcription product thereof is or is derivable (preferably, derived) from a transposable element or an insertion sequence.

In some embodiments, the target nucleic acid or transcription product thereof is or is derivable (preferably, derived) from an antibiotic resistance gene.

In some embodiments, the target nucleic acid or transcription product thereof is or is derivable (preferably, derived) from a nucleic acid encoding a virulence factor.

In some embodiments, the virulence factor is selected from the group consisting of a toxin-, an internalin- and a hemolysin-encoding nucleic acid.

In some embodiments, the one or more cas genes and the two or more CRISPR repeats are or are derivable (preferably, derived) from the same cell.

In some embodiments, the one or more cas genes and the two or more CRISPR repeats naturally co-occur in the same cell.

In some embodiments, the CRISPR spacers are or are derivable (preferably, derived) from an organism that is different to the cell from which the one or more cas genes and/or the two or more CRISPR repeats are or are derivable (preferably, derived).

In some embodiments, the cell is a recipient cell or a host cell.

In some embodiments, the one or more cas genes or proteins and/or the two or more CRISPR repeats are or are derivable (preferably, derived) from the same cell.

In some embodiments, the spacers are or are derivable (preferably, derived) from an organism that is different to the cell comprising the one or more cas genes or proteins and/or the two or more CRISPR repeats.

In some embodiments, the one or more cas genes or proteins and the two or more CRISPR repeats naturally co-occur in the same cell.

In some embodiments, said modification comprises inserting one or more CRISPR spacers and/or pseudo CRISPR spacers into the cell.

In some embodiments, the spacer of the cell has 100% homology to the CRISPR spacer or pseudo CRISPR spacer of the organism.

In some embodiments, said modification comprises genetically engineering the CRISPR spacer of the cell.

In some embodiments, all or part of the spacer in the cell is modified.

In some embodiments, said modification comprises the modification of a recombinant spacer.

In some embodiments, said modification occurs through spontaneous mutation or mutagenesis.

In some embodiments, the at least one or more CRISPR spacer(s) in the cell are deleted.

In some embodiments, at least one or more CRISPR repeat(s) in the cell are deleted.

In some embodiments, one or more cas genes are deleted,

In some embodiments, CRISPR and/or one or more cas genes are deleted.

In some embodiments, the one or more cas genes or proteins and/or two or more CRISPR repeats in the cell are deleted.

In some embodiments, the nucleotide sequences of the cas gene and the CRISPR repeat are or are derivable (preferably, derived) from the same or different strains.

In some embodiments, the nucleotide sequences of the cas gene and the CRISPR repeat are or are derivable (preferably, derived) from the same or different species.

In some embodiments, the nucleotide sequences of the cas gene and the CRISPR repeat are or are derivable (preferably, derived) from the same or different genera.

In some embodiments, the nucleotide sequences of the cas gene and the CRISPR repeat are or are derivable (preferably, derived) from the same or different organisms.

In some embodiments, the target nucleic acid in the bacteriophage is a highly conserved nucleic acid sequence.

In some embodiments, the target nucleic acid in the bacteriophage encodes a host specificity protein.

In some embodiments, the target nucleic acid in the bacteriophage encodes a protein that is essential for survival, replication or growth of the bacteriophage.

In some embodiments, the target nucleic acid in the bacteriophage encodes a helicase, a primase, a head or tail structural protein, a protein with a conserved domain (eg. holin, lysin, and others) or a conserved sequences amongst important phage genes.

In some embodiments, the method for determining the resistance of a cell to a target nucleic acid or a transcription product thereof comprises the additional step of comparing the sequence of the one or more CRISPR spacers in the cell with the sequence of the target nucleic acid.

In some embodiments, the method for determining the resistance of a cell to a target nucleic acid or a transcription product thereof comprises the additional step of determining the resistance profile of the cell.

In some embodiments, said culture is a starter culture or a probiotic culture.

FIGURES

FIG. 1

Schematic representation of CRISPR1 of *S. thermophilus* CNRZ1066 (42 repeats).

FIG. 2

Dotplot analysis of Cas protein sequences (A) and CRISPR locus sequences (B). Organism names (genus, species, strain) are indicated on the right side of each dotplot (for example Sth_LMG18311=*S. thermophilus* strain LMG18311).

FIG. 3

Spacer sequences of *S. thermophilus* CNRZ1066 CRISPR locus were blasted (short nearly exact sequence searches using BlastN at the NCBI website) against the viruses database, and aligned with the subsequent matches in *S. thermophilus* bacteriophages. (A) The table indicates the spacer sequences of CNRZ1066 CRISPR presenting significant sequence identities with phage sequences (dark cells). (B) Alignment of the sequence of interspacing sequence #29 with eight phage sequences. (Remark: spacer #20 shows similarity to a number of host specificity proteins).

FIG. 4

Putative stem-loop secondary structure of a CRISPR repeat sequence of *S. thermophilus*. Only one DNA strand is shown.

FIG. 5

Integration of a CRISPR spacer into the CRISPR locus of *Streptococcus thermophilus* provides resistance against a bacteriophage that the CRISPR spacer shows identity to. The parent DGCC7710 is phage sensitive, and the BIM DGCC7710RH1 is phage resistant. The BIM DGCC7710RH1 has a new spacer (Sn) in the CRISPR locus, which shows 100% identity to phage sequence. In step (b) the strain is challenged with phage 858 and a phage resistant mutant is selected. In step (c) the CRISPR I locus of the mutant has an additional spacer which shares 100% identity with region 31.921-31.950 bp of the phage.

FIG. 6

Integration of a CRISPR spacer into the CRISPR locus of *Streptococcus thermophilus* provides resistance against a bacteriophage that the CRISPR spacer shows identity to. The parent DGCC7710 is phage sensitive, and the BIM DGCC7710RH2 is phage resistant. The BIM DGCC7710 ORH2 has a new spacer (Sn) in the CRISPR locus, which shows 100% identity to phage sequence. In step (b) the strain is challenged with phage 858 and a phage resistant mutant is selected. In step (c) The experiment was independently repeated and another mutant was selected. The CRISPR I locus of the mutant has an additional spacer (different from that in RH1) which shares 100% identity with region 17.125-17.244 bp of the phage.

FIG. 7

Spacer arrangement of CRISPR I in various *Streptococcus thermophilus* strains. Numbers indicate the position of the spacer. Strain names are listed on the left. Letters indicate CRISPR spacer type, with identical spacers described with a similar 2-letter code. Spacers with single nucleotide polymorphisms are labeled with identical letter combination, complemented with a "prime" label. Unique spacers are not described by a letter combination, and are left blank.

FIG. 8

Homology of CRISPR spacers with known sequences, including bacterial chromosomal sequences (shaded in gray), plasmid DNA sequences (black squares) and phage genomic sequences (shaded in black).

FIG. 9

A graphical representation of the plasmid system used to genetically engineer a number of constructs in *Streptococcus thermophilus* as described by Russell, M. W., and T. R. Klaenhammer (2001) Efficient system for directed integration into the *Lactobacillus acidophilus* and *Lactobacillus gasseri* chromosomes via homologous recombination. *Applied and Environmental Microbiology* 67:4361-4364.

FIG. 10

A graphical representation of the plasmid used to subclone PCR products of the various constructs described herein (cas1 KO, cas4 KO, RT and S1S2). The plasmid is available commercially from Invitrogen in the TOPO TA Cloning® kit.

FIG. 11

A graphical representation of the plasmid used for homologous recombination in one embodiment of the present invention.

FIG. 12

A graphical representation illustrating the preparation of the CAS1KO construct in which the cas1 gene is disrupted by homologous recombination.

FIG. 13

A graphical representation illustrating the preparation of the CAS4KO construct in which the cas4 gene is disrupted by homologous recombination.

FIG. 14

A graphical representation illustrating the SIS2 construct engineering using specific primers and iterative PCR reactions. The first panel illustrates all primers used and the set up for the first two PCR reactions (reaction #1 with primers P1 and P2 and reaction #2 with primers P2 and P3). The second panel shows the PCR products obtained from the first two PCR reactions, with the product from reaction #1 on the left and the product from reaction #2 on the right. The third panel shows the third PCR reaction, using a combination of the products from the first two PCRs as the template for the third PCR reaction, and primer P1 from the first reaction along with primer P4 from the second reaction. The fourth panel shows the product of PCR #3, which technically generates the S1S2 construct.

FIG. 15

A graphical representation of the details for primer design for primers 2 and 3, which contain key sequences for the experiment, derived from spacers identical to phage sequences (the PCR products derived from these PCR primers will generate the spacers that will ultimately provide resistance to the phages).

FIG. 16

A graphical representation of the integration of the S1S2 construct.

FIG. 17

A graphical representation of the preparation of the RT construct using a restriction enzyme to generate the RT construct from the SIS2 construct. There are BglI restriction sites within the repeats allow the "middle" part of the construct to be cut. Following enzymatic digestion, a ligase is used to patch together the two end pieces, thus generating a new construct that has RT, but no spacers.

FIG. 18

A graphical representation of the integration of the RT construct.

FIG. 19

A graphical representation of the RT' construct.

FIG. 20

A graphical representation of the RT' construct.

DETAILED DESCRIPTION OF THE INVENTION

CRISPR Locus

CRISPR loci are a distinct class of interspersed short sequence repeats (SSRs) that were first recognized in *E. coli* (Ishino et al. (1987) *J. Bacteriol.* 169:5429-5433; Nakata et al. (1989) *J. Bacteriol.* 171:3553-3556). Similar interspersed SSRs have been identified in *Haloferax mediterranei, Streptococcus pyogenes, Anabaena*, and *Mycobacterium tuberculosis* (Groenen et al. (1993) *Mol. Microbiol.* 10:1057-1065; Hoe et al. (1999) *Emerg. Infect. Dis.* 5:254-263; Masepohl et al. (1996) *Biochim. Biophys. Acta* 1307:26-30; Mojica et al. (1995) *Mol. Microbiol.* 17:85-93). The CRISPR loci differ from other SSRs by the structure of the repeats, which have been termed short regularly spaced repeats (SRSRs) (Janssen et al. (2002) *OMICS J. Integ. Biol.* 6:23-33; Mojica et al. (2000) *Mol. Microbiol.* 36:244-246). The repeats are short elements that occur in clusters, that are always regularly spaced by unique intervening sequences with a constant length (Mojica et al. (2000) *Mol. Microbiol.* 36:244-246). Although the repeat sequences are highly conserved between strains, the number of interspersed repeats and the sequences of the spacer regions differ from strain to strain (van Embden et al. (2000) *J. Bacteriol.* 182:2393-2401).

The common structural characteristics of CRISPR loci are described in Jansen. et al. (2002) as (i) the presence of multiple short direct repeats, which show no or very little sequence variation within a given locus; (ii) the presence of non-repetitive spacer sequences between the repeats of similar size; (iii) the presence of a common leader sequence of a few hundred basepairs in most species harbouring multiple CRISPR loci; (iv) the absence of long open reading frames within the locus; and (v) the presence of one or more cas genes.

CRISPRs are typically short partially palindromic sequences of 24-40 bp containing inner and terminal inverted repeats of up to 11 bp. Although isolated elements have been detected, they are generally arranged in clusters (up to about 20 or more per genome) of repeated units spaced by unique intervening 20-58 bp sequences. CRISPRs are generally homogenous within a given genome with most of them being identical. However, there are examples of heterogeneity in, for example, the Archaea (Mojica et al. 2000).

By way of example, the genome of *Streptococcus thermophilus* LMG18311 contains 3 CRISPR loci; the 36-bp repeated sequences are different in CRISPR1 (34 repeats), CRISPR2 (5 repeats), and CRISPR3 (a single sequence). Nevertheless, they are perfectly conserved within each locus. CRISPR1 and CRISPR2 repeats are respectively interspaced by 33 and 4 sequences of 30 bp in length. All these interspacing sequences are different from each other. They are also different from those found in strain CNRZ1066 (41 interspacing sequences within CRISPR1) and in strain LMD-9 (16 within CRISPR1 and 8 within CRISPR3), which both are *S. thermophilus*. FIG. 1 describes one of the CRISPRs identified in *S. thermophilus.*

Various methods for identifying CRISPR loci are already known in the art. By way of example, Jensen et al. (2002) describe a computer based approach in which nucleotide sequences are searched for CRISPR motifs using the PATSCAN program at the server of the Mathematics and Computer Science Division at the Argonne National Laboratory, Argonne, Ill., USA. The algorithm that was used for identifying CRISPR motifs was p1=a . . . b c . . . d p1 c . . . d p1 c . . . d p1, where a and b are the lower and upper size limit of the repeat and p1 and c and d are the lower and upper size limit of the spacer sequences. The values of a, b, c and d may be varied from about 15 to about 70 bp at increments of about 5 bp.

CRISPR loci may be identified using dotplots (using, for example, a computer program called Dotter).

Sequence similarity analysis may be performed using various methods that are well known in the art. By way of example, analysis may be performed using NCBI BLAST with a microbial genomes database (http://www.ncbi.nlm-.nih.gov) and GenBank.

The amplification of CRISPR loci has been described in, for example, Mojica et al. (2005) and Pourcel et al. (2005). Amplification of the desired region of DNA may be achieved by any method known in the art, including polymerase chain reaction (PCR). By "amplification" we mean the production of additional copies of a nucleic acid sequence. This is generally carried out using PCR technologies well known in the art (Dieffenbach and Dveksler (1995) *PCR Primer, a Laboratory Manual* (Cold Spring Harbor Press, Plainview, N.Y.).

By "polymerase chain reaction" or "PCR" we mean a method such as that disclosed in U.S. Pat. Nos. 4,683,195 and 4,683,202, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as "PCR". Because the desired amplified segments of the target sequence become the predominant sequences (in terms of concentration) in the mixture, they are said to be "PCR amplified."

In the PCR approach, oligonucleotide primers can be designed for use in PCR reactions to amplify all or part of a CRISPR locus. By "primer" we mean an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced (i.e., in the presence of nucleotides and an inducing agent—such as DNA polymerase and at a suitable temperature and pH). The primer may be single stranded for maximum efficiency in amplification, but may alternatively be double stranded. If double stranded, the primer is first treated to separate its strands before being used to prepare extension products. The primer may be an oligodeoxyribonucleotide. The primer must be sufficiently long to prime the synthesis of extension products in the presence of the inducing agent. The exact lengths of the primers will depend on many factors, including temperature, source of primer, and the use of the method. PCR primers are typically at least about 10 nucleotides in length, and most typically at least about 20 nucleotides in length.

Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially mismatched primers, and the like.

The CRISPR loci may comprise, consist or consist essentially of DNA or RNA of genomic, synthetic or recombinant origin.

The CRISPR loci may be double-stranded or single-stranded whether representing the sense or antisense strand or combinations thereof.

The CRISPR loci may be prepared by use of recombinant DNA techniques (e.g. recombinant DNA), as described herein.

Nucleotide sequences described herein may be obtained from databases—such as GenBank or the JGI website at http://genome.jgi-psf.org/mic_home.html.

CRISPR Orientation

For the avoidance of doubt, in the context of the present invention the CRISPR locus is orientated as follows.

The CRISPR leader is a conserved DNA segment of defined size. For example, the leader sequence of *S. thermophilus* CRISPR1 is the DNA segment starting immediately after the stop codon of gene str0660, and ending just before the first repeat. The CRISPR leader is located at the 5' end of the CRISPR locus. The CRISPR leader is located immediately upstream of the first CRISPR repeat of the CRISPR locus.

The CRISPR trailer is a conserved DNA segment of defined size. For example, the trailer sequence of *S. thermophilus* CRISPR1 is the DNA segment starting immediately after the terminal repeat, and ending just before the stop codon of gene str0661 (located on the opposite DNA strand). The CRISPR trailer is located at the 3' end of the CRISPR locus. The CRISPR trailer is located immediately downstream of the terminal repeat.

By way of example, the CRISPR leader and CRISPR trailer sequences in the CRISPR1 locus of *Streptococcus thermophilus* strain CNRZ1066 are:

```
CRISPR leader
5'-CAAGGACAGTTATTGATTTTATAATCACTATGTGGGTATAAAAACGT

CAAAATTTCATTTGAG-3'

CRISPR trailer
5'-TTGATTCAACATAAAAAGCCAGTTCAATTGAACTTGGCTTT-3'
```

The CRISPR leader corresponds to positions 625038 to 625100, and the CRISPR trailer corresponds to positions 627845 to 627885 in the full genome (CP000024) of *Streptococcus thermophilus.*

For the avoidance of doubt "upstream" means in the 5' direction and "downstream" means in the 3' direction.

CAS

As used herein, the term "cas gene" has the conventional meaning as used in the art and refers to one or more cas genes that are generally coupled, associated or close to or in the vicinity of flanking CRISPR loci.

A comprehensive review of the Cas protein family is presented in Haft et al. (2005) *Computational Biology* 1, 6 e60. As described therein, 41 CRISPR-associated (cas) gene families are described, in addition to the four previously known gene families. It shows that CRISPR systems belong to different classes, with different repeat patterns, sets of genes, and species ranges.

The number of cas genes at a given CRISPR locus can vary between species.

In one aspect, the present invention relates to the use of one or more cas genes or proteins for modulating resistance in a cell (eg. a recipient cell) against a target nucleic acid or a transcription product thereof.

In a further aspect, the present invention relates to the use of one or more cas genes or proteins and one more CRISPR spacers for modulating resistance in, a cell (eg. a recipient cell) against a target nucleic acid or a transcription product thereof.

In some embodiments, one or more of the cas genes and/or proteins may naturally occur in a recipient cell and one or more heterologous spacers may be integrated or inserted adjacent to the one or more of the cas genes or proteins.

In some embodiments, suitably one or more of the cas genes and/or proteins may be heterologous to the recipient cell and one or more of the spacers may be homologous or heterologous. In this instance, the spacers may be integrated or inserted adjacent to the one or more of the cas gene or proteins.

In one aspect, the present invention relates to the use of one or more cas genes or proteins and at least two CRISPR repeats for modulating resistance in a cell (eg. a recipient cell) against a target nucleic acid or a transcription product thereof.

In one aspect, the present invention relates to the use of one or more cas genes or proteins, at least two CRISPR repeats and at least one CRISPR spacer for modulating resistance in a cell (eg. a recipient cell) against a target nucleic acid or a transcription product thereof.

CRISPR structures are typically found in the vicinity of four genes named cas1 to cas4. The most common arrangement of these genes is cas3-cas4-cas1-cas2. The Cas3 protein appears to be a helicase, whereas Cas4 resembles the RecB family of exonucleases and contains a cysteine-rich motif, suggestive of DNA binding. Cas1 is generally highly basic and is the only Cas protein found consistently in all species that contain CRISPR loci. Cas2 remains to be characterized. cas1-4 are typically characterized by their close proximity to the CRISPR loci and their broad distribution across bacterial and archaeal species. Although not all cas1-4 genes associate with all CRISPR loci, they are all found in multiple subtypes.

Bolotin et al. (2005) have recently reported another cluster of three genes associated with CRISPR structures in many bacterial species, named here as cas1B, cas5 and cas6.

The cas gene may be cas1, cas2, cas3, cas4, cas1B, cas5 and/or cas6. In one embodiment, the cas gene is cas1.

The cas gene may be cas1, cas2, cas3, cas4, cas1B, cas5 and/or cas6 or a fragment, variant, homologue or derivative thereof.

The cas genes may be cas1, cas2, cas3, cas4, cas1B, cas5 and/or cas6 or a plurality thereof or a combination thereof—such as cas1 and cas2; cas1 and cas3; cas1 and cas4; cas1 and cas1B; cas1 and cas5; cas1 and cas6; cas2 and cas3; cas2 and cas4; cas2 and cas1B; cas2 and cas5; cas2 and cas6; cas3 and cas4; cas3 and cas1B; cas3 and cas5; cas3 and cas6; cas4 and cas1B; cas4 and cas5; cas4 and cas6; cas1B and cas5; cas1B and cas6; cas1, cas2 and cas3; cas1, cas2 and cas4; cas1, cas2 and cas1B; cas1, cas2, cas3 and cas4; cas1, cas2, cas3 and cas1B; cas1, cas2, cas3 and cas5; cas1, cas2, cas3 and cas6; cas1, cas2, cas3, cas4 and cas1B; cas1, cas2, cas3, cas4 and cas5; cas1, cas2, cas3, cas4, cas1B and cas6; cas1, cas2, cas3, cas4, cas1B, cas5; cas1, cas2, cas3, cas4, cas1B and cas6; cas1, cas2, cas3, cas4, cas1B, cas5 and cas6; cas2, cas3 and cas4; cas2, cas3 and cas1B; cas2, cas3 and cas5; cas2, cas3 and cas6; cas2, cas3, cas4 and cas1B; cas2, cas3, cas4, and cas5; cas2, cas3, cas4 and cas6; cas2, cas3, cas4, cas1B and cas5; cas2, cas3, cas4, cas1B and cas6; cas2, cas3, cas4, cas1B, cas5 and cas6; cas3, cas4 and cas1B; cas3, cas4 and cas5; cas3, cas4 and cas6; cas3, cas4, cas1B and cas5; cas3, cas4, cas1B and cas6; cas3, cas4, cas1B, cas5 and cas6; cas4, cas1B and cas5; cas4, cas1B and cas6; cas4, cas1B, cas5 and cas6; cas5 and cas6 or combinations thereof.

The cas genes may be cas1 and cas2; cas1 and cas3; cas1 and cas4; cas1 and cas1B; cas1 and cas5; cas1 and cas6; cas2 and cas3; cas2 and cas4; cas2 and cas1B; cas2 and cas5; cas2 and cas6; cas3 and cas4; cas3 and cas1B; cas3 and cas5; cas3 and cas6; cas4 and cas1B; cas4 and cas5; cas4 and cas6; cas1B and cas5 or cas1B and cas6 or combinations thereof.

The cas genes may be a cas1, cas2 and cas3; cas1, cas2 and cas4; cas1, cas2 and cas1B; cash cas2, cas3 and cas4; cas1, cas2, cas3 and cas1B; cas1, cas2, cas3 and cas5; cas1, cas2, cas3 and cas6; cas1, cas2, cas3, cas4 and cas1B; cas1, cas2, cas3, cas4 and cas5; cas1, cas2, cas3, cas4, cas1B and cas6; cas1, cas2, cas3, cas4, cas1B and cas5; cas1, cas2, cas3, cas4, cas1B and cas6; cas1, cas2, cas3, cas4, cas1B, cas5 and cas6 or combinations thereof.

The cas genes may be cas2, cas3 and cas4; cas2, cas3 and cas1B; cas2, cas3 and cas5; cas2, cas3 and cas6; cas2, cas3, cas4 and cas1B; cas2, cas3, cas4, and cas5; cas2, cas3, cas4 and cas6; cas2, cas3, cas4, cas1B and cas5; cas2, cas3, cas4, cas1B and cas6; cas2, cas3, cas4, cas1B, cas5 and cas6 or combinations thereof.

The cas genes may be cas3, cas4 and cas1B; cas3, cas4 and cas5; cas3, cas4 and cas6; cas3, cas4, cas1B and cas5; cas3, cas4, cas1B and cas6; cas3, cas4, cas1B, cas5 and cas6; cas4, cas1B and cas5; cas4, cas1B and cas6; cas4, cas1B, cas5 and cas6; cas5 and cas6 or combinations thereof.

The cas gene may be one or more of cas1, cas2, cas3, cas4, cas1B, cas5 and/or cas6 or a plurality thereof—such as a plurality of any 2 cas genes, any 3 cas genes, any 4 cas genes, any 5 cas genes, any 6 cas genes, or any 7 cas genes.

The plurality of cas genes may comprise, consist or consist essentially of a plurality of the same cas genes—such as 2 cas genes, 3 cas genes, 4 cas genes, 5 cas genes, 6 cas genes, 7 cas genes, 8 cas genes, 9 cas genes, 10 cas genes, 15 cas genes, 20 cas genes, 25 cas genes, 30 cas genes, 35 cas genes, 40 cas genes or even 50 or more cas genes.

The plurality of cas genes may comprise, consist or consist essentially of a plurality of different cas genes—such as 2 different cas genes, 3 different cas genes, 4 different cas genes, 5 different cas genes, 6 different cas genes, 7 different cas genes, 8 different cas genes, 9 different cas genes, 10 different cas genes, 15 different cas genes, 20 different cas genes, 25 different cas genes, 30 different cas genes, 35 different cas genes, 40 different cas genes or even 50 or more different cas genes.

The plurality of cas genes may comprise, consist or consist essentially of a plurality of the same and/or different cas genes—such as 2 different cas genes, 3 different cas genes, 4 different cas genes, 5 different cas genes, 6 different cas genes, 7 different cas genes, 8 different cas genes, 9 different cas genes, 10 different cas genes, 15 different cas genes, 20 different cas genes, 25 different cas genes, 30 different cas genes, 35 different cas genes, 40 different cas genes or even 50 or more different cas genes. The same cas gene may be duplicated a plurality of times.

Suitably, the term "cas gene" refers to a plurality of cas genes—such as between 2 and 12 cas genes, more preferably, between 3 and 11 cas genes, more preferably, between 4 and 10 cas genes, more preferably, between 4 and 9 cas genes, more preferably, between 4 and 8 cas genes, more preferably, between 4 and 7 cas genes—such as 4, 5, 6, or 7 cas genes.

The cas gene(s) may comprise, consist or consist essentially of DNA or RNA of genomic, synthetic or recombinant origin.

The cas gene(s) may be double-stranded or single-stranded whether representing the sense or antisense strand or combinations thereof.

The cas gene(s) may be prepared by use of recombinant DNA techniques (e.g. recombinant DNA), as described herein.

As described herein below, the cas gene may be a fragment of a cas gene, thereby indicating hat the cas gene comprises a fraction of a wild-type sequence. Suitably, the sequence comprises at least 30%, at least 40%, at least 50%, at least 60%, at least 65%, at least 70%, at least 75%, at least 80%, at least 85%, at least 90%, at least 95%, at least 96%, at least 97%, at least 98%, or least 99% of the wild-type sequence.

For some embodiments it is preferred that the cas gene is the cas gene that is closest to the leader sequence or the first CRISPR repeat at the 5' end of the CRISPR locus—such as cas4 or cas6.

The Cas protein may be Cas, Cas2, Cas3, Cas4, Cas1B, Cas5 and/or Cas6.

The Cas protein may be Cas1, Cas2, Cas3, Cas4, Cas1B, Cas5 and/or Cas6 or a fragment, variant, homologue or derivative thereof.

The Cas protein may be Cas1, Cas2, Cas3, Cas4, Cas1B, Cas5 and/or Cas6 or a combination thereof—such as Cas1 and Cas2; Cas1 and Cas3; Cas1 and Cas4; Cas1 and Cas1B; Cas1 and Cas5; Cas1 and Cas6; Cas2 and Cas3; Cas2 and Cas4; Cas2 and Cas1B; Cas2 and Cas5; Cas2 and Cas6; Cas3 and Cas4; Cas3 and Cas1B; Cas3 and Cas5; Cas3 and Cas6; Cas4 and Cas1B; Cas4 and Cas5; Cas4 and Cas6; Cas1B and Cas5; Cas1B and Cas6; Cas1, Cas2 and Cas3; Cas1, Cas2 and Cas4; Cas1, Cas2 and Cas1B; Cas1, Cas2, Cas3 and Cas4; Cas1, Cas2, Cas3 and Cas1B; Cas1, Cas2, Cas3 and Cas5; Cas1, Cas2, Cas3 and Cas6; Cas1, Cas2, Cas3, Cas4 and Cas1B; Cas1, Cas2, Cas3, Cas4 and Cas5; Cas1, Cas2, Cas3, Cas4, Cas1B and Cas6; Cas1, Cas2, Cas3, Cas4, Cas1B and Cas5; Cas1, Cas2, Cas3, Cas4, Cas1B and Cas6; Cas1, Cas2, Cas3, Cas4, Cas1B, Cas5 and Cas6; Cas2, Cas3 and Cas4; Cas2, Cas3 and Cas1B; Cas2, Cas3 and Cas5; Cas2, Cas3 and Cas6; Cas2, Cas3, Cas4 and Cas1B;

Cas2, Cas3, Cas4, and Cas5; Cas2, Cas3, Cas4 and Cas6; Cas2, Cas3, Cas4, Cas1B and Cas5; Cas2, Cas3, Cas4, Cas1B and Cas6; Cas2, Cas3, Cas4, Cas1B, Cas5 and Cas6; Cas3, Cas4 and Cas1B; Cas3, Cas4 and Cas5; Cas3, Cas4 and Cas6; Cas3, Cas4, Cas1B and Cas5; Cas3, Cas4, Cas1B and Cas6; Cas3, Cas4, Cas1B, Cas5 and Cas6; Cas4, Cas1B and Cas5; Cas4, Cas1B and Cas6 or Cas4, Cas1B, Cas5 and Cas6, Cas5 and Cas6.

The Cas protein may be Cast and Cas2; Cas1 and Cas3; Cast and Cas4; Cast and Cas1B; Cas1 and Cas5; Cast and Cas6; Cas2 and Cas3; Cas2 and Cas4; Cas2 and Cas1B; Cas2 and Cas5; Cas2 and Cas6; Cas3 and Cas4; Cas3 and Cas1B; Cas3 and Cas5; Cas3 and Cas6; Cas4 and Cas1B; Cas4 and Cas5; Cas4 and Cas6; Cas1B and Cas5 or Cas1B and Cas6 or combinations thereof.

The Cas protein may be Cas1, Cas2 and Cas3; Cas1, Cas2 and Cas4; Cas1, Cas2 and Cas1B; Cas1, Cas2, Cas3 and Cas4; Cas1, Cas2, Cas3 and Cas1B; Cas1, Cas2, Cas3 and Cas5; Cas1, Cas2, Cas3 and Cas6; Cas1, Cas2, Cas3, Cas4 and Cas1B; Cas1, Cas2, Cas3, Cas4 and Cas5; Cas1, Cas2, Cas3, Cas4, Cas1B and Cas6; Cast, Cas2, Cas3, Cas4, Cas1B and Cas5; Cas1, Cas2, Cas3, Cas4, Cas1B and Cas6; Cas1, Cas2, Cas3, Cas4, Cas1B, Cas5 and Cas6 or combinations thereof.

The Cas protein may be Cas2, Cas3 and Cas4; Cas2, Cas3 and Cas1B; Cas2, Cas3 and Cas5; Cas2, Cas3 and Cas6; Cas2, Cas3, Cas4 and Cas1B; Cas2, Cas3, Cas4, and Cas5; Cas2, Cas3, Cas4 and Cas6; Cas2, Cas3, Cas4, Cas1B and Cas5S; Cas2, Cas3, Cas4, Cas1B and Cas6; Cas2, Cas3, Cas4, Cas1B, Cas5 and Cas6 or combinations thereof.

The Cas protein may be Cas3, Cas4 and Cas1B; Cas3, Cas4 and Cas5; Cas3, Cas4 and Cas6; Cas3, Cas4, Cas1B and Cas5; Cas3, Cas4, Cas1B and Cas6; Cas3, Cas4, Cas1B, Cas5 and Cas6; Cas4, Cas1B and Cas5; Cas4, Cas1B and Cas6; Cas4, Cas1B, Cas5 and Cas6; Cas5 and Cas6 or combinations thereof.

The Cas protein may be one or more of Cas1, Cas2, Cas3, Cas4, Cas1B, Cas5 and/or Cas6 or a plurality thereof—such as a plurality of any 2 Cas genes, any 3 Cas genes, any 4 Cas genes, any 5 Cas genes, any 6 Cas genes, or any 7 Cas genes.

The plurality of Cas proteins may comprise, consist or consist essentially of a plurality of the same Cas proteins—such as 2 Cas proteins, 3 Cas proteins, 4 Cas proteins, 5 Cas proteins, 6 Cas proteins, 7 Cas proteins, 8 Cas proteins, 9 Cas proteins, Cas proteins, 15 Cas proteins, 20 Cas proteins, 25 Cas proteins, 30 Cas proteins, 35 Cas proteins, 40 Cas proteins or even 50 or more Cas proteins.

The plurality of Cas proteins may comprise, consist or consist essentially of a plurality of different Cas proteins—such as 2 different Cas proteins, 3 different Cas proteins, 4 different Cas proteins, 5 different Cas proteins, 6 different Cas proteins, 7 different Cas proteins, 8 different Cas proteins, 9 different Cas proteins, 10 different Cas proteins, 15 different Cas proteins, 20 different Cas proteins, 25 different Cas proteins, 30 different Cas proteins, 35 different Cas proteins, 40 different Cas proteins or even 50 or more different Cas proteins.

The plurality of Cas proteins may comprise, consist or consist essentially of a plurality of the same and/or different Cas proteins—such as 2 different Cas proteins, 3 different Cas proteins, 4 different Cas proteins, 5 different Cas proteins, 6 different Cas proteins, 7 different Cas proteins, 8 different Cas proteins, 9 different Cas proteins, 10 different Cas proteins, 15 different Cas proteins, 20 different Cas proteins, 25 different Cas proteins, 30 different Cas proteins, 35 different Cas proteins, 40 different Cas proteins or even 50 or more different Cas proteins. The same Cas proteins may be duplicated a plurality of times.

Suitably, the term "Cas protein" refers to a plurality of Cas proteins—such as between 2 and 12 Cas proteins, more preferably, between 3 and 11 Cas proteins, more preferably, between 4 and 10 Cas proteins, more preferably, between 4 and 9 Cas proteins, more preferably, between 4 and 8 Cas proteins, more preferably, between 4 and 7 proteins genes—such as 4, 5, 6; or 7 Cas proteins.

The Cas protein(s) may be encoded by a cas gene which may comprise DNA or RNA of genomic, synthetic or recombinant origin.

The Cas protein(s) may be encoded by a cas gene which may be double-stranded or single-stranded whether representing the sense or antisense strand or combinations thereof.

The Cas protein(s) may be prepared by use of recombinant DNA techniques (e.g. recombinant DNA), as described herein.

In a further aspect, there is provided a method for identifying a cas gene for use in modulating the resistance of a cell against a target nucleic acid or transcription product thereof comprising the steps of: (i) preparing a cell comprising at least one CRISPR spacer and at least two CRISPR repeats; (ii) engineering the cell such that it comprises at least one cas gene; and (iii) determining if the cell modulates resistance against the target nucleic acid or transcription product thereof, wherein modulation of the resistance of the cell against the target nucleic acid or transcription product thereof is indicative that the cas gene can be used to modulate the resistance of the cell.

One or more of the cas genes may be used to engineer a cell—such as a recipient cell. In particular, one or more cas genes may be used to engineer a cell—such as a recipient cell—that in combination with one or more, preferably, two or more CRISPR repeats and one or more CRISPR spacers can be used to modulate the resistance of a cell against a target nucleic acid or a transcription product thereof. By way of example, the cas gene(s) may be inserted into the DNA of a cell (eg. a recipient cell)—such as plasmid DNA or genomic DNA of a cell—using various methods that are well known in the art. By way of further example, the cas genes may be used as a template upon which to modify (eg. mutate) the DNA of a cell (eg. a recipient cell)—such as plasmid DNA or genomic DNA—such that cas genes are created or formed in the DNA of the cell. By way of further example, the cas genes may be cloned into a construct, a plasmid or a vector and the like which is then transformed into the cell, using methods such as those described herein.

The cas genes may comprise or consist of a cas cluster selected from the group consisting of any one or more of SEQ ID No. 461, SEQ ID No. 466, SEQ ID No. 473, SEQ ID No. 478, SEQ ID No. 488, SEQ ID No. 493, SEQ ID No. 498, SEQ ID No. 504, SEQ ID No. 509, SEQ ID No. 517

The cas genes may comprise or consist of any one or more of SEQ ID Nos. 462-465, 467-472, 474-477, 479-487, 489-492, 494-497, 499-503, 505-508, 510-516 and/or 517-521.

Suitably, the one or more cas genes or proteins are used together with or in combination with one or more, preferably, two or more CRISPR repeats and optionally one or more CRISPR spacers.

CRISPR Repeat

As used herein, the term "CRISPR repeat" has the conventional meaning as used in the art ie. multiple short direct repeats, which show no or very little sequence variation within a given CRISPR locus.

As used herein, the term "CRISPR" is synonymous with the term "CRISPR repeat".

The number of nucleotides in a repeat is generally about 20 to about 40 base pairs, but may be about 20 to about 39 base pairs, about 20 to about 37 base pairs, about 20 to about 35 base pairs, about 20 to about 33 base pairs, about 20 to about 30 base pairs, about 21 to about 40 base pairs, about 21 to about 39 base pairs, about 21 to about 37 base pairs, about 23 to about 40 base pairs, about 23 to about 39 base pairs, about 23 to about 37 base pairs, about 25 to about 40 base pairs, about 25 to about 39 base pairs, about 25 to about 37 base pairs, about 25 to about 35 base pairs, or about 28 or 29 base pairs. The number of repeats may range from about 1 to about 140, from about 1 to about 100, from about 2 to about 100, from about 5 to about 100, from about 10 to about 100, from about 15 to about 100, from about 20 to about 100, from about 25 to about 100, from about 30 to about 100, from about 35 to about 100, from about 40 to about 100, from about 45 to about 100, from about 50 to about 100, from about 1 to about 135, from about 1 to about 130, from about 1 to about 125, from about 1 to about 120, from about 1 to about 115, from about 1 to about 110, from about 1 to about 105, from about 1 to about 100, from about 1 to about 95, from about 1 to about 90, from about 1 to about 80, from about 1 to about 70, from about 1 to about 60, from about 1 to about 50, from about 10 to about 140, from about 10 to about 130, from about 10 to about 120, from about 10 to about 110, from about 10 to about 95, from about 10 to about 90, from about 20 to about 80, from about 30 to about 70, from about 30 to about 60, from about 30 to about 50, from about 30 to about 40, or about 32.

Suitably, the number of nucleotides in a repeat is generally about 20 to about 40 base pairs, but may be about 20 to about 39 base pairs, about 20 to about 37 base pairs, about 20 to about 35 base pairs, about 20 to about 33 base pairs, about 20 to about 30 base pairs, about 21 to about 40 base pairs, about 21 to about 39 base pairs, about 21 to about 37 base pairs, about 23 to about 40 base pairs, about 23 to about 39 base pairs, about 23 to about 37 base pairs, about 25 to about 40 base pairs, about 25 to about 39 base pairs, about 25 to about 37 base pairs, about 25 to about 35 base pairs, or about 28 or 29 base pairs.

Suitably, the number of repeats may range from about 2 to about 140, from about 2 to about 100, from about 2 to about 100, from about 5 to about 100, from about 10 to about 100, from about 15 to about 100, from about 20 to about 100, from about 25 to about 100, from about 30 to about 100, from about 35 to about 100, from about 40 to about 100, from about 45 to about 100, from about 50 to about 100.

Suitably, the number of repeats may range from about 2 to about 135, from about 2 to about 130, from about 2 to about 125, from about 2 to about 120, from about 2 to about 115, from about 2 to about 110, from about 2 to about 105, from about 2 to about 100, from about 2 to about 95, from about 2 to about 90, from about 2 to about 80, from about 2 to about 70, from about 2 to about 60, from about 2 to about 50, from about 2 to about 40, from about 2 to about 30, from about 2 to about 20, from about 2 to about 10, from about 2 to about 9, from about 2 to about 8, from about 2 to about 7, from about 2 to about 6, from about 2 to about 5, from about 2 to about 4, or from about 2 to about 3.

The CRISPR repeat(s) may comprise, consist or consist essentially of DNA or RNA of genomic, synthetic or recombinant origin.

The CRISPR repeat(s) may be double-stranded or single-stranded whether representing the sense or antisense strand or combinations thereof.

The CRISPR repeat(s) may be prepared by use of recombinant DNA techniques (e.g. recombinant DNA), as described herein.

One or more of the CRISPR repeats may be used to engineer a cell—such as a recipient cell. In particular, one or more, preferably, two or more CRISPR repeats may be used to engineer a cell—such as a recipient cell—that in combination with one or more cas genes or proteins and one or more CRISPR spacers can be used to modulate the resistance of a cell against a target nucleic acid or a transcription product thereof. By way of example, the CRISPR repeat(s) may be inserted into the DNA of a cell (eg. a recipient cell)—such as plasmid DNA or genomic DNA of a cell—using various methods that are well known in the art. By way of further example, the CRISPR repeat(s) may be used as a template upon which to modify (eg. mutate) the DNA of a cell (eg. a recipient cell)—such as plasmid DNA or genomic DNA—such that CRISPR repeat(s) are created or engineered in the DNA of the cell. By way of further example, CRISPR repeat(s) may be cloned into a construct, a plasmid or a vector and the like which is then transformed into the cell, using methods such as those described herein.

In a further aspect of the present invention, there is also provided a method for identifying a CRISPR repeat for use in modulating the resistance of a cell against a target nucleic acid or transcription product thereof comprising the steps of: (i) preparing a cell comprising at least one CRISPR spacer and at least one cas gene; (ii) engineering the cell such that it contains a CRISPR repeat; and (iii) determining if the cell modulates resistance against the target nucleic acid or transcription product thereof, wherein modulation of the resistance of the cell against the target nucleic acid or transcription product thereof is indicative that the CRISPR repeat can be used to modulate resistance.

Suitably, one or more cas genes or proteins are used together with or in combination with one or more, preferably, two or more CRISPR repeats and optionally one or more CRISPR spacers. Suitably, the cas gene(s) or protein(s) and CRISPR repeat(s) form a functional combination as described below.

A CRISPR spacer is flanked by two CRISPR repeats. In other words, a CRISPR spacer has at least one CRISPR repeat on each side.

The CRISPR repeats may comprise or consist of the nucleotide sequence set forth in any one or more of SEQ ID Nos. 1-22.

Functional Combination

As mentioned above, surprisingly, the inventors have discovered that a given set of cas genes or proteins is always associated with a given repeated sequence within a particular CRISPR locus. In other words, cas genes or proteins seem to be specific for a given DNA repeat, meaning that cas genes or proteins and the repeated sequence form a functional pair.

Accordingly, particular combinations of one or more cas genes or proteins and one or more, preferably, two or more CRISPR repeats are used in order for a CRISPR spacer to confer resistance against a target nucleic acid or transcription product thereof in a cell (eg. a recipient cell). Accordingly, it has been surprisingly found that it is not possible to merely use any cas genes or proteins or any CRISPR repeat. Instead it is a feature of the present invention that the combination is functional.

In the context of the CRISPR repeat-cas gene or protein combination described herein, the term "functional" means that the combination is able to confer resistance to a target nucleic acid or a transcription product thereof when used together with a CRISPR spacer which aligns with or is homologous to a target nucleic acid or transcription product thereof.

As used herein the term "functional CRISPR repeat-cas combination" and "functional CRISPR repeat-cas gene combination" includes a functional combination in which cas is a cas gene or a Cas protein.

Suitably, the one or more cas genes or proteins and/or the one or more, preferably, two or more CRISPR repeats are or are derivable (preferably, derived) from the same cell (eg. the same recipient cell).

In one embodiment, the term "derivable" is synonymous with the term "obtainable".

In one embodiment, the term "derived" is synonymous with the term "obtained".

Suitably, the one or more cas genes or proteins and/or the one or more, preferably, two or more CRISPR repeats are derivable (preferably, derived) from the same CRISPR locus within a genome or plasmid, preferably a genome or plasmid of the same strain, species or genera.

Suitably, the one or more cas genes or proteins and/or the one or more, preferably, two or more CRISPR repeats are derivable (preferably, derived) from the same CRISPR locus within a single genome or plasmid, preferably a single genome or plasmid of the same strain, species or genera.

Suitably, the one or more cas genes or proteins and the one or more, preferably, two or more CRISPR repeats naturally co-occur.

Suitably, the one or more cas genes or proteins and the one or more, preferably, two or more CRISPR repeats naturally co-occur in the same cell (eg. recipient cell).

Suitably, the one or more cas genes or proteins and the one or more, preferably, two or more CRISPR repeats naturally co-occur in the same genome of a cell (eg. recipient cell).

Suitably, the one or more cas genes or proteins and the one or more, preferably, two or more CRISPR repeats naturally co-occur in the same genome of a strain, species or genera.

Accordingly, in a further aspect, there is provided a combination or nucleic acid consisting essentially of at least two CRISPR repeats and at least one cas gene or protein.

In one embodiment, the term "consists essentially of" refers to a combination of at least two CRISPR repeats and at least one cas gene or protein and excluding at least one further component of a CRISPR locus—such as the absence of one or more CRISPR spacer(s) and/or the absence of one or more common leader sequence(s) of a CRISPR locus.

In one embodiment, the term "consists essentially of" refers to a combination of at least two CRISPR repeats and at least one cas gene or protein only and excluding all other components of a CRISPR locus—such as a naturally occurring CRISPR locus.

In a further embodiment, the term "consists essentially of" refers to a combination of at least two CRISPR repeats and at least one cas gene or protein only and excluding at least one further component of a CRISPR locus—preferably excluding at least one further component of a naturally occurring CRISPR locus.

In a further embodiment, the term "consists essentially of" refers to a combination of at least two CRISPR repeats and at least one cas gene or protein with the proviso that at least one further component of the natural CRISPR locus is absent (eg. substantially absent).

Suitably, there is provided a combination of at least two CRISPR repeats and at least one cas gene or protein with the proviso that all other components of the CRISPR locus are absent (eg. substantially absent), preferably that all other components of the CRISPR locus of the natural combination of CRISPR repeat(s) and cas gene(s) are absent.

Suitably, the one or more cas genes or proteins are used in combination or together with one or more CRISPR spacers.

Suitably, the one or more cas genes or proteins are used in combination or together with at least one or more CRISPR spacers and at least one or more, preferably, two or more CRISPR repeats.

In one embodiment, the CRISPR spacer(s) are or are derivable (preferably, derived) from an organism (eg. a donor organism) that is different to the cell (eg. the recipient cell) from which the one or more cas genes or proteins and/or the one or more, preferably, two or more CRISPR repeats are or are derivable (preferably, derived).

Various arrangements of CRISPR repeats(s) and cas gene(s) or protein(s)—such as functional CRISPR repeat-cas combinations—are contemplated.

The combination may comprise, consist or consist essentially of at least any of 9, 10, 11, 12, 13, 14, 15, 16, 17, 18, 19 or 20 CRISPR repeat (s) in combination with any of 1, 2, 3, 4, 5, 6, 7, 8, 9, 10, 11, 12, 13, 14, 15, 16, 17, 18, 19 or 20 cas genes or proteins—such as 16 CRISPR repeat and 12 cas genes or proteins or 18 CRISPR repeats and 20 cas genes or proteins or any other combinations thereof.

The CRISPR repeat(s) and cas gene(s) may be arranged in various ways.

The combination may be cas1-repeat (wherein the repeat is at least two repeats, preferably, with at least one spacer in between the repeats), cas2-repeat (wherein the repeat is at least two repeats, preferably, with at least one spacer in between the repeats), cas3-repeat (wherein the repeat is at least two repeats, preferably, with at least one spacer in between the repeats), cas4-repeat (wherein the repeat is at least two repeats, preferably, with at least one spacer in between the repeats), cas1B-repeat (wherein the repeat is at least two repeats, preferably, with at least one spacer in between the repeats), cas5-repeat (wherein the repeat is at least two repeats, preferably, with at least one spacer in between the repeats), and/or cas6-repeat (wherein the repeat is at least two repeats, preferably, with at least one spacer in between the repeats).

The cas gene may be cas1, cas2, cas3, cas4, cas1B, cas5 and/or cas6 or a fragment, variant, homologue or derivative thereof.

The cas genes may be cas1, cas2, cas3, cas4, cas1B, cas5 and/or cas6 or a plurality thereof or a combination thereof—such as cas1 and cas2-repeat (wherein the repeat is at least two repeats, preferably, with at least one spacer in between the repeats); cas1 and cas3-repeat (wherein the repeat is at least two repeats, preferably, with at least one spacer in between the repeats); cas1 and cas4-repeat (wherein the repeat is at least two repeats, preferably, with at least one spacer in between the repeats); cas1 and cas1B-repeat (wherein the repeat is at least two repeats, preferably, with at least one spacer in between the repeats); cas) and cas5-repeat (wherein the repeat is at least two repeats, preferably, with at least one spacer in between the repeats); cas1 and cas6-repeat (wherein the repeat is at least two repeats, preferably, with at least one spacer in between the repeats); cas2 and cas3-repeat (wherein the repeat is at least two repeats, preferably, with at least one spacer in between the repeats); cas2 and cas4-repeat (wherein the repeat is at least two repeats, preferably, with at least one spacer in between the repeats); cas2 and cas1B-repeat (wherein the repeat is at least two repeats, preferably, with at least one spacer in between the repeats); cas2 and cas5-repeat (wherein the repeat is at least two repeats, preferably, with at least one spacer in between the repeats); cas2 and cas6-repeat (wherein the repeat is at least two repeats, preferably, with at least one spacer in between the repeats); cas3 and cas4-repeat (wherein the repeat is at least two repeats, preferably, with at least one spacer in between the repeats); cas3 and cas1B-repeat (wherein the repeat is at least two repeats, preferably, with at least one spacer in between the repeats); cas3 and cas5-repeat (wherein the repeat is at least two repeats, preferably, with at least one spacer in between the repeats); cas3 and cas6-repeat (wherein the repeat is at least two repeats, preferably, with at least one spacer in between the repeats); cas4 and cas1B-repeat (wherein the repeat is at least two repeats, preferably, with at least one spacer in between the repeats); cas4 and cas5-repeat (wherein the repeat is at least two repeats, preferably, with at least one spacer in between the repeats); cas4 and cas6-repeat (wherein the repeat is at least two repeats, preferably, with at least one spacer in between the repeats); cas1B and cas5-repeat (wherein the repeat is at least two repeats, preferably, with at least one spacer in between the repeats); cas1B and cas6-repeat (wherein the repeat is at least two repeats, preferably, with at least one spacer in between the repeats); cas1, cas2 and cas3-repeat (wherein the repeat is at least two repeats, preferably, with at least one spacer in between the repeats); cas1, cas2 and cas4-repeat (wherein the repeat is at least two repeats, preferably, with at least one spacer in between the repeats); cas1, cas2 and cas1B-repeat (wherein the repeat is at least two repeats, preferably, with at least one spacer in between the repeats); cas1, cas2, cas3 and cas4-repeat (wherein the repeat is at least two repeats, preferably, with at least one spacer in between the repeats); cas1 cas2, cas3 and cas1B-repeat (wherein the repeat is at least two repeats, preferably, with at least one spacer in between the repeats); cas1, cas2, cas3 and cas5-repeat (wherein the repeat is at least two repeats, preferably, with at least one spacer in between the repeats); cas1, cas2, cas3 and cas6-repeat (wherein the repeat is at least two repeats, preferably, with at least one spacer in between the repeats); cas1, cas2, cas3, cas4 and cas1B-repeat (wherein the repeat is at least two repeats, preferably, with at least one spacer in between the repeats); cas1, cas2, cas3, cas4 and cas5-repeat (wherein the repeat is at least two repeats, preferably, with at least one spacer in between the repeats); cas1, cas2, cas3, cas4, cas1B and cas6-repeat (wherein the repeat is at least two repeats, preferably, with at least one spacer in between the repeats); cas1, cas2, cas3, cas4, cas1B, cas5-repeat (wherein the repeat is at least two repeats, preferably, with at least one spacer in between the repeats); cas1, cas2, cas3, cas4, cas1B and cas6-repeat (wherein the repeat is at least two repeats, preferably, with at least one spacer in between the repeats); cas1, cas2, cas3, cas4, cas1B, cas5 and cas6-repeat (wherein the repeat is at least two repeats, preferably, with at least one spacer in between the repeats); cas2, cas3 and cas4-repeat (wherein the repeat is at least two repeats, preferably, with at least one spacer in between the repeats); cas2, cas3 and cas1B-repeat (wherein the repeat is at least two repeats, preferably, with at least one spacer in between the repeats); cas2, cas3 and cas5-repeat (wherein the repeat is at least two repeats, preferably, with at least one spacer in between the repeats): cas2, cas3 and cas6-repeat (wherein the repeat is at least two repeats, preferably, with at least one spacer in between the repeats); cas2, cas3, cas4 and cas1B-repeat (wherein the repeat is at least two repeats, preferably, with at least one spacer in between the repeats); cas2, cas3, cas4, and cas5-repeat (wherein the repeat is at least two repeats, preferably, with at least one spacer in between the repeats); cas2, cas3, cas4 and cas6-repeat (wherein the repeat is at least two repeats, preferably, with at least one spacer in between the repeats); cas2, cas3, cas4, cas1B and cas5-repeat (wherein the repeat is at least two repeats, preferably, with at least one spacer in between the repeats); cas2, cas3, cas4, cas1B and cas6-repeat (wherein the repeat is at least two repeats, preferably, with at least one spacer in between the repeats); cas2, cas3, cas4, cas1B, cas5 and cas6-repeat (wherein the repeat is at least two repeats, preferably, with at least one spacer in between the repeats); cas3, cas4 and cas1B-repeat (wherein the repeat is at least two repeats, preferably, with at least one spacer in between the repeats); cas3, cas4 and cas5-repeat (wherein the repeat is at least two repeats, preferably, with at least one spacer in between the repeats); cas3, cas4 and cas6 repeat (wherein the repeat is at least two repeats, preferably, with at least one spacer in between the repeats); cas3, cas4, cas1B and cas5-repeat (wherein the repeat is at least two repeats, preferably, with at least one spacer in between the repeats); cas3, cas4, cas1B and cas6-repeat (wherein the repeat is at least two repeats, preferably, with at least one spacer in between the repeats); cas3, cas4, cas1B, cas5 and cas6-repeat (wherein the repeat is at least two repeats, preferably, with at least one spacer in between the repeats); cas4, cas1B and cas5-repeat (wherein the repeat is at least two repeats, preferably, with at least one spacer in between the repeats); cas4, cas1B and cas6-repeat (wherein the repeat is at least two repeats, preferably, with at least one spacer in between the repeats); cas4, cas1B, cas5 and cas6-repeat (wherein the repeat is at least two repeats, preferably, with at least one spacer in between the repeats); cas5 and cas6-repeat (wherein the repeat is at least two repeats, preferably, with at least one spacer in between the repeats) or combinations thereof.

The cas genes may be cas1 and cas2-repeat (wherein the repeat is at least two repeats, preferably, with at least one spacer in between the repeats); cas1 and cas3-repeat (wherein the repeat is at least two repeats, preferably, with at least one spacer in between the repeats); cas1 and cas4-repeat (wherein the repeat is at least two repeats, preferably, with at least one spacer in between the repeats); cas1 and cas1B-repeat (wherein the repeat is at least two repeats, preferably, with at least one spacer in between the repeats); cas1 and cas5-repeat (wherein the repeat is at least two repeats, preferably, with at least one spacer in between the repeats); cas1 and cas6-repeat (wherein the repeat is at least two repeats, preferably, with at least one spacer in between the repeats); cas2 and cas3-repeat (wherein the repeat is at least two repeats, preferably, with at least one spacer in between the repeats); cas2 and cas4-repeat (wherein the repeat is at least two repeats, preferably, with at least one spacer in between the repeats); cas2 and cas1B-repeat (wherein the repeat is at least two repeats, preferably, with at least one spacer in between the repeats); cas2 and cas5-repeat (wherein the repeat is at least two repeats, preferably, with at least one spacer in between the repeats); cas2 and cas6-repeat (wherein the repeat is at least two repeats, preferably, with at least one spacer in between the repeats); cas3 and cas4-repeat (wherein the repeat is at least two repeats, preferably, with at least one spacer in between the repeats); cas3 and cas1B-repeat (wherein the repeat is at least two repeats, preferably, with at least one spacer in between the repeats); cas3 and cas5-repeat (wherein the repeat is at least two repeats, preferably, with at least one spacer in between the repeats); cas3 and cas6-repeat (wherein the repeat is at least two repeats, preferably, with at least one spacer in between the repeats); cas4 and cas1B- repeat (wherein the repeat is at least two repeats, preferably, with at least one spacer in between the repeats); cas4 and cas5-repeat (wherein the repeat is at least two repeats, preferably, with at least one spacer in between the repeats); cas4 and cas6-repeat (wherein the repeat is at least two repeats, preferably, with at least one spacer in between the repeats); cas1B and cas5-repeat (wherein the repeat is at least two repeats, preferably, with at least one spacer in between the repeats) or cas1B and cas6-repeat (wherein the repeat is at least two repeats, preferably, with at least one spacer in between the repeats) or combinations thereof.

The cas genes may be a cas1, cas2 and cas3-repeat (wherein the repeat is at least two repeats, preferably, with at least one spacer in between the repeats); cas1, cas2 and cas4-repeat (wherein the repeat is at least two repeats, preferably, with at least one spacer in between the repeats); cas1, cas2 and cas1B-repeat (wherein the repeat is at least two repeats, preferably, with at least one spacer in between the repeats); cas1, cas2, cas3 and cas4-repeat (wherein the repeat is at least two repeats, preferably, with at least one spacer in between the repeats); cas1, cas2, cas3 and cas1B-repeat (wherein the repeat is at least two repeats, preferably, with at least one spacer in between the repeats); cas1, cas2, cas3 and cas5-repeat (wherein the repeat is at least two repeats, preferably, with at least one spacer in between the repeats); cas1, cas2, cas3 and cas6-repeat (wherein the repeat is at least two repeats, preferably, with at least one spacer in between the repeats); cas1, cas2, cas3, cas4 and cas1B-repeat (wherein the repeat is at least two repeats, preferably, with at least one spacer in between the repeats); cas1, cas2, cas3, cas4 and cas5-repeat (wherein the repeat is at least two repeats, preferably, with at least one spacer in between the repeats); cas1, cas2, cas3, cas4, cas1B and cas6-repeat (wherein the repeat is at least two repeats, preferably, with at least one spacer in between the repeats); cas1, cas2, cas3, cas4, cas1B and cas5-repeat (wherein the repeat is at least two repeats, preferably, with at least one spacer in between the repeats); cas1, cas2, cas3, cas4, cas1B and cas6-repeat (wherein the repeat is at least two repeats, preferably, with at least one spacer in between the repeats); cas1, cas2, cas3, cas4, cas1B, cas5 and cas6-repeat (wherein the repeat is at least two repeats, preferably, with at least one spacer in between the repeats) or combinations thereof.

The cas genes may be cas2, cas3 and cas4-repeat (wherein the repeat is at least two repeats, preferably, with at least one spacer in between the repeats); cas2, cas3 and cas1B-repeat (wherein the repeat is at least two repeats, preferably, with at least one spacer in between the repeats); cas2, cas3 and cas5-repeat (wherein the repeat is at least two repeats, preferably, with at least one spacer in between the repeats); cas2, cas3 and cas6-repeat (wherein the repeat is at least two repeats, preferably, with at least one spacer in between the repeats); cas2, cas3, cas4 and cas1B-repeat (wherein the repeat is at least two repeats, preferably, with at least one spacer in between the repeats); cas2, cas3, cas4, and cas5-repeat (wherein the repeat is at least two repeats, preferably, with at least one spacer in between the repeats); cas2, cas3, cas4 and cas6-repeat (wherein the repeat is at least two repeats, preferably, with at least one spacer in between the repeats); cas2, cas3, cas4, cas1B and cas5-repeat (wherein the repeat is at least two repeats, preferably, with at least one spacer in between the repeats); cas2, cas3, cas4, cas1B and cas6-repeat (wherein the repeat is at least two repeats, preferably, with at least one spacer in between the repeats); cas2, cas3, cas4, cas1B, cas5 and cas6-repeat (wherein the repeat is at least two repeats, preferably, with at least one spacer in between the repeats) or combinations thereof.

The cas genes may be cas3, cas4 and cas1B-repeat (wherein the repeat is at least two repeats, preferably, with at least one spacer in between the repeats); cas3, cas4 and cas5-repeat (wherein the repeat is at least two repeats, preferably, with at least one spacer in between the repeats); cas3, cas4 and cas6-repeat (wherein the repeat is at least two repeats, preferably, with at least one spacer in between the repeats); cas3, cas4, cas1B and cas5-repeat (wherein the repeat is at least two repeats, preferably, with at least one spacer in between the repeats); cas3, cas4, cas1B and cas6-repeat (wherein the repeat is at least two repeats, preferably, with at least one spacer in between the repeats); cas3, cas4, cas1B, cas5 and cas6-repeat (wherein the repeat is at least two repeats, preferably, with at least one spacer in between the repeats); cas4, cas1B and cas5-repeat (wherein the repeat is at least two repeats, preferably, with at least one spacer in between the repeats); cas4, cas1B and cas6-repeat (wherein the repeat is at least two repeats, preferably, with at least one spacer in between the repeats); cas4, cas1B, cas5 and cas6-repeat (wherein the repeat is at least two repeats, preferably, with at least one spacer in between the repeats); cas5 and cas6-repeat (wherein the repeat is at least two repeats, preferably, with at least one spacer in between the repeats) or combinations thereof.

Where the combination of a cas gene and a CRISPR repeat comprises more than one cas gene, it will be understood that the CRISPR repeat may be inserted at the 3' end of the cas genes, the 5' end of the cas genes, or even in between the cas genes, provided that at least one of the cas genes remains functional.

In one embodiment, a first CRISPR repeat-cas gene or protein combination (comprising at least one cas gene or protein and at least two CRISPR repeats, wherein both are derivable (preferably, derived) from the same CRISPR locus within a genome) may be used in combination with a second CRISPR repeat-cas gene or protein combination (comprising at least one cas gene or protein and at least two CRISPR repeats, wherein both are derivable (preferably, derived) from the same or a different CRISPR locus within a genome). Accordingly, in this embodiment of the invention, the first and second combination are derivable (preferably, derived) from the same or different CRISPR loci within a genome.

Thus the first and second CRISPR repeat-cas gene or protein combinations may even be from different genomes—such as different genomes within the same cluster, as described in further detail herein.

In a still further embodiment of the present invention, a first and/or a second CRISPR repeat-cas gene or protein combination (comprising at least one cas gene and at least two CRISPR repeats derivable (preferably, derived) from the same CRISPR locus within a genome) may be used in combination with 3, 4, 5, 6, 7, 8, 9 or 10 or more CRISPR repeat-cas gene or protein combinations (each comprising at least one cas gene or protein and at least two CRISPR repeats derivable (preferably, derived) from the same or a different CRISPR loci within a genome). Accordingly, in this embodiment of the invention, the combinations are derivable (preferably, derived) from the same or different CRISPR loci within a genome.

In a further embodiment of the invention, the combinations may even be from different genomes—such as different genomes within the same cluster, as described in further detail herein.

In other words, for the CRISPR-repeat-cas gene or protein combination to confer resistance, in some embodiments, the CRISPR-repeat(s) and cas gene(s) or protein(s) naturally co-occur within a given CRISPR locus of a genome. In some embodiments, the CRISPR-repeat(s) and cas gene(s) or protein(s) naturally co-occur within the same CRISPR locus of a genome. These functional combinations together may confer resistance against a target nucleic acid or a transcription product thereof.

In a further aspect, there is provided a method for identifying a functional combination of a cas gene or protein and a CRISPR repeat comprising the steps of: (i) analysing the sequences (eg. nucleic acid or protein sequences) of the cas gene or protein and the CRISPR repeat; (ii) identifying one or more clusters of cas genes or proteins; (iii) identifying one or more clusters of CRISPR repeats; and (iv) combining those cas gene or protein and CRISPR repeat sequences that fall within the same cluster.

In a further aspect, there is provided a method for identifying a functional combination of a cas gene or protein and a CRISPR repeat for use in modulating the resistance of a cell against a target nucleic acid or a transcription product thereof comprising the steps of: (i) preparing a cell comprising a combination of one or more cas genes or proteins and one or more, preferably, two or more CRISPR repeats; (ii) engineering the cell such that it contains one or more CRISPR spacers; and (iii) determining if the cell modulates resistance against a target nucleic acid, wherein modulation of the resistance of the cell against the target nucleic acid or a transcription product thereof is indicative that the combination can be used to modulate the resistance of the cell against the target nucleic acid.

Suitably, the sequences of the cas gene or protein and the CRISPR repeat are or are derivable (preferably, derived) from the same or different strains.

Suitably, the sequences of the cas gene or protein and the CRISPR repeat are or are derivable (preferably, derived) from the same or different species.

Suitably, the sequences of the cas gene or protein and the CRISPR repeat are or are derivable (preferably, derived) from the same or different genera.

Suitably, the sequences of the cas gene or protein and the CRISPR repeat are or are derivable (preferably, derived) from the same or different organisms.

Suitably, the analysis is performed using dotplot analysis.

The combination may comprise, consist or consist essentially of DNA or RNA of genomic, synthetic or recombinant origin.

The combination may comprise, consist or consist essentially of DNA and RNA of genomic, synthetic or recombinant origin.

The combination may comprise, consist or consist essentially of a DNA CRISPR repeat of genomic, synthetic or recombinant origin.

The combination may comprise, consist or consist essentially of a RNA CRISPR repeat of genomic, synthetic or recombinant origin.

The combination may comprise, consist or consist essentially of a DNA cas gene repeat of genomic, synthetic or recombinant origin.

The combination may comprise, consist or consist essentially of a RNA cas gene of genomic, synthetic or recombinant origin.

The combination may comprise, consist or consist essentially of a DNA CRISPR repeat and DNA cas gene of genomic, synthetic or recombinant origin.

The combination may comprise, consist or consist essentially of a DNA CRISPR repeat and RNA cas gene of genomic, synthetic or recombinant origin.

The combination may comprise, consist or consist essentially of a RNA CRISPR repeat and DNA cas gene of genomic, synthetic or recombinant origin.

The combination may comprise, consist or consist essentially of a RNA CRISPR repeat and RNA cas gene of genomic, synthetic or recombinant origin.

The CRISPR repeat may be double-stranded or single-stranded whether representing the sense or antisense strand or combinations thereof.

The cas gene may be double-stranded or single-stranded whether representing the sense or antisense strand or combinations thereof.

The CRISPR repeat may be double-stranded or single-stranded whether representing the sense or antisense strand or combinations thereof and the cas gene may be double-stranded or single-stranded whether representing the sense or antisense strand or combinations thereof.

The CRISPR repeat may be double-stranded whether representing the sense or antisense strand or combinations thereof and the cas gene may be double-stranded whether representing the sense or antisense strand or combinations thereof.

The CRISPR repeat may be double-stranded whether representing the sense or antisense strand or combinations thereof and the cas gene may be single-stranded whether representing the sense or antisense strand or combinations thereof.

The CRISPR repeat may be single-stranded whether representing the sense or antisense strand or combinations thereof and the cas gene may be double-stranded whether representing the sense or antisense strand or combinations thereof.

The CRISPR repeat may be single-stranded whether representing the sense or antisense strand or combinations thereof and the cas gene may be single-stranded whether representing the sense or antisense strand or combinations thereof.

One or more of the functional combinations as described above may be used to engineer a cell—such as a recipient cell. In particular, one or more functional combinations may be used to engineer a cell—such as a recipient cell—that in combination with one or more CRISPR spacers can be used to modulate the resistance of a cell against a target nucleic acid or a transcription product thereof. By way of example, the functional combinations may be inserted into the DNA of a cell (eg. a recipient cell)—such as plasmid DNA or genomic DNA of a cell—using various methods that are well known in the art. By way of further example, the functional combinations may be used as a template upon which to modify (eg. mutate) the DNA of a cell (eg. a recipient cell)—such as plasmid DNA or genomic DNA—such that functional combinations are created in the DNA of the cell. By way of further example, functional combinations may be cloned into a construct, a plasmid or a vector and the like which are then transformed into the cell, using methods such as those described herein.

In one embodiment, the functional combination is obtained or obtainable by a method comprising the steps of: (a) analysing the sequences of a cas gene and a CRISPR repeat; (b) identifying one or more clusters of cas genes; (c) identifying one or more clusters of CRISPR repeats; and (d) combining those cas gene and CRISPR repeat sequences that fall within the same cluster, wherein the combination of the cas gene and CRISPR repeat sequences within the same cluster is indicative that the combination is a functional combination.

Clusters are described in further detail below.

CRISPR Spacer

As used herein, the term "CRISPR spacer" has the conventional meaning as used in the art and refers to the non-repetitive spacer sequences that are found between multiple short direct repeats (i.e. CRISPR repeats) of CRISPR loci. In other words, a CRISPR spacer is found between two CRISPR repeats.

It has been found that CRISPR spacer sequences in prokaryotes often have significant similarities to a variety of DNA molecules—such as genetic elements (including, but not limited to, chromosomes, bacteriophages, and conjugative plasmids). Interestingly, cells carrying these CRISPR spacers are unable to be infected by DNA molecules containing sequences homologous to the spacers (Mojica et al. 2005).

Typically, the CRISPR spacer is naturally present in between two identical multiple short direct repeats that are palindromic.

Suitably, the CRISPR spacer is homologous to the target nucleic acid or a transcription product thereof or an identified sequence. Although homology can also be considered in terms of similarity, in the context of the present invention it is preferred to express homology in terms of sequence identity. A homologous sequence is taken to include a CRISPR spacer, which may be at least 70, 75, 80, 85 or 90% identical, or at least 91, 92, 93, 94, 95, 96, 97, 98 or 99% identical to the target nucleic acid sequence or a transcription product thereof or an identified sequence.

In some embodiments, the CRISPR spacer is 100% identical to the target nucleic acid sequence.

The number of CRISPR spacers at a given CRISPR loci or locus can vary between species.

Suitably, the number of spacers may range from about 1 to about 140, from about 1 to about 100, from about 2 to about 100, from about 5 to about 100, from about 10 to about 100, from about 15 to about 100, from about 20 to about 100, from about 25 to about 100, from about 30 to about 100, from about 35 to about 100, from about 40 to about 100, from about 45 to about 100, from about 50 to about 100.

Suitably, the number of spacers may range from about 1 to about 135, from about 1 to about 130, from about 1 to about 125, from about 1 to about 120, from about 1 to about 115, from about 1 to about 110, from about 1 to about 105, from about 1 to about 100, from about 1 to about 95, from about 1 to about 90, from about 1 to about 80, from about 1 to about 70, from about 1 to about 60, from about 1 to about 50, from about 1 to about 40, from about 1 to about 30, from about 1 to about 20, from about 1 to about 10, from about 1 to about 9, from about 1 to about 8, from about 1 to about 7, from about 1 to about 6, from about 1 to about 5, from about 1 to about 4, from about 1 to about 3, from about 1 to about 2.

Typically, CRISPR spacers are identified by sequence analysis as the DNA stretches located in between two repeats.

As described herein, the inventors have surprisingly discovered that the use of one or more cas genes or proteins in combination with one or more, preferably, two or more CRISPR repeats (preferably, functional combination(s) thereof) provides for the specificity of immunity to be conferred by one or more CRISPR spacers in a cell—such as a recipient cell.

As used herein, the term "specificity of immunity" means that immunity can be conferred against a specific nucleic acid sequence or transcription product thereof using a specific CRISPR spacer (or pseudo CRISPR spacer) sequence. Accordingly, a given CRISPR spacer does not confer resistance against any nucleic acid sequence or transcription product thereof but only to those sequences against which the CRISPR spacer (or pseudo CRISPR spacer) is homologous—such as 100% identical.

The CRISPR spacer(s) may be or may be derivable (preferably, derived) from an organism—such as a donor organism—that is different to the cell—such as the recipient cell or even a further donor organism—from which the one or more cas genes or proteins and/or the one or more, preferably, two or more CRISPR repeats are or are derivable (preferably, derived). The CRISPR spacers may be or may be derivable (preferably, derived) from an organism—such as a donor organism—that is heterologous to the cell—such as the recipient cell or even a further donor organism—from which the one or more cas genes or proteins and/or the one or more, preferably, two or more CRISPR repeats are or are derivable (preferably, derived). The one or more cas genes or proteins and/or the one or more, preferably, two or more CRISPR repeats may be or may be derivable (preferably, derived) from a homologous (ie. the same) cell—such as a homologous recipient cell.

For the avoidance of doubt, the CRISPR spacer(s) may be designed and produced synthetically (eg. using recombinant DNA techniques).

In one embodiment, the CRISPR spacers are heterologous (ie. different) to the cell—such as the recipient cell—from which the one or more cas genes or proteins and/or the one or more, preferably, two or more CRISPR repeats are or are derivable (preferably, derived) and the one or more cas genes or proteins and/or the one or more, preferably, two or more CRISPR repeats are or are derivable (preferably, derived) from a homologous cell—such as a homologous recipient cell.

In another embodiment, the CRISPR spacers are heterologous (ie. different) to the cell—such as the recipient cell—from which the one or more cas genes or proteins are or are derivable (preferably, derived).

In another embodiment, the CRISPR spacers are heterologous to the cell—such as the recipient cell and the one or more cas genes or proteins and/or the one or more, preferably, two or more CRISPR repeats are or are derivable (preferably, derived) from a homologous cell—such as a homologous recipient cell.

In another embodiment, the CRISPR spacers are heterologous to the cell—such as the recipient cell—whereas the one or more cas genes or proteins and/or the one or more, preferably, two or more CRISPR repeats is/are homologous to the cell—such as the recipient cell.

In another embodiment, the CRISPR spacers are heterologous to the recipient cell, whereas the recipient cell is homologous for the one or more cas genes or proteins and/or the one or more, preferably, two or more CRISPR repeats.

In another embodiment, the CRISPR spacer used in accordance with the present invention is one which is not naturally associated with the CRISPR repeat and/or cas genes and/or functional CRISPR repeat-cas gene combination. In other words, the CRISPR spacer in the recombinant CRISPR locus according to the present invention is heterologous to the CRISPR repeat and/or cas genes of the CRISPR locus.

One or more of CRISPR spacers may be used to engineer a cell—such as a recipient cell. In particular, one or more CRISPR spacers may be used to engineer a cell—such as a recipient cell—that in combination with one or more cas genes or proteins and/or one or more, preferably, two or more CRISPR repeats (preferably, one or more functional combination thereof) can be used to modulate the resistance of a cell against a target nucleic acid or a transcription product thereof.

Suitably one or more of CRISPR spacers may be used to engineer a cell—such as a recipient cell. In particular, one or more CRISPR spacers are used to engineer a cell—such as a recipient cell—that in combination with one or more cas genes or proteins can be used to modulate the resistance of a cell against a target nucleic acid or a transcription product thereof.

By way of example, the CRISPR spacers may be inserted into the DNA of a cell (eg. a recipient cell)—such as plasmid DNA or genomic DNA of a cell—using various methods that are well known in the art.

By way of further example, the CRISPR spacers may be used as a template upon which to modify (eg. mutate) the DNA of a cell (eg. a recipient cell)—such as plasmid DNA or genomic DNA—such that CRISPR spacers are created in the DNA of the cell.

By way of further example, CRISPR spacers may be cloned into a construct, a plasmid or a vector and the like which are then transformed into the cell, using methods such as those described herein.

In a further aspect, there is also provided a method for identifying a CRISPR spacer for use in modulating the resistance of a cell against a target nucleic acid or a transcription product thereof comprising the steps of: (i) preparing a cell comprising at least two CRISPR repeats and at least one cas gene or protein; (ii) identifying at least one CRISPR spacer in an organism—such as a donor organism; (iii) modifying the sequence of the CRISPR spacer of the cell such that it has homology to the CRISPR spacer of the donor organism comprising the target nucleic acid; and (iv) determining if the cell modulates resistance against the target nucleic acid, wherein modulation of the resistance of the cell against the target nucleic acid or transcription product thereof is indicative that the CRISPR spacer modulates the resistance of the cell against the target nucleic acid.

The CRISPR spacers may comprise or consist of the nucleotide sequence set forth any one or more of in any of SEQ ID Nos. 23-460 and/or SEQ ID Nos. 522-665.

A CRISPR spacer is flanked by two CRISPR repeats. In other words, a CRISPR spacer has at least one CRISPR repeat on each side.

Without wishing to be bound by any particular theory, the further a given CRISPR spacer is from the 5' end of the CRISPR locus (comprising the cas gene(s) and/or the leader sequence), the lower the resistance conferred by that CRISPR spacer may be. Accordingly, in one embodiment of the present invention it is preferred that one or more of the first 100 CRISPR spacers from the 5' end of the CRISPR locus (comprising the cas genes and/or the leader sequence) are modified, more preferably, that one or more of the first 50 CRISPR spacers from the 5' end of the CRISPR locus (comprising the cas genes and/or the leader sequence) are modified, more preferably, that one or more of the first 40 CRISPR spacers from the 5' end of the CRISPR locus (comprising the cas genes and/or the leader sequence) are modified, more preferably, that one or more of the first 30 CRISPR spacers from the 5' end of the CRISPR locus (comprising the cas genes and/or the leader sequence) are modified, more preferably, that one or more of the first 20 CRISPR spacers from the 5' end of the CRISPR locus (comprising the cas genes and/or the leader sequence) are modified, more preferably, that one or more of the first 15 CRISPR spacers from the 5' end of the CRISPR locus (comprising the cas genes and/or the leader sequence) are modified, more preferably, that one or more of the first 10 CRISPR spacers from the 5' end of the CRISPR locus (comprising the cas genes and/or the leader sequence) are modified.

As will be appreciated by the skilled person, different bacteria have different numbers of CRISPR spacers.

CRISPR Spacer Core

For a specific CRISPR type within a microbial species, the CRISPR spacer is typically represented by a defined predominant length, but the size may vary. CRISPR types described to date have been found to contain a predominant spacer length of between about 20 bp and about 58 bp.

As used herein, the term "CRISPR spacer core" means the length of the shortest observed spacer within a CRISPR type. Thus, by way of example, within *Streptococcus thermophilus* CRISPR Type 1, the dominant spacer length is 30 bp with a minority of spacers between 28 bp and 32 bp in size. So in this particular example (*S. thermophilus* CRISPR Type 1), the CRISPR spacer core is defined as a continuous stretch of 28 bp.

Suitably, the CRISPR spacer core is homologous to the target nucleic acid or a transcription product thereof or an identified sequence over the length of the core sequence. Although homology can also be considered in terms of similarity, in the context of the present invention it is preferred to express homology in terms of sequence identity. A homologous sequence is taken to include a CRISPR spacer core, which may be at least 90% identical or at least 91, 92, 93, 94, 95, 96, 97, 98 or 99% identical to the target nucleic acid sequence or a transcription product thereof or an identified sequence over the length of the core sequence.

Suitably, the CRISPR spacer core is 100% identical to the target nucleic acid sequence or a transcription product thereof or an identified sequence over the length of the core sequence.

Pseudo-CRISPR Spacer

As used herein, the term "pseudo-CRISPR spacer" refers to a nucleic acid sequence present in an organism (eg. a donor organism)—such as a bacteriophage—which is preferably essential for function and/or survival and/or replication and/or infectivity and the like, and which forms a CRISPR spacer sequence; and/or can be used to form or prepare a CRISPR spacer sequence which is complementary to or homologous to the pseudo-CRISPR spacer; and/or can be used to modulate resistance.

One or more of pseudo CRISPR spacers or CRISPR spacer(s) which is/are complementary or homologous to the one or more pseudo CRISPR spacer(s) may be used to engineer a cell—such as a recipient cell. In particular, one or more pseudo CRISPR spacers or CRISPR spacer(s) which is/are complementary or homologous to the one or more pseudo CRISPR spacer(s) may be used to engineer a cell—such as a recipient cell—that in combination with one or more cas genes or proteins and/or one or more CRISPR repeats (eg, one or more functional combinations thereof) can be used to modulate the resistance of a cell against a target nucleic acid or a transcription product thereof.

One or more pseudo CRISPR spacers or CRISPR spacer(s) which is/are complementary or homologous to the one or more pseudo CRISPR spacer(s) may be used to engineer a cell—such as a recipient cell—that in combination with one or more cas genes or proteins can be used to modulate the resistance of a cell against a target nucleic acid or a transcription product thereof.

By way of example, the pseudo CRISPR spacers or CRISPR spacer(s) which is/are complementary or homologous to the one or more pseudo CRISPR spacer(s) may be inserted into the DNA of a cell (eg. a recipient cell)—such as plasmid DNA or genomic DNA of a cell—using various methods that are well known in the art.

By way of further example, the pseudo CRISPR spacers may be used as a template upon which to modify (eg. mutate) the DNA of a cell (eg. a recipient cell)—such as plasmid DNA or genomic DNA—such that CRISPR spacers are created in the DNA of the cell. By way of further example, pseudo CRISPR spacers or CRISPR spacer(s) which is/are complementary or homologous to the one or more pseudo CRISPR spacer(s) may be cloned into a construct, a plasmid or a vector and the like which are then transformed into the cell, using methods such as those described herein.

Nucleic Acid Sequence

In a further aspect, there is provided a nucleic acid sequence (eg. a recombinant or an isolated nucleic acid sequence) consisting essentially of at least one cas gene or protein.

The nucleic acid sequence may be DNA or RNA of genomic, synthetic or recombinant origin e.g. cDNA. The nucleotide sequence may be double-stranded or single-stranded whether representing the sense or antisense strand or combinations thereof. Recombinant nucleic acid sequences may be prepared by use of recombinant DNA techniques, as described herein. The target nucleic acid sequence may be or may be derived from a gene.

As used herein, the term "consisting essentially of" in the context of the nucleic acid sequence refers to a nucleic acid sequence comprising one or more cas genes and excluding at least one further component of a CRISPR locus—such as the CRISPR repeats, the CRISPR spacers and/or the common leader sequence.

Accordingly, in one embodiment, there is provided a nucleic acid sequence consisting essentially of at least one cas gene and at least two CRISPR repeats.

In a further embodiment, there is provided a nucleic acid sequence consisting essentially of at least one cas gene and at least one CRISPR spacer.

In a further embodiment, there is provided a nucleic acid sequence consisting essentially of at least one cas gene, at least one CRISPR spacer and at least two CRISPR repeats.

In a further embodiment, there is provided a nucleic acid sequence comprising at least one cas gene with the proviso that at least one further component of a CRISPR locus is absent, suitably, with the proviso that at least one further component of a natural CRISPR locus is absent (eg. substantially absent).

In a further embodiment, there is provided a nucleic acid sequence comprising at least one cas gene with the proviso that the CRISPR spacers of the CRISPR locus are absent, suitably, with the proviso that CRISPR spacers of a natural CRISPR locus are absent (eg. substantially absent).

In a further embodiment, there is provided a nucleic acid sequence comprising at least one cas gene with the proviso that the CRISPR repeats of the CRISPR locus are absent, suitably, with the proviso that the CRISPR repeats of a natural CRISPR, locus are absent.

In a further embodiment, there is provided a nucleic acid sequence comprising at least one cas gene with the proviso that the common leader sequences of the CRISPR locus are absent, suitably, with the proviso that the common leader sequences of the natural CRISPR locus are absent.

In a further embodiment, there is provided a nucleic acid sequence comprising at least one cas gene with the proviso that the CRISPR spacers and the CRISPR repeats of the CRISPR locus are absent, suitably, with the proviso that the CRISPR spacers and the CRISPR repeats of the natural CRISPR locus are absent.

In a further embodiment, there is provided a nucleic acid sequence comprising at least one cas gene with the proviso that the CRISPR spacers and the CRISPR repeats of the CRISPR locus are absent, suitably, with the proviso that the CRISPR spacers and the CRISPR repeats of the natural CRISPR locus are absent.

In a further embodiment, there is provided a nucleic acid sequence comprising at least one cas gene with the proviso that the CRISPR spacers and the common leader sequences of the CRISPR locus are absent, suitably, with the proviso that the CRISPR spacers and the common leader sequences of the natural CRISPR locus are absent.

In a further embodiment, there is provided a nucleic acid sequence comprising at least one cas gene with the proviso that the CRISPR repeats and the common leader sequences of the CRISPR locus are absent, suitably, with the proviso that the CRISPR repeats and the common leader sequences of the natural CRISPR locus are absent.

In further embodiment, there is provided a nucleic acid sequence comprising at least one cas gene with the proviso that the CRISPR repeats, the CRISPR spacers and the common leader sequences of the CRISPR locus are absent, suitably, with the proviso that the CRISPR repeats, the CRISPR spacers and the common leader sequences of the natural CRISPR locus are absent.

The nucleic acid sequence and the nucleic acids may be isolated or substantially purified. By "isolated" or "substantially purified" is intended that the nucleic acid molecules, or biologically active fragments or variants, homologues, or derivatives thereof are substantially or essentially free from components normally found in association with the nucleic acid in its natural state. Such components include other cellular material, culture media from recombinant production, and various chemicals used in chemically synthesising the nucleic acids.

An "isolated" nucleic acid sequence or nucleic acid is typically free of nucleic acid sequences that flank the nucleic acid of interest in the genomic DNA of the organism from which the nucleic acid was derived (such as coding sequences present at the 5' or 3' ends). However, the molecule may include some additional bases or moieties that do not deleteriously affect the basic characteristics of the composition.

The nucleic acid sequence(s) may be used in the engineering of a cell—such as a recipient cell. By way of example, the nucleic acid sequence may be inserted into the DNA—such as plasmid DNA or genomic DNA—of a recipient cell, using methods—such as homologous recombination. By way of further example, the nucleic acid sequence(s) may be used as a template upon which to modify (eg. mutate) the DNA of a cell (eg. a recipient cell)—such as plasmid DNA or genomic DNA—such that the nucleic acid sequence(s) are created in the DNA of the cell. By way of further example, the nucleic acid sequence(s) may be cloned into a construct, a plasmid or a vector and the like which are then transformed into the cell, using methods such as those described herein.

A CRISPR spacer is flanked by two CRISPR repeats. In other words, a CRISPR spacer has at least one CRISPR repeat on each side.

Target Nucleic Acid Sequence

As used herein, the term "target nucleic acid sequence" refers to any nucleic acid sequence or transcription product thereof, against which resistance in a cell—such as a recipient cell—is to be modulated.

The resistance may be against the target nucleic acid sequence per se. Advantageously, this confers resistance to a cell against a donor organism from which the target nucleic acid(s) is derivable (preferably, derived). Thus, by way of example, the insertion of a pseudo CRISPR spacer derivable (preferably, derived) from a bacteriophage or a CRISPR spacer(s) which is/are complementary or homologous to the one or more pseudo CRISPR spacer(s) into a cell—such as a recipient cell—may confer resistance to the bacteriophage. Thus, by way of further example, insertion between two CRISPR repeats of a pseudo CRISPR spacer derivable (preferably, derived) from a bacteriophage or CRISPR spacer(s) which is/are complementary or homologous to the one or more pseudo CRISPR spacer(s) into a cell—such as a recipient cell—may confer resistance to the bacteriophage.

The resistance may be against a transcription product of the target nucleic acid sequence—such as a transcript of the target nucleic acid sequence (eg. an RNA (eg. mRNA) transcript (eg. a sense or an antisense RNA transcript) or even a polypeptide transcription product. Advantageously, this confers resistance to a cell against a donor organism from which the transcription product is derivable (preferably, derived).

The target nucleotide sequence may be DNA or RNA of genomic, synthetic or recombinant origin.

The nucleotide sequence may be double-stranded or single-stranded whether representing the sense or antisense strand or combinations thereof.

The nucleotide sequence may be prepared by use of recombinant DNA techniques (e.g. recombinant DNA).

The nucleotide sequence may be the same as a naturally occurring form, or may be derivable (preferably, derived) therefrom.

The target nucleic acid sequence may be or may be derivable (preferably, derived) from a gene.

The target nucleic acid sequence may be or may be derivable (preferably, derived) from a variant, homologue, fragment or derivative of a gene.

In one embodiment, the target nucleic sequence is or is derivable (preferably, derived) from bacteriophage.

In one embodiment, the target nucleic sequence is or is derivable (preferably, derived) from plasmid DNA.

In one embodiment, the target nucleic sequence is or is derivable (preferably, derived) from a mobile genetic element.

In one embodiment, the target nucleic sequence is or is derivable (preferably, derived) from a transposable element or an insertion sequence.

In one embodiment, the target nucleic sequence is or is derivable (preferably, derived) from a gene that confers resistance.

In one embodiment, the target nucleic sequence is or is derivable (preferably, derived) from a gene that confers resistance to an antibiotic.

In one embodiment, the target nucleic sequence is or is derivable (preferably, derived) from a virulence factor.

In one embodiment, the target nucleic sequence is or is derivable (preferably, derived) from a toxin, an internalin or a hemolysin.

Modulating Resistance

In a further aspect, there is provided a method for modulating the resistance of a cell—such as a recipient cell—against a target nucleic acid or a transcription product thereof.

As used herein, the term "modulating resistance" may refer to suppressing, reducing, decreasing, inducing, conferring, restorating, elevating, increasing or otherwise affecting the resistance of a cell to a target nucleic acid.

As used herein, the term "resistance" is not meant to imply that a cell is 100% resistant to a target nucleic acid or a transcription product thereof, but includes cells that are tolerant of the target nucleic acid or a transcription product thereof.

As used herein the term "resistance to target nucleic acid or transcription product thereof" means that resistance is conferred against a cell or an organism—such as a phage—that comprises or produces the target nucleic acid or transcription product thereof.

Without being bound by any particular theory, we believe that resistance or immunity is not linked to the "entry" of foreign DNA into a cell (ie. penetration through the cell membrane). Immunity or resistance would rather correspond to an obstruction, hurdle, impediment, barrier or avoidance to persistency, maintenance or survival of the incoming nucleic acid (either, for example, in a free linear form, or integrated within the bacterial chromosome, outside from a CRISPR locus or within a circular molecule—such as a plasmid), or to a obstruction, hurdle, impediment, barrier or avoidance to its replication and/or transcription and/or expression.

In one embodiment, the minimal components conferring immunity or resistance against a target nucleic acid or expression product thereof is at least one cas gene (or one Cas protein) and at least two CRISPR repeats flanking a spacer.

In one embodiment, it is preferred that "modulating resistance" means inducing, conferring, elevating or increasing the resistance of a cell to a target nucleic acid.

In one aspect, there is provided a method for modulating (e.g. conferring or increasing) the resistance of a cell against a target nucleic acid or a transcription product thereof comprising the steps of: (i) identifying a sequence (eg. a conserved sequence) in an organism (preferably, a sequence essential to the function or survival of the organism); (ii) preparing a CRISPR spacer which is a sequence homologous, (suitably 100% identical), to the identified sequence; (iii) preparing a nucleic acid comprising at least one cas gene and at least two CRISPR repeats together with the CRISPR spacer; and (iv) transforming a cell with said nucleic acid thus to render the cell resistant to said target nucleic acid or transcription product thereof.

As used herein, the term "conserved sequence" in the context of identifying a conserved sequence in an organism does not necessarily have to be conserved in its strictest sense since the knowledge of one sequence from a given organism will be enough. Furthermore the sequence does not need to be part of an essential entity, since we believe that a spacer inspired from an essential gene would be more efficient in conferring immunity or resistance.

In one embodiment, the conserved sequence is a sequence that is essential for function and/or survival and/or replication and/or infectivity and the like of an organism or a cell. By way of example, the conserved sequence may be a helicase, a primase a head or tail structural protein, a protein with a conserved domain (eg. holing, lysine, and others) or a conserved sequences amongst important phage genes.

In a further aspect, there is provided a method for modulating (eg. conferring or increasing) the resistance of a cell against a target nucleic acid or a transcription product thereof comprising the steps of: (i) identifying one or more CRISPR spacers in an organism resistant to the target nucleic acid or transcription product thereof; (ii) preparing a recombinant nucleic acid comprising at least one cas gene or protein and at least two CRISPR repeats together with said identified one or more spacers; and (iii) transforming a cell with said recombinant nucleic acid thus to render the recipient cell resistant to said target nucleic acid or transcription product thereof.

In a further aspect, there is provided a method for modulating (eg. conferring or increasing) the resistance of a cell comprising at least one or more cas genes or proteins and one or more, preferably, two or more CRISPR repeats against a target nucleic acid or a transcription product thereof comprising the steps of: (i) identifying one or more CRISPR spacers in an organism resistant to the target nucleic acid or transcription product thereof; and (ii) modifying the sequence of one or more CRISPR spacer(s) in the cell such that the CRISPR spacer(s) has homology to the CRISPR spacer(s) in the organism.

In one embodiment, one or more CRISPR spacers in a cell—such as a recipient cell—are modified (eg. genetically engineered) such that the CRISPR spacer(s) have homology to one or more CRISPR spacer(s) in an organism—such as a donor organism—that is substantially resistant to a target nucleic acid or a transcription product thereof in order to render the cell resistant to the target nucleic acid.

Suitably, the one or more cas genes or proteins and one or more, preferably, two or more CRISPR repeats in the cell are a functional combination as described herein.

The genetic engineering may include, but is not limited to, adding (eg. inserting), deleting (eg. removing) or modifying (eg. mutating) the sequence of the one or more CRISPR spacers or in a cell such that the CRISPR spacer has homology (eg. increased homology after the genetic engineering) to one or more CRISPR spacers of a donor organism. This engineering step will result in a cell that was substantially sensitive to a target nucleic acid or a transcription product thereof being substantially resistant to the target nucleic acid or a transcription product thereof.

The genetic engineering may even include, but is not limited to, adding (eg. inserting) or deleting (eg. removing) the sequence of the one or more pseudo CRISPR spacers in to a cell. This engineering step will result in a cell that was substantially sensitive to a target nucleic acid or a transcription product thereof being substantially resistant to the target nucleic acid or a transcription product thereof.

In another embodiment, "modulating resistance" means suppressing, reducing or decreasing the resistance of a cell to a target nucleic acid.

Thus, in a further aspect, there is provided a method for decreasing or reducing the resistance of a cell—such as a recipient cell—comprising at least one or more cas genes or proteins and one or more, preferably, two or more CRISPR repeats against a target nucleic acid or a transcription product thereof.

According to this embodiment, the method comprises the steps of: (i) identifying one or more CRISPR spacers in an organism that is substantially resistant to the target nucleic acid or a transcription product thereof; and (ii) modifying the sequence of one or more CRISPR spacer(s) in the cell such that the CRISPR spacer(s) has a reduced degree of homology to the CRISPR spacer(s) in the organism.

In another embodiment, there is provided a method for modulating (eg. decreasing) the resistance of a cell comprising one or more cas genes or proteins and one or more, preferably, two or more CRISPR repeats against a target nucleic acid or transcription product thereof comprising the steps of: (i) identifying a CRISPR spacer or a pseudo CRISPR spacer in an organism comprising a target nucleic acid or transcription product thereof against which resistance is to be modulated; and (ii) identifying the CRISPR spacer in the organism in which resistance is to be modulated; and (iii) adapting the sequence of the CRISPR spacer in the organism in which resistance is to be modulated such that the CRISPR spacer has a lower degree of homology to the CRISPR spacer or pseudo CRISPR spacer of the organism comprising the target nucleic acid or transcription product thereof against which resistance is to be modulated.

One or more CRISPR spacers in a substantially resistant cell are engineered in order to render the cell sensitive to a target nucleic acid. The genetic engineering may include, but is not limited to, the addition (eg. insertion), deletion (eg. removal) or modification of one or more functional CRISPR repeat-cas combinations or portions or fragments thereof in the substantially resistant cell and/or the addition (eg. insertion), deletion (eg. removal) or modification of one or more CRISPR spacers or portions or fragments thereof in the substantially resistant cell.

This engineering step will then result in a cell that was substantially resistant to a target nucleic acid or a transcription product thereof becoming substantially sensitive to a target nucleic acid or a transcription product thereof.

Typically, in order to confer sensitivity to a cell, it is expected that one or more CRISPR spacers, one or more cas genes or proteins, one or more, preferably, two or more CRISPR repeats or one or more functional CRISPR repeat-cas combinations from a substantially resistant cell will be removed, deleted or modified such that resistance is no longer conferred.

Advantageously, cells that are sensitive to a target nucleic acid or a transcription product thereof may be prepared such that their levels within a given culture—such as a starter culture—may be modulated (eg. decreased) as desired. Thus, by way of example, a starter culture comprising two or more bacterial strains may be developed such that all members of the culture are sensitive to the same agent (eg. bacteriophage). Accordingly, at a time when it is no longer desired for the culture to be alive, the culture may be contacted with the same single agent in order to kill all members of the culture.

Moreover, it may even be possible to modulate the sensitivity of a cell to one or more agents (eg. bacteriophage) such that the agent kills only a certain proportion of the cells in a given culture—such as 10, 20, 30, 40, 50, 60, 70, 80, 90 or 95% of the cells in a given culture.

In one aspect, a cell—such as a recipient cell—may be engineered such that it comprises a CRISPR spacer or a sequence corresponding to a pseudo CRISPR spacer thereby rendering the cell resistant to a target nucleic acid or transcription product thereof. Suitably, the cell is engineered such that the CRISPR spacer or sequence corresponding to the pseudo CRISPR spacer is used together with a functional cas gene-CRISPR repeat combination, as described herein.

In one aspect, a cell that is resistant to a target nucleic acid or transcription product thereof is engineered such that the CRISPR spacer conferring the immunity against the target nucleic acid or transcription product thereof is inserted into a cell that comprises a functional cas gene-CRISPR repeat combination, thereby rendering the cell resistant to the target nucleic acid or transcription product thereof.

In one aspect, the sequence of one or more CRISPR spacers or pseudo CRISPR spacers of a cell that is resistant to a target nucleic acid or transcription product thereof is determined. A cell—such as a recipient cell—is then engineered such that it comprises the sequence of the CRISPR spacer and a functional cas gene-CRISPR repeat combination, thereby rendering the cell resistant to the target nucleic acid or transcription product thereof.

In one aspect, a CRISPR spacer from a cell—such as a recipient cell—and a functional cas gene-CRISPR repeat combination from the same or different cell—such as the same or different recipient cell—are prepared. A further cell—such as a recipient cell—is then engineered such that is comprises the CRISPR spacer sequence and functional cas gene-CRISPR repeat combination thereby rendering the cell resistant to the target nucleic acid or transcription product thereof.

A CRISPR spacer is flanked by two CRISPR repeats. In other words, a CRISPR spacer has at least one CRISPR repeat on each side.

Bacteriophage

In a particularly preferred aspect of the present invention, the resistance of a cell against a bacteriophage is modulated.

The bacteriophage is virulent to the cell.

The bacteriophage may be a virulent or a temperate bacteriophage.

As used herein, the term "bacteriophage" has its conventional meaning as understood in the art ie. a virus that selectively infects prokaryotes—such as bacteria. Many bacteriophages are specific to a particular genus or species or strain of cell.

The bacteriophage may be a lytic bacteriophage or a lysogenic bacteriophage.

A lytic bacteriophage is one that follows the lytic pathway through completion of the lytic cycle, rather than entering the lysogenic pathway. A lytic bacteriophage undergoes viral replication leading to lysis of the cell membrane, destruction of the cell, and release of progeny bacteriophage particles capable of infecting other cells.

A lysogenic bacteriophage is one capable of entering the lysogenic pathway, in which the bacteriophage becomes a dormant, passive part of the cell's genome through prior to completion of its lytic cycle.

The term "bacteriophage" is synonymous with the term "phage".

Whilst resistance against any bacteriophage (including wild type, naturally occurring, isolated or recombinant bacteriophage) may be employed, bacteriophage active against bacteria are preferred. More suitably, bacteriophage active against bacteria that are pathogenic to plants and/or animals (including humans) are of particular interest.

By way of example, the bacteriophage include, but are not limited to, those bacteriophage capable of infecting a bacterium that naturally comprises one or more CRISPR loci. CRISPR loci have been identified in more than 40 prokaryotes (Jansen et al. 2002b; Mojica et al., 2005; Haft et al., 2005) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listerta, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthamonas, Yersinia, Treponema* and *Thermotoga.*

By way of example, the bacteriophage include, but are not limited to, those bacteriophage capable of infecting bacteria belonging to the following. genera: *Escherichia, Shigella, Salmonella, Erwinia, Yersinia, Bacillus, Vibrio, Legionella, Pseudomonas, Neisseria, Bordetella, Helicobacter, Listeria, Agrobacterium, Staphylococcus, Streptococcus, Enterococcus, Clostridium, Corynebacterium, Mycobacterium, Treponema, Borrelia, Francisella, Brucella* and *Xanthomonas.*

By way of further example, the bacteriophage include, but are not limited to, those bacteriophage capable of infecting (or transducing) lactic acid bacteria species, a *Bifidobacterium* species, a *Brevibacterium* species, a *Propionibacterium* species, a *Lactococcus* species, a *Streptococcus* species, a *Lactobacillus* species including the *Lactobacillus acidophilus, Enterococcus species, Pediococcus* species, a *Leuconostoc* species and *Oenococcus* species.

By way of further example, the bacteriophage include, but are not limited to, those bacteriophage capable of infecting *Lactococcus lactis*, including *Lactococcus lactis* subsp. *lactis* and *Lactococcus lactis* subsp. *cremoris, Lactococcus lactis* subsp. *lactis* biovar *diacetylactfis, Streptococcus thermophilus, Lactobacillus delbrueckii* subsp. *bulgaricus, Lactobacillus helveticus, Bifidobacterium lactis, Lactobacillus acidophilus, Lactobacillus casei, Bifidobacterium infantis, Lactobacillus paracasei, Lactobacillus salivarius, Lactobacillus plantarum, Lactobacillus reuteri, Lactobacillus gasseri, Lactobacillus johnsonii* or *Bifidobacterium longum.*

By way of further example, the bacteriophages include, but are not limited to, those bacteriophage capable of infecting any fermentative bacteria susceptible to disruption by bacteriophage infection, including but not limited to processes for the production of antibiotics, amino acids, and solvents. Products produced by fermentation which are known to have encountered bacteriophage infection, and the corresponding infected fermentation bacteria, include Cheddar and cottage cheese (*Lactucoccus lactis* subsp. *lactis, Lactococcus lactis* subsp. *cremoris*), Yogurt (*Lactobacillus delbrueckii* subsp. *bulgaricus, Streptococcus thermophilus*), Swiss cheese (*S. thermophilus, Lactobacillus lactis, Lactobacillus helveticus*), Blue cheese (*Leuconostoc cremoris*), Italian cheese (*L. bulgaricus, S. thermophilus*), Viili (*Lactococcus lactis* subsp. *cremoris, Lactococcus lactis* subsp. *lactis* biovar *diacetylactis, Leuconostoc cremoris*), Yakult (*Lactobacillus casei*), casein (*Lactococcus lactis* subsp. *cremoris*), Natto (*Bacillus subtilis* var. natto), Wine (*Leuconostoc oenos*), Sake (*Leuconostoc mesenteroides*), Polymyxin (*Bacillus polymyxa*), Colistin (*Bacillus colistrium*), Bacitracin (*Bacillus licheniformis*), L-Glutamic acid (*Brevibacterium lactofermentum, Microbacterium ammoniaphilum*), and acetone and butanol (*Colstridium acetobutylicum, Clostridium saccharoperbutylacetonicum*).

Preferred bacteria are *S. thermophilus, L. delbrueckii* subsp. *bulgaricus* and/or *L. acidophilus.*

By way of further example, the bacteriophages include, but are not limited to, those bacteriophage capable of infecting a bacterium that comprises one or more heterologous CRISPR loci. The bacterium may comprise one or more heterologous CRISPR loci, one or more heterologous cas genes, one or more heterologous CRISPR repeats and/or one or more heterologous CRISPR spacers.

Bacteriophages may include, but are not limited to, bacteriophages that belong to any of the following virus families: Corticoviridae, Cystoviridae, Inoviridae, Leviviridae, Microviridae, Myoviridae, Podoviridae, Siphoviridae, or Tectiviridae.

To cause bacteriophage infection of cells, it "infects" a cell when it injects or transfers its nucleic acid into the cell, with the phage nucleic acid existing independently of the cell's genome. Infection may lead to expression (transcription and translation) of the bacteriophage nucleic acid within the cell and continuation of the bacteriophage life cycle. In the case of recombinant bacteriophage, recombinant sequences within the phage genome, such as reporter nucleic acids, may be expressed as well.

It has been found that CRISPR spacer sequences in prokaryotes often have significant similarities to a variety of DNA molecules—such as genetic elements (including, but not limited to, chromosomes, bacteriophages, conjugative plasmids). Interestingly, cells carrying these CRISPR spacers are unable to be infected by DNA molecules containing sequences homologous to the spacers (Mojica et al. 2005).

In the context of the present invention, one or more particular pseudo-spacers derivable or derived from bacteriophage DNA or CRISPR spacer(s) which is/are complementary or homologous to the one or more pseudo-CRISPR spacer(s) can be added within a CRISPR locus of a cell—such as a recipient cell—in order to modulate (eg. provide) resistance against a particular bacteriophage, thus substantially preventing phage attack.

Typically, particular regions within the phage genome may be targeted to prepare the pseudo-spacers—such as genes coding for host specificity proteins—that provide particular phage-host recognition—such as helicases, primase, head or tail structural proteins, proteins with a conserved domain (eg. holing, lysine, and others) or conserved sequences amongst important phage genes.

Any nucleic acid originating from the phage genome may confer immunity against the phage when inserted, for example, between two repeats in an active CRISPR locus. Immunity may be more "efficient" if the CRISPR spacer corresponds to an internal sequence of a phage gene, and even more "efficient" when this gene encodes "essential" proteins (eg. the antireceptor).

Accordingly, in a further aspect, there is provided a method for conferring resistance to a cell (suitably, a bacterial cell) against a bacteriophage comprising the steps of: (a) providing one or more pseudo CRISPR. spacers from at least one bacteriophage; (b) identifying one or more functional CRISPR repeat-cas combinations in at least one cell that is substantially sensitive to the bacteriophage; and (c) engineering the one or more CRISPR loci in the substantially sensitive cell such that they comprise one or more pseudo CRISPR spacers from a bacteriophage or one or more CRISPR spacer(s) which is/are complementary or homologous to the one or more pseudo CRISPR spacer(s) to render the cell resistant.

In a further aspect, there is provided a method for conferring resistance to a cell (suitably, a bacterial cell) against a bacteriophage comprising the steps of (a) providing one or more pseudo CRISPR spacers from at least one bacteriophage; (b) identifying one or more functional CRISPR repeat-cas combinations in at least one cell that is substantially sensitive to the bacteriophage; and (c) inserting one or more pseudo CRISPR spacers from the bacteriophage or one or more CRISPR spacer(s) which is/are complementary or homologous to the one or more pseudo CRISPR spacer(s) into the substantially sensitive cell such that the cell is rendered substantially resistant to the bacteriophage.

In a further aspect, there is provided a method for modulating the lysotype of a bacterial cell comprising the steps of: (a) providing one or more pseudo CRISPR spacers from, at least one bacteriophage; (b) identifying one or more functional CRISPR repeat-cas combinations in at least one cell that is substantially sensitive to the bacteriophage; and (c) engineering the one or more CRISPR loci in the substantially sensitive cell such that they comprise one or more pseudo CRISPR spacers from a bacteriophage or one or more CRISPR spacer(s) which is/are complementary or homologous to the one or more pseudo CRISPR spacer(s).

In a further aspect, there is provided a method for modulating the lysotype of a bacterial cell comprising the steps of: (a) providing one or more pseudo CRISPR spacers from at least one bacteriophage; (b) identifying one or more functional CRISPR repeat-cas combinations in at least one cell that is substantially sensitive to the bacteriophage; and (c) inserting one or more one or more pseudo CRISPR spacers from the bacteriophage or one or more CRISPR spacer(s) which is/are complementary or homologous to the one or more pseudo CRISPR spacer(s) into the substantially sensitive cell.

In a further aspect, there is provided a method for conferring resistance to a cell (suitably, a bacterial cell) against a bacteriophage comprising the steps of: (i) identifying a pseudo CRISPR spacer in a bacteriophage comprising a target nucleic acid or a transcription product thereof against which resistance is to be modulated; and (ii) modifying the sequence of the CRISPR spacer of the cell such that the CRISPR spacer of the cell has homology to the pseudo CRISPR spacer of the bacteriophage comprising the target nucleic acid.

In a further aspect, there is provided a method for conferring resistance to a cell (suitably, a bacterial cell) against a bacteriophage comprising the steps of: (i) identifying a pseudo CRISPR spacer in a bacteriophage comprising a target nucleic acid or a transcription product thereof against which resistance is to be modulated; and (ii) modifying the sequence of the CRISPR spacer of the cell such that the CRISPR spacer of the cell has 100% homology or identity to the pseudo CRISPR spacer of the bacteriophage comprising the target nucleic acid.

In a further aspect, there is provided a method for modulating the lysotype of a bacterial cell comprising the steps of: comprising the steps of: (i) identifying a pseudo CRISPR spacer in a bacteriophage comprising a target nucleic acid or a transcription product thereof against which resistance is to be modulated; and (ii) modifying the sequence of the CRISPR spacer of the cell such that the CRISPR spacer of the cell has homology to the pseudo CRISPR spacer of the bacteriophage comprising the target nucleic acid.

In a further aspect, there is provided a method for modulating the lysotype of a bacterial cell comprising the steps of: (i) identifying a pseudo CRISPR spacer in a bacteriophage comprising a target nucleic acid or a transcription product thereof against which resistance is to be modulated; and (ii) modifying the sequence of the CRISPR spacer of the cell such that the CRISPR spacer of the cell has 100% homology or identity to the pseudo CRISPR spacer of the bacteriophage comprising the target nucleic acid:

Suitably, the CRISPR spacer of the bacterial cell will have 100% homology or identity to a sequence—such as a pseudo CRISPR spacer—in the bacteriophage comprising the target nucleic acid.

Suitably, the CRISPR spacer of the bacterial cell will form a component part of a CRISPR locus comprising a functional CRISPR repeat-cas combination as described herein.

Suitably, the target nucleic acid or a transcription product thereof in the bacteriophage is a highly conserved nucleic acid sequence.

Suitably, the target nucleic acid or transcription product thereof in the bacteriophage is a gene coding for a host specificity protein.

Suitably, the target nucleic acid or transcription product thereof in the bacteriophage encodes an enzyme that is essential for survival, replication or growth of the bacteriophage.

Suitably, the target nucleic acid or transcription product thereof in the bacteriophage encodes a helicase, a primase, a head or tail structural protein, or a protein with a conserved domain (eg. holing, lysine, and others).

Advantageously, bacterial cells may be prepared according to the present invention that have a "reduced susceptibility to bacteriophage multiplication or infection". As used herein, this term refers to the bacterium as having a low or no susceptibility to bacteriophage multiplication or infection when compared to the wild-type bacterium when cultured, in for example, a dairy medium.

In one embodiment, the term "low susceptibility to bacteriophage multiplication" refers to the level of bacteriophage multiplication in a bacterium being below a level, which would cause a deleterious effect to a culture in a given period of time. Such deleterious effects on a culture include, but are not limited to, no coagulation of milk during production of fermented milk products (such as yoghurt or cheese), inadequate or slow lowering of the pH during production of fermented milk products (such as yoghurt or cheese), slow ripening of cheese and deterioration of a food's texture to the point where it is unappetising or unsuitable for human consumption.

For an equivalent set of culture conditions the susceptibility towards a bacteriophage of a bacterium of the present invention is, in comparison to the wild-type bacterium, 100 times lower (efficiency of plaquing [EOP]=$10^{-2}$), preferably 1000 times lower (EOP=$10^{-3}$), preferably 10 000 times lower (EOP=$10^{-4}$), more preferably 100 000 times lower (EOP=$10^{-5}$). Preferably, the level of bacteriophage multiplication in a culture is measured after about 14 hours incubation of the culture, more preferably after about 12 hours, more preferably after about 7 hours, more preferably after about 6 hours, more preferably after about 5 hours and more preferably after about 4 hours.

In a further aspect, there is provided a method for conferring sensitivity to a cell (preferably, a bacterial cell) against a bacteriophage comprising the steps of: (a) providing a pseudo CRISPR spacer from at least one bacteriophage; (b) identifying one or more functional CRISPR repeat-cas combinations in a cell that is substantially resistant to the bacteriophage; and (c) engineering the one or more CRISPR loci in the substantially, sensitive cell such that they comprise one or more pseudo CRISPR spacers or one or more CRISPR spacer(s) which is/are complementary or homologous to the one or more pseudo CRISPR spacer(s) that have a reduced degree of homology as compared to the one or more CRISPR loci in the substantially resistant cell.

In a further aspect, there is provided a method for modulating (eg. reducing) the lysotype of a cell (preferably a bacterial cell), comprising one or more cas genes or proteins and one or more, preferably, two or more CRISPR repeats comprising the steps of: (i) identifying a pseudo CRISPR spacer in a bacteriophage against which resistance is to be modulated; and (ii) modifying the sequence of the CRISPR spacer of the cell such that the CRISPR spacer of the cell has a reduced degree of homology to the pseudo CRISPR spacer of the bacteriophage comprising the target nucleic acid.

In still a further aspect, there is provided a method for modulating (eg. reducing or decreasing) the resistance of a bacterial cell comprising one or more cas genes or proteins and one or more, preferably, two or more CRISPR repeats against a bacteriophage comprising the steps of: (i) identifying one or more pseudo CRISPR spacers in a bacteriophage against which resistance is to be modulated; (ii) identifying a CRISPR spacer in the bacterial cell in which resistance is to be modulated that is homologous to the pseudo CRISPR spacer(s); and (iii) modifying the sequence of the CRISPR spacer in the bacterial cell in which resistance is to be modulated such that the CRISPR spacer has a lower degree of homology to the pseudo CRISPR spacer(s) of the bacteriophage against which resistance is to be modulated.

Suitably, the CRISPR spacer of the cell will have a reduced degree of homology—such as a 1, 2, 3, 4, 5, 6, 7, 8, 9, 10, 15, 20, 25, 30, 35, 40, 45, 50, 55, 60, 65, 70, 75, 80, 90 or 95% reduction in homology as compared to the pseudo CRISPR spacer(s) of the bacteriophage against which resistance is to be modulated.

Bacterial cells may therefore be prepared according to the present invention that have an "increased susceptibility to bacteriophage multiplication". As used herein, this term refers to the bacterium as having an increased or high susceptibility to bacteriophage multiplication when compared to the wild-type bacterium when cultured, in for example, a dairy medium.

In one embodiment, the term "high susceptibility to bacteriophage multiplication" refers to the level of bacteriophage multiplication in a bacterium being above a level, which would cause a deleterious effect to a culture in a given period of time. Such deleterious effects on a culture include, but are not limited to, no coagulation of milk during production of fermented milk products (such as yoghurt or cheese), inadequate or slow lowering of the pH during production of fermented milk products (such as yoghurt or cheese), slow ripening of cheese and deterioration of a food's texture to the point where it is unappetising or unsuitable for human consumption. For an equivalent set of culture conditions the susceptibility towards a bacteriophage of a bacterium of the present invention is, in comparison to the wild-type bacterium, 100 times higher, 1000 times higher, 10 000 times higher, or 100 000 times higher (EOP=$10^{-5}$). The level of bacteriophage multiplication in a culture. is measured after about 14 hours incubation of the culture, more preferably after about 12 hours, more preferably after about 7 hours, more preferably after about 6 hours, more preferably after about 5 hours and in a highly preferred embodiment after about 4 hours.

A CRISPR spacer is flanked by two CRISPR repeats. In other words, a CRISPR spacer has at least one CRISPR repeat on each side.

Bacteria

In a further embodiment, the target nucleic sequence or a transcription product thereof may be or may be derivable (preferably, derived) from one or more bacteria. Accordingly, resistance of a cell, eg. a bacterial cell, against bacteria or a component thereof may be modulated.

The target nucleotide sequence may be or may be derived from a gene that is or is associated with resistance to plasmid transfer in bacteria. According to this embodiment of the present invention, one or more CRISPR spacers in the cell are modified such that the CRISPR spacer of the cell has homology to the CRISPR spacer and/or pseudo CRISPR spacer contained in the plasmid DNA of the bacterial cell so as to provide resistance against the particular plasmid(s), thus preventing transfer of foreign DNA into the cell. Specifically, particular regions within the plasmid DNA can be targeted as to provide immunity against plasmid DNA, such as sequences within the plasmids origin of replication or sequences within genes coding for replication proteins.

Thus, according to this aspect, the method comprises the steps of: (i) identifying a CRISPR spacer and/or pseudo CRISPR spacer derivable (preferably, derived) from the plasmid DNA of a bacterial cell against which resistance is to be modulated; and (ii) modifying the sequence of a CRISPR spacer in the cell in which resistance is to be modulated such that the CRISPR spacer of the cell has homology to the CRISPR spacer and/or pseudo CRISPR spacer contained in the plasmid DNA of the bacterial cell.

In still a further aspect, there is provided a further method for conferring resistance to a cell against plasmid transfer comprising the steps of: (a) identifying a CRISPR spacer and/or pseudo CRISPR spacer derivable (preferably, derived) from plasmid DNA; (b) identifying one or more functional CRISPR repeat-cas gene combinations in a cell that is substantially sensitive to the plasmid; and (c) engineering the one or more CRISPR loci in the substantially sensitive cell such that they comprise one or more CRISPR spacers and/or pseudo CRISPR spacers from the plasmid to render the cell resistant.

The target nucleotide sequence may be or may be derived from a gene that is or is associated with resistance to one or more mobile genetic elements. Particular CRISPR spacers and/or pseudo CRISPR spacers derivable (preferably, derived) from one or more mobile genetic elements can be added within a CRISPR locus of a cell so as to provide resistance against mobile genetic elements—such as transposable elements and insertion sequences, thus preventing transfer of foreign DNA and genetic drift. Specifically, particular regions within transposons and insertion sequences can be targeted so as to provide immunity against mobile genetic elements. For example, targets can include conjugative transposons (Tn916), class II transposons (Tn501), insertions sequences (IS26) or transposase genes.

Thus, according to this aspect, the method comprises the steps of: (i) identifying a CRISPR spacer and/or pseudo CRISPR spacer derivable (preferably, derived) from one or more mobile genetic elements of a cell against which resistance is to be modulated; and (ii) modifying the sequence of a CRISPR spacer in a cell in which resistance is to be modulated such that the CRISPR spacer and/or pseudo CRISPR spacer of the cell has homology to the CRISPR spacer contained in the mobile genetic element(s) of the cell.

In still a further aspect, there is provided a further method for conferring resistance to a cell against one or more mobile genetic elements comprising the steps of: (a) identifying a CRISPR spacer and/or pseudo CRISPR spacer derivable (preferably, derived) from one or more mobile genetic elements; (b) identifying one or more functional CRISPR repeat-cas combinations in a cell that is substantially sensitive to the one or more mobile genetic elements; and (c) engineering the one or more CRISPR loci in the substantially sensitive cell such that they comprise or have homology to one or more CRISPR spacers and/or pseudo CRISPR spacers from the one or more mobile genetic elements to render the cell resistant.

The target nucleotide sequence may be or may be derived from a gene that is or is associated with resistance to antibiotics. By "antibiotic" is understood a chemical composition or moiety which decreases the viability or which inhibits the growth or reproduction of microbes. Antibiotic resistance genes include, but are not limited to $bla_{tem}$, $bla_{rob}$, $bla_{shv}$, aadB, aacC1, aacC2, aacC3, aacA4, mecA, vanA, vanH, vanX satA, aacA-aphH, vat, vga, msrA sul, and/or int. The antibiotic resistance genes include those that are or are derivable (preferably, derived) from bacterial species that include but are not limited to the genera *Escherichia, Klebsiella, Pseudomonas, Proteus, Streptococcus, Staphylococcus, Enterococcus, Haemophilus* and *Moraxella*. The antibiotic resistance genes also include those that are or are derivable (preferably, derived) from bacterial species that include but are not limited to *Escherichia coli, Klebsiella pneumoniae, Pseudomonas aeruginosa, Proteus mirabilis, Streptococcus pneumoniae, Staphylococcus aureus, Staphylococcus epidermidis, Enterococcus faecalis, Staphylococcus saprophyticus, Streptococcus pyogenes, Haemophilus influenzae*, and *Moraxella catarrhalis*.

Particular CRISPR spacers and/or pseudo CRISPR spacers derivable (preferably, derived) from antibiotic resistance encoding genes can be added within a CRISPR locus of a cell—such as a recipient cell—so as to prevent transfer of genes conferring resistance to antibiotics into the cell, thus reducing the risk of acquiring antibiotic resistance markers. By way of example, targets can also include vanR, (a gene conferring resistance to vancomycin), or tetR, a gene conferring resistance to tetracycline, or targeting beta-lactamase inhibitors.

Thus, according to this aspect, the method comprises the steps of: (i) identifying one or more CRISPR spacers and/or pseudo CRISPR spacers derivable (preferably, derived) from a cell that comprises one or more antibiotic resistance genes or markers; and (ii) modifying the sequence of the CRISPR spacer in a cell that does not comprise or does not express the antibiotic resistance genes or markers such that the CRISPR spacer of the cell has homology to the one or more CRISPR spacers and/or pseudo CRISPR spacers contained in the cell that comprises one or more antibiotic resistance genes or markers.

In still a further aspect, there is provided a method for modulating the acquisition of antibiotic resistance markers in a cell comprising the steps of: (a) identifying one or more CRISPR spacers and/or pseudo. CRISPR spacers derivable (preferably, derived) from a cell that comprises one or more antibiotic resistance genes or markers; (b) identifying one or more CRISPR loci in a cell that does not comprise or does not express the antibiotic resistance genes or markers; and (c) modifying the sequence of the CRISPR spacer in the cell that does not comprise or does not express the antibiotic resistance genes or markers such that the CRISPR spacer and/or pseudo CRISPR spacers has homology to the CRISPR spacer contained in the cell resistant to the transfer of genes conferring resistance to one or more antibiotics.

The target nucleotide sequence may be or may be derived from a gene that is or is associated with genes encoding virulence factors. Particular CRISPR spacers and/or pseudo CRISPR spacers derivable (preferably, derived) from genes encoding virulence factors can be added within a bacterium CRISPR locus to provide resistance against the transfer of genes conferring virulence into the bacterium. For example, factors commonly contributing to virulence in microbial pathogens can be targeted, such as toxins, internalins and hemolysins.

Thus, according to this aspect, the method comprises the steps of: (i) identifying one or more CRISPR spacers and/or pseudo CRISPR spacers derivable (preferably, derived) from a cell that comprises one or more virulence factors; and (ii) modifying the sequence of the CRISPR spacer in a cell that does not comprise or does not express the virulence factor(s) or marker(s) such that the CRISPR spacer of the cell has homology to the one or more CRISPR spacers and/or pseudo CRISPR spacers contained in the cell that comprises one or more virulence factors.

In still a further aspect, there is provided a further method for conferring resistance to a cell against one or more virulence factor(s) or marker(s) comprising the steps of: (a) identifying a CRISPR spacer and/or pseudo CRISPR spacer derivable (preferably, derived) from one or more virulence factor(s) or marker(s); (b) identifying one or more functional CRISPR repeat-cas combinations in a cell that is substantially sensitive to the one or more virulence factor(s) or marker(s); and (c) engineering the one or more CRISPR loci in the substantially sensitive cell such that they comprise one or more CRISPR spacers and/or pseudo CRISPR spacers from the one or more virulence factor(s) or marker(s) to render the cell resistant.

A CRISPR spacer is flanked by two CRISPR repeats. In other words, a CRISPR spacer has at least one CRISPR repeat on each side.

Modification

Nucleic acid sequences may be modified by genetically engineering nucleic acid sequences.

All or part of a nucleic acid sequence may be modified.

All or part of one or more CRISPR spacers, cas genes or proteins, CRISPR repeats or CRISPR loci may be modified.

Recombinant CRISPR spacers, cas genes or proteins, CRISPR repeats or CRISPR loci may be modified.

Naturally occurring CRISPR spacers, cas genes or proteins, CRISPR repeats or CRISPR loci may be modified.

Naturally co-occurring cas genes or proteins and CRISPR repeats may be modified.

The genetic engineering may be mediated using various methods that are known in the art and will typically include well known methods—such as PCR amplification, cloning and site-directed mutagenesis. Mutations may be introduced using synthetic oligonucleotides. These oligonucleotides contain nucleotide sequences flanking the desired mutation sites. A suitable method is disclosed in Morinaga et al., (*Biotechnology* (1984) 2, p 646-649). Another method of introducing mutations into enzyme-encoding nucleotide sequences is described in Nelson and Long (*Analytical Biochemistry* (1989), 180, p 147-151). A further method is described in Sarkar and Sommer (*Biotechniques* (1990), 8, p 404-407—"The megaprimer method of site directed mutagenesis"). Commercially available kits are also now widely available for performing site directed mutagenesis. Genetic engineering methods are described in detail in J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA Methods* in Enzymology, Academic Press.

The genetic engineering step may even include methods such as homologous recombination which may be particularly useful when, for example, CRISPR spacers are being inserted or deleted.

The genetic engineering step may even include the activation of one or more nucleic acid sequences—such as one CRISPR loci, CRISPR repeats, CRISPR spacers, cas genes or proteins, functional combinations of cas genes or proteins and CRISPR repeats or even combinations thereof.

Suitably, one or more CRISPR spacers or pseudo CRISPR spacers may be inserted into at least one CRISPR locus.

In one embodiment, the modification does not interrupt one or more cas genes of the at least one CRISPR locus. In another embodiment, the one or more cas genes remain intact.

In one embodiment, the modification does not interrupt one or more CRISPR repeats of the at least one CRISPR locus. In one embodiment, the one or more CRISPR repeats remain intact.

Suitably, one or more CRISPR spacers or pseudo CRISPR spacers may be inserted into or within at least one CRISPR locus.

Suitably, one or more CRISPR spacers or pseudo CRISPR spacers, may be inserted at the 5' end of at least one CRISPR locus.

In one embodiment, the modification comprises inserting at least one CRISPR spacer or pseudo CRISPR spacers into a cell—such as a recipient cell. In another embodiment, the modification comprises inserting one or more CRISPR spacers or pseudo CRISPR spacers into (eg. to modify or replace) one or more CRISPR spacers of a cell—such as a recipient cell.

In one embodiment, the modification comprises inserting at least one CRISPR spacer or pseudo CRISPR spacer from an organism—such as a donor organism—into the cell. In another embodiment, the modification comprises inserting one or more CRISPR spacers or pseudo CRISPR spacers from an organism—such as a donor organism—into (eg. to modify or replace) one or more CRISPR spacers, or pseudo CRISPR spacers of a cell.

In one embodiment, one or more CRISPR spacers or pseudo CRISPR spacers—such as one or more CRISPR spacers or pseudo CRISPR spacers from an organism—such as a donor organism—are inserted into (eg. to modify or replace) one or more CRISPR spacers or pseudo CRISPR spacers of the cell.

In one embodiment, one or more CRISPR spacers or pseudo CRISPR spacers—such as one or more CRISPR spacers or pseudo CRISPR spacers from an organism-such as a donor organism—are inserted into (eg. to modify or replace) one or more, preferably, two or more CRISPR repeats of the cell. In this embodiment of the invention, it is preferred that at least one functional CRISPR repeat-cas combination remains intact in the cell.

In one embodiment, one or more CRISPR spacers or pseudo CRISPR spacers—such as one or more CRISPR spacers or pseudo CRISPR spacers from an organism—such as a donor organism—are inserted into (eg. to modify or replace) the same or different CRISPR spacers of the cell.

In one embodiment, one or more CRISPR spacers or pseudo CRISPR spacers—such as one or more CRISPR spacers or pseudo CRISPR spacers from an organism—such as a donor organism—are inserted adjacent to (eg. to modify or replace) one or more CRISPR spacers or pseudo CRISPR spacers of the cell.

In the context of the present invention, the term "adjacent" means "next to" in its broadest sense and includes "directly adjacent". Thus, in one embodiment, one or more CRISPR spacers or pseudo CRISPR spacers from an organism may be inserted "directly adjacent" to one or more CRISPR spacers or pseudo CRISPR spacers of the cell. ie.

the CRISPR spacer(s) or pseudo CRISPR spacer(s) is inserted such that there are no intervening nucleotides between the spacers.

In another embodiment, the CRISPR spacer(s) or pseudo CRISPR spacer(s) are inserted such that there are at least 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 10,000, 100,000 or even 1,000,000 or more intervening nucleotides between the spacers.

In another embodiment, the intervening nucleotide may be called a leader sequence. These terms are used interchangeably herein. The leader sequence can be of a different length in different bacteria. Suitably the leader sequence is at least 20, 25, 30, 35, 40, 45, 50, 55, 60, 65, 70, 75, 80, 85, 90, 95, 100, 200, 300, 400 or 500 or more nucleotides in length. Suitably the leader sequence is between the last cas gene (at the 3' end) and the first CRISPR repeat (at the 5' end) of the CRISPR locus.

In one embodiment the leader sequence may be between about 20-500 nucleotides in length.

In one embodiment, one or more CRISPR spacers or pseudo CRISPR spacers—such as one or more CRISPR spacers or pseudo CRISPR spacers from a donor organism—are inserted adjacent to one or more, preferably, two or more CRISPR repeats of the cell.

In another embodiment, one or more CRISPR spacers or pseudo CRISPR spacers—such as one or more CRISPR spacers or pseudo CRISPR spacers from a donor organism—are inserted adjacent to one or more cas genes of the cell.

In another embodiment, one or more CRISPR spacers or pseudo CRISPR spacers—such as one or more CRISPR spacers or pseudo CRISPR spacers from a donor organism—are inserted adjacent to the same or different spacers of the recipient cell.

In another embodiment, one or more CRISPR spacers or pseudo CRISPR spacers—such as one or more CRISPR spacers or pseudo CRISPR spacers from a donor organism—are each inserted adjacent to the same or different CRISPR repeats of the cell.

In another embodiment, one or more CRISPR spacers or pseudo CRISPR spacers—such as one or more CRISPR spacers or pseudo CRISPR spacers from a donor organism—are each inserted adjacent to the same or different cas genes of the recipient cell.

In another embodiment, two or more CRISPR spacers or pseudo CRISPR spacers—such as two or more CRISPR spacers or pseudo CRISPR spacers from a donor organism—are each inserted adjacent to the same or different CRISPR spacers or pseudo CRISPR spacers and/or CRISPR repeats and/or cas genes of the recipient cell.

In another embodiment, the sequence of the CRISPR spacer—such as one or more CRISPR spacers from a donor organism—of the recipient cell is modified such that the CRISPR spacer has homology to the CRISPR spacer of the donor organism.

In another embodiment, the sequence of the spacer of the cell is modified such that it has homology to the CRISPR spacer or pseudo CRISPR spacer of the organism.

In one embodiment, the CRISPR spacer has 100% homology to the CRISPR spacer of the donor organism.

The CRISPR spacer(s) or pseudo CRISPR spacers may comprise DNA or RNA of genomic, synthetic or recombinant origin.

The CRISPR spacer (s) or pseudo CRISPR spacers may be double-stranded or single-stranded whether representing the sense or antisense strand or combinations thereof.

The CRISPR spacer (s) or pseudo CRISPR spacers may be prepared by use of recombinant DNA techniques (e.g. recombinant DNA), as described herein.

The modification may comprise inserting one or more CRISPR spacers or pseudo CRISPR spacers from an organism—such as a donor organism—that is substantially resistant to a target nucleic acid or a transcription product thereof into one or more CRISPR loci of a substantially sensitive cell.

The modification may comprise inserting one or more CRISPR spacers or pseudo CRISPR spacers from an organism—such as a donor organism—that is substantially resistant to a target nucleic acid or a transcription product thereof into (eg. between) a functional combination of at least two CRISPR repeats and at least one cas gene in a substantially sensitive cell.

The modification may even comprise modifying (eg. mutating) the DNA of a cell (eg. a recipient cell)—such as plasmid DNA or genomic DNA—such that one or more cas genes are created in the DNA of the cell. By way of further example, the cas genes may be cloned into a construct, a plasmid or a vector and the like which is then transformed into the cell, using methods such as those described herein.

The modification may even comprise modifying (eg. mutating) the DNA of a cell (eg. a recipient cell)—such as plasmid DNA or genomic DNA—such that one or more, preferably, two or more CRISPR repeats are created in the DNA of the cell. By way of further example, the CRISPR repeats may be cloned into a construct, a plasmid or a vector and the like which is then transformed into the cell, using methods such as those described herein.

The modification may even comprise modifying (eg. mutating) the DNA of a cell (eg. a recipient cell)—such as plasmid DNA or genomic DNA—such that one or more cas-CRISPR repeat functional combinations are created in the DNA of the cell. By way of further example, the cas-CRISPR repeat functional combinations may be cloned into a construct, a plasmid or a vector and the like which is then transformed into the cell, using methods such as those described herein.

The modification may even comprise modifying (eg. mutating) the DNA of a cell (eg. a recipient cell)—such as plasmid DNA or genomic DNA—such that one or more CRISPR spacers are created in the DNA of the cell. By way of further example, the CRISPR spacers may be cloned into a construct, a plasmid or a vector and the like which is then transformed into the cell, using methods such as those described herein.

In one embodiment, a CRISPR spacer is flanked by two CRISPR repeats. In other words, a CRISPR spacer has at least one CRISPR repeat on each side.

Suitably, the modification comprises inserting one or more CRISPR spacers (eg. heterologous CRISPR spacers) in the vicinity of (eg. adjacent to, suitably, directly adjacent to) one or more cas genes and/or the leader sequence. Suitably, according to this embodiment of the present invention, the organisation of the naturally occurring CRISPR locus is maintained following insertion of the one or more CRISPR spacers.

Cluster

It has also been surprisingly found that it is not possible to merely exchange CRISPR repeat-cas combinations between any cells (eg. any strains, species or genera of cells) since it is believed that this will not necessarily result in functional CRISPR repeat-cas combinations.

Rather, for the CRISPR repeat-cas combination(s) to be functional they should be compatible. Accordingly, it is believed that it is not possible to switch cas genes or CRISPR repeats between different CRISPR loci unless they are from the same cluster.

Even more surprising is that the clusters do not follow the "organism" phylogeny. Specifically, within one organism, there may be more than one CRISPR. These CRISPR(s) can belong to different clusters, even though they are present in the same organism. As a result, it is believed that a functional CRISPR repeat-cas. combination requires that the combination be switched within a cluster as opposed to within an organism.

For the avoidance of doubt, the term "cluster" as used herein does not refer to a—cluster of genes located at the same locus (typically forming an operon) but to the output from sequence comparison analysis—such as multiple sequence comparison analysis and/or multiple sequence alignments and/or dot plot analysis. Accordingly, cluster analysis of CRISPR loci may be performed using various methods that are known in the art—such as dot-plot analysis as taught herein below for example or multiple alignment followed by dendrogram calculation.

Advantageously, the use of naturally co-occurring CRISPR repeat-cas combination(s) provides for the interchange of the combination both within and between a given species, thereby making it possible to engineer the resistance of one strain using the combination from a different strain.

The cluster may be a class, a family or a group of sequences.

Determining Resistance

In a further aspect, there is provided a method for determining the resistance profile of a cell against a target nucleic acid. As used herein, the term "resistance profile" means one or more entities against which the cell is sensitive or resistant. Accordingly, the resistance profile of a cell may be that the cell is resistant to a first bacteriophage, sensitive to a second bacteriophage, resistant to a first mobile genetic element and sensitive to a first antibiotic resistance gene etc.

One or more cas genes or proteins, and/or one or more, preferably, two or more CRISPR repeats and/or one or more CRISPR spacers etc. within a cell may be detected or sequenced so as to predict/determine the likely resistance profile of a particular cell.

Suitably, one or more CRISPR spacers within a cell are detected or sequenced so as to predict/determine the likely resistance profile of a particular cell.

Suitable detection methods may include PCR, DNA-DNA hybridization (or DNA-RNA hybridization ie. using DNA or RNA probes that could be synthetic, labelled oligonucleotides, for example). DNA microarrays may also be used.

One or more cas-CRISPR repeat functional combinations and/or one or more CRISPR spacers within a cell may be detected or sequenced so as to predict/determine the likely resistance profile of a particular cell. By way of example, it is possible to predict/determine the likely resistance profile of a particular bacterial cell to one or more bacteriophage which can be used as a lysotype predictor for microbial selection.

One or more Cas genes and/or one or more CRISPR repeats may be sequenced in addition to one or more CRISPR spacers in order to verify the compatibility of the Cas gene-CRISPR repeat combination or even to identify new pairs of compatible cas/repeats.

Recipient Cell

As used herein, the term "recipient cell" refers to any cell in which resistance against a target nucleic acid or a transcription product thereof is modulated or is to be modulated.

In one embodiment, the recipient cell refers to any cell comprising the recombinant nucleic acid according to the present invention.

The recipient cell may comprise one or more, preferably, two or more CRISPR repeats and one or more cas genes or proteins. Suitably, the CRISPR repeats and the cas genes or proteins form a functional combination in the recipient cell, as described herein.

The recipient cell may comprise one or more modified CRISPR repeats and/or one or more modified cas genes or proteins. Suitably, the modified CRISPR repeats and/or the modified cas genes or proteins form a functional combination in the recipient cell, as described herein.

The recipient cell may comprise one or more genetically engineered CRISPR repeats and/or one or more genetically engineered cas genes or proteins. Suitably, the genetically engineered CRISPR repeats and/or the genetically engineered cas genes or proteins form a functional combination in the recipient cell, as described herein.

The recipient cell may comprise one or more recombinant CRISPR repeats and/or one or more recombinant cas genes or proteins. Suitably, the recombinant CRISPR repeats and/or the recombinant cas genes or proteins form a functional combination in the recipient cell, as described herein.

The recipient cell may comprise one or more naturally occurring CRISPR repeats and one or more naturally occurring cas genes or proteins. Suitably, the CRISPR repeats(s) and the cas gene(s) or proteins form a functional combination.

By "naturally occurring" we mean occurring naturally in nature.

The recipient cell may even comprise combinations of one or more modified, genetically engineered, recombinant or naturally occurring CRISPR repeats and one or more modified, genetically engineered, recombinant or naturally occurring cas genes or proteins. Suitably, the one or more modified, genetically engineered, recombinant or naturally occurring CRISPR spacer(s) or the one or more modified, genetically engineered, recombinant or naturally occurring cas gene(s) or proteins form a functional combination.

Suitably, the recipient cell is a prokaryotic cell.

Suitably, the recipient cell is a bacterial cell. Suitable bacterial cells are described herein.

The bacterial cell may be selected from a lactic acid bacteria species, a *Bifidobacterium* species, a *Brevibacterium* species, a *Propionibacterium* species, a. *Lactococcus* species, a *Streptococcus* species, a *Lactobacillus* species including the *Enterococcus* species, *Pediococcus* species, a *Leuconostoc* species and *Oenococcus* species.

Suitable species include, but are not limited to *Lactococcus lactis*, including *Lactococcus lactis* subsp. *lactis* and *Lactococcus lactis* subsp. *cremoris, Lactococcus lactis* subsp. *cremoris, Leuconostoc* sp., *Lactococcus lactis* subsp. *lactis* biovar, *Streptococcus thermophilus, Lactobacillus delbrueckii* subsp. *bulgaricus* and *Lactobacillus helveticus, Bifidobacterium lactis, Lactobacillus acidophilus, Lactobacillus casei.*

The cell in which resistance is to be modulated may be a bacterial cell used for the fermentation of meat (including beef, pork, and poultry) including, but not limited to, lactic acid bacteria, *Pediococcus cerevisiae, Lactobacillus plantarum, Lactobacillus brevis, Micrococcus species, Lactobacillus sakei, Lactobacillus curvatus, Pediococcus pentosaceus, Staphylococcus xylosus* and *Staphylococcus vitulinus* and mixtures thereof (Food Biotechnology, 538-39 (D. Knorr Ed. 1987); C. Pederson, Microbiology of Fermented Foods, 210-34 (2d ed. 1979); U.S. Pat. No. 2,225,783).

The cell in which resistance is to be modulated may be a bacterial cell used for the fermentation of vegetables (e.g., carrots, cucumbers, tomatoes, peppers, and cabbage) including, but not limited to, *Lactobacillus plantatum, Lactobacillus brevis, Leuconostoc mesenteroides, Pediococcus pentosaceus*, and mixtures thereof (Food Biotechnology, 540 (D. Knorr Ed. 1987); C. Pederson, Microbiology of Fermented Foods, 153-209 (2d ed. 1979); U.S. Pat. Nos. 3,024,116; 3,403,032; 3,932,674; and 3,897,307).

The cell in which resistance is to be modulated may be a bacterial cell used for the fermentation of dough formed from cereals (e.g., wheat, rye, rice, oats, barley, and corn).

The cell in which resistance is to be modulated may be a bacterial cell used for the production of wine. Typically, this is achieved by the fermentation of fruit juice, typically grape juice.

The cell in which resistance is to be modulated may be a bacterial cell used for the fermentation of milk to produce cheese—such as *Lactobacillus delbrueckii* subsp. *bulgaricus, Lactobacillus helveticus, Streptococcus thermophilus, Lactococcus lactis* subsp. *lactis, Lactococcus lactis* subsp. *cremoris, Lactococcus lactis* subsp. *lactis* biovar *diacetylactis, Bifidobacteria* and *Enterococci* etc and mixtures thereof (Food Biotechnology, 530 (D. Knorr Ed. 1987); C. Pederson, Microbiology of Fermented Foods, 135-51 (2d ed. 1979)).

The cell in which resistance is to be modulated may be a bacterial cell used for the fermentation of milk to produce cheese—such as *Lactobacillus bulgaricus, Lactobacillus helveticus, Streptococcus thermophilus, Lactococcus lactis* subsp. *lactis, Lactococcus lactis* subsp. *cremoris, Lactococcus lactis* subsp. *lactis* biovar, *Lactococci, Bifidobacteria* and *Enterococci* etc and mixtures thereof (Food Biotechnology, 530 (D. Knorr Ed. 1987); C. Pederson, Microbiology of Fermented Foods, 135-51 (2d ed. 1979)). The cell in which resistance is to be modulated may be a bacterial cell used for the fermentation of egg—such as *Pediococcus pentosaceus, Lactobacillus plantarum*, and mixtures thereof (Food Biotechnology, 538-39 (D. Knorr Ed. 1987)).

The cell in which resistance is to be modulated may be a bacterium that naturally comprises one or more CRISPR loci. CRISPR loci have been identified in more than 40 prokaryotes (Jansen et al. 2002b; Mojica et al., 2005; Haft et al., 2005) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthamonas, Yersinia, Treponema* and *Thermotoga.*

The cell in which resistance is to be modulated may be a bacterium for use in cosmetic or pharmaceutical compositions. Such compositions may comprise a microbial culture and/or labelled bacterium and/or a. cell culture according to the present invention. Thus the microbial culture and/or labelled bacterium and/or a cell culture according to the present invention may be compatible in cosmetics or in pharmacy or in therapy.

Donor Organism

In one embodiment, the term "donor-organism" refers to an organism or cell from which the CRISPR repeat and/or cas gene and/or combination(s) thereof and/or CRISPR spacers are derivable (preferably, derived). These can be the same or different.

In one embodiment, the term "donor organism" refers to an organism or cell from which the one or more, preferably, two or more CRISPR repeats and/or one or more cas gene and/or combination(s) thereof and/or CRISPR spacers are derivable (preferably, derived). These can be the same or different.

In one embodiment, the CRISPR spacer or pseudo CRISPR spacer is synthetically derived.

In one embodiment, the donor organism or cell comprises one or more CRISPR spacers, which confers the specific of immunity against a target nucleic acid or transcription product thereof.

In one embodiment, the donor organism or cell from which the cas gene and/or CRISPR repeat and/or combination thereof is derivable (preferably derived) is also the recipient cell/organism for the recombinant CRISPR locus. These can be the same or different.

In one embodiment, the donor organism or cell from which the CRISPR spacer is derivable (preferably derived) is also the recipient cell/organism for the recombinant CRISPR locus. These can be the same or different.

When it is the case that the donor organism is a bacterial cell then the donor organism will typically comprise a CRISPR spacer which confers the specific immunity against the target nucleic acid or transcription product thereof.

The organism may be a bacterial cell or a bacteriophage.

Suitably, the organism is a bacteriophage.

Host Cells

As used herein, the term "host cell" refers to any cell that comprises the combination, the construct or the vector and the like according to the present invention.

Host cells may be transformed or transfected with a nucleotide sequence contained in a vector e.g. a cloning vector. Said nucleotide sequence may be carried in a vector for the replication and/or expression of the nucleotide sequence. The cells will be chosen to be compatible with the said vector and may, for example, be prokaryotic (for example bacterial) cells.

Aspects of the present invention also relate to host cells comprising the combination, construct or the vector of the present invention. The construct or the vector may comprise a nucleotide sequence for replication and expression of the sequence. The cells will be chosen to be compatible with the vector and may, for example, be prokaryotic (for example bacterial) cells.

Construct

In a further aspect, there is provided a construct comprising one or more of the nucleic acid sequences described herein.

The term "construct"—which is synonymous with terms such as "conjugate", "cassette" and "hybrid"—includes a nucleotide sequence directly or indirectly attached to another sequence—such as a regulatory sequence (eg. a promoter). By way of example, the present invention covers a construct comprising a nucleotide sequence operably linked to such a regulatory sequence. The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

The construct may even contain or express a marker, which allows for the selection of the nucleotide sequence construct in, for example, a bacterium. Various markers exist which may be used, for example those markers that provide for antibiotic resistance—e.g. resistance to bacterial antibiotics—such as Erythromycin, Ampicillin, Streptomycin and Tetracycline.

Vector

The construct may be or may be included in a vector (eg. a plasmid).

Thus, in a further aspect there is provided a vector comprising one or more of the constructs or sequences described herein.

The term "vector" includes expression vectors and transformation vectors and shuttle vectors.

The term "transformation vector", means a construct capable of being transferred from one entity to another entity—which may be of the species or may be of a different species. If the construct is capable of being transferred from one species to another then the transformation vector is sometimes called a "shuttle vector".

The vectors may be transformed into a suitable cell (eg. a host cell) as described below.

The vectors may be for example, plasmid or phage vectors provided with an origin of replication, optionally a promoter for the expression of the said polynucleotide and optionally a regulator of the promoter.

The vectors may contain one or more selectable marker nucleotide sequences. The most suitable selection systems for industrial micro-organisms are those formed by the group of selection markers which do not require a mutation in the host organism.

The vectors may be used in vitro, for example for the production of RNA or used to transfect or transform a host cell.

Thus, polynucleotides may be incorporated into a recombinant vector (typically a replicable vector), for example, a cloning or expression vector. The vector may be used to replicate the nucleic acid in a compatible host cell.

Transfection

Introduction of a nucleic acid (eg. a construct or vector) into a cell can be effected by various methods. For example, calcium phosphate transfection, DEAE-dextran mediated transfection, cationic lipid-mediated transfection, electroporation, transduction or infection may be used. Such methods are described in many standard laboratory manuals—such as Sambrook et al., Molecular Cloning: A Laboratory Manual, 2d ed. (1989) Cold Spring Harbor Laboratory Press, Cold Spring Harbor, N.Y.

Cells containing the nucleic acid (eg. a construct or vector) may be selected by using, for example, Erythromycin for cells transfected with a nucleic acid (eg. a construct or vector) carrying a resistance selectable marker.

Transformation

Teachings on the transformation of cells are well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

A cell may be transformed with a nucleic acid (eg. a construct or vector). Cells transformed with the nucleotide sequence may be cultured under conditions suitable for the replication or expression of the nucleotide sequence.

Introducing

In the context of introducing a nucleic acid into a cell, in one embodiment it is preferred that the term "introducing" means one or more of transforming, transfecting, conjugating or transducing.

Starter Cultures

Starter cultures are used extensively in the food industry in the manufacture of fermented products including milk products—such as yoghurt and cheese, meat products, bakery products, wine and vegetable products.

Starter cultures used in the manufacture of many fermented milk, cheese and butter products include cultures of bacteria, generally classified as lactic acid bacteria. Such bacterial starter cultures impart specific features to various dairy products by performing a number of functions.

Commercial non-concentrated cultures of bacteria are referred to in industry as 'mother cultures', and are propagated at the production site, for example a dairy, before being added to an edible starting material, such as milk, for fermentation. The starter culture propagated at the production site for inoculation into an edible starting material is referred to as the 'bulk starter'.

Suitable starter cultures for use in the present invention may include any organism which is of use in the food, cosmetic or pharmaceutical industry.

For example, the starter culture may be suitable for use in the dairy industry. When used in the dairy industry the starter culture may be selected from a lactic acid bacteria species, a *Bifidobacterium* species, a *Brevibacterium* species, a *Propionibacterium* species. Suitable starter cultures of the lactic acid bacteria group include commonly used strains of a *Lactococcus* species, a *Streptococcus* species, a *Lactobacillus* species including the *Lactobacillus acidophilus, Enterococcus* species, *Pediococcus* species, a *Leuconostoc* species and *Oenococcus* species.

Cultures of lactic acid bacteria are commonly used in the manufacture of fermented milk products—such as buttermilk, yoghurt or sour cream, and in the manufacture of butter and cheese, for example Brie or Harvati. *Lactococcus* species include the widely used *Lactococcus lactis*, including *Lactococcus lactis* subsp. *lactis* and *Lactococcus lactis* subsp. *cremoris*.

Other lactic acid bacteria species include *Leuconostoc* sp., *Streptococcus thermophilus, Lactobacillus delbrueckii* subsp. *bulgaricus* and *Lactobacillus helveticus*. In addition, probiotic strains—such as *Lactococcus* species—include the widely used *Lactococcus lactis*, including *Lactococcus lactis* subsp. *lactis* and *Lactococcus lactis* subsp. *cremoris*. Mesophilic cultures of lactic acid bacteria commonly used in the manufacture of fermented milk products such as buttermilk, yoghurt or sour cream, and in the manufacture of butter and cheese, for example Brie or Harvati. Other *Lactococcus* species include *Lactococcus lactis* subsp. *cremoris, Lactococcus lactis, Leuconostoc* sp., *Lactococcus lactis* subsp. *lactis* biovar, *Streptococcus thermophilus, Lactobacillus delbrueckii* subsp. *bulgaricus* and *Lactobacillus helveticus*. In addition, probiotic strains such as *Bifidobacterium lactis, Lactobacillus acidophilus, Lactobacillus casei* may be added during said manufacturing to enhance flavour or to promote health.

Cultures of lactic acid bacteria commonly used in the manufacture of cheddar and Monterey Jack cheeses include *Streptococcus thermophilus, Lactococcus lactis* subsp. *lactis* and *Lactococcus lactis* subsp. *cremoris* or combinations thereof.

Thermophilic cultures of lactic acid bacteria commonly used in the manufacture of Italian cheeses such as Pasta filata or parmesan, include *Streptococcus thermophilus* and

*Lactobacillus delbrueckii* subsp *bulgaricus*. Other *Lactobacillus* species—such as *Lactobacillus helveticus*—may be added during manufacturing to obtain a desired flavour.

Advantageously, the starter culture organism may comprise or consist of a genetically modified strain (prepared according to the methods desired herein) of one of the above lactic acid bacteria strains or any other starter culture strain.

The selection of organisms for the starter culture of the invention will depend on the particular type of products to be prepared and treated. Thus, for example, for cheese and butter manufacturing, mesophillic cultures of *Lactococcus* species, *Leuconostoc* species and *Lactobacillus* species are widely used, whereas for yoghurt and other fermented milk products, thermophillic strains of *Streptococcus* species and of *Lactobacillus* species are typically used.

The starter culture may even be a dried starter culture.

The starter culture may be a concentrated starter culture.

The starter culture may be a concentrated starter culture used in direct inoculation.

The starter culture may be a frozen starter culture.

The starter culture may consist of one bacterial strain, ie., a pure culture. In this case, substantially. all, or at least a significant portion of the bacterial starter culture would generally comprise the same bacterium.

In the alternative, the starter culture may comprise several bacterial strains, ie., a defined mixed culture.

Lactic Acid Bacteria

Particularly suitable starter cultures, in particular dried starter cultures, for use in the present invention comprise lactic acid bacteria.

As used herein the term "lactic acid bacteria" refers to Gram positive, microaerophillic or anaerobic bacteria which ferment sugar with the production of acids including lactic acid as the predominantly produced acid, acetic acid, formic acid and propionic acid. The industrially most useful lactic acid bacteria are found among *Lactococcus* species, such as *Lactococcus lactis, Lactobacillus* species, *Bifidobacterium* species, *Streptococcus* species, *Leuconostoc* species, *Pediococcus* species and *Propionibacterium* species.

The starter cultures of the present invention may comprise one or more lactic acid bacteria species such as, *Lactococcus lactis, Lactobacillus delbrueckii* subsp. *bulgaricus* and *Streptococcus thermophilus* or combinations thereof.

Lactic acid bacteria starter cultures are commonly used in the food industry as mixed strain cultures comprising one or more species. For a number of mixed strain cultures, such as yoghurt starter cultures comprising strains of *Lactobacillus delbrueckii* subsp. *bulgaricus* and *Streptococcus thermophilus*, a symbiotic relationship exists between the species wherein the production of lactic acid is greater compared to cultures of single strain lactic acid bacteria (Rajagopal et al. J. Dairy Sci., 73, p. 894-899, 1990).

Preparing Starter Cultures

Starter cultures may be prepared by techniques well known in the art such as those disclosed in U.S. Pat. No. 4,621,058. By way of example, starter cultures may be prepared by the introduction of an inoculum, for example a bacterium, to a growth medium to produce an inoculated medium and ripening the inoculated medium to produce a starter culture.

Preparing Dried Starter Cultures

Dried starter cultures may be prepared by techniques well known in the art, such as those discussed in U.S. Pat. Nos. 4,423,079 and 4,140,800.

Dried starter cultures for use in the present invention may be in the form of solid preparations. Examples of solid preparations include, but are not limited to tablets, pellets, capsules, dusts, granules and powders which may be wettable, spray-dried, freeze-dried or lyophilised.

The dried starter cultures for use in the present. invention may be in either a deep frozen pellet form or freeze-dried powder form. Dried starter cultures in a deep frozen pellet or freeze-dried powder form may be prepared according to the methods known in the art.

The starter cultures for use in the present invention may be in the form of concentrates which comprise a substantially high concentration of one or more bacteria. Suitably the concentrates may be diluted with water or resuspended in water or other suitable diluents, for example, an appropriate growth medium or mineral or vegetable oils, for use in the present invention. The dried starter cultures of the present invention in the form of concentrates may be prepared according to the methods known in the art, for example by centrifugation, filtration or a combination of such techniques.

Product

Suitable products for use in the present invention include, but are not limited to, a foodstuffs, cosmetic products or pharmaceutical products.

Any product, which is prepared from, or comprises, a culture is contemplated in accordance with the present invention. These include, but are not limited to, fruits, legumes, fodder crops and vegetables including derived products, grain and grain-derived products, dairy foods and dairy food-derived products, meat, poultry, seafood, cosmetic and pharmaceutical products.

The term "food" is used in a broad sense and includes feeds, foodstuffs, food ingredients, food supplements, and functional foods.

As used herein the term "food ingredient" includes a formulation, which is or can be added to foods and includes formulations which can be used at low levels in a wide variety of products that require, for example, acidifying or emulsifying.

As used herein, the term "functional food" means a food which is capable of providing not only a nutritional effect and/or a taste satisfaction, but is also capable of delivering a further beneficial effect to consumer. Although there is no legal definition of a functional food, most of the parties with an interest in this area agree that there are foods marketed as having specific health effects.

The term "food" covers food for humans as well as food for animals (i.e. a feed). In a preferred aspect, the food is for human consumption.

The cells described herein may be—or may be added to—a food ingredient, a food supplement, or a functional food.

The food may be in the form of a solution or as a solid—depending on the use and/or the mode of application and/or the mode of administration.

The cells described herein can be used in the preparation of food products such as one or more of: confectionery products, dairy products, meat products, poultry products, fish products and bakery products.

By way of example, the bacterium can be used as ingredients to soft drinks, a fruit juice or a beverage comprising whey protein, health teas, cocoa drinks, milk drinks and lactic acid bacteria drinks, yoghurt, drinking yoghurt and wine.

There is also provided a method of preparing a food, the method comprising admixing the cells according to the present invention with a food ingredient (such as a starting material for a food). The method for preparing a food is also another aspect of the present invention.

Suitably a food as described herein is a dairy product. More preferably a dairy product as described herein is one or more of the following: a yoghurt, a cheese (such as an acid curd cheese, a hard cheese, a semi-hard cheese, a cottage cheese), a buttermilk, quark, a sour cream, kefir, a fermented whey-based beverage, a koumiss, a milk drink and a yoghurt drink.

Here, the term "food" is used in a broad sense—and covers food for humans as well as food for animals (i.e. a feed). In a preferred aspect, the food is for human consumption.

The term feed as used herein includes raw and processed plant material and non plant material. The feed may be any feed suitable for consumption by an animal, including livestock (animal) feed, for example poultry feed, fish feed or crustacean feed for example.

Variants/Homologues/Derivatives/Fragments

The present invention encompasses the use of variants, homologues, derivatives and fragments thereof, including variants, homologues, derivatives and fragments of CRISPR loci, CRISPR spacers, pseudo CRISR spacers, cas genes or proteins, CRISPR repeats, functional CRISPR repeat-cas gene combinations and target nucleic acid sequences or transcription products thereof.

The term "variant" is used to mean a naturally occurring polypeptide or nucleotide sequences which differs from a wild-type sequence.

The term "fragment" indicates that, a polypeptide or nucleotide sequence comprises a fraction of a wild-type sequence. It may comprise one or more large contiguous sections of sequence or a plurality of small sections. The sequence may also comprise other elements of sequence, for example, it may be a fusion protein with another protein. Preferably the sequence comprises at least 50%, more preferably at least 65%, more preferably at least 80%, more preferably at least 85%, more preferably at least 90%, more preferably at least 95%, more preferably at least 96%, more preferably at least 97%, more preferably at least 98%, most preferably at least 99% of the wild-type sequence.

Preferably, the fragment retains 50%, more preferably 60%, more preferably 70%, more preferably 80%, more preferably 85%, more preferably 90%, more preferably 95%, more preferably 96%, more preferably 97%, more preferably 98%, or most preferably 99% activity of the wild-type polypeptide or nucleotide sequence.

Preferably, a CRISPR spacer or pseudo CRISPR spacer comprises at least 50%, more preferably at least 65%, more preferably at least 80%, more preferably at least 85%, more preferably at least 90%, more preferably at least 95%, more preferably at least 96%, more preferably at least 97%, more preferably at least 98%, most preferably at least 99% of the wild-type sequence. Preferably, a CRISPR spacer retains 50%, more preferably 60%, more preferably 70%, more preferably 80%, more preferably 85%, more preferably 90%, more preferably 95%, more preferably 96%, more preferably 97%, more preferably 98%, or most preferably 99% activity of the wild-type polypeptide or nucleotide sequence.

Preferably, a cas gene comprises at least 50%, more preferably at least 65%, more preferably at least 80%, more preferably at least 85%, more preferably at least 90%, more preferably at least 95%, more preferably at least 96%, more preferably at least 97%, more preferably at least 98%, most preferably at least 99% of the wild-type sequence. Preferably, a cas gene retains 50%, more preferably 60%, more preferably 70%, more preferably 80%, more preferably 85%, more preferably 90%, more preferably 95%, more preferably 96%, more preferably 97%, more preferably 98%, or most preferably 99% activity of the wild-type polypeptide or nucleotide sequence.

Preferably, a Cas protein comprises at least 50%, more preferably at least 65%, more preferably at least 80%, more preferably at least 85%, more preferably at least 90%, more preferably at least 95%, more preferably at least 96%, more preferably at least 97%, more preferably at least 98%, most preferably at least 99% of the wild-type sequence. Preferably, a Cas protein retains 50%, more preferably 60%, more preferably 70%, more preferably 80%, more preferably 85%, more preferably 90%, more preferably 95%, more preferably 96%, more preferably 97%, more. preferably 98%, or most preferably 99% activity of the wild-type polypeptide or nucleotide sequence.

Preferably, a CRISPR repeat comprises at least 50%, more preferably at least 65%, more preferably at least 80%, more preferably at least 85%, more preferably at least 90%, more preferably at least 95%, more preferably at least 96%, more preferably at least 97%, more preferably at least 98%, most preferably at least 99% of the wild-type sequence. Preferably, a CRISPR repeat retains 50%, more preferably 60%, more preferably 70%, more preferably 80%, more preferably 85%, more preferably 90%, more preferably 95%, more preferably 96%, more preferably 97%, more preferably 98%, or most preferably 99% activity of the wild-type polypeptide or nucleotide sequence.

Preferably, a functional CRISPR repeat-cas combination comprises at least 50%, more preferably at least 65%, more preferably at least 80%, more preferably at least 85%, more preferably at least 90%, more preferably at least 95%, more preferably at least 96%, more preferably at least 97%, more preferably at least 98%, most preferably at least 99% of the wild-type sequence. Preferably, functional CRISPR repeat-cas combination retains 50%, more preferably 60%, more preferably 70%, more preferably 80%, more preferably 85%, more preferably 90%, more preferably 95%, more preferably 96%, more preferably 97%, more preferably 98%, or most preferably 99% activity of the wild-type polypeptide or nucleotide sequence.

Preferably, a target nucleic acid sequence comprises at least 50%, more preferably at least 65%, more preferably at least 80%, more preferably at least 85%, more preferably at least 90%, more preferably at least 95%, more preferably at least 96%, more preferably at least 97%, more preferably at least 98%, most preferably at least 99% of the wild-type sequence. Preferably, a target nucleic acid sequence retains 50%, more preferably 60%, more preferably 70%, more preferably 80%, more preferably 85%, more preferably 90%, more preferably 95%, more preferably 96%, more preferably 97%, more preferably 98%, or most preferably 99% activity of the wild-type polypeptide or nucleotide sequence.

The fragment may be a functional fragment.

By a "functional fragment" of a molecule is understood a fragment retaining or possessing substantially the same biological activity as the intact molecule. In all instances, a functional fragment of a molecule retains at least 10% and at least about 25%, 50%, 75%, 80%, 85%, 90%, 95%, 96%, 97%, 98% or 99% of the biological activity of the intact molecule.

The term "homologue" means an entity having a certain homology with the subject amino acid sequences and the subject nucleotide sequences. Here, the term "homology" can be equated with "identity".

In the present context, a homologous sequence is taken to include an amino acid sequence, which may be at least 75, 85 or 90% identical, preferably at least 95%, 96%, 97%, 98% or 99% identical to the subject sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence, which may be at least 75, 85 or 90% identical, preferably at least 95%, 96%, 97%, 98% or 99% identical to the subject sequence. Although homology can also be considered in terms of similarity (i.e. amino acid residues having similar chemical properties/functions), in the context of the present invention it is preferred to express homology in terms of sequence identity.

Homology comparisons may be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a, sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410), the GENEWORKS suite of comparison tools and CLUSTAL. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix—such as BLOSUM62.

Once the software has produced an optimal alignment, it is possible to calculate % homology, preferably % sequence identity. The software typically does this as part of the sequence comparison and generates a numerical result.

Should Gap Penalties be used when determining sequence identity, then suitably the following parameters are used:

| FOR BLAST | |
|---|---|
| GAP OPEN | 0 |
| GAP EXTENSION | 0 |

| FOR CLUSTAL | DNA | PROTEIN | |
|---|---|---|---|
| WORD SIZE | 2 | 1 | K triple |
| GAP PENALTY | 10 | 10 | |
| GAP EXTENSION | 0.1 | 0.1 | |

For polypeptide sequence comparison the following settings may be used: GAP creation penalty of 3.0 and GAP extension penalty of 0.1. Suitably, the degree of identity with regard to an amino acid sequence is determined over at least 5 contiguous amino acids, determined over at least 10 contiguous amino acids, over at least 15 contiguous amino acids, over at least 20 contiguous amino acids, over at least 30 contiguous amino acids, over at least 40 contiguous amino acids, over at least 50 contiguous amino acids, or over at least 60 contiguous amino acids.

The sequences may also have deletions, insertions or substitutions of amino acid residues, which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example, according to the Table below. Amino acids in the same block in the second column and suitably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) may occur i.e. like-for-like substitution—such as basic for basic, acidic for acidic, polar for polar etc. Non-homologous substitution may also occur i.e. from one class of residue to another or alternatively involving the inclusion of unnatural amino acids—such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids—such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone #*, L-norleucine*, L-norvaline*, p-nitro-L-phenylalanine*, L-hydroxyproline#, L-thioproline*, methyl derivatives of phenylalanine (Phe)—such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * has been utilised for the purpose of the discussion above (relating to homologous or non=homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups—such as methyl, ethyl or propyl groups—in addition to amino acid spacers—such as glycine or β-alanine residues. A further form of variation involves the presence of one or more amino acid residues in peptoid form will be well understood by those skilled in the art. For the avoidance of doubt, "the peptoid form" is used to refer to variant. amino acid residues wherein the α-carbon substituent group is on the residue's nitrogen atom rather than the α-carbon. Processes for preparing peptides in the peptoid form are known in the art, for example, Simon R J et al., PNAS (1992) 89(20), 9367-9371 and Horwell D C, Trends Biotechnol. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences may be modified by any method available in the art. Such modifications may be carried out to enhance the in vive activity or life span of nucleotide sequences useful in the present invention.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*; ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

The invention will now be further described by way of Examples, which are meant to serve to assist one of ordinary skill in the art in carrying out the invention and are not intended in any way to limit the scope of the invention.

EXAMPLES

Example 1

Insertion of a phage specific spacer into an existing, functional CRISPR to provide resistance to the corresponding phage.

Strain—*Streptococcus thermophilus* ST0089

Phage—2972

*Streptococcus thermophilus* ST0089 is an industrially important strain used in the manufacture of yogurt, is genetically amenable to manipulation, and susceptible to virulent phage 2972. The full genome sequence for phage 2972 was recently determined.

The CRISPR loci is determined in strain ST0089. This is determined preferentially by sequencing the entire genome of ST0089. Alternatively, the CRISPR loci is identified via PCR using primer sets with sequences identical to *S. thermophilus* CRISPR elements previously identified.

Once identified, the CRISPR loci sequence is determined as well as the proximal regions which should contain the relevant cas genes.

At least one particular CRISPR-cas locus is selected for further manipulation. Functionality of this locus is ascertained through in silico analysis of the spacer regions and their homologies to phage DNA sequences (i.e. absence and/or presence of spacer sequences and correlation to phage infectivity with strain ST0089). In the absence of this correlation, functionality is assumed based on the presence of all documented elements (i.e. repeats, spacers, leader sequences, cas genes—putatively encoding full length proteins).

A suitable spacer sequence(s) is chosen from the genome of phage 2972. The criteria of the selected spacer is based on: 1) length of the spacers within the selected CRISPR locus; 2) about 100% identity to the phage sequence; 3) theoretically any phage sequence may be selected.

In the simplest example, a CRISPR unit consisting of a phage 2972 spacer sequence, flanked by two repeating elements (identical to the selected CRISPR locus) is chemically synthesized. By definition this synthetic "CRISPR unit" is approximately 100 bp in length and is too short for ensuing integration into the CRISPR locus.

Therefore, additional flanking DNA is constructed along with the CRISPR unit A minimum of 500 bp of homologous DNA, identical to the targeted CRISPR locus flanks the synthetic CRISPR unit, to facilitate integration.

There are at least two approaches. One construct emulates the addition of a new spacer onto the existing CRISPR. Alternatively, the entire CRISPR locus is replaced with the synthetic CRISPR unit.

The resulting CRISPR integrant is verified through DNA sequencing of the CRISPR locus prior to biological testing.

Phage sensitivity patterns of the CRISPR integrant against phage 2972 is tested and compared with the parental strain.

The constructed CRISPR integrant successfully demonstrates the direct correlation between the presence of a specific spacer within the proper context of CRISPR-cas.

Example 2

A spacer homologous to a phage DNA is inserted into a cell—such as recipient cell. The cell becomes resistant to the phage. In a CRISPR locus within the selected strain, a new CRISPR spacer is designed from phage DNA (with 100% identity to phage DNA) within the anti-receptor gene and inserted into the cell. The anti-receptor gene is targeted because CRISPR spacers from other strains have been found to show similarity to phage anti-receptor genes. Four strains bearing spacers showing identity to phage anti-receptor genes are resistant to the particular phage. The mutant is exposed to phage and it becomes resistant to it.

Example 3

A plasmid comprising a CRISPR spacer is prepared, and we show that this plasmid cannot be transferred into a cell that contains the same spacer, whereas the plasmid without the spacer can be transformed into the cell.

Example 4

A spacer is inserted into an original host, but not in a CRISPR locus, and the resulting mutant retains its sensitivity to the phage, showing that the spacer needs to be in a particular environment within a CRISPR and cas genes Example 5

A whole CRISPR repeat-cas combination is inserted into a cell—such as a recipient cell—to provide immunity against incoming nucleic acid.

Example 6

For a particular CRISPR repeat-cas combination present in two different strains, the "exchange" of spacers modifies their phenotypes (phage sensitivity/resistance).

Example 7

One or more cas genes (from a functional CRISPR-cas unit) are deleted. Cas genes are necessary for immunity to be provided. Cas mutants are still sensitive to the phage, despite the presence of the spacer identical to phage DNA.

Example 8

The deleted cas genes are cloned on a plasmid. It is possible to provide the cas genes in trans to the host. Where the cas gene is knocked out, immunity can be restored.

Example 9

Different cas-CRISPR-repeat combinations are prepared. Not only are cas genes or proteins required, but also, specific cas-CRISPR repeat pairs are required for functionality. When cas genes or proteins are provided from another CRISPR locus, the strain remains sensitive to the phage.

Example 10

When a particular CRISPR spacer is deleted from a naturally occurring CRISPR locus, this removes immunity against a given phage and the host becomes sensitive (looses resistance) to the phage to which the spacer is homologous to.

Example 11

Integration of a CRISPR spacer into the CRISPR locus of a bacterium provides resistance against a bacteriophage that the CRISPR spacer shows identity to
(A) *Streptococcus thermophilus* strain DGCC7710RH1
*Streptococcus thermophilus*

*Streptococcus thermophilus* strain DGCC7710 (deposited at the French "Collection Nationale de Cultures de Microorganismes" under number CNCM I-2423) possesses at least 3 CRISPR loci: CRISPR1, CRISPR2, and CRISPR3. In strains CNRZI066 and LMG18311 for which the complete genome sequence is known (Bolotin et al., 2004), CRISPR1 is located at the same chromosomal locus: between str0660 (or stu0660) and str0661 (or stu0661).

In strain DGCC7710, CRISPR1 is also located at the same chromosomal locus, between highly similar genes. CRISPR1 of strain DGCC7710 contains 33 repeats (including the terminal repeat), and thus 32 spacers.

All these spacers are different from each other. Most of these spacers are new (not yet described within CRISPR loci), but four spacers close to the CRISPR1 trailer are identical to already known CRISPR1 spacers:
  the $28^{th}$ spacer of DGCC7710 is 100% identical to the $31^{st}$ CRISPR1 spacer of strain CNRZ1575 (Genbank accession number DQ072991);
  the $30^{th}$ spacer of DGCC7710 is 100% identical to the $27^{th}$ CRISPR1 spacer of strain CNRZ703 (Genbank accession number DQ072990);
  the $31^{st}$ spacer of DGCC7710 is 100% identical to the $28^{th}$ CRISPR1 spacer of strain CNRZ703 (Genbank accession number DQ072990);
  the $32^{nd}$ spacer of DGCC7710 is 100% identical to the $30^{th}$ CRISPR1 spacer of strain CNRZ703 (Genbank accession number DQ072990).
Virulent Bacteriophage
  D858 is a bacteriophage belonging to the Siphoviridae family of viruses. Its genome sequence has been completely determined but is not published yet. This phage is virulent to *S. thermophilus* strain DGCC7710.

Phage Resistant Mutant

*Streptococcus thermophilus* strain DGCC7710RH1 has been isolated as a natural phage resistant mutant using DGCC7710 as the parental strain, and phage D858 as the virulent phage.

CRISPR1 of strain DGCC7710-RH1 contains 34 repeats (including the terminal repeat), and thus 33 spacers. When compared to the CRISPR1 sequence of *Streptococcus thermophilus* strain DGCC7710, the CRISPR1 sequence of *Streptococcus thermophilus* strain DGCC7710-RH1 possesses one additional new spacer (and of course one additional repeat which flanks the new spacer) at one end of the CRISPR locus (ie. close to the leader, at the 5' end of the CRISPR locus).

All the other spacers of CRISPR1 locus are unchanged.

The CRISPR1 sequence (5'-3') of strain DGCC7710-RH1 is:

```
>CRISPR1_DGCC7710-RH1,
caaggacagttattgattttataatcactatgtgggtataaaaacgtcaaaatttcatttgag

GTTTTTGTACTCTCAAGATTTAAGTAACTGTACAACtcaacaattgcaacatcttataacccactt

GTTTTTGTACTCTCAAGATTTAAGTAACTGTACAACtgtttgacagcaaatcaagattcgaattgt

GTTTTTGTACTCTCAAGATTTAAGTAACTGTACAACaatgacgaggagctattggcacaacttaca

GTTTTTGTACTCTCAAGATTTAAGTAACTGTACAACcgatttgacaatctgctgaccactgttatc

GTTTTTGTACTCTCAAGATTTAAGTAACTGTACAACacacttggcaggcttattactcaacagcga

GTTTTTGTACTCTCAAGATTTAAGTAACTGTACAACctgttccttgttcttttgttgtatcttttc

GTTTTTGTACTCTCAAGATTTAAGTAACTGTACAACttcattcttccgtttttgtttgcgaatcct

GTTPTTGTACTCTCAAGATTTAAGTAACTGTACAACgctggcgaggaaacgaacaaggcctcaaca

GTTTTTGTACTCTCAAGATTTAAGTAACTGTACAACCatagagtggaaaactagaaacagattcaa

GTTTTTGTACTCTCAAGATTTAAGTAACTGTACAACataatgccgttgaattacacggcaaggtca

GTTTTTGTACTCTCAAGATTTAAGTAACTGTACAACgagcgagctcgaaataatcttaattacaag

GTTTTTGTACTCTCAAGATTTAAGTAACTGTACAACgttcgctagcgtcatgtggtaacgtattta

GTTTTTGTACTCTCAAGATTTAAGTAACTGTACAACggcgtcccaatcctgattaatacttactcg

GTTTTTGTACTCTCAAGATTTAAGTAACTGTACAACaacacagcaagacaagaggatgatgctatg

GTTTTTGTACTCTCAAGATTTAAGTAACTGTACAACcgacacaagaacgtatgcaagagttcaag

GTTTTTGTACTCTCAAGATTTAAGTAACTGTACAACacaattcttcatccggtaactgctcaagtg

GTTTTTGTACTCTCAAGATTTAAGTAACTGTACAACaattaagggcatagaaagggagacaacatg

GTTTTTGTACTCTCAAGATTTAAGTAACTGTACAACcgatatttaaaatcattttcataacttcat

GTTTTTGTACTCTCAAGATTTAAGTAACTGTACAACgcagtatcagcaagcaagctgttagttact

GTTTTTGTACTCTCAAGATTTAAGTAACTGTACAACataaactatgaaattttataattttaaga

GTTTTTGTACTCTCAAGATTTAAGTAACTGTACAACaataatttatggtatagcttaatatcattg

GTTTTTGTACTCTCAAGATTTAAGTAACTGTACAACtgcatcgagcacgttcgagtttaccgtttc

GTTTTTGTACTCTCAAGATTTAAGTAACTGTACAACtctatatcgaggtcaactaacaattatgct

GTTTTTGTACTCTCAAGATTTAAGTAACTGTACAACaatcgttcaaattctgttttaggtacattt

GTTTTTGTACTCTCAAGATTTAAGTAACTGTACAACaatcaatacgacaagagttaaaatggtctt

GTTTTTGTACTCTCAAGATTTAAGTAACTGTACAACgcttagctgtccaatccacgaacgtggatg

GTTTTTGTACTCTCAAGATTTAAGTAACTGTACAACcaaccaacggtaacagctactttttacagt

GTTTTTGTACTCTCAAGATTTAAGTAACTGTACAACataactgaaggataggagcttgtaaagtct

GTTTTTGTACTCTCAAGATTTAAGTAACTGTACAACtaatgctacatctcaaaggatgatcccaga

GTTTTTGTACTCTCAAGATTTAAGTAACTGTACAACaagtagttgatgacctctacaatggtttat

GTTTTTGTACTCTCAAGATTTAAGTAACTGTACAACacctagaagcatttgagcgtatattgattg

GTTTTTGTACTCTCAAGATTTAAGTAACTGTACAACaattttgccccttctttgccccttgactag

GTTTTTGTACTCTCAAGATTTAAGTAACTGTACAACaccattagcaatcatttgtgcccattgagt
```

-continued

```
GTTTTTGTACTCTCAAGATTTAAGTAACTGTACAGT

ttgattcaacataaaaagccagttcaattgaacttggcttt

Legend
Leader sequence:
5'-caaggacagttattgattttataatcactatgtgggtataaaaacgtcaaaatttcatttgag-
3'

Integrated sequence comprising a CRISPR Repeat in upper case and a
CRISPR spacer (ie. tagging sequence) in lower case.

CRISPR Repeats

Terminal repeat:
5' gtttttgtactctcaagatttaagtaactgtacagt-3'

Trailer sequence:
5' ttgattcaacataaaaagccagttcaattgaacttggcttt3'
```

The sequence of the new spacer exists within the D858 phage genome and is represented herein as SEQ ID No. 534.

The sequence of the spacer is found between positions 31921 and 31950 bp (ie. on the plus strand) of D858's genome (and has 100% identity to the D858 genomic sequence over 30 nucleotides):

```
spa-        1 tcaacaattgcaacatcttataacccactt    30
cer           ||||||||||||||||||||||||||||||
D858    31921 tcaacaattgcaacatcttataacccactt 31950
```

Figure 5:
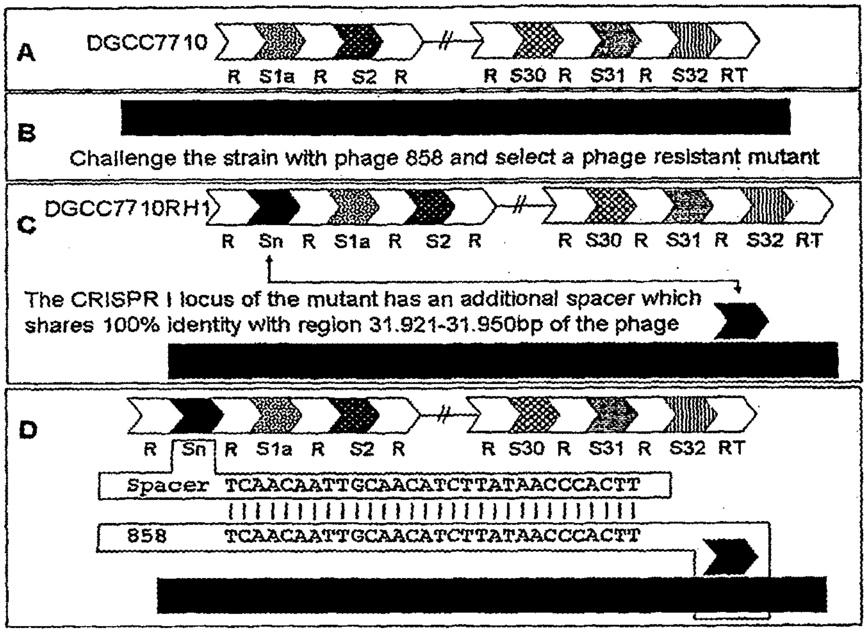

The new spacer that is integrated into the CRISPR1 locus of *Streptococcus thermophilus* strain DGCC7710-RH1 confers to this strain resistance to phage D858, as represented in FIG. 5 and Table 1.

(B) *Streptococcus thermophilus* Strain DGCC7710RH2

*Streptococcus thermophilus* strain DGCC7710-RH2 has been isolated as a natural phage resistant mutant using *Streptococcus thermophilus* strain DGCC7710 as the parental strain, and phage D858 as the virulent phage.

CRISPR1 of *Streptococcus thermophilus* strain DGCC7710-RH2 contains 34 repeats (including the terminal repeat), and thus 33 spacers. When compared to the CRISPR1 sequence of *Streptococcus thermophilus* strain DGCC7710, the CRISPR1 sequence of *Streptococcus thermophilus* strain DGCC7710-RH2 possesses one additional new spacer (and of course one additional repeat which flanks the new spacer) at one end of the CRISPR locus (ie. close to the leader, at the 5' end of the CRISPR locus). All the other spacers of CRISPR1 locus are unchanged.

The CRISPR1 sequence (5'-3') of strain DGCC7710-RH2 is:

```
<CRISPR1__DGCC7710-RH2
caaggacagttattgattttataatcactatgtgggtataaaaacgtcaaaatttcatttgag

GTTTTTGTACTCTCAAGATTTAAGTAACTGTACAACttacgtttgaaaagaatatcaaatcaatga

GTTTTTGTACTCTCAAGATTTAAGTAACTGTACAACtgtttgacagcaaatcaagattcgaattgt

GTTTTTGTACTCTCAAGATTTAAGTAACTGTACAACaatgacgaggagctattggcacaacttaca

GTTTTTGTACTCTCAAGATTTAAGTAACTGTACAACcgatttgacaatctgctgaccactgttatc

GTTTTTGTACTCTCAAGATTTAAGTAACTGTACAACacacttggcaggcttattactcaacagcga

GTTTTTGTACTCTCAAGATTTAAGTAACTGTACAACctgttccttgttcttttgttgtatcttttc

GTTTTTGTACTCTCAAGATTTAAGTAACTGTACAACttcattcttccgtttttgtttgcgaatcct

GTTTTTGTACTCTCAAGATTTAAGTAACTGTACAACgctggcgaggaaacgaacaaggcctcaaca

GTTTTTGTACTCTCAAGATTTAAGTAACTGTACAACcatagagtggaaaactagaaacagattcaa

GTTTTTGTACTCTCAAGATTTAAGTAACTGTACAACataatgccgttgaattacacggcaaggtca

GTTTTTGTACTCTCAAGATTTAAGTAACTGTACAACgagcgagctcgaaataatcttaattacaag

GTTTTTGTACTCTCAAGATTTAAGTAACTGTACAACgttcgctagcgtcatgtggtaacgtattta

GTTTTTGTACTCTCAAGATTTAAGTAACTGTACAACggcgtcccaatcctgattaatacttactcg

GTTTTTGTACTCTCAAGATTTAAGTAACTGTACAACaacacagcaagacaagaggatgatgctatg

GTTTTTGTACTCTCAAGATTTAAGTAACTGTACAACcgacacaagaacgtatgcaagagttcaag

GTTTTTGTACTCTCAAGATTTAAGTAACTGTACAACacaattcttcatccggtaactgctcaagtg

GTTTTTGTACTCTCAAGATTTAAGTAACTGTACAACaattaagggcatagaaagggagacaacatg

GTTTTTGTACTCTCAAGATTTAAGTAACTGTACAACcgatatttaaaatcattttcataacttcat
```

-continued

```
GTTTTTGTACTCTCAAGATTTAAGTAACTGTACAACgcagtatcagcaagcaagctgttagttact

GTTTTTGTACTCTCAAGATTTAAGTAACTGTACAACataaactatgaaattttataattttttaaga

GTTTTTGTACTCTCAAGATTTAAGTAACTGTACAACaataatttatggtatagcttaatatcattg

GTTITTGTACTCTCAAGATTTAAGTAACTGTACAACtgcatcgagcacgttcgagtttaccgtttc

GTTTTTGTACTCTCAAGATTTAAGTAACTGTACAACtctatatcgaggtcaactaacaattatgct

GTTTTTGTACTCTCAAGATTTAAGTAACTGTACAACaatcgttcaaattctgttttaggtacattt

GTTTTTGTACTCTCAAGATTTAAGTAACTGTACAACaatcaatacgacaagagttaaaatggtctt

GTTTTTGTACTCTCAAGATTTAAGTAACTGTACAACgcttagctgtccaatccacgaacgtggatg

GTTTTTGTACTCTCAAGATTVAAGTAACTGTACAACcaaccaacggtaacagctactttttacagt

GTTTTTGTACTCTCAAGATTTAAGTAACTGTACAACataactgaaggataggagcttgtaaagtct

GTTTTTGTACTCTCAAGATTTAAGTAACTGTACAACtaatgctacatctcaaaggatgatcccaga

GTTTTTGTACTCTCAAGATTTAAGTAACTGTACAACaagtagttgatgacctctacaatggtttat

GTTTTTGTACTCTCAAGATTTAAGTAACTGTACAACacctagaagcatttgagcgtatattgattg

GTTTTTGTACTCTCAAGATTTAAGTAACTGTACAACaattttgccccttctttgccccttgactag

GTTTTTGTACTCTCAAGATTTAAGTAACTGTACAACaccattagcaatcatttgtgcccattgagt

GTTTTTGTACTCTCAAGATTTAAGTAACTGTACAGT

ttgattcaacataaaaagccagttcaattgaacttggcttt

Legend
Leader sequence:
5'caaggacagttattgattttataatcactatgtgggtataaaaacgtcaaaatttcatttgag 3'

Integerated sequence comprising a CRISPR Repeat in upper case and a
CRISPR spacer (ie. tagging sequence) in lower case.

CRISPR Repeats
Terminal repeat:
5' gtttttgtactctcaagatttaagtaactgtacagt 3'

Trailer sequence:
5' ttgattcaacataaaaagccagttcaattgaacttggcttt3'
```

It has been shown that the sequence of the new spacer exists within the D858 phage genome.

The sequence of the spacer (represented herein as SEQ ID No. 535) is found between positions 17215 and 17244 bp (ie. on the plus strand) of D858's genome (and has 100% identity to the D858 genomic sequence over 30 nucleotides):

```
spa-        1 ttacgtttgaaaagaatatcaaatcaatga    30
cer           ||||||||||||||||||||||||||||||
D858    17215 ttacgtttgaaaagaatatcaaatcaatga 17244
```

Figure 6:
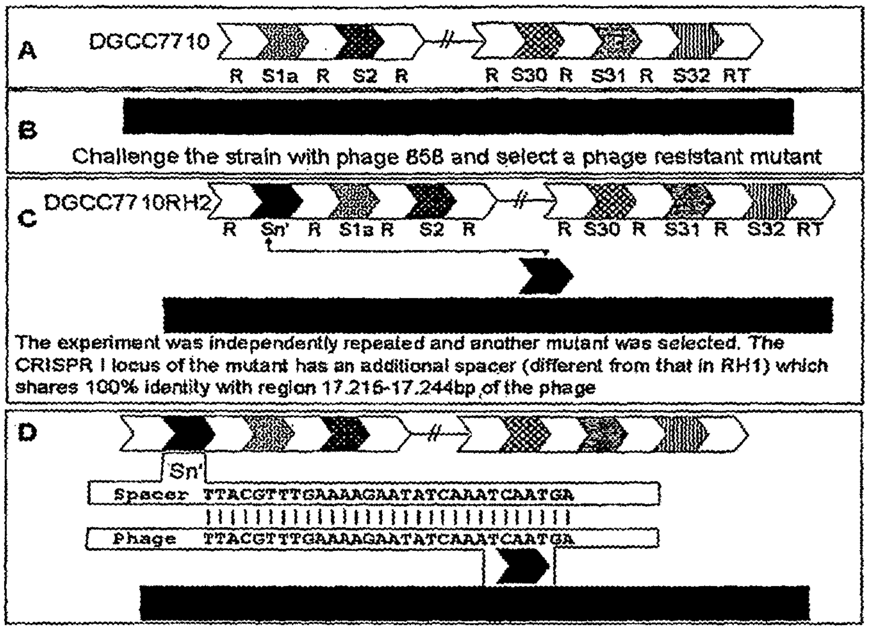
Figure 7:
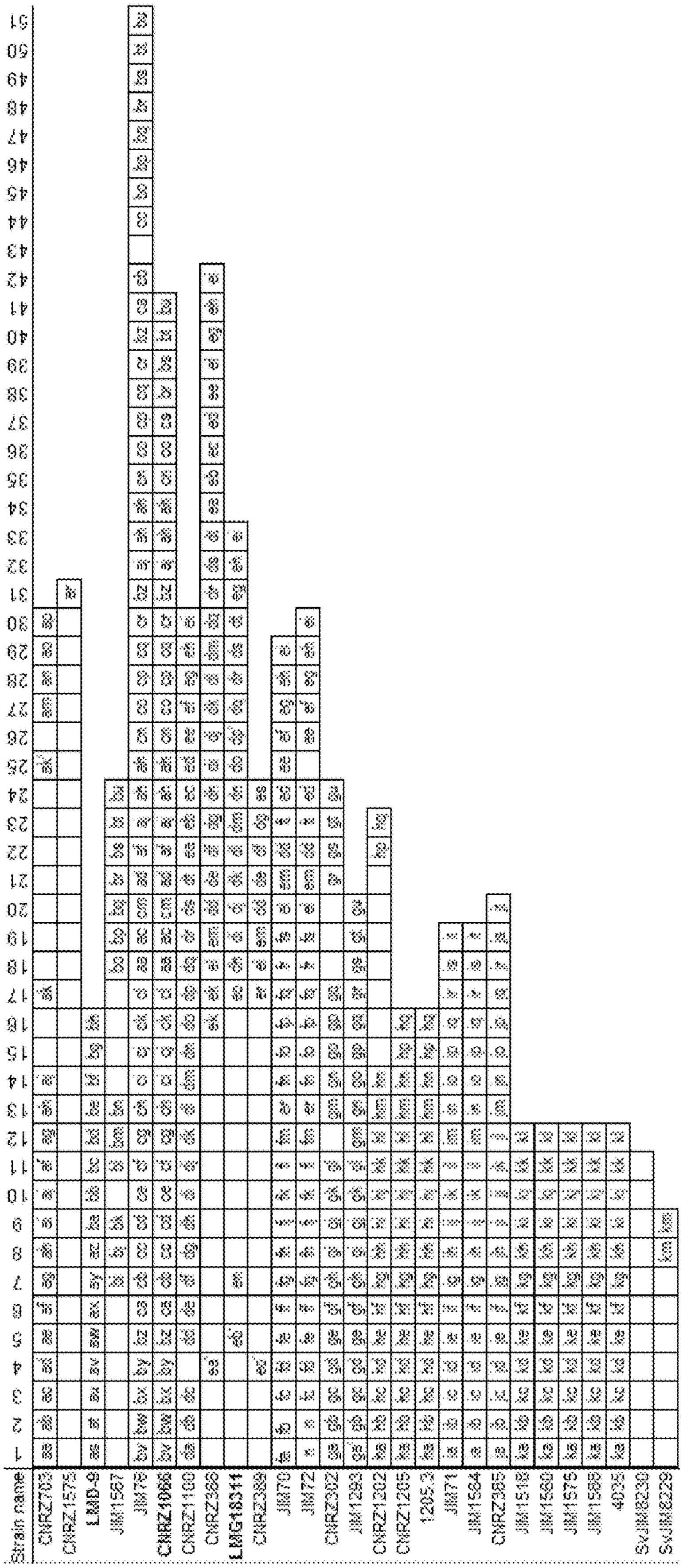
Figure 8:
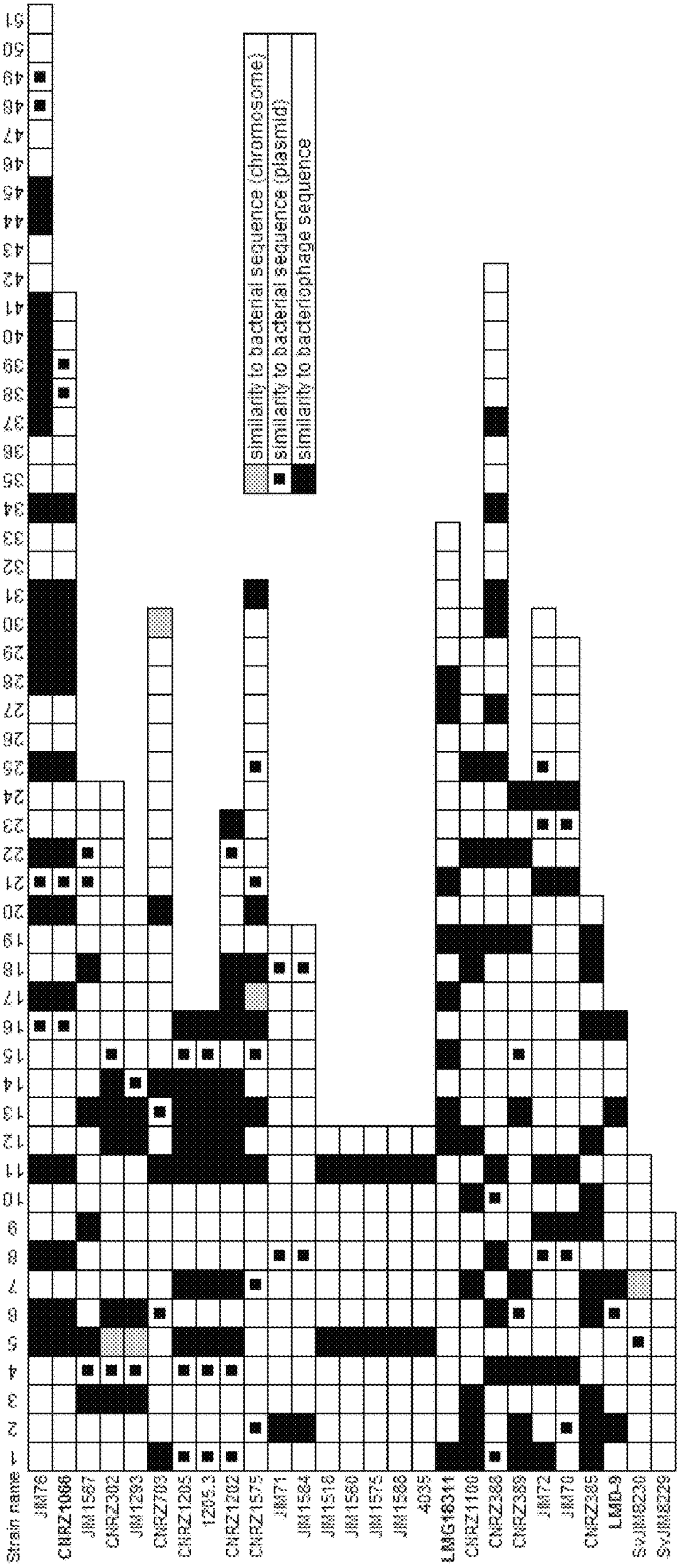
Figure 9:
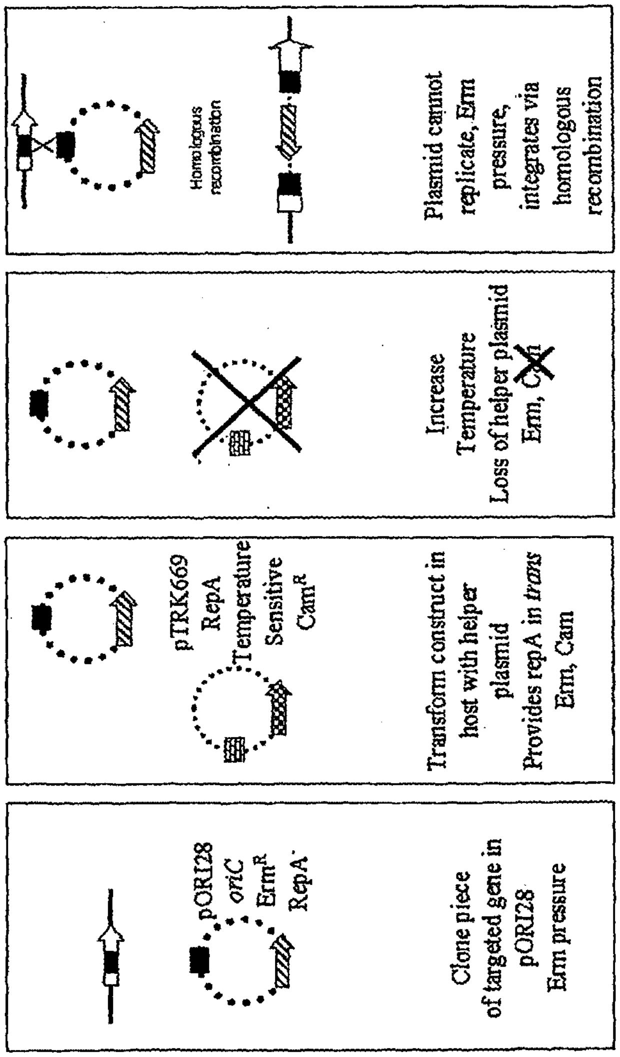
Figure 10:
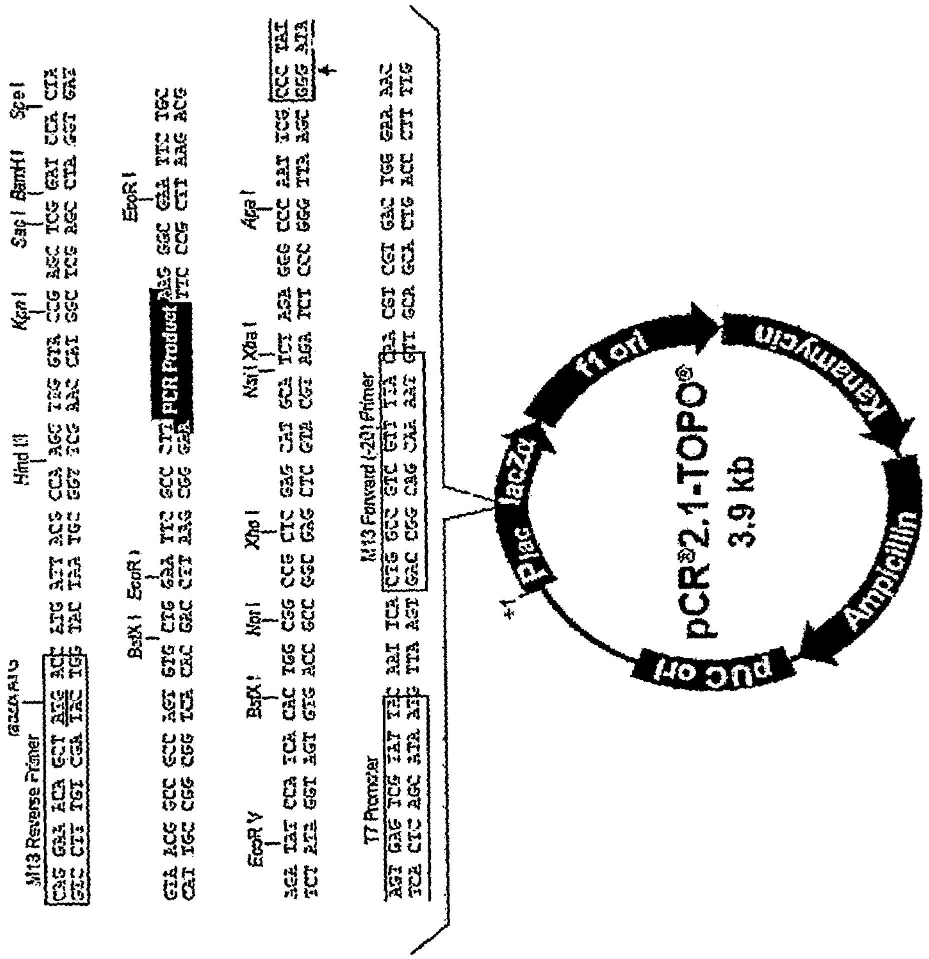
Figure 11:
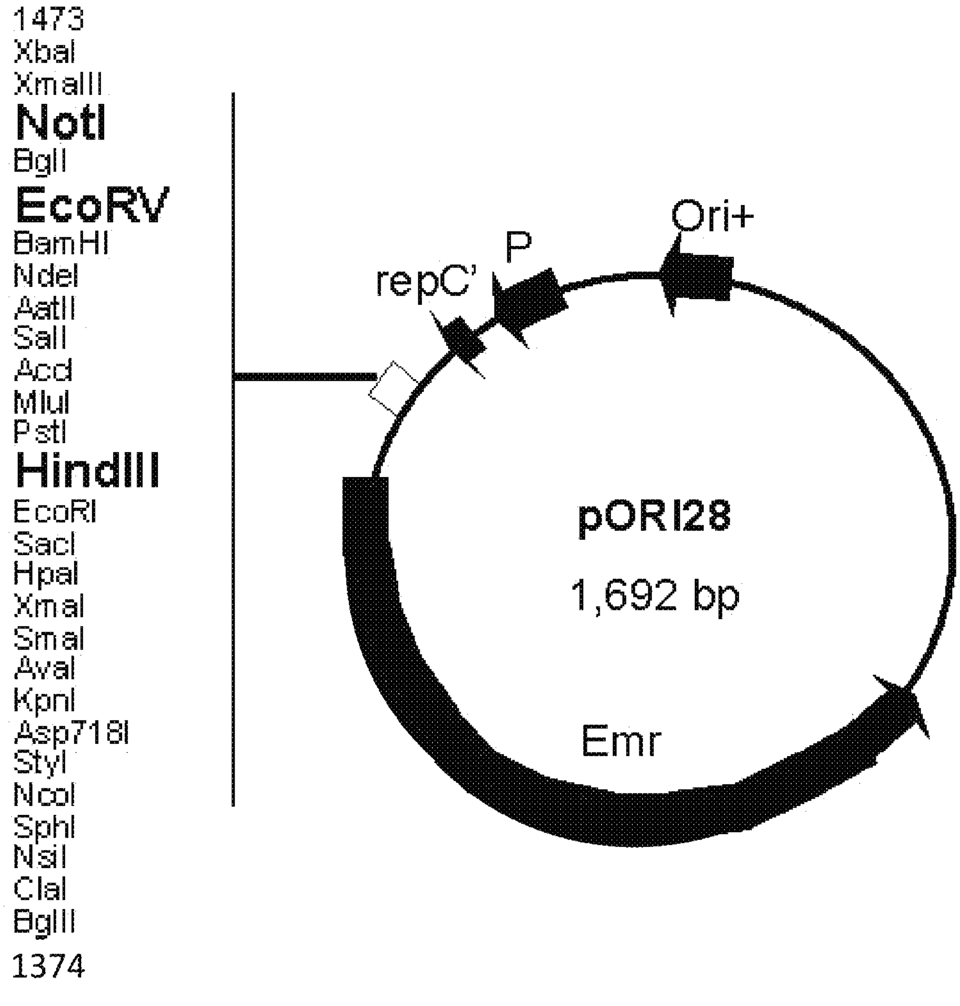

The new spacer that is integrated into the CRISPR1 locus of *Streptococcus thermophilus* strain DGCC7710-RH2 confers to *Streptococcus thermophilus* strain DGCC7710-RH2 a resistance to phage D858, as represented in FIG. 6 and Table 1.

Example 12

Construct Integration and Knockout

Materials and Methods

Strains and Plasmids

*Streptococcus thermophilus* DGCC7710 parent strain, sensitive to phages 858 and 2972

*Streptococcus thermophilus* DGCC7778 CRISPR mutant resistant to 858

*Streptococcus thermophilus* DGCC7778cas1KO

*Streptococcus thermophilus* DGCC7778cas4KO

*Streptococcus thermophilus* DGCC7778RT

*Streptococcus thermophilus* DGCC7778RT'

*Streptococcus thermophilus* DGCC7710R2 CRISPR mutant resistant to 2972

*Streptococcus thermophilus* DGCC7710R2S1S2

*Escherichia coli* EC1,000 provides pORI28 (Russell and Klaenhammer, 2001)

*Escherichia coli* pCR2.1TOPO provides pTOPO (Invitrogen catalog # K4500-01)

pTOPO is a plasmid used for sub-cloning of the various constructs pTOPOcas1ko contains an integral fragment of cas1 pTOPOcas4ko contains an integral fragment of cas4 pTOPOS1S2 contains the S1S2 spacer construct pTOPO RT contains the RT terminal repeat construct pORI28 is a plasmid used for integration of the various constructs in the chromosome of *Streptococcus thermophilus* strains.

pORIcas1ko contains an integral fragment of cas1 pORIcas4ko contains an integral fragment of cas4 pORIS1S2 contains the S1S2 spacer construct purist contains the RT terminal repeat construct Primers

```
Cas1
5'-caaatggatagagaaacgc-3'
and

5'-ctgataaggtgttcgttgtcc-3'

Cas4
5'-ggagcagatggaatacaagaaagg-3'
and

5'-gagagactaggttgtctcagca-3'

S1S2 and RT
P1
5'-acaaacaacagagaagtatctcattg-3'

P2
5'-aacgagtacactcactatttgtacg-3'

P3
5'-tccactcacgtacaaatagtgagtgtactcgtttttgtattctcaag

atttaagtaactgtacagtttgattcaacataaaaag-3'

P4
5'-attecttcatcctcgctttggtt-3'
```

Strains and phages were obtained from the Danisco Culture Collection, or from referenced material (Russell and Klaenhammer, Applied and Environmental Microbiology 2001, 67:43691-4364; Levesque et al., Applied and Environmental Microbiology 2005 71:4057-4068).

Phage preparation, purification and tests were carried out using methods described previously (Duplessis et al., Virology 2005, 340:192-208; Levesque et al., Applied and Environmental Microbiology 2005 71:4057-4068).

*Streptococcus thermophilus* strains were grown at 37 C or 42 C in M17 (Difco Laboratories) supplemented with 0.5% lactose or sucrose. For phage infection, 10 mM CaCl2 were added to the medium prior to phage infection, as described previously (Duplessis et al., Virology 2005, 340:192-208; Levesque et al., Applied and Environmental Microbiology 2005 71:4057-4068).

Enzymes used to carry out restriction digests and PCR were purchased from Invitrogen and used according to the manufacturer's instructions. PCRs were carried out on an Eppendorf Mastercycler Gradient thermocycler as described previously (Barrangou et al., 2002 *Applied and Environmental Microbiology* 68:2877-2884).

Gene inactivation and site-specific plasmid insertion via homologous recombination in the *Streptococcus thermophilus* chromosome were carried out by sub-cloning into the Invitrogen pCR2.1TOPO system, subsequent cloning in the pORI system using *Escherichia coli* as a host and the constructs were ultimately purified and transformed into *Streptococcus thermophilus* as previously described (Russell and Klaenhammer, *Applied and Environmental Microbiology* 2001, 67:43691-4364)

(1) RT Construct Integration

Figure 17:
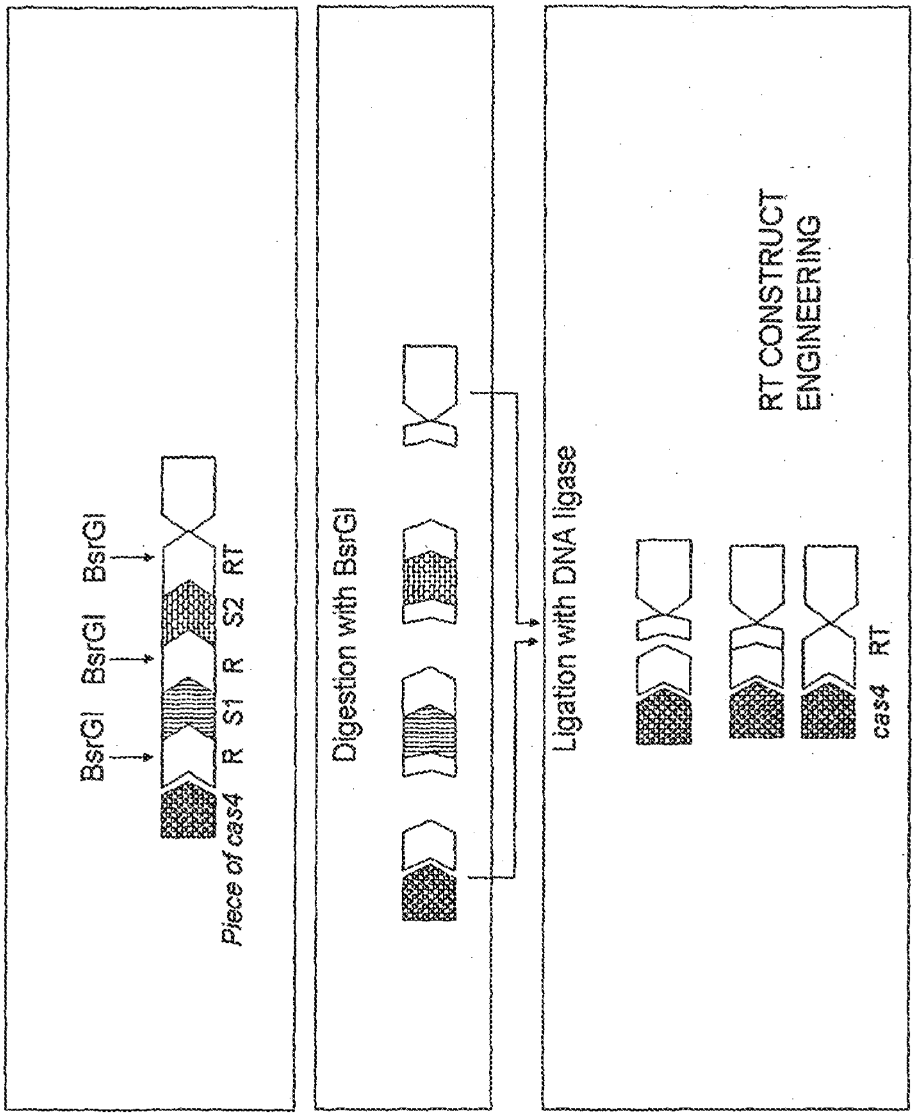
Figure 18:
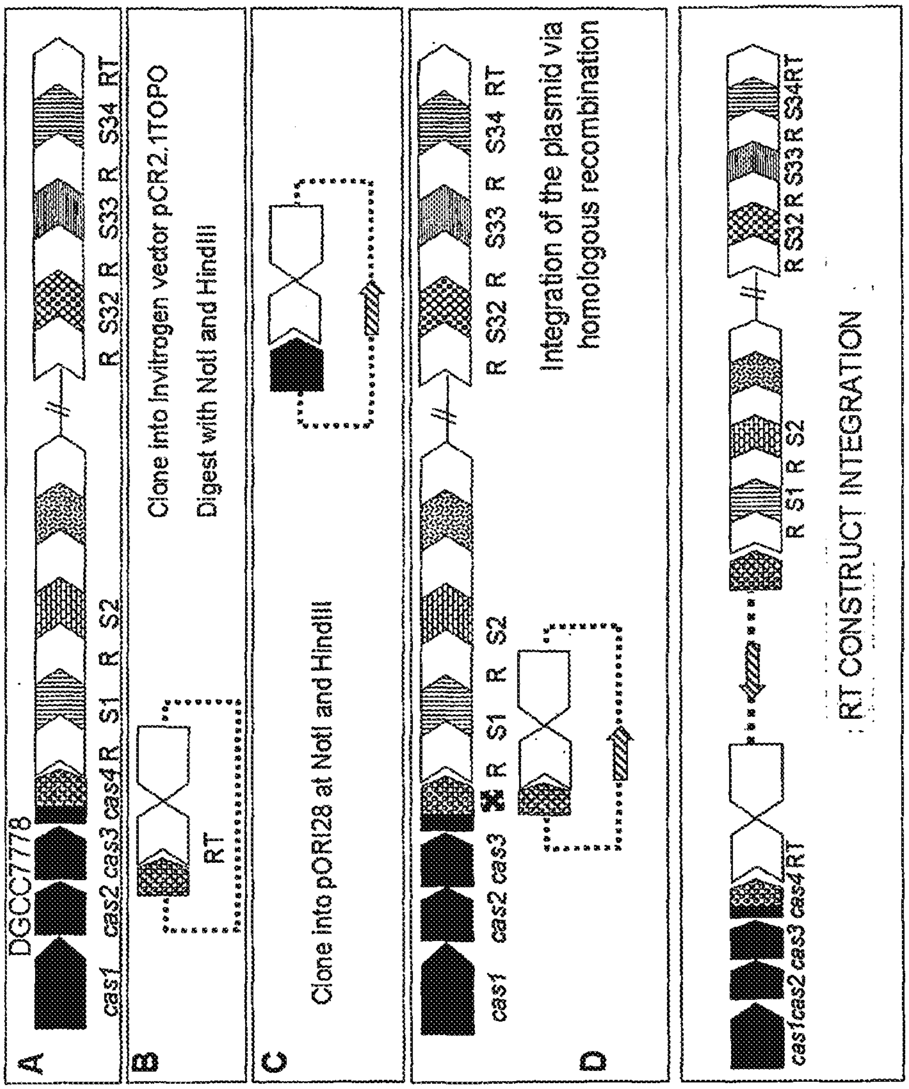
Figure 19:
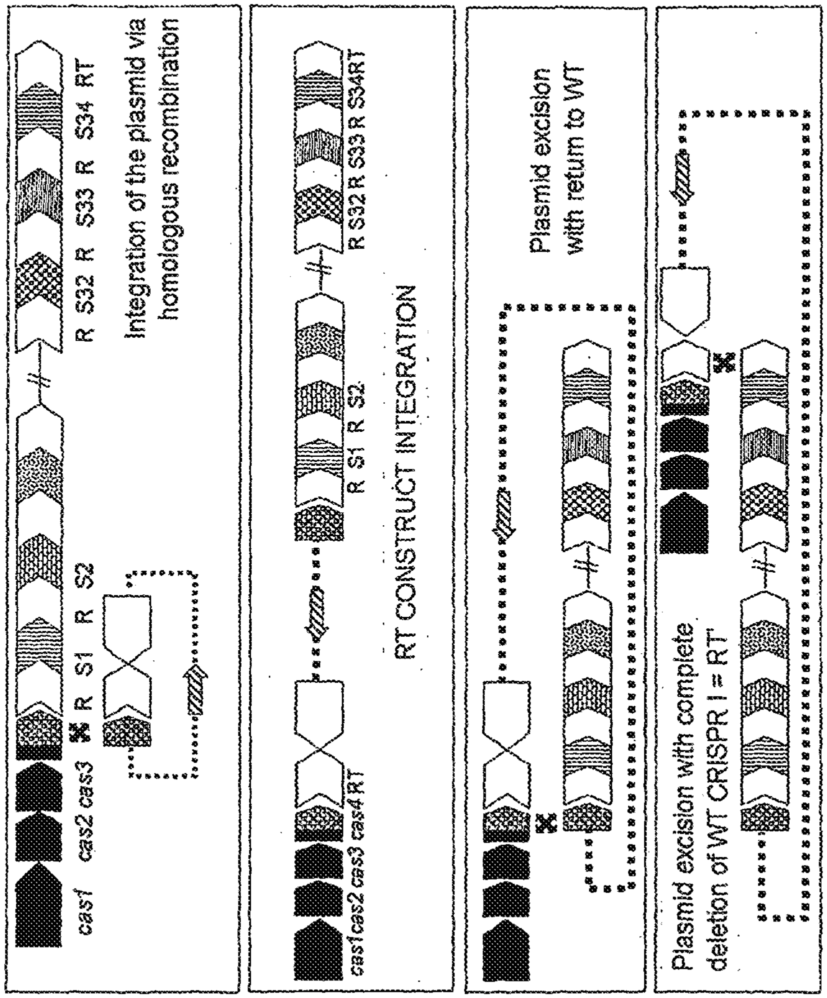
Figure 20:
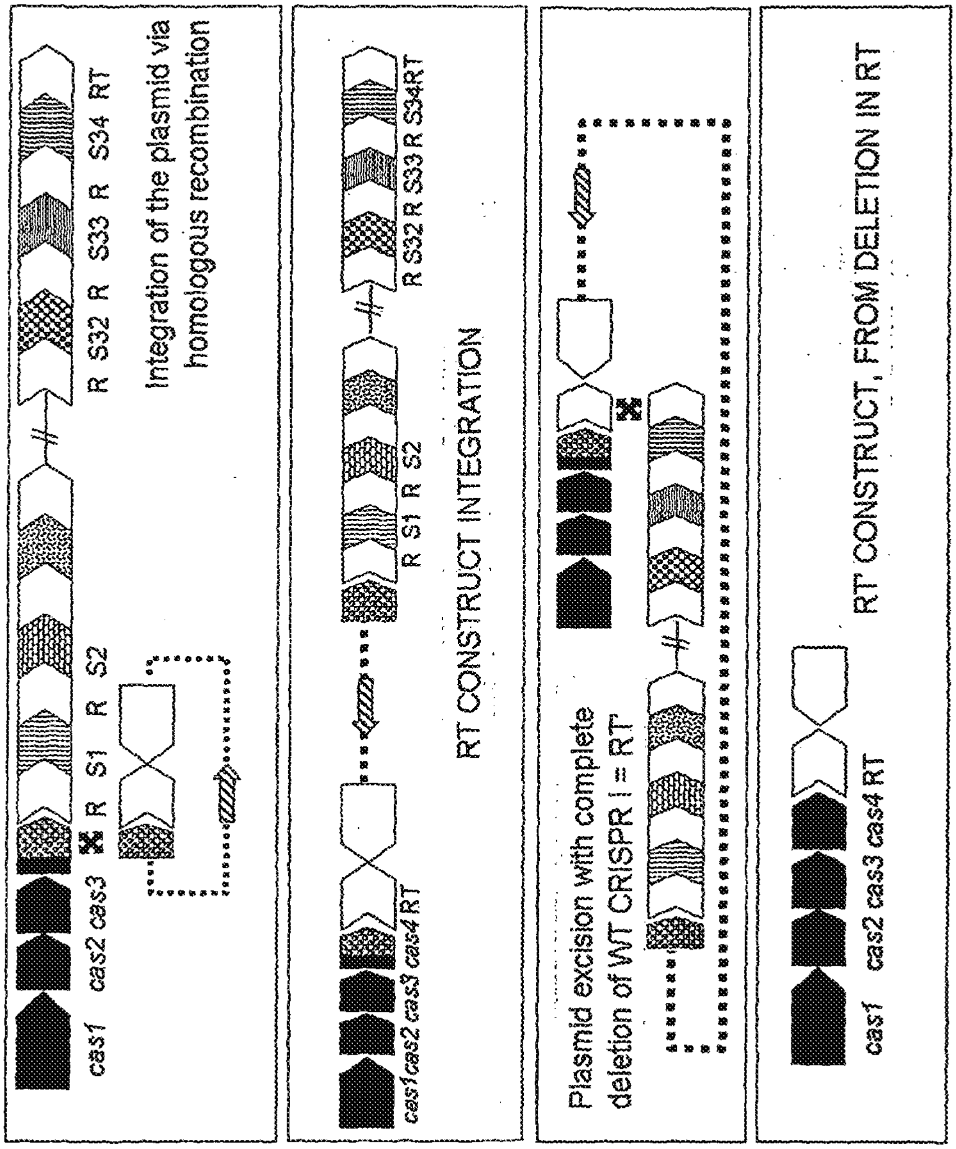

Using the RT Construct engineered as shown in FIG. 17, the construct was inserted just after cas4, as shown in FIG. 18.

The parent DGCC7778 is resistant to phage 858.

The parent has two spacers (S1 and D2) which are identical to phage 858 DNA.

The resulting strain (RT) loses resistance to phage 858, as shown in Table 1. This demonstrates that cas genes need to be in the immediate vicinity of the spacer(s) to confer resistance.

(2) Cas1 Knockout

Figure 12:
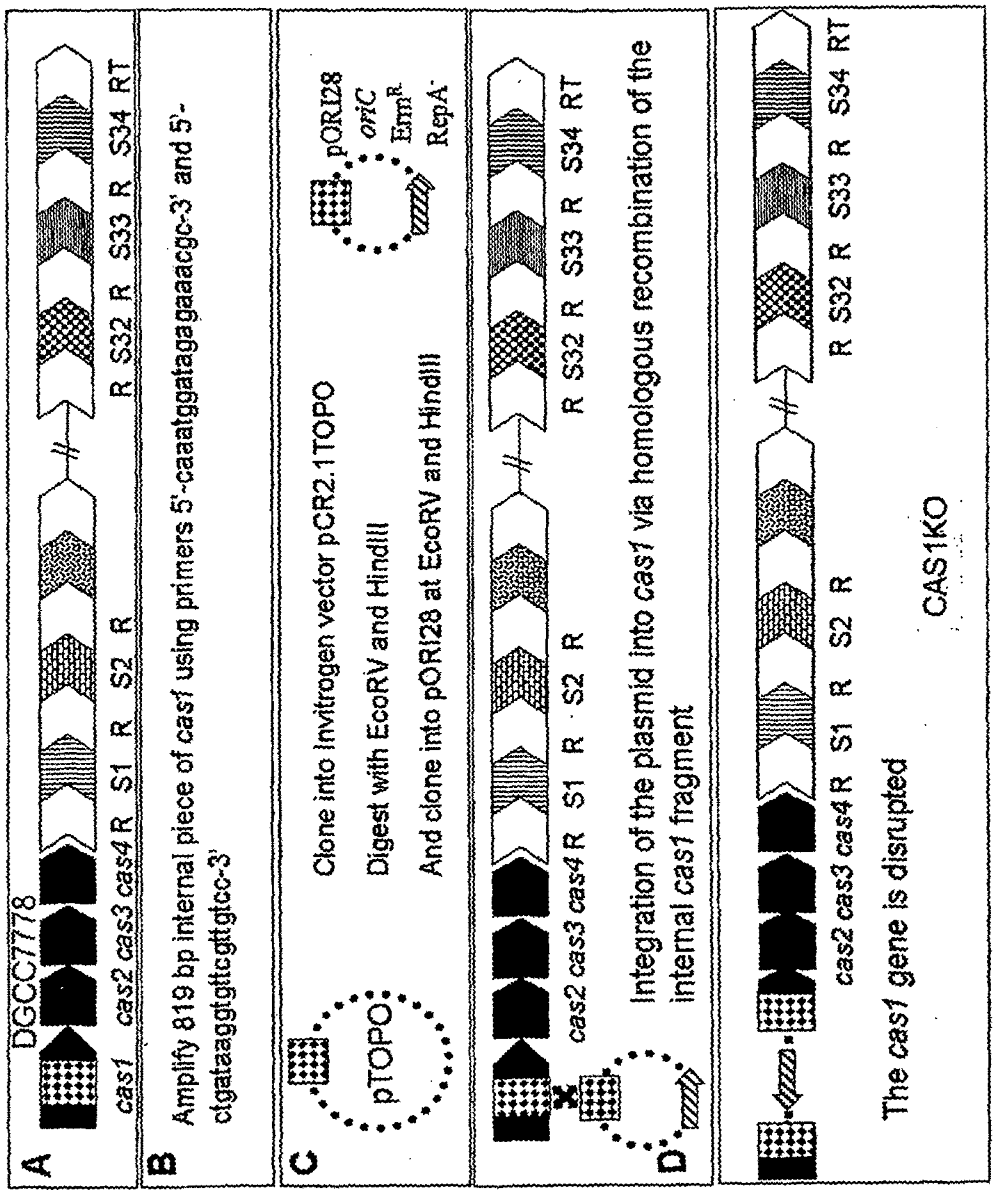
Figure 13:
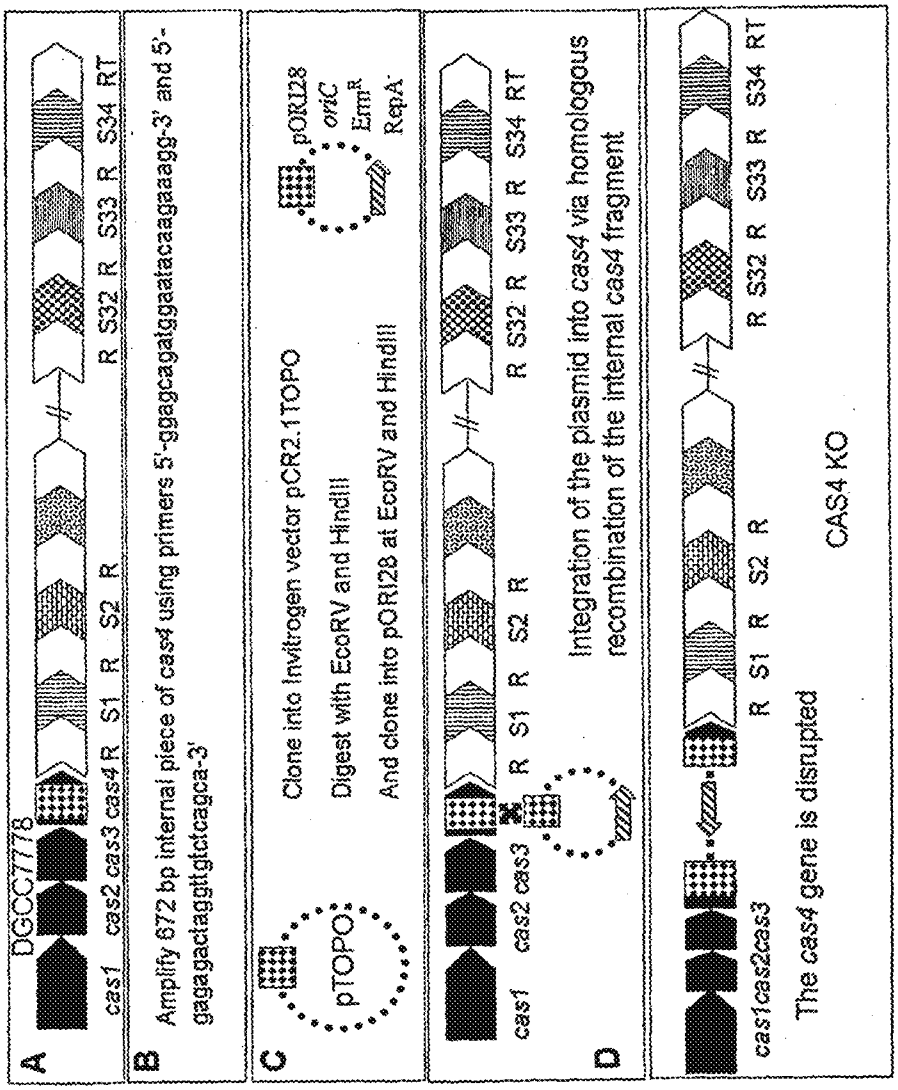

As shown in FIG. 12 the parent DGCC7778 is engineered such that the cas1 gene is disrupted. As shown in Table 1, this results in a loss of resistance, meaning that cas1 is needed to confer resistance.

(3) Cas4 Knockout

As shown in FIG. 12 the parent DGCC7778 is engineered such that the cas4 gene is disrupted.

(4) S1S2 Construct Integration

Figure 14:
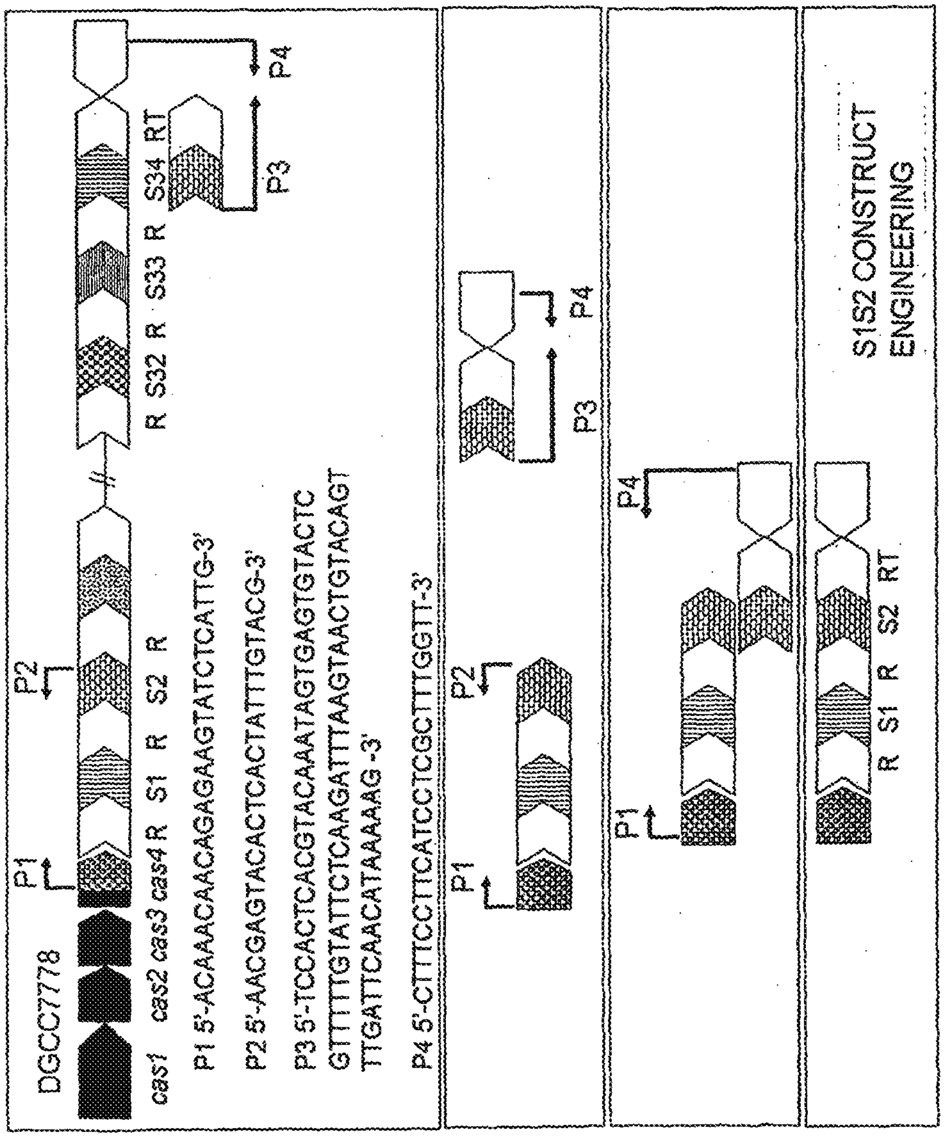
Figure 16:
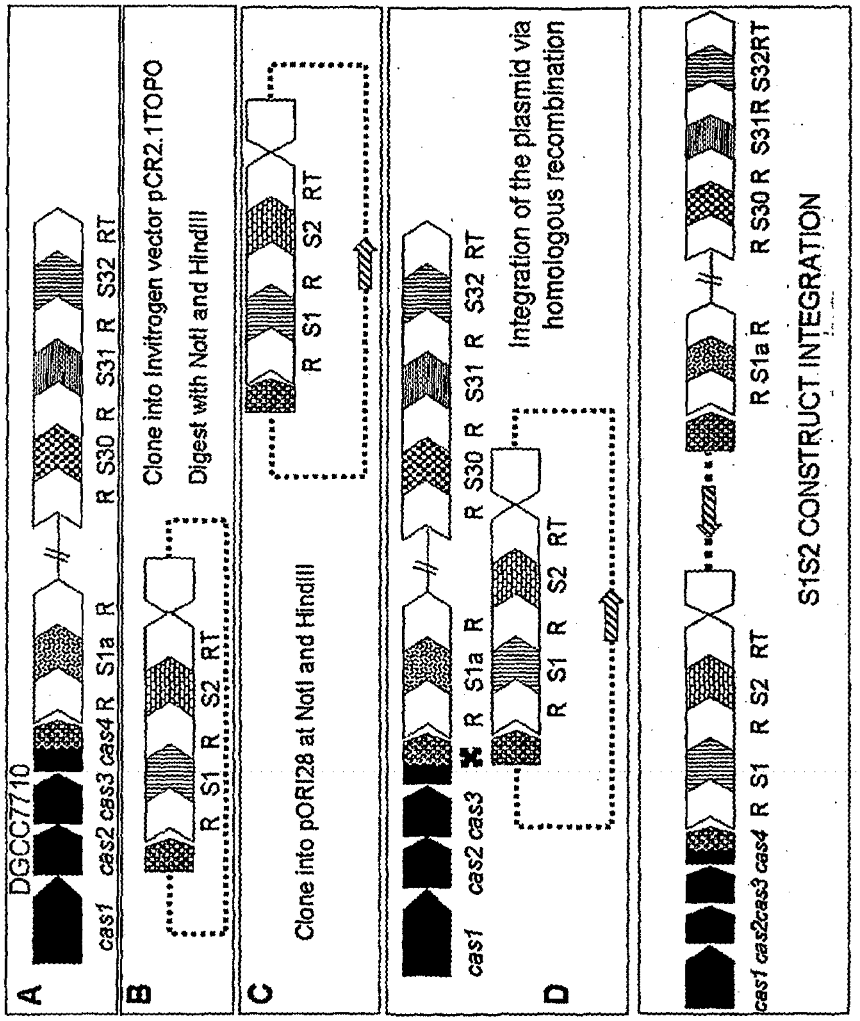

As shown in FIGS. 14-16 the a S1S2 construct is integrated into the parent DGCC7710.

Summary

CRISPRs (Clustered Regularly Interspaced Short Palindromic Repeats) (a.k.a. SPIDR—SPacer Interspersed Direct Repeats) constitute a family of recently described DNA loci widespread throughout prokaryotic genomes. They are constituted of short and highly conserved DNA palindromic repeats which are regularly interspaced by highly polymorphic sequences of about the same length. Additionally, cas genes (CRISPR-associated genes) are usually present in the vicinity of CRISPR sequences. In the literature no clear physiological function has been attributed yet to CRISPR sequences or cas genes.

Here we suggest that CRISPR sequences in combination with cas genes may be used to provide resistance against incoming nucleic acid. Particularly, we propose that the spacers within CRISPR loci provide the specificity for immunity against incoming nucleic acid. As a result, we suggest that cas genes in association with CRISPR sequences be used to provide cells with resistance against particular nucleic acid sequences—such as bacteriophages, plasmids, transposons, and insertion sequences. Additionally, these elements can be manipulated to generate targeted immunity against particular nucleic acid sequences, such as phage components, antibiotic resistance genes, virulence factors, novel sequences, undesirable elements and the like. Thus, the simple knowledge of inter alia CRISPR spacer sequences for a given bacterial strain would be an advantage to determine its lysotype (the lysotype defines the resistance/sensitivity of a given bacterium to various bacteriophages) and predict its ability to survive exposure to defined nucleic acid sequences. Consequently, characterisation of CRISPR loci in bacteria could help to determine, predict and modify host-phage interaction. Particular application of CRISPR genetic engineering, by addition, deletion or modification of spacer sequences, could lead to phage resistant bacterial variants.

CRISPRs (Clustered Regularly Interspaced Short Palindromic Repeats), also known as SPIDR (SPacer Interspersed Direct Repeats), form a new family of repeated sequences which have been identified in complete genome sequences, in numerous prokaryotes, mostly on chromosomes but also on plasmids (Mojica et al., 2000; Jansen et al., 2002a). CRISPR loci are constituted of short and highly conserved DNA repeats (24 to 40 bp, repeated from 1 to 140 times) which are partially palindromic. While there are certain limits to the base degeneracy between repeats from different loci and species, there is no absolute conserved sequence throughout all observed repeats. Moreover the repeats are seemingly oriented within a particular locus, with regards to the neighbouring genes. These repeated sequences (usually specific to a species) are interspaced by polymorphic sequences of constant length (20 to 58 bp depending on the CRISPR) which are designated as "spacers". Up to 20 different CRISPR loci have been found within a single chromosome. FIG. 1 describes one of the CRISPR identified in *Streptococcus thermophilus* CNRZ1066.

For example, the genome of *S. thermophilus* LMG18311 contains 3 CRISPR loci. The 36-bp repeated sequences are different in CRISPR1 (34 repeats), CRISPR2 (5 repeats), and CRISPR3 (one single sequence); nevertheless, they are perfectly conserved within each locus. CRISPR1 and CRISPR2 repeats are respectively interspaced by 33 and 4 sequences of 30 bp in length. All these spacers are different from each other (apart from minor exceptions: very few spacers may be present twice within a given CRISPR locus). They are also different from those found in other strains—such as CNRZ1066 (41 spacers within CRISPR1) or LMD-9 (16 spacers within CRISPR1 and 8 within CRISPR3), which are *S. thermophilus* strains that have very similar genomes.

Although the biological function of CRISPR loci is unknown some hypotheses have been proposed. For example, it has been proposed that they may be involved in the attachment of the chromosome to a cellular structure, or in the chromosome replication and replicon. partitioning, but no experimental demonstration has been reported to confirm these hypotheses.

Figure 2A:
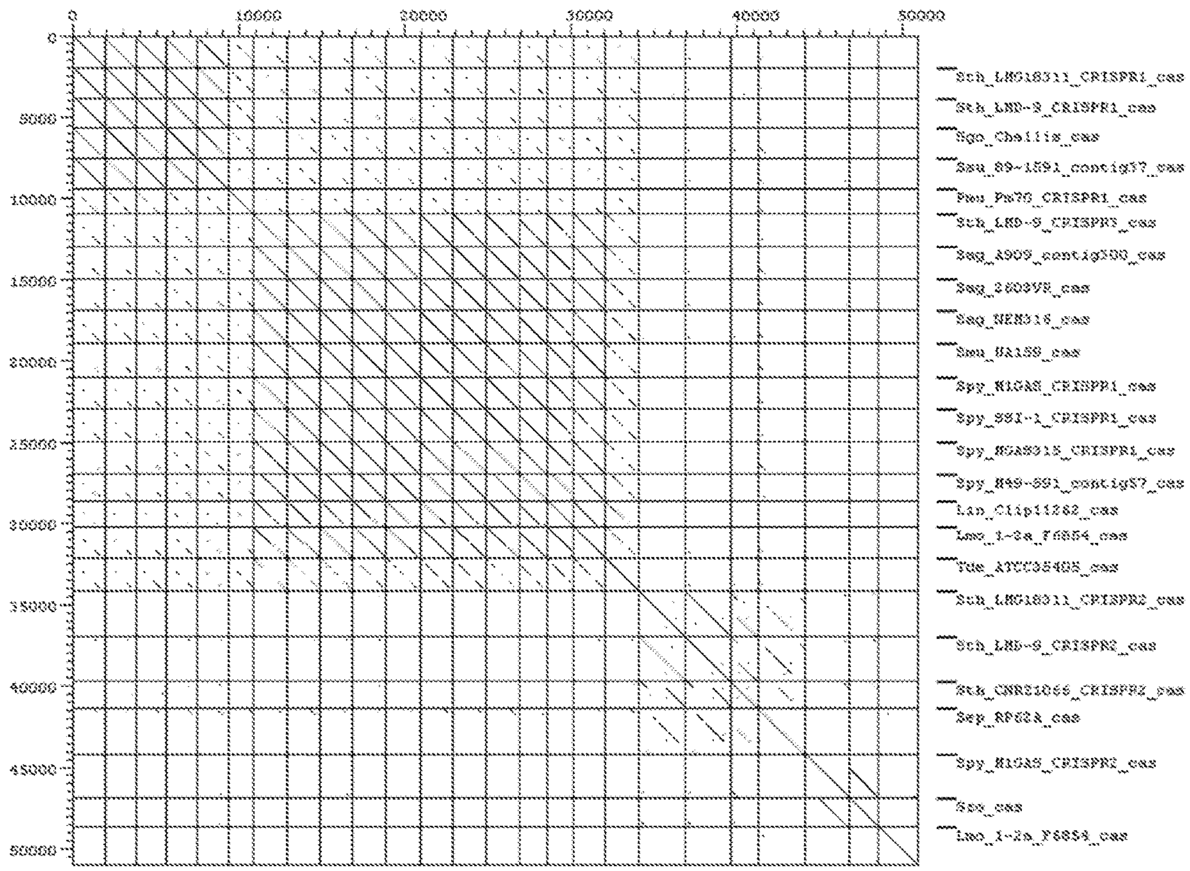
Figure 2B:
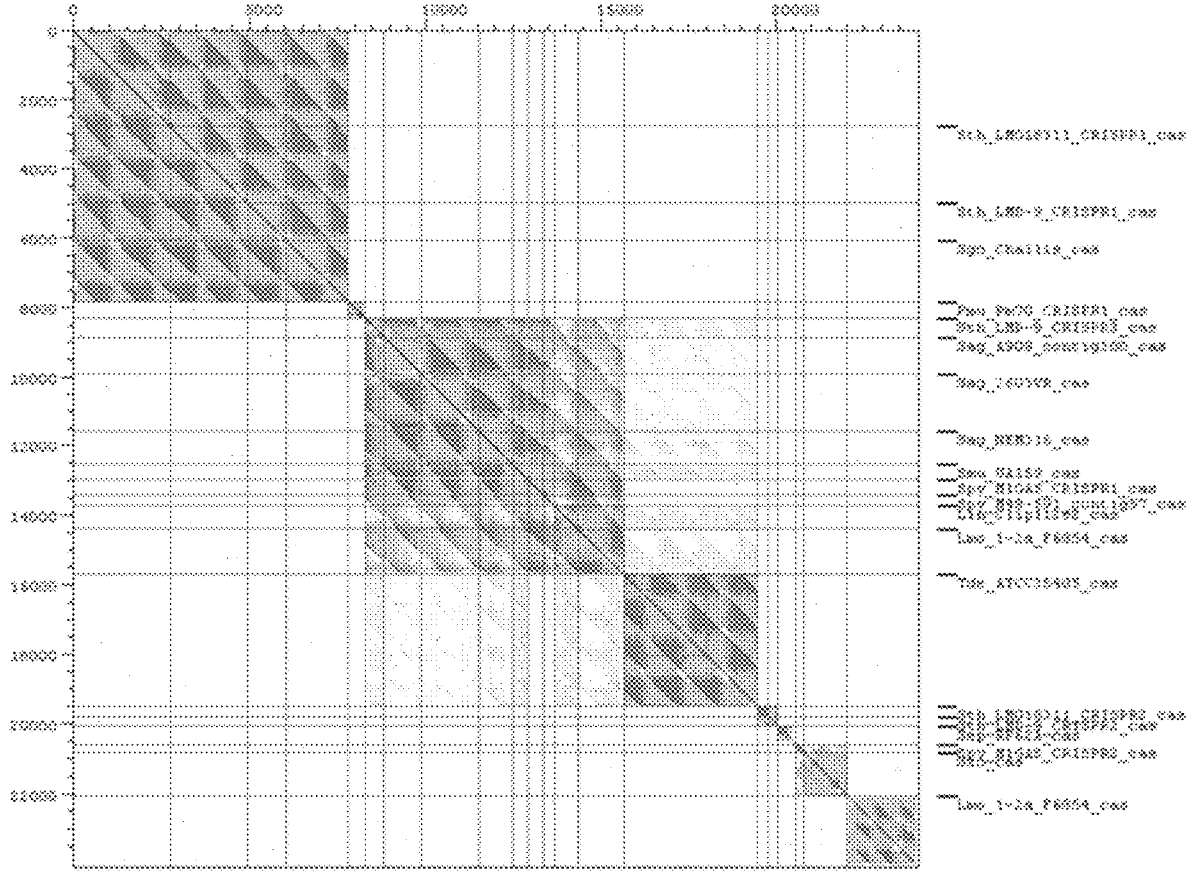

Generally CRISPR loci. are immediately adjacent to a group of 4 to 7. genes which have been called cas (CRISPR-associated) genes (Jansen et al., 2002b). At the present time no clear physiological role has been attributed to Cas proteins, but for some of them the presence of particular protein motifs suggests that they could act as a DNA gyrase or a DNA polymerase. These clusters of 4 to 7 cas genes, either originating from different loci within a given genome or originating from different microorganisms, can be distinguished and grouped into different types on the basis of sequence similarity. One of our major findings is that a given set of cas genes is always associated with a given repeated sequence within a particular CRISPR locus. In other words, cas genes [or Cas proteins] seem to be specific for a. given DNA repeat, meaning that cas genes [or Cas proteins] and the repeated sequence could form a functional pair. Dotplot analyses indicate that the clusters and groups obtained when analyzing Cas protein sequences are similar to those obtained when analyzing CRISPR repeats (as shown in FIG. 2).

Figure 4:
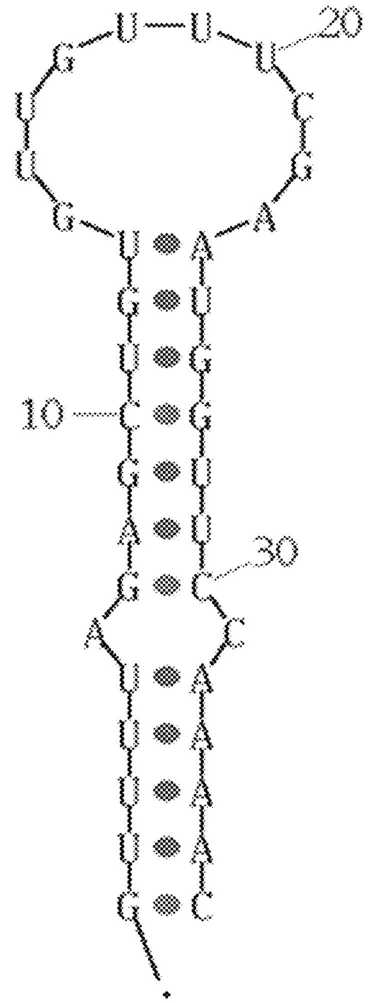

In *S. thermophilus*, a bacterial species for which several phage genomes have been sequenced, the 30-bp spacers are often identical to phage DNA (FIG. 3). This observation has also been made for the spacer sequences of many other bacterial genera and species for which phage DNA sequences are known. Furthermore it has been previously mentioned in at least two recent publications (Pourcel et al., 2005; Mojica et al., 2005). On the other hand the absence of significant sequence similarity for the remaining spacer sequences may be explained by the fact that only a few phage genomes are available at this time. On the basis of very high DNA sequence similarities between some CRISPR spacers and bacteriophage sequences, we propose that the specificity of the CRISPR spacers participates in the determination of the strain lysotype. To support the proposal of an effect of CRISPR spacer sequences on the bacterial immunity against bacteriophages, it was found that a significant proportion of matches for spacers in bacteriophage genome sequences occur within genes likely involved in the host specificity (see FIG. 3). Another hypothesis could be that the spacer sequences are recognized by the bacterium as foreign DNA. Thus, the bacterium would eliminate the nucleic acid molecule bearing this sequence when entering the cell. One argument supporting this idea is the deduced peculiar structure of CRISPR. Indeed, we propose that the repeat elements provide a structural feature while the spacers containing the sequence providing specific immunity against incoming nucleic acid. The palindromic repeats have the potential to form very stable hairpin (stem-loop) structures (see FIG. 4), and they are separated by spacers whose size corresponds to roughly 3 turns of the DNA helix (although it can vary between 2 and 5). Thus any CRISPR locus could be highly structured into a series of regularly spaced DNA hairpins.

Advantageously, the lysotype of a given bacterial strain may be modified either by natural generation of resistant derivatives (Bacteriophage Insensitive Mutants), or by genetic engineering. Specifically, genetic engineering solutions may be designed by, for example, addition, by deletion, or by modification of the spacer sequences or even a complete CRISPR locus.

Examples of applications of this invention include, but are not limited to:

(i) Phage resistance. Particular CRISPR spacers derived from bacteriophage DNA may be added within a bacterial host CRISPR locus as to provide resistance against this particular bacteriophage, thus preventing phage attack. Additionally, particular regions within the phage genome (host specificity proteins) can be targeted that provide particular phage-host recognition, or that are highly conserved within phage DNA, such as sequences from helicase or primase genes, head and tail structural proteins, or proteins with conserved domains (eg. helicase, holing, lysine, and others) or conserved sequences amongst important phage genes.

(ii) Resistance to plasmid transfer. Particular CRISPR spacers derived from plasmid DNA can be added within a bacterium CRISPR locus as to provide resistance against this particular plasmid, thus preventing transfer of foreign DNA into the microbe. Specifically, particular regions within the plasmid DNA can be targeted as to provide immunity against plasmid DNA, such as sequences within the plasmid's origin of replication.

(iii) Resistance to mobile genetic elements. Particular CRISPR spacers derived from mobile genetic element DNA can be added within a bacterium CRISPR locus as to provide resistance against mobile genetic elements such as transposable elements and insertion sequences, thus preventing transfer of foreign DNA and genetic drift. Specifically, particular regions within transposons and insertion sequences can be targeted as to provide immunity against mobile genetic elements. For example, targets can include conjugative transposons (Tn916), class II transposons (Tn501), or insertions sequences (IS26).

(iv) Resistance to antibiotic resistance genes. Particular CRISPR spacers derived from antibiotic resistance encoding genes can be added within a bacterium CRISPR locus as to prevent transfer of genes conferring resistance to antibiotics into the bacterial host, thus reducing the risk of acquiring antibiotic resistance markers. For example, targets can include vanR, a gene conferring resistance to vancomycin, or tetR, a gene conferring resistance to tetracycline, or targeting beta-lactamase inhibitors.

(v) Resistance to genes encoding virulence factors. Particular CRISPR spacers derived from genes encoding virulence factors can be added within a bacterium CRISPR locus as to provide resistance against the transfer of genes conferring virulence into the bacterium. For example, factors commonly contributing to virulence in microbial pathogens can be targeted, such as toxins, internalins and hemolysins.

(vi) Diagnostics. The CRISPR spacers within a particular bacterium may be detected or sequenced as to predict/ determine the likely sensitivity of particular microbes to bacteriophage, and thus be used as a lysotype predictor for microbial selection.

(vii) Resistance to novel sequences. Novel spacer sequences can be synthesized de novo, engineered and integrated into a CRISPR within a selected bacterial host as to provide resistance to a particular identical and novel sequence present into an infecting DNA molecule.

Since CRISPRs are wide-spread among bacterial species, the aforementioned applications could be used in a large variety of organisms. CRISPR loci have been described in a number of Gram-positive (including lactic acid bacteria) and Gram-negative bacteria. Thus, CRISPR loci in association with cas genes can be used to characterize/modify strain lysotype and generate resistance to nucleic acid in a wide range of bacteria. In addition to potential applications for phage resistance, it has been mentioned in the literature that CRISPR sequences show some homology to mobile genetic elements such as plasmids and transposons (Mojica et al., 2005).

In a further aspect, there is provided the use of a combination of a CRISPR locus and one or more cas genes to provide resistance against a defined nucleic acid.

Suitably, the nucleic acid is DNA.

Suitably, the nucleic acid is RNA.

Suitably, the nucleic acid is derivable (preferably, derived) from a phage.

Suitably, the nucleic acid is derivable (preferably, derived) from a plasmid.

Suitably, the nucleic acid is derivable (preferably, derived) from a mobile genetic element.

Suitably, the nucleic acid is derivable (preferably, derived) from a transposon (Tn).

Suitably, the nucleic acid is derivable (preferably, derived) from an insertion sequence (IS).

Suitably, the nucleic acid nucleic acid is derivable (preferably, derived) from undesirable targeted genetic elements.

Suitably, the nucleic acid is derivable (preferably, derived) from an antibiotic resistance gene.

Suitably, the nucleic acid is derivable (preferably, derived) from a virulence factor.

Suitably, the nucleic acid is derivable (preferably, derived) from a pathogenicity island.

Suitably, the nucleic acid nucleic acid is derivable (preferably, derived) from a novel sequence, so as to provide resistance against entities carrying this particular molecule.

In a further aspect, there is provided the use of CRISPR for identification and typing.

In a further aspect, there is provided the use of one or more cas genes and one or more CRISPR elements (eg. one or more CRISPR repeats and/or CRISPR spacers) for modulating resistance in a cell against a target nucleic acid or a transcription product thereof.

TABLE 1

| | | Phage 2972 | | Phage 858 | |
|---|---|---|---|---|---|
| Strains | BIM on[1] | Phage sensitivity[2] | Spacer-phage homology[3] | Phage sensitivity[2] | Spacer-phage homology[3] |
| DGCC7710 | — | S | Ctrl | S | Ctrl |
| DGCC7778 | 858 | S | >10 SNPs | R | 100% (2 spacers) |
| DGCC7710•RH1 | 858 | R | 100% | R | 100% |
| DGCC7710•RH2 | 858 | R | 100% | R | 100% |
| DGCC7778RT | 858 | S | >10 SNPs | S | 100% but not next to cas |
| DGCC7778RT' | 858 | S | >10 SNPs | S | No spacers left |
| DGCC7778cas1 | 858 | S | >10 SNPs | S | 100% (2 spacers) but cas1 KO |
| DGCC7778cas4 | 858 | S | >10 SNPs | R | 100% (2 spacers) but cas4 KO |
| DGCC7710-R2 | 2972 | R | 100% (1 spacer) | S | 5 SNPs |
| DGCC7710-R2S1S2 | 2972 | S | 100% but not next to cas | R | S1S2 are 100% identical to phase 858 |

[1]Phage used to generate Bacteriophage Insensitive Mutants (BIMs)
[2]Phage sensitivity of the strain, S = sensitive, R = resistant as determined by spot and plaque assays
[3]Homology between the new spacer of the mutant, and the DNA sequence of the phage used to generate the mutant
Phages retained the ability to adsorb to the mutants

REFERENCES

Bolotin A, Quinquis B, Sorokin A, Ehrlich S D (2005). Clustered regularly interspaced short palindrome repeats (CRISPRs) have spacers of extrachromosomal origin. *Microbiology* 151(8):2551-61.

Groenen P M, Bunschoten A E, van Soolingen D, & J D van Embden (1993). Nature of DNA polymorphism in the direct repeat cluster of *Mycobacterium tuberculosis*; application for strain differentiation by a novel typing method. Molecular Microbiology 10:1057-1065.

Hoe N, Nakashima K, Grigsby D, Pan X, Dou S J, Naidich S, Garcia M, Kahn E, Bergmire-Seat D, & J M Musser (1999). Rapid molecular genetic subtyping of serotype M1 group A *Streptococcus* strains. Emerging Infectious Diseases 5:254-263.

Jansen R, Van Embden J D A, Gaastra W, & L M Schouls (2002a). Identification of a novel family of sequence repeats among prokaryotes. OMICS 6:23-33.

Jansen R, Van Embden J D A, Gaastra W, & L M Schouls (2002b). Identification of genes that are associated with DNA repeats in prokaryotes. Molecular Microbiology 43:1565-1575

Kamerbeek J, Schouls L, Kolk A, Van Agterveld M, Van Soolingen D, Kuijper S, Bunschoten A, Molhuizen H, Shaw R, Goyal M, & J Van Embden (1997). Simultaneous detection and strain differentiation of *Mycobacterium tuberculosis* for diagnosis and epidemiology. Journal of Clinical Microbiology 35:907-914

Mojica F J M, Diez-Villasenor C, Soria E, & G Juez (2000). Biological significance of a family of regularly spaced repeats in the genomes of Archaea, Bacteria and mitochondria. Molecular Microbiology 36:244-246

Mojica F J M, Diez-Villasenor C, Garcia-Martinez J, & E Soria (2005). Intervening sequences of regularly spaced prokaryotic repeats derive from foreign genetic elements. Journal of Molecular Evolution 60:174-182

Pourcel C, Savignol G, & G Vergnaud (2005). CRISPR elements in *Yersinia pestis* aquire new repeats by preferential uptake of bacteriophage DNA and provide additional tools for evolutionary studies. Microbiology 151: 653-663

Saunders N F W, Goodchild A, Raftery M, Guilhaus M, Curmi P M G, & R Cavicchioli (2005). Predicted roles for hypothetical proteins in the low-temperature expressed proteome of the antartic archaeon *Methanococcoides burtonii*. Journal of Proteome Research 4:464-472

Mongodin E F, Hance I R, DeBoy R T, Gill S R, Daugherty S, Huber R, Fraser C M, Stetter K, & K E Nelson (2005). Gene transfer and genome plasticity in *Thermotoga maritima*, a model hyperthermophilic species. Journal of Bacteriology 187:4935-4944

Peng X, Brugger K, Shen L, She Q, & R A Garrett (2003). Genus-specific protein binding to the large clusters of DNA repeats (Short Regularly Spaced Repeats) present in *Sulfolobus* genomes. Journal of Bacteriology 185:2410-2417

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry, microbiology and molecular biology or related fields are intended to be within the scope of the following claims.

The invention claimed is:

1. A DNA construct comprising a cas gene and a heterologous regulatory sequence, which is heterologous to the source of the cas gene, operably linked to at least one nucleotide sequence component of the construct, wherein the cas gene comprises one of the nucleotide sequences of the SEQ ID NO:s selected from the group consisting of SEQ ID NO:s 505-508, 510-516, and 518-521 or a cas gene encoding a polypeptide having at least 100% identity to a polypeptide encoded by one of the nucleotide sequences of the SEQ ID NO:s selected from the group consisting of SEQ ID NO:s 505-508, 510-516 and 518-521.

2. The construct according to claim 1, comprising one or more CRISPR repeat(s) which are from the same CRISPR locus as the cas gene and originate from a genome or a plasmid.

3. A vector comprising the construct of claim 1.

4. A host cell comprising the construct of claim 1.

5. A cell culture comprising the host cell of claim 4.

6. A cell culture according to claim 5, wherein said culture is a starter culture or a probiotic culture.

7. A food or feed produced from the host cell of claim 4.

8. A construct according to claim 1 wherein said cas gene encodes a Cas protein which keeps the ability to form a functional combination with a CRISPR repeat as set forth in SEQ ID NO:s 18-19.

9. A DNA construct comprising a cas gene having one of the nucleotide sequences of the SEQ ID NO:s selected from the group consisting of SEQ ID NO:s 505-508, 510-516, and 518-521 wherein said cas gene is operably linked to a heterologous regulatory sequence which is heterologous to the source of the cas gene.

* * * * *